US010584350B2

(12) United States Patent
He et al.

(10) Patent No.: US 10,584,350 B2
(45) Date of Patent: Mar. 10, 2020

(54) STRUCTURALLY MODIFIED COI1

(71) Applicant: Board of Trustees of Michigan State University, East Lansing, MI (US)

(72) Inventors: Sheng Yang He, Okemos, MI (US); Li Zhang, Lansing, MI (US); Jian Yao, Kalamazoo, MI (US); Rahul Banerjee, Rockville, MD (US); John Withers, East Lansing, MI (US)

(73) Assignee: Board of Trustees of Michigan State University, East Lansing, MI (US)

(*) Notice: Subject to any disclaimer, the term of this patent is extended or adjusted under 35 U.S.C. 154(b) by 139 days.

(21) Appl. No.: 15/796,311

(22) Filed: Oct. 27, 2017

(65) Prior Publication Data
US 2018/0135070 A1    May 17, 2018

Related U.S. Application Data

(60) Provisional application No. 62/413,850, filed on Oct. 27, 2016.

(51) Int. Cl.
*C12N 15/82* (2006.01)
*C07K 14/415* (2006.01)
*A01N 53/00* (2006.01)

(52) U.S. Cl.
CPC ........ *C12N 15/8274* (2013.01); *C07K 14/415* (2013.01); *C12N 15/82* (2013.01); *C12N 15/8281* (2013.01); *C12N 15/8286* (2013.01); *A01N 53/00* (2013.01)

(58) Field of Classification Search
None
See application file for complete search history.

(56) References Cited

U.S. PATENT DOCUMENTS

| | | | |
|---|---|---|---|
| 5,384,253 | A | 1/1995 | Krzyzek et al. |
| 5,472,869 | A | 12/1995 | Krzyzek et al. |
| 5,489,520 | A | 2/1996 | Adams et al. |
| 5,538,877 | A | 7/1996 | Lundquist et al. |
| 5,538,880 | A | 7/1996 | Lundquist et al. |
| 9,297,017 | B2 * | 3/2016 | Sheard .................. C07K 14/415 |

FOREIGN PATENT DOCUMENTS

| | | |
|---|---|---|
| EP | 0604662 A1 | 7/1994 |
| EP | 0672752 A1 | 9/1995 |
| WO | WO-9/506127 A1 | 3/1995 |
| WO | WO-95/06128 A2 | 3/1995 |

OTHER PUBLICATIONS

Bell, K.S., et al., "Genome sequence of the enterobacterial phytopathogen *Erwinia carotovora* subsp. *atroseptica* and characterization of virulence factors", Pro. Natl. Acad. Sci. USA, 101(30), (2004), 11105-11110.

Bender, C. L., et al., "*Pseudomonas syringae* phytotoxins: Mode of action, regulation, and biosynthesis by peptide and polyketide synthetases", Microbiol Mol Biol Rev, 63(2), (1999), 266-292.

Block, A., et al., "The *Pseudomonas syringae* type III effector HopD1 suppresses effector-triggered immunity, localizes to the endoplasmic reticulum, and targets the *Arabidopsis* transcription factor NTL9", New Phytol 201(4), (2014), 1358-1370.

Brooks, D. M., et al., "Identification and characterization of a well-defined series of coronatine biosynthetic mutants of *Pseudomonas syringae* pv. *tomato* DC3000", Mol Plant Miscrobe Interact, 17(2), (2004), 162-174.

Browse, J., et al., "Jasmonte Passes Muster: A Receptor and Targets for the Defense Hormone", Annu Rev Plant Biol., 60, (2009), 183-205.

Case, D. A., et al., "AMBER 12 Reference Manual (University of California, San Francisco)", Available at ambermd.org/doc12/Amber12.pdf. Accessed Oct. 20, 2015, (2012), 1-348 (350 pgs.).

Chandler, V. L., et al., "Two Regulatory Genes of the Maize Anthocyanin Pathway are Homologous: Isolation of B Utilizing R Genomic Sequences", The Plant Cell, 1(12), (1989), 1175-1183.

Chini, A., et al., "The ZIM domain mediates homo- and heteromeric interactions between *Arabidopsis* JAZ proteins", Plant J., 59(1), (2009), 77-87.

Christou, P., et al., "Stable transformation of soybean by electroporation and root formation from transformed callus", Proc. Natl. Acad. Sci. USA, 84(12), (1987), 3962-3966.

Chung, H. S., et al., "A Critical Role for the TIFY Motif in Repression of Jasmonate Signaling by a Stabilized Splice Variant of the Jasmonate ZIM-Domain Protein JAZ10 in *Arabidopsis*", The Plant Cell, 21(1), (2009), 131-145.

Chung, H. S., et al., "Regulation and Function of *Arabidopsis* Jasmonate ZIM-Domain Genes in Response to Wounding and Herbivory", Plant Physiol, 146(3), (2008), 952-964.

Cipollini, D., et al., "Salicylic acid inhibits jasmonic acid-induced resistance of *Arabidopsis thaliana* to *Spodoptera exigua*", Mol Ecol, 13(6), (2004), 1643-1653.

Clark, J., et al., "A Future for Transgenic Livestock", Nature Reviews Genetics, 4, (2003), 825-833.

Clough, S. J., et al., "Floral dip: A simplified method for *Agrobacterium*-mediated transformation of *Arabidopsis thaliana*", The Plant J., 16(6), (1998), 735-743.

Coruzzi, G., et al., "Tissue-specific and light-regulated expression of a pea nuclear gene encoding the small subunit of ribulose-1,5-bisphosphate carboxylase.", The EMBO Journal, 3(8), (1984), 1671-1679.

Creelman, R. A., et al., "Biosynthesis and Action of Jasmonates in Plants", Annu Rev Plant Mol. Biol., 48, (1997), 355-381.

Cui, J., et al., "*Pseudomonas syringae* manipulates systemic plant defenses against pathogens and herbivores.", Proc Natl Acad Sci USA, 102(5), (2013), 1791-1796.

Dekeyser, R A., et al., "Transient Gene Expression in Intact and Organized Rice Tissues", The Plant Cell, 2(7), (Jul. 1990), 591-602.

(Continued)

*Primary Examiner* — Eileen B O Hara
(74) *Attorney, Agent, or Firm* — Schwegman Lundberg & Woessner, P.A.

(57) ABSTRACT

Described herein are plants that are resistant to herbicides, such as herbicide compositions comprising coronatine, where the herbicide-resistant plants express a modified CORONATINE INSENSITIVE 1 (COI1) protein.

28 Claims, 14 Drawing Sheets

Specification includes a Sequence Listing.

(56) References Cited

OTHER PUBLICATIONS

Dong, X., et al., "Induction of *Arabidopsis* Defense Genes by Virulent and Avirulent *Pseudomonas syringae* Strains and by a Cloned Avirulence Gene", The Plant Cell, 3(1), (1991), 61-72.
Dou, D., et al., "Phytopathogen Effectors Subverting Host Immunity: Different Foes, Similar Battleground", Cell Host Microbe, 12(4), (2012), 484-495.
Ebert, P. R., et al., "Identification of an essential upstream element in the nopaline synthase promoter by stable and transient assays", Proc. Natl. Acad. Sci. USA, 84(16), (1987), 5745-5749.
Feys, B., et al., "*Arabidopsis* Mutants Selected for Resistance to the Phytotoxin Coronatine Are Male Sterile, Insensitive to Methyl Jasmonate, and Resistant to a Bacterial Pathogen", The Plant Cell, 6(5), (1994), 751-759.
Fonseca, S., et al., "(+)-7-iso-Jasmonoyl-L-isoleucine is the endogenous bioactive jasmonate", Nat Chem Biol, 5(5), (2009), 344-350.
Fyans, J. K., et al., "Characterization of the Coronatine-Like Phytotoxins Produced by the Common Scab Pathogen *Streptomyces scabies*", Mol Plant Microbe Interact, 28(4), (2015), 443-454.
Geng, X., et al., "The phytotoxin coronatine is a multifunctional component of the virulence armament of *Pseudomonas syringae*", Planta, 240(6), (2014), 1149-1165.
Gimenez-Ibanez, S., et al., "The Bacterial Effector HopX1 Targets JAZ Transcriptional Repressors to Activate Jasmonate Signaling and Promote Infection in *Arabidopsis*", PLoS Biol, 12(2):e1001792, (2014), 1-15.
Glazebrook, J., "Contrasting mechanisms of defense against biotrophic and necrotrophic pathogens", Annu Rev Phytopathol, 43, (2005), 205-227.
Gordon-Kamm, W. J., et al., "Transformation of Maize Cells and Regeneration of Fertile Transgenic Plants", The Plant Cell, 2, (1990), 603-618.
Groen, S. C., et al., "Pathogen-Triggered Ethylene Signaling Mediates Systemic-Induced Susceptibility to Herbivory in *Arabidopsis*", The Plant Cell, 25(11), (2013), 4755-4766.
Gupta, V., et al., "*Arabidopsis thaliana* EDS4 Contributes to Salicylic Acid (SA)-Dependent Expression of Defense Responses: Evidence for Inhibition of Jasmonic Acid Signaling by SA", Molec Plant-Microbe Interact, 13(5), (2000), 503-511.
Hayashimoto, A., et al., "A Polyethylene Glycol-Mediated Protoplast Transformation System for Production of Fertile Transgenic Rice Plants.", Plant Physiol., 93(3), (1990), 857-863.
Herde, M., et al., "Chapter 5—Elicitation of Jasmonate-Mediated Defense Responses by Mechanical Wounding and Insect Herbivory", Methods Mol Biol., 1011, (2013), 51-61.
Horsch, R. B., et al., "A Simple and General Method for Transferring Genes into Plants", Science, 227(4691), (Mar. 8, 1985), 1229-1231.
Hudspeth, R. L., et al., "Structure and expression of the maize gene encoding the phosphoenolpyruvate carboxylase isozyme involved in $C_4$ photosynthesis", Plant Molecular Biology, 12(5), (May 1989), 579-589.
Irvine, N. M., et al., "Synthesis and characterization of synthetic analogs of cinnacidin, a novel phytotoxin from *Nectria* sp.", Pest Manag Sci, 64, (2008), 891-899.
Jefferson, R. A., "Assaying Chimeric Genes in Plants: The GUS Gene Fusion System", Plant Mol. Biol. Rep., 5(4), (1987), 387-405.
Jiang, S., et al., "Bacterial Effector Activates Jasmonate Signaling by Directly Targeting JAZ Transcriptional Repressors", PLoS Pathog, 9(10):e1003715, (2013), 1-12.
Katsir, L., et al., "COI1 is a critical component of a receptor for jasmonate and the bacterial virulence factor coronatine", Proc. Natl. Acad. Sci. USA, 105(19), (2008), 7100-7105.
Lawton, M. A., et al., "Expression of a soybean ß-conclycinin gene under the control of the Cauliflower Mosaic Virus 35S and 19S promoters in transformed petunia tissues", Plant Molecular Biology. 9(4), (Jul. 1987), 315-324.

McCabe, D. E., et al., "Stable Transformation of Soybean (*Glycine max*) by Particle Acceleration", Bio/Technology, 6, (Aug. 1988), 923-926.
McElroy, D., et al., "Isolation of an Efficient Actin Promoter for Use in Rice Transformation", The Plant Cell, 2, (Feb. 1990), 163-171.
Melotto, M., et al., "A critical role of two positively charged amino acids in the Jas motif of *Arabidopsis* JAZ proteins in mediating coronatine- and jasmonoyl isoleucine-dependent interactions with the COI1 F-box protein", Plant J., 55(6), (2008), 979-988.
Mewis, I., et al., "Major Signaling Pathways Modulate *Arabidopsis* Glucosinolate Accumulation and Response to Both Phloem-Feeding and Chewing Insects", Plant Physiol, 138(2), (2005), 1149-1162.
Monte, I., et al., "Rational design of a ligand-based antagonist of jasmonate perception", Nat Chem Biol, 10(8), (2014), 671-676.
Nakagawa, S., et al., "Effect size, confidence interval and statistical significance: A practical guide for biologists", Biol Rev Camb Philos Soc., 82(4), (2007), 591-605.
Odell, J., et al., "Identification of DNA Sequences Required for Activity of the Cauliflower Mosaic Virus 35S Promoter", Nature, 313, (1985), 810-812.
Park, S.-Y., et al., "Agrochemical control of plant water use using engineered abscisic acid receptors", Nature, 520(7548), (2015), 545-548 (17 pgs,).
Pauwels, L., et al., "NINJA connects the co-repressor TOPLESS to jasmonate signalling", Nature, 464(7289), (2010), 788-791 (6 pgs.).
Pauwels, L., et al., "The JAZ Proteins: A Crucial Interface in the Jasmonate Signaling Cascade", The Plant Cell, 23(9), (2011), 3089-3100.
Pieterse, C. M., et al., "Hormonal Modulation of Plant Immunity", Annu Rev Cell Dev Biol., 28, (2012), 489-521.
Plett, J. M., et al., "Effector MiSSP7 of the mutualistic fungus *Laccaria bicolor* stabilizes the *Populus* JAZ6 protein and represses jasmonic acid (JA) responsive genes", Proc Natl Acad Sci USA, 111(22), (2014), 8299-8304.
Qi, M., "Genome Sequence Analyses of *Pseudomonas savastanoi* pv. *glycinea* and Subtractive Hybridization-Based Comparative Genomics with Nine Pseudomonads", PLoS One, 6(1):e16451, (2011), 1-15.
Robert-Seilaniantz, A., et al., "Hormone Crosstalk in Plant Disease and Defense: More Than Just Jasmonate-Salicylate Antagonism", Annu Rev Phytopathol, 49, (2011), 317-343.
Santner, A., et al., "Recent advances and emerging trends in plant hormone signalling", Nature, 459(7250), (2009), 1071-1078.
Sengupta-Gopalan, C., et al., "Developmentally regulated expression of the bean β-phaseolin gene in tobacco seed", Proc. Natl. Acad. Sci. USA. 82(100, (1985), 3320-3324.
Sheard, L. B., et al., "Jasmonate perception by inositol-phosphate-potentiated COI1-JAZ co-receptor", Nature, 468(7322), (2010), 400-405 (8 pgs,).
Song, S., et al., "Jasmonate signaling and crosstalk with gibberellin and ethylene", Curr Opin Plant Biol., 21, (2014), 112-119.
Staswick, P. E., et al., "The Oxylipin Signal Jasmonic Acid Is Activated by an Enzyme That Conjugates It to Isoleucine in *Arabidopsis*", Plant Cell, 16(8), (2004), 2117-2127.
Stumpe, M., et al., "The moss *Physcomitrella patens* contains cyclopentenones but no jasmonates: Mutations in allene oxide cyclase lead to reduced fertility and altered sporophyte morphology", New Phytol, 188(3), (2010), 740-749.
Sullivan, T. D., et al., "Isolation and characterization of a maize chlorophyll a/b binding protein gene that produces high levels of mRNA in the dark", Mol. Gen. Genet., 215(3), (1989), 431-440.
Tan, X., et al., "Mechanism of auxin perception by the TIR1 ubiquitin ligase", Nature, 446(7136), (2007), 640-645.
Thaler, J. S., et al., "Evolution of jasmonate and salicylate signal crosstalk", Trends Plant Sci, 17(5), (2012), 260-270.
Thines, B., et al., "JAZ repressor proteins are targets of the $SCF^{COI1}$ complex during jasmonate signalling", Nature, 448(7154), (2007), 661-665 (6 pgs.).
Tsuda, K., et al., "Transcriptional networks in plant immunity", New Phytol., 206(3), (2015), 932-947.

(56) References Cited

OTHER PUBLICATIONS

Vidhyasekaran, P., et al., "Chapter 3—Jasmonate Signaling System in Plant Innate Immunity", In: Plant Hormone Signaling Systems in Plant Innate Immunity (Part of the Signaling and Communication in Plants book series (Springer, The Netherlands), (2015), 123-194.

Walker, J. C., et al., "DNA sequences required for anaerobic expression of the maize alcohol dehydrogenase 1 gene", Proc. Natl. Acad. Sci. USA, 84(19), (1987), 6624-6628.

Wang, C., et al., "Insights into the Origin and Evolution of the Plant Hormone Signaling Machinery", Plant Physiol, 167(3), Liu_etal, (2015), 872-886.

Wang, J., et al., "Antechamber, An Accessory Software Package for Molecular Mechanical Calculation", Abstract 135, Section COMP, Abstracts of Papers, 222nd National Meeting of the American Chemical Society, Chicago, IL, Aug. 26-30, 2001, (2001), 1 pg.

Wang, Y., et al., "Characterization of cis-Acting Elements Regulating Transcription from the Promoter of a Constitutively Active Rice Actin Gene", Mol. Cell. Biol., 12(8), (1992), 3399-3406.

Wasternack, C., et al., "Jasmonates: An Update on Biosynthesis, Signal Transduction and Action in Plant Stress Response, Growth and Development", Ann of Botany (Lond), 100(4), (2007), 681-697.

Wasternack, C., et al., "Jasmonates: biosynthesis, perception, signal transduction and action in plant stress response, growth and development. An update to the 2007 review in *Annals of Botany*", Annuals of Botany (Lond), 111(6), (2013), 1021-1058.

Whalen, M. C., et al., "Identification of *Pseudomonas syringae* pathogens of *Arabidopsis* and a bacterial locus determining avirulence on both *Arabidopsis* and soybean", The Plant Cell, 3(1), (1991), 49-59.

Xin, X. F., et al., "*Pseudomonas syringae* pv. *tomato* DC3000: A Model Pathogen for Probing Disease Susceptibility and Hormone Signaling in Plants", Annu Rev Phytopathol, 51, (2013), 473-498.

Xu, L., et al., "The SCF$^{COI1}$ Ubiquitin-Ligase Complexes Are Required for Jasmonate Response in *Arabidopsis*", The Plant Cell, 14(8), (2002), 1919-1935.

Yan, J., et al., "The *Arabidopsis* Coronatine Insensitive1 Protein Is a Jasmonate Receptor", The Plant Cell, 21(8), (2009), 2220-2236.

Yan, Y., et al., "A Downstream Mediator in the Growth Repression Limb of the Jasmonate Pathway", The Plant Cell, 19(8), (2007), 2470-2483.

Yang, D. L., et al., "Plant hormone jasmonate prioritizes defense over growth by interfering with gibberellin signaling cascade", Proc. Natl. Acad. Sci. USA, 109(19), (2012), E1192-E1200.

Yang, N. S., et al., "Maize sucrose synthase-1 promoter directs phloem cell-specific expression of Gus gene in transgenic tobacco plants.", Proc. Natl. Acad. Sci. USA, 87(11), (1990), 4144 4148.

Yao, J., et al., "*Pseudomonas syringae* infection assays in *Arabidopsis*", Methods Mol Biol., 1011, (2013), 63-81.

Zeng, W., et al., "A Genetic Screen Reveals *Arabidopsis* Stomatal and/or Apoplastic Defenses against *Pseudomonas syringae* pv. *tomato* DC3000", PLoS Pathog, 7(10): e1002291., (2011), 1-13.

Zhang, F., et al., "Structural basis of JAZ repression of MYC transcription factors in jasmonate signaling", Nature, 525(7568), (2015), 269-273 (17 pgs.).

Zhang, L., et al., "Host target modifification as a strategy to counter pathogen hijacking of the jasmonate hormone receptor", Proc. Natl. Acad. Sci. USA, 112(46), (2015), 14354-14359.

Zheng, X.Y., et al., "Coronatine Promotes *Pseudomonas syringae* Virulence in Plants by Activating a Signaling Cascade that Inhibits Salicylic Acid Accumulation", Cell Host Microbe, 11(6), (2012), 587-596.

\* cited by examiner

Alanine substitution mutants of COI1

| | K81 | R85 | M88 | F89 | L91 | R121 | K147 | E173 | R348 | R351 | D354 | E355 |
|---|---|---|---|---|---|---|---|---|---|---|---|---|
| JAZ9 | | | | | | | | | | | | |

| | Q356 | G357 | Y380 | D407 | R409 | L410 | V411 | L412 | L413 | R415 | R440 | F443 |
|---|---|---|---|---|---|---|---|---|---|---|---|---|
| JAZ9 | | | | | | | | | | | | |

| | W467 | L469 | L470 | Y472 | Q491 | K492 | R496 | R516 | COI1 | BD | AD | |
|---|---|---|---|---|---|---|---|---|---|---|---|---|
| JAZ9 | | | | | | | | | | | | |

FIG. 1A

Alanine substitution mutants of COI1

| | COI1 | BD | H54 | S77 | K79 | H118 | K144 | M201 | L301 | Y302 | R326 | Y444 |
|---|---|---|---|---|---|---|---|---|---|---|---|---|
| JAZ9 | | | | | | | | | | | | |

FIG. 1B

SEQUENCE LISTING

<160> NUMBER OF SEQ ID NOS: 61

<210> SEQ ID NO 1
<211> LENGTH: 592
<212> TYPE: PRT
<213> ORGANISM: Arabidopsis thaliana

<400> SEQUENCE: 1

```
Met Glu Asp Pro Asp Ile Lys Arg Cys Lys Leu Ser Cys Val Ala Thr
 1               5                  10                  15

Val Asp Asp Val Ile Glu Gln Val Met Thr Tyr Ile Thr Asp Pro Lys
            20                  25                  30

Asp Arg Asp Ser Ala Ser Leu Val Cys Arg Arg Trp Phe Lys Ile Asp
        35                  40                  45

Ser Glu Thr Arg Glu His Val Thr Met Ala Leu Cys Tyr Thr Ala Thr
 50                  55                  60

Pro Asp Arg Leu Ser Arg Arg Phe Pro Asn Leu Arg Ser Leu Lys Leu
 65                  70                  75                  80

Lys Gly Lys Pro Arg Ala Ala Met Phe Asn Leu Ile Pro Glu Asn Trp
                85                  90                  95

Gly Gly Tyr Val Thr Pro Trp Val Thr Glu Ile Ser Asn Asn Leu Arg
            100                 105                 110

Gln Leu Lys Ser Val His Phe Arg Arg Met Ile Val Ser Asp Leu Asp
        115                 120                 125

Leu Asp Arg Leu Ala Lys Ala Arg Ala Asp Asp Leu Glu Thr Leu Lys
130                 135                 140

Leu Asp Lys Cys Ser Gly Phe Thr Thr Asp Gly Leu Leu Ser Ile Val
145                 150                 155                 160

Thr His Cys Arg Lys Ile Lys Thr Leu Leu Met Glu Glu Ser Ser Phe
                165                 170                 175

Ser Glu Lys Asp Gly Lys Trp Leu His Glu Leu Ala Gln His Asn Thr
            180                 185                 190

Ser Leu Glu Val Leu Asn Phe Tyr Met Thr Glu Phe Ala Lys Ile Ser
        195                 200                 205

Pro Lys Asp Leu Glu Thr Ile Ala Arg Asn Cys Arg Ser Leu Val Ser
210                 215                 220

Val Lys Val Gly Asp Phe Glu Ile Leu Glu Leu Val Gly Phe Phe Lys
225                 230                 235                 240

Ala Ala Ala Asn Leu Glu Glu Phe Cys Gly Gly Ser Leu Asn Glu Asp
                245                 250                 255

Ile Gly Met Pro Glu Lys Tyr Met Asn Leu Val Phe Pro Arg Lys Leu
            260                 265                 270

Cys Arg Leu Gly Leu Ser Tyr Met Gly Pro Asn Glu Met Pro Ile Leu
        275                 280                 285

Phe Pro Phe Ala Ala Gln Ile Arg Lys Leu Asp Leu Tyr Ala Leu
290                 295                 300

Leu Glu Thr Glu Asp His Cys Thr Leu Ile Gln Lys Cys Pro Asn Leu
305                 310                 315                 320

Glu Val Leu Glu Thr Arg Asn Val Ile Gly Asp Arg Gly Leu Glu Val
                325                 330                 335

Leu Ala Gln Tyr Cys Lys Gln Leu Lys Arg Leu Arg Ile Glu Arg Gly
            340                 345                 350

Ala Asp Glu Gln Gly Met Glu Asp Glu Glu Gly Leu Val Ser Gln Arg
        355                 360                 365
```

Gly Leu Ile Ala Leu Ala Gln Gly Cys Gln Glu Leu Glu Tyr Met Ala
            370                 375                 380

Val Tyr Val Ser Asp Ile Thr Asn Glu Ser Leu Glu Ser Ile Gly Thr
385                 390                 395                 400

Tyr Leu Lys Asn Leu Cys Asp Phe Arg Leu Val Leu Leu Asp Arg Glu
                405                 410                 415

Glu Arg Ile Thr Asp Leu Pro Leu Asp Asn Gly Val Arg Ser Leu Leu
                420                 425                 430

Ile Gly Cys Lys Lys Leu Arg Arg Phe Ala Phe Tyr Leu Arg Gln Gly
            435                 440                 445

Gly Leu Thr Asp Leu Gly Leu Ser Tyr Ile Gly Gln Tyr Ser Pro Asn
450                 455                 460

Val Arg Trp Met Leu Leu Gly Tyr Val Gly Glu Ser Asp Glu Gly Leu
465                 470                 475                 480

Met Glu Phe Ser Arg Gly Cys Pro Asn Leu Gln Lys Leu Glu Met Arg
                485                 490                 495

Gly Cys Cys Phe Ser Glu Arg Ala Ile Ala Ala Val Thr Lys Leu
            500                 505                 510

Pro Ser Leu Arg Tyr Leu Trp Val Gln Gly Tyr Arg Ala Ser Met Thr
            515                 520                 525

Gly Gln Asp Leu Met Gln Met Ala Arg Pro Tyr Trp Asn Ile Glu Leu
530                 535                 540

Ile Pro Ser Arg Arg Val Pro Glu Val Asn Gln Gly Glu Ile Arg
545                 550                 555                 560

Glu Met Glu His Pro Ala His Ile Leu Ala Tyr Tyr Ser Leu Ala Gly
                565                 570                 575

Gln Arg Thr Asp Cys Pro Thr Thr Val Arg Val Leu Lys Glu Pro Ile
            580                 585                 590

<210> SEQ ID NO 2
<211> LENGTH: 592
<212> TYPE: PRT
<213> ORGANISM: Arabidopsis thaliana

<400> SEQUENCE: 2

Met Glu Asp Pro Asp Ile Lys Arg Cys Lys Leu Ser Cys Val Ala Thr
1               5                   10                  15

Val Asp Asp Val Ile Glu Gln Val Met Thr Tyr Ile Thr Asp Pro Lys
                20                  25                  30

Asp Arg Asp Ser Ala Ser Leu Val Cys Arg Arg Trp Phe Lys Ile Asp
            35                  40                  45

Ser Glu Thr Arg Glu His Val Thr Met Ala Leu Cys Tyr Thr Ala Thr
50                  55                  60

Pro Asp Arg Leu Ser Arg Phe Pro Asn Leu Arg Ser Leu Lys Leu
65                  70                  75                  80

Lys Gly Lys Pro Arg Ala Ala Met Phe Asn Leu Ile Pro Glu Asn Trp
                85                  90                  95

Gly Gly Tyr Val Thr Pro Trp Val Thr Glu Ile Ser Asn Asn Leu Arg
            100                 105                 110

Gln Leu Lys Ser Val His Phe Arg Arg Met Ile Val Ser Asp Leu Asp
            115                 120                 125

Leu Asp Arg Leu Ala Lys Ala Arg Ala Asp Asp Leu Glu Thr Leu Lys
            130                 135                 140

Leu Asp Lys Cys Ser Gly Phe Thr Thr Asp Gly Leu Leu Ser Ile Val
145                 150                 155                 160

-continued

```
Thr His Cys Arg Lys Ile Lys Thr Leu Leu Met Glu Glu Ser Ser Phe
                165                 170                 175

Ser Glu Lys Asp Gly Lys Trp Leu His Glu Leu Ala Gln His Asn Thr
            180                 185                 190

Ser Leu Glu Val Leu Asn Phe Tyr Met Thr Glu Phe Ala Lys Ile Ser
        195                 200                 205

Pro Lys Asp Leu Glu Thr Ile Ala Arg Asn Cys Arg Ser Leu Val Ser
    210                 215                 220

Val Lys Val Gly Asp Phe Glu Ile Leu Glu Leu Val Gly Phe Phe Lys
225                 230                 235                 240

Ala Ala Ala Asn Leu Glu Glu Phe Cys Gly Gly Ser Leu Asn Glu Asp
                245                 250                 255

Ile Gly Met Pro Glu Lys Tyr Met Asn Leu Val Phe Pro Arg Lys Leu
            260                 265                 270

Cys Arg Leu Gly Leu Ser Tyr Met Gly Pro Asn Glu Met Pro Ile Leu
        275                 280                 285

Phe Pro Phe Ala Ala Gln Ile Arg Lys Leu Asp Leu Leu Tyr Ala Leu
    290                 295                 300

Leu Glu Thr Glu Asp His Cys Thr Leu Ile Gln Lys Cys Pro Asn Leu
305                 310                 315                 320

Glu Val Leu Glu Thr Arg Asn Val Ile Gly Asp Arg Gly Leu Glu Val
                325                 330                 335

Leu Ala Gln Tyr Cys Lys Gln Leu Lys Arg Leu Arg Ile Glu Arg Gly
            340                 345                 350

Ala Asp Glu Gln Gly Met Glu Asp Glu Glu Gly Leu Val Ser Gln Arg
        355                 360                 365

Gly Leu Ile Ala Leu Ala Gln Gly Cys Gln Glu Leu Glu Tyr Met Val
    370                 375                 380

Val Tyr Val Ser Asp Ile Thr Asn Glu Ser Leu Glu Ser Ile Gly Thr
385                 390                 395                 400

Tyr Leu Lys Asn Leu Cys Asp Phe Arg Leu Val Leu Leu Asp Arg Glu
                405                 410                 415

Glu Arg Ile Thr Asp Leu Pro Leu Asp Asn Gly Val Arg Ser Leu Leu
            420                 425                 430

Ile Gly Cys Lys Lys Leu Arg Arg Phe Ala Phe Tyr Leu Arg Gln Gly
        435                 440                 445

Gly Leu Thr Asp Leu Gly Leu Ser Tyr Ile Gly Gln Tyr Ser Pro Asn
    450                 455                 460

Val Arg Trp Met Leu Leu Gly Tyr Val Gly Glu Ser Asp Glu Gly Leu
465                 470                 475                 480

Met Glu Phe Ser Arg Gly Cys Pro Asn Leu Gln Lys Leu Glu Met Arg
                485                 490                 495

Gly Cys Cys Phe Ser Glu Arg Ala Ile Ala Ala Val Thr Lys Leu
            500                 505                 510

Pro Ser Leu Arg Tyr Leu Trp Val Gln Gly Tyr Arg Ala Ser Met Thr
        515                 520                 525

Gly Gln Asp Leu Met Gln Met Ala Arg Pro Tyr Trp Asn Ile Glu Leu
    530                 535                 540

Ile Pro Ser Arg Arg Val Pro Glu Val Asn Gln Gln Gly Glu Ile Arg
545                 550                 555                 560

Glu Met Glu His Pro Ala His Ile Leu Ala Tyr Tyr Ser Leu Ala Gly
                565                 570                 575
```

| Gln | Arg | Thr | Asp | Cys | Pro | Thr | Thr | Val | Arg | Val | Leu | Lys | Glu | Pro | Ile |
|---|---|---|---|---|---|---|---|---|---|---|---|---|---|---|---|
| | | 580 | | | | | 585 | | | | | 590 | | | |

<210> SEQ ID NO 3
<211> LENGTH: 2512
<212> TYPE: DNA
<213> ORGANISM: Arabidopsis thaliana

<400> SEQUENCE: 3

```
gcaaaaatga aaagaaaaac atagaagtag agagaagatc gcatctcgac cgtcaacttc    60
agtgtatgaa ataatgatcg tcccacttga tcctcaaaaa tattattaac caaacaaaat   120
ttgattccat cgtcccactt tcttcttctt cctcccaatc cgcctcttct tcctacgcgt   180
gtcttcttct ccctcactct ctcaatctct agtcttctcc gattcaccgg atctttcctt   240
tcttacttct ttcttctcac tctggtggtt atgtgtggat ctgcgacctc gatttcaatt   300
cgaagtcgtc ggtttcttct ctaaatcgaa tctttccagg attcgtttgt ttttttcttt   360
tgttttttt tcgatccgat ggaggatcct gatatcaaga ggtgtaaatt gagctgcgtc   420
gcgacggttg atgatgtcat cgagcaagtc atgacctata taactgaccc gaaagatcgc   480
gattcggctt ctttggtgtg tcggagatgg ttcaagattg attccgagac gagagagcat   540
gtgactatgg cgctttgcta cactgcgacg cctgatcgtc ttagccgtcg attcccgaac   600
ttgaggtcgc tcaagcttaa aggcaagcct agagcagcta tgtttaatct gatccctgag   660
aactggggag gttatgttac tccttgggtt actgagattt ctaacaaccct taggcagctc   720
aaatcggtgc acttccgacg gatgattgtc agtgacttag atctagatcg tttagctaaa   780
gctagagcag atgatcttga actttgaag ctagacaagt gttctggttt tactactgat   840
ggacttttga gcatcgttac acactgcagg aaaataaaaa ctttgttaat ggaagagagt   900
tcttttagtg aaaaggatgg taagtggctt catgagcttg ctcagcacaa cacatctctt   960
gaggttttaa acttctacat gacggagttt gccaaaatca gtcccaaaga cttggaaacc  1020
atagctagaa attgccgctc tctggtatct gtgaaggtcg gtgactttga gattttggaa  1080
ctagttgggt tctttaaggc tgcagctaat cttgaagaat tttgtggtgg ctccttgaat  1140
gaggatattg gaatgcctga gaagtacatg aatctggttt ttccccgaaa actatgtcgg  1200
cttggtctct cttacatggg acctaatgaa atgccaatac tatttccatt cgcggcccaa  1260
atccgaaagc tggatttgct ttatgcattg ctagaaactg aagaccattg tacgcttatc  1320
caaaagtgtc ctaatttgga agttctcgag acaaggaatg taatcggaga tagggtcta  1380
gaggtccttg cacagtactg taagcagttg aagcggctga ggattgaacg cggtgcagat  1440
gaacaaggaa tggaggacga agaaggctta gtctcacaaa gaggattaat cgctttggct  1500
cagggctgcc aggagctaga atacatggcg gtgtatgtct cagatataac taacgaatct  1560
cttgaaagca taggcacata tctgaaaaac ctctgtgact ccgccttgt cttactcgac  1620
cgggaagaaa ggattacaga tctgccactg acaacggag tccgatctct tttgattgga  1680
tgcaagaaac tcagacgatt tgcattctat ctgagacaag gcggcttaac cgacttgggc  1740
ttaagctaca tcggacagta cagtccaaac gtgagatgga tgctgctggg ttacgtaggt  1800
gaatcagatg aaggtttaat ggaattctca agaggctgtc caaatctaca gaagctagag  1860
atgagaggtt gttgcttcag tgagcgagca atcgctgcag cggttacaaa attgccttca  1920
ctgagatact tgtgggtaca aggttacaga gcatcgatga cgggacaaga tctaatgcag  1980
atggctagac cgtactggaa catcgagctg attccatcaa gaagagtccc ggaagtgaat  2040
```

-continued

```
caacaaggag agataagaga gatggagcat ccggctcata tattggctta ctactctctg    2100
gctggccaga gaacagattg tccaacaact gttagagtcc tgaaggagcc aatatgatat    2160
gacccaaaaa acaggtttgt atataaagat ttttagtctc gagttttggg gtttccacaa    2220
actgtgtact atactacttt ggttctttt ttgtttcatg ttgtgtcgtc gatgttttg     2280 ggagattaca tagagtcagt cttgtttgtt gtatggtcat tacttcttta ttttttcctca   2340 ggggtctgtt tactttaatt tctttaataa aaccccgaag attttgagag atttctttat    2400
cgtccatggt gttgacttct gagagctata tttgtttgga ttggcatctg aaactttatt    2460
tgtggttgtg attgttttga taacattagt aaaaaggcaa ataatagagt ac            2512
```

<210> SEQ ID NO 4
<211> LENGTH: 590
<212> TYPE: PRT
<213> ORGANISM: Brassica rapa

<400> SEQUENCE: 4

```
Met Glu Asp Pro Asp Ile Lys Lys Cys Arg Leu Ser Ser Val Thr Val
1               5                   10                  15

Asp Asp Val Ile Glu Gln Val Met Pro Tyr Ile Thr Asp Pro Lys Asp
            20                  25                  30

Arg Asp Ser Ala Ser Leu Val Cys Arg Arg Trp Phe Glu Ile Asp Ser
        35                  40                  45

Glu Thr Arg Glu His Val Thr Met Ala Leu Cys Tyr Thr Ser Thr Pro
    50                  55                  60

Asp Arg Leu Ser Arg Arg Phe Pro Asn Leu Arg Ser Ile Lys Leu Lys
65                  70                  75                  80

Gly Lys Pro Arg Ala Ala Met Phe Asn Leu Ile Pro Glu Asn Trp Gly
                85                  90                  95

Gly Phe Val Thr Pro Trp Val Asn Glu Ile Ala Ser Ser Leu Arg Arg
            100                 105                 110

Leu Lys Ser Val His Phe Arg Arg Met Ile Val Ser Asp Leu Asp Leu
        115                 120                 125

Asp Val Leu Ala Lys Ala Arg Leu Asp Glu Leu Glu Ala Leu Lys Leu
    130                 135                 140

Asp Lys Cys Ser Gly Phe Ser Thr Asp Gly Leu Phe Ser Ile Val Lys
145                 150                 155                 160

His Cys Arg Lys Met Lys Thr Leu Leu Met Glu Glu Ser Ser Phe Val
                165                 170                 175

Glu Lys Asp Gly Asn Trp Leu His Glu Leu Ala Leu His Asn Thr Ser
            180                 185                 190

Leu Glu Val Leu Asn Phe Tyr Met Thr Glu Phe Ala Lys Ile Asn Ala
        195                 200                 205

Lys Asp Leu Glu Ser Ile Ala Arg Asn Cys Arg Ser Leu Val Ser Val
    210                 215                 220

Lys Ile Gly Asp Phe Glu Met Leu Glu Leu Val Gly Phe Phe Lys Ala
225                 230                 235                 240

Ala Thr Asn Leu Glu Glu Phe Cys Gly Gly Ser Leu Asn Glu Ile
                245                 250                 255

Gly Arg Pro Glu Lys Tyr Met Asn Leu Thr Phe Pro Pro Lys Leu Cys
            260                 265                 270

Cys Leu Gly Leu Ser Tyr Met Gly Pro Asn Glu Met Pro Ile Leu Phe
        275                 280                 285

Pro Phe Ala Ala Gln Ile Arg Lys Leu Asp Leu Ile Tyr Ala Leu Leu
```

```
Ala Thr Glu Asp His Cys Thr Leu Ile Gln Lys Cys Pro Asn Leu Glu
305                 310                 315                 320

Val Leu Glu Thr Arg Asn Val Ile Gly Asp Arg Gly Leu Glu Val Leu
            325                 330                 335

Gly Gln Cys Cys Lys Lys Leu Lys Arg Leu Arg Ile Glu Arg Gly Glu
                340                 345                 350

Asp Glu Gln Gly Met Glu Asp Glu Gly Leu Val Ser Gln Arg Gly
            355                 360                 365

Leu Val Ala Leu Ala Gln Gly Cys Gln Glu Leu Glu Tyr Met Ala Val
            370                 375                 380

Tyr Val Ser Asp Ile Thr Asn Glu Ser Leu Glu Ser Ile Gly Thr Tyr
385                 390                 395                 400

Leu Lys Asn Leu Cys Asp Phe Arg Leu Val Leu Asp Gln Glu Glu
                405                 410                 415

Arg Ile Thr Asp Leu Pro Leu Asp Asn Gly Val Arg Ser Leu Leu Ile
                420                 425                 430

Gly Cys Lys Lys Leu Arg Arg Phe Ala Phe Tyr Leu Arg Gln Gly Gly
            435                 440                 445

Leu Thr Asp Val Gly Leu Ser Tyr Ile Gly Gln Tyr Ser Pro Asn Val
    450                 455                 460

Arg Trp Met Leu Leu Gly Tyr Val Gly Glu Ser Asp Glu Gly Leu Met
465                 470                 475                 480

Glu Phe Ser Arg Gly Cys Pro Lys Leu Gln Lys Leu Glu Met Arg Gly
                485                 490                 495

Cys Cys Phe Ser Glu Arg Ala Ile Ala Ala Val Leu Lys Ile Pro
            500                 505                 510

Ser Leu Arg Tyr Leu Trp Val Gln Gly Tyr Arg Ala Ser Thr Thr Gly
            515                 520                 525

Gln Asp Leu Arg Leu Met Ser Arg Pro Tyr Trp Asn Ile Glu Leu Ile
            530                 535                 540

Pro Ala Arg Lys Val Pro Glu Val Asn Gln Leu Gly Glu Val Arg Glu
545                 550                 555                 560

Met Glu His Pro Ala His Ile Leu Ala Tyr Tyr Ser Leu Ala Gly Glu
            565                 570                 575

Arg Thr Asp Cys Pro Pro Thr Val Lys Val Leu Arg Glu Ala
            580                 585                 590

<210> SEQ ID NO 5
<211> LENGTH: 590
<212> TYPE: PRT
<213> ORGANISM: Brassica rapa

<400> SEQUENCE: 5

Met Glu Asp Pro Asp Ile Lys Lys Cys Arg Leu Ser Ser Val Thr Val
1               5                   10                  15

Asp Asp Val Ile Glu Gln Val Met Pro Tyr Ile Thr Asp Pro Lys Asp
                20                  25                  30

Arg Asp Ser Ala Ser Leu Val Cys Arg Arg Trp Phe Glu Ile Asp Ser
            35                  40                  45

Glu Thr Arg Glu His Val Thr Met Ala Leu Cys Tyr Thr Ser Thr Pro
        50                  55                  60

Asp Arg Leu Ser Arg Arg Phe Pro Asn Leu Arg Ser Ile Lys Leu Lys
65                  70                  75                  80
```

-continued

Gly Lys Pro Arg Ala Ala Met Phe Asn Leu Ile Pro Glu Asn Trp Gly
                85                  90                  95

Gly Phe Val Thr Pro Trp Val Asn Glu Ile Ala Ser Ser Leu Arg Arg
            100                 105                 110

Leu Lys Ser Val His Phe Arg Arg Met Ile Val Ser Asp Leu Asp Leu
        115                 120                 125

Asp Val Leu Ala Lys Ala Arg Leu Asp Glu Leu Glu Ala Leu Lys Leu
    130                 135                 140

Asp Lys Cys Ser Gly Phe Ser Thr Asp Gly Leu Phe Ser Ile Val Lys
145                 150                 155                 160

His Cys Arg Lys Met Lys Thr Leu Leu Met Glu Glu Ser Ser Phe Val
                165                 170                 175

Glu Lys Asp Gly Asn Trp Leu His Glu Leu Ala Leu His Asn Thr Ser
            180                 185                 190

Leu Glu Val Leu Asn Phe Tyr Met Thr Glu Phe Ala Lys Ile Asn Ala
        195                 200                 205

Lys Asp Leu Glu Ser Ile Ala Arg Asn Cys Arg Ser Leu Val Ser Val
    210                 215                 220

Lys Ile Gly Asp Phe Glu Met Leu Glu Leu Val Gly Phe Phe Lys Ala
225                 230                 235                 240

Ala Thr Asn Leu Glu Glu Phe Cys Gly Gly Ser Leu Asn Glu Glu Ile
                245                 250                 255

Gly Arg Pro Glu Lys Tyr Met Asn Leu Thr Phe Pro Pro Lys Leu Cys
            260                 265                 270

Cys Leu Gly Leu Ser Tyr Met Gly Pro Asn Glu Met Pro Ile Leu Phe
        275                 280                 285

Pro Phe Ala Ala Gln Ile Arg Lys Leu Asp Leu Ile Tyr Ala Leu Leu
    290                 295                 300

Ala Thr Glu Asp His Cys Thr Leu Ile Gln Lys Cys Pro Asn Leu Glu
305                 310                 315                 320

Val Leu Glu Thr Arg Asn Val Ile Gly Asp Arg Gly Leu Glu Val Leu
                325                 330                 335

Gly Gln Cys Cys Lys Lys Leu Lys Arg Leu Arg Ile Glu Arg Gly Glu
            340                 345                 350

Asp Glu Gln Gly Met Glu Asp Glu Glu Gly Leu Val Ser Gln Arg Gly
        355                 360                 365

Leu Val Ala Leu Ala Gln Gly Cys Gln Glu Leu Glu Tyr Met Val Val
    370                 375                 380

Tyr Val Ser Asp Ile Thr Asn Glu Ser Leu Glu Ser Ile Gly Thr Tyr
385                 390                 395                 400

Leu Lys Asn Leu Cys Asp Phe Arg Leu Val Leu Leu Asp Gln Glu Glu
                405                 410                 415

Arg Ile Thr Asp Leu Pro Leu Asp Asn Gly Val Arg Ser Leu Leu Ile
            420                 425                 430

Gly Cys Lys Lys Leu Arg Arg Phe Ala Phe Tyr Leu Arg Gln Gly Gly
        435                 440                 445

Leu Thr Asp Val Gly Leu Ser Tyr Ile Gly Gln Tyr Ser Pro Asn Val
    450                 455                 460

Arg Trp Met Leu Leu Gly Tyr Val Gly Glu Ser Asp Glu Gly Leu Met
465                 470                 475                 480

Glu Phe Ser Arg Gly Cys Pro Lys Leu Gln Lys Leu Glu Met Arg Gly
                485                 490                 495

Cys Cys Phe Ser Glu Arg Ala Ile Ala Ala Ala Val Leu Lys Ile Pro

|  |  | 500 |  |  | 505 |  |  | 510 |  |
|---|---|---|---|---|---|---|---|---|---|

Ser Leu Arg Tyr Leu Trp Val Gln Gly Tyr Arg Ala Ser Thr Thr Gly
    515      520      525

Gln Asp Leu Arg Leu Met Ser Arg Pro Tyr Trp Asn Ile Glu Leu Ile
  530      535      540

Pro Ala Arg Lys Val Pro Glu Val Asn Gln Leu Gly Glu Val Arg Glu
545      550      555      560

Met Glu His Pro Ala His Ile Leu Ala Tyr Tyr Ser Leu Ala Gly Glu
    565      570      575

Arg Thr Asp Cys Pro Pro Thr Val Lys Val Leu Arg Glu Ala
    580      585      590

<210> SEQ ID NO 6
<211> LENGTH: 2157
<212> TYPE: DNA
<213> ORGANISM: Brassica rapa

<400> SEQUENCE: 6

```
gccacttctt cctcctctcc tcacgctcca cgtccctgc tagcatccct cccgcttcct      60
cctccgatct ctgctcgtct tatcttcact ctctactgta ttactttgga tctgcgagag    120
attcgtgtaa ttgaaatcga tctcgtccct cagctggtat tcgaatttgt tgattgtttt    180
ggtttgtttt agattcgatt tcgatttgtt acatggagga tccggatatc aagaagtgca    240
gattgagctc cgtgacggtc gatgacgtca tcgagcaggt catgccttac ataaccgatc    300
cgaaagatcg agactccgct tccctcgtgt gccggaggtg gttcgagatc gactccgaga    360
cgagggagca cgtgaccatg gccttgtgct cacctcgac gcccgatcgt ctcagccgta    420
ggtttcccaa tctgaggtcg atcaagctca aagggaagcc gagagcagct atgttcaatc    480
tcatccccga gaactgggga gggtttgtta ccccttgggt caacgagata gcttcgtcgc    540
tgcgaaggct caagtctgtg cattttaggc ggatgattgt gagcgatttg gatctggatg    600
ttttggctaa ggcgaggttg gatgagctcg aggcgttgaa gcttgataag tgctcgggtt    660
tctctacgga tggacttttc agcatcgtta agcactgcag gaaaatgaaa acattgttaa    720
tggaagagag ttcttttgtt gaaaaggatg gtaactggct tcatgaactt gctctgcaca    780
acacttctct cgaggttcta aatttctaca tgactgagtt tgcaaaaatc aatgccaaag    840
acttggaaag catagctaga aattgccgct ctctggtttc tgtgaagatc ggtgactttg    900
agatgttgga actagtcggg ttctttaaag ctgcaactaa tcttgaagaa ttttgtggtg    960
gctccttaaa tgaagaaatt ggaagaccgg agaagtatat gaatctgact ttccctccaa   1020
aactatgttg tctgggcctt tcttacatgg gacctaatga aatgccaata ctgttttccat  1080
tcgctgccca atccggaag ctggatctga tctatgcatt gctcgcaact gaggatcatt   1140
gtacacttat tcaaaagtgt cctaatttgg aagttctcga gacaaggaat gtaattggag   1200
atagggggtct agaggttctt ggacagtgct gtaagaagtt gaagcggctg aggattgaac   1260
ggggtgaaga tgaacaagga atggaggatg aagaaggctt agtctcacaa agaggattag   1320
tcgctttggc tcagggctgc caggagctag aatacatggc ggtgtatgtc tcagatataa   1380
ccaacgagtc tctcgaaagc ataggcacat atctgaaaaa cctctgtgac ttccgcctcg   1440
tcttactcga ccaagaagag agaataacag atctgccact ggacaacgga gtcagatccc   1500
tcttgatcgg atgcaaaaaa ctcagacggt ttgcattcta tctcagacaa ggcggcttaa   1560
cagacgtggg gttaagctac atcggacagt acagtccaaa cgtgaggtgg atgcttctcg   1620
```

-continued

```
gttacgttgg tgaatcagac gaaggcctaa tggaattctc aagaggatgt ccgaaactac    1680
agaagctgga gatgagaggt tgttgcttca gcgagcgagc aatagctgca gcggtactga    1740
aaatcccttc gctgagatac ctgtgggtac aaggctatag agcatcgacg acgggacaag    1800
acctgaggct aatgtctaga ccgtactgga acatcgagct gattccggca agaaaagtcc    1860
cggaagtgaa tcagcttgga gaggtgagag agatggagca tcctgctcat atactggctt    1920
actactctct ggctggtgag agaacagatt gtccaccaac ggttaaagtc ctgggggagg    1980
catgatgatg atgatgaaaa gcaggtttgt acataaagat ttggttttga ggtttccacg    2040
aactgtcgaa tggattctat tttttcttta tggtgtatt gtctgtagtt ttgagagatt     2100
ccataaagac ttttgagaga ttgaaataag aagagagaaa actagtcttt cagaaga       2157
```

<210> SEQ ID NO 7
<211> LENGTH: 703
<212> TYPE: PRT
<213> ORGANISM: Brassica napus

<400> SEQUENCE: 7

```
Met Leu Gln Arg Ile Phe Trp Met Phe Phe Phe Ser Phe Asn Met Leu
1               5                   10                  15

Thr Arg Tyr Phe Ile Lys Thr Pro Pro Gly Tyr Phe Cys Arg Leu Ala
            20                  25                  30

Arg Cys Ala Ala Tyr Ala Thr Arg Leu Thr Lys Gln Thr Asp Ser Ile
        35                  40                  45

Ala Ser Ser Pro Pro Ser Ile Tyr Ile Lys Asn Asn Asn Tyr Pro Leu
    50                  55                  60

Cys Pro Leu Asp Pro Lys Leu Leu Leu Leu Ser Thr Leu Leu Ile
65                  70                  75                  80

Pro Ser Phe Thr His Thr Tyr Ala Thr Ser Ser Ser Pro His Ala
                85                  90                  95

Pro Gln Ile Arg Val Ile Glu Ile Asp Leu Ile Arg Phe Arg Phe Val
            100                 105                 110

Thr Met Glu Asp Pro Asp Ile Lys Lys Cys Arg Leu Ser Ser Val Thr
        115                 120                 125

Val Asp Asp Val Ile Glu Gln Val Met Pro Tyr Ile Thr Asp Pro Lys
    130                 135                 140

Asp Arg Asp Ser Ala Ser Leu Val Cys Arg Arg Trp Phe Glu Ile Asp
145                 150                 155                 160

Ser Glu Thr Arg Glu His Val Thr Met Ala Leu Cys Tyr Thr Ser Thr
                165                 170                 175

Pro Asp Arg Leu Ser Arg Arg Phe Pro Asn Leu Arg Ser Ile Lys Leu
            180                 185                 190

Lys Gly Lys Pro Arg Ala Ala Met Phe Asn Leu Ile Pro Glu Asn Trp
        195                 200                 205

Gly Gly Phe Val Thr Pro Trp Val Asn Glu Ile Ala Ser Ser Leu Arg
    210                 215                 220

Arg Leu Lys Ser Val His Phe Arg Arg Met Ile Val Ser Asp Leu Asp
225                 230                 235                 240

Leu Asp Val Leu Ala Lys Ala Arg Leu Asp Glu Leu Glu Ala Leu Lys
                245                 250                 255

Leu Asp Lys Cys Ser Gly Phe Ser Thr Asp Gly Leu Phe Ser Ile Val
            260                 265                 270

Lys His Cys Arg Lys Met Lys Thr Leu Leu Met Glu Glu Ser Ser Phe
        275                 280                 285
```

```
Val Glu Lys Asp Gly Asn Trp Leu His Glu Leu Ala Leu His Asn Thr
    290                 295                 300
Ser Leu Glu Val Leu Asn Phe Tyr Met Thr Glu Phe Ala Lys Ile Asn
305                 310                 315                 320
Ala Lys Asp Leu Glu Ser Ile Ala Arg Asn Cys Arg Ser Leu Val Ser
                325                 330                 335
Val Lys Ile Gly Asp Phe Glu Met Leu Glu Leu Val Gly Phe Phe Lys
                340                 345                 350
Ala Ala Thr Asn Leu Glu Glu Phe Cys Gly Gly Ser Leu Asn Glu Glu
            355                 360                 365
Ile Gly Arg Pro Glu Lys Tyr Met Asn Leu Thr Phe Pro Pro Lys Leu
    370                 375                 380
Cys Cys Leu Gly Leu Ser Tyr Met Gly Pro Asn Glu Met Pro Ile Leu
385                 390                 395                 400
Phe Pro Phe Ala Ala Gln Ile Arg Lys Leu Asp Leu Ile Tyr Ala Leu
                405                 410                 415
Leu Ala Thr Glu Asp His Cys Thr Leu Ile Gln Lys Cys Pro Asn Leu
                420                 425                 430
Glu Val Leu Glu Thr Arg Asn Val Ile Gly Asp Arg Gly Leu Glu Val
            435                 440                 445
Leu Gly Gln Cys Cys Lys Lys Leu Lys Arg Leu Arg Ile Glu Arg Gly
    450                 455                 460
Glu Asp Glu Gln Gly Met Glu Asp Glu Glu Gly Leu Val Ser Gln Arg
465                 470                 475                 480
Gly Leu Val Ala Leu Ala Gln Gly Cys Gln Glu Leu Glu Tyr Met Ala
                485                 490                 495
Val Tyr Val Ser Asp Ile Thr Asn Glu Ser Leu Glu Ser Ile Gly Thr
                500                 505                 510
Tyr Leu Lys Asn Leu Cys Asp Phe Arg Leu Val Leu Leu Asp Gln Glu
            515                 520                 525
Glu Arg Ile Thr Asp Leu Pro Leu Asp Asn Gly Val Arg Ser Leu Leu
    530                 535                 540
Ile Gly Cys Lys Lys Leu Arg Arg Phe Ala Phe Tyr Leu Arg Gln Ser
545                 550                 555                 560
Gly Leu Thr Asp Val Gly Leu Ser Tyr Ile Gly Gln Tyr Ser Pro Asn
                565                 570                 575
Val Arg Trp Met Leu Leu Gly Tyr Val Gly Glu Ser Asp Glu Gly Leu
                580                 585                 590
Met Glu Phe Ser Arg Gly Cys Pro Lys Leu Gln Lys Leu Glu Met Arg
            595                 600                 605
Gly Cys Cys Phe Ser Glu Arg Ala Ile Ala Ala Val Leu Lys Ile
    610                 615                 620
Pro Ser Leu Arg Tyr Leu Trp Val Gln Gly Tyr Arg Ala Ser Thr Thr
625                 630                 635                 640
Gly Gln Asp Leu Arg Leu Met Ser Arg Pro Tyr Trp Asn Ile Glu Leu
                645                 650                 655
Ile Pro Ala Arg Lys Val Pro Glu Val Asn Gln Leu Gly Glu Val Arg
                660                 665                 670
Glu Met Glu His Pro Ala His Ile Leu Ala Tyr Tyr Ser Leu Ala Gly
            675                 680                 685
Glu Arg Thr Asp Cys Pro Pro Thr Val Lys Val Leu Arg Glu Ala
    690                 695                 700
```

<210> SEQ ID NO 8
<211> LENGTH: 703
<212> TYPE: PRT
<213> ORGANISM: Brassica napus

<400> SEQUENCE: 8

```
Met Leu Gln Arg Ile Phe Trp Met Phe Phe Phe Ser Phe Asn Met Leu
 1               5                  10                  15

Thr Arg Tyr Phe Ile Lys Thr Pro Pro Gly Tyr Phe Cys Arg Leu Ala
            20                  25                  30

Arg Cys Ala Ala Tyr Ala Thr Arg Leu Thr Lys Gln Thr Asp Ser Ile
        35                  40                  45

Ala Ser Ser Pro Pro Ser Ile Tyr Ile Lys Asn Asn Asn Tyr Pro Leu
    50                  55                  60

Cys Pro Leu Asp Pro Lys Leu Leu Leu Leu Ser Thr Leu Leu Ile
65                  70                  75                  80

Pro Ser Phe Thr His Thr Tyr Ala Thr Ser Ser Ser Pro His Ala
                85                  90                  95

Pro Gln Ile Arg Val Ile Glu Ile Asp Leu Ile Arg Phe Arg Phe Val
            100                 105                 110

Thr Met Glu Asp Pro Asp Ile Lys Lys Cys Arg Leu Ser Ser Val Thr
        115                 120                 125

Val Asp Asp Val Ile Glu Gln Val Met Pro Tyr Ile Thr Asp Pro Lys
130                 135                 140

Asp Arg Asp Ser Ala Ser Leu Val Cys Arg Arg Trp Phe Glu Ile Asp
145                 150                 155                 160

Ser Glu Thr Arg Glu His Val Thr Met Ala Leu Cys Tyr Thr Ser Thr
                165                 170                 175

Pro Asp Arg Leu Ser Arg Arg Phe Pro Asn Leu Arg Ser Ile Lys Leu
            180                 185                 190

Lys Gly Lys Pro Arg Ala Ala Met Phe Asn Leu Ile Pro Glu Asn Trp
        195                 200                 205

Gly Gly Phe Val Thr Pro Trp Val Asn Glu Ile Ala Ser Ser Leu Arg
    210                 215                 220

Arg Leu Lys Ser Val His Phe Arg Arg Met Ile Val Ser Asp Leu Asp
225                 230                 235                 240

Leu Asp Val Leu Ala Lys Ala Arg Leu Asp Glu Leu Ala Leu Lys
                245                 250                 255

Leu Asp Lys Cys Ser Gly Phe Ser Thr Asp Gly Leu Phe Ser Ile Val
            260                 265                 270

Lys His Cys Arg Lys Met Lys Thr Leu Leu Met Glu Glu Ser Ser Phe
        275                 280                 285

Val Glu Lys Asp Gly Asn Trp Leu His Glu Leu Ala Leu His Asn Thr
    290                 295                 300

Ser Leu Glu Val Leu Asn Phe Tyr Met Thr Glu Phe Ala Lys Ile Asn
305                 310                 315                 320

Ala Lys Asp Leu Glu Ser Ile Ala Arg Asn Cys Arg Ser Leu Val Ser
                325                 330                 335

Val Lys Ile Gly Asp Phe Glu Met Leu Glu Leu Val Gly Phe Phe Lys
            340                 345                 350

Ala Ala Thr Asn Leu Glu Glu Phe Cys Gly Gly Ser Leu Asn Glu Glu
        355                 360                 365

Ile Gly Arg Pro Glu Lys Tyr Met Asn Leu Thr Phe Pro Pro Lys Leu
    370                 375                 380
```

```
Cys Cys Leu Gly Leu Ser Tyr Met Gly Pro Asn Glu Met Pro Ile Leu
385                 390                 395                 400

Phe Pro Phe Ala Ala Gln Ile Arg Lys Leu Asp Leu Ile Tyr Ala Leu
                405                 410                 415

Leu Ala Thr Glu Asp His Cys Thr Leu Ile Gln Lys Cys Pro Asn Leu
            420                 425                 430

Glu Val Leu Glu Thr Arg Asn Val Ile Gly Asp Arg Gly Leu Glu Val
        435                 440                 445

Leu Gly Gln Cys Cys Lys Lys Leu Lys Arg Leu Arg Ile Glu Arg Gly
450                 455                 460

Glu Asp Glu Gln Gly Met Glu Asp Glu Glu Gly Leu Val Ser Gln Arg
465                 470                 475                 480

Gly Leu Val Ala Leu Ala Gln Gly Cys Gln Glu Leu Glu Tyr Met Val
                485                 490                 495

Val Tyr Val Ser Asp Ile Thr Asn Glu Ser Leu Glu Ser Ile Gly Thr
            500                 505                 510

Tyr Leu Lys Asn Leu Cys Asp Phe Arg Leu Val Leu Leu Asp Gln Glu
        515                 520                 525

Glu Arg Ile Thr Asp Leu Pro Leu Asp Asn Gly Val Arg Ser Leu Leu
530                 535                 540

Ile Gly Cys Lys Lys Leu Arg Arg Phe Ala Phe Tyr Leu Arg Gln Ser
545                 550                 555                 560

Gly Leu Thr Asp Val Gly Leu Ser Tyr Ile Gly Gln Tyr Ser Pro Asn
                565                 570                 575

Val Arg Trp Met Leu Leu Gly Tyr Val Gly Glu Ser Asp Glu Gly Leu
            580                 585                 590

Met Glu Phe Ser Arg Gly Cys Pro Lys Leu Gln Lys Leu Glu Met Arg
        595                 600                 605

Gly Cys Cys Phe Ser Glu Arg Ala Ile Ala Ala Val Leu Lys Ile
610                 615                 620

Pro Ser Leu Arg Tyr Leu Trp Val Gln Gly Tyr Arg Ala Ser Thr Thr
625                 630                 635                 640

Gly Gln Asp Leu Arg Leu Met Ser Arg Pro Tyr Trp Asn Ile Glu Leu
                645                 650                 655

Ile Pro Ala Arg Lys Val Pro Glu Val Asn Gln Leu Gly Glu Val Arg
            660                 665                 670

Glu Met Glu His Pro Ala His Ile Leu Ala Tyr Tyr Ser Leu Ala Gly
        675                 680                 685

Glu Arg Thr Asp Cys Pro Pro Thr Val Lys Val Leu Arg Glu Ala
690                 695                 700

<210> SEQ ID NO 9
<211> LENGTH: 592
<212> TYPE: PRT
<213> ORGANISM: Brassica oleracea

<400> SEQUENCE: 9

Met Thr Met Glu Asp Pro Asp Ile Lys Lys Cys Arg Leu Ser Ser Val
1               5                   10                  15

Thr Val Asp Asp Val Ile Glu Gln Val Met Pro Tyr Ile Thr Asp Pro
            20                  25                  30

Lys Asp Arg Asp Ser Ala Ser Leu Val Cys Arg Arg Trp Phe Glu Ile
        35                  40                  45

Asp Ser Glu Thr Arg Glu His Val Thr Met Ala Leu Cys Tyr Thr Ser
```

```
            50                  55                  60
Thr Pro Asp Arg Leu Ser Arg Phe Pro Asn Leu Arg Ser Ile Lys
 65                  70                  75                  80

Leu Lys Gly Lys Pro Arg Ala Ala Met Phe Asn Leu Ile Pro Glu Asn
                 85                  90                  95

Trp Gly Gly Phe Val Thr Pro Trp Val Asn Glu Val Ala Ser Ser Leu
                100                 105                 110

Pro Arg Leu Lys Ser Val His Phe Arg Arg Met Ile Val Ser Asp Leu
            115                 120                 125

Asp Leu Asp Val Leu Ala Lys Ala Arg Leu Asp Glu Leu Glu Ala Leu
    130                 135                 140

Lys Leu Asp Lys Cys Ser Gly Phe Ser Thr Asp Gly Leu Phe Ser Ile
145                 150                 155                 160

Val Lys His Cys Arg Lys Met Lys Thr Leu Leu Met Glu Glu Ser Ser
                165                 170                 175

Phe Val Glu Lys Asp Gly Asn Trp Leu His Glu Leu Ala Leu His Asn
            180                 185                 190

Thr Ser Leu Glu Val Leu Asn Phe Tyr Met Thr Glu Phe Ala Lys Ile
        195                 200                 205

Asn Ala Lys Asp Leu Glu Ser Ile Ala Arg Asn Cys Arg Ser Leu Val
210                 215                 220

Ser Val Lys Ile Gly Asp Phe Glu Met Leu Glu Leu Val Gly Phe Phe
225                 230                 235                 240

Lys Ala Ala Thr Asn Leu Glu Glu Phe Cys Gly Gly Ser Phe Asn Glu
                245                 250                 255

Glu Ile Gly Arg Pro Glu Lys Tyr Met Asn Leu Thr Phe Pro Pro Lys
            260                 265                 270

Leu Cys Cys Leu Gly Leu Ser Tyr Met Gly Pro Asn Glu Met Pro Ile
            275                 280                 285

Leu Phe Pro Phe Ala Ala Gln Ile Arg Lys Leu Asp Leu Ile Tyr Ala
        290                 295                 300

Leu Leu Ala Thr Glu Asp His Cys Thr Leu Ile Gln Lys Cys Pro Asn
305                 310                 315                 320

Leu Glu Val Leu Glu Thr Arg Asn Val Ile Gly Asp Arg Gly Leu Glu
                325                 330                 335

Val Leu Gly Gln Cys Cys Lys Lys Leu Lys Arg Leu Arg Ile Glu Arg
            340                 345                 350

Gly Glu Asp Glu Gln Gly Met Glu Asp Glu Glu Gly Leu Val Ser Gln
            355                 360                 365

Arg Gly Leu Val Ala Leu Ala Gln Gly Cys Gln Glu Leu Glu Tyr Met
    370                 375                 380

Ala Val Tyr Val Ser Asp Ile Thr Asn Glu Ser Leu Glu Ser Ile Gly
385                 390                 395                 400

Thr Tyr Leu Lys Asn Leu Cys Asp Phe Arg Leu Val Leu Leu Asp Gln
                405                 410                 415

Glu Glu Arg Ile Thr Asp Leu Pro Leu Asp Asn Gly Val Arg Ser Leu
            420                 425                 430

Leu Ile Gly Cys Lys Lys Leu Arg Arg Phe Ala Phe Tyr Leu Arg Gln
            435                 440                 445

Gly Gly Leu Thr Asp Val Gly Leu Ser Tyr Ile Gly Gln Tyr Ser Pro
    450                 455                 460

Asn Val Arg Trp Met Leu Leu Gly Tyr Val Gly Glu Ser Asp Glu Gly
465                 470                 475                 480
```

```
Leu Met Glu Phe Ser Arg Gly Cys Pro Lys Leu Gln Lys Leu Glu Met
            485                 490                 495

Arg Gly Cys Cys Phe Ser Glu Arg Ala Ile Ala Ala Val Leu Lys
            500                 505                 510

Ile Pro Ser Leu Arg Tyr Leu Trp Val Gln Gly Tyr Arg Ala Ser Thr
            515                 520                 525

Thr Gly Gln Asp Leu Arg Leu Met Ser Arg Pro Tyr Trp Asn Ile Glu
            530                 535                 540

Leu Ile Pro Ala Arg Lys Val Pro Glu Val Asn Gln Leu Gly Glu Val
545                 550                 555                 560

Arg Glu Met Glu His Pro Ala His Ile Leu Ala Tyr Tyr Ser Leu Ala
            565                 570                 575

Gly Glu Arg Thr Asp Cys Pro Pro Thr Val Lys Val Leu Arg Glu Ala
            580                 585                 590

<210> SEQ ID NO 10
<211> LENGTH: 592
<212> TYPE: PRT
<213> ORGANISM: Brassica oleracea

<400> SEQUENCE: 10

Met Thr Met Glu Asp Pro Asp Ile Lys Lys Cys Arg Leu Ser Ser Val
1               5                   10                  15

Thr Val Asp Asp Val Ile Glu Gln Val Met Pro Tyr Ile Thr Asp Pro
                20                  25                  30

Lys Asp Arg Asp Ser Ala Ser Leu Val Cys Arg Arg Trp Phe Glu Ile
            35                  40                  45

Asp Ser Glu Thr Arg Glu His Val Thr Met Ala Leu Cys Tyr Thr Ser
        50                  55                  60

Thr Pro Asp Arg Leu Ser Arg Arg Phe Pro Asn Leu Arg Ser Ile Lys
65                  70                  75                  80

Leu Lys Gly Lys Pro Arg Ala Ala Met Phe Asn Leu Ile Pro Glu Asn
                85                  90                  95

Trp Gly Gly Phe Val Thr Pro Trp Val Asn Glu Val Ala Ser Ser Leu
            100                 105                 110

Pro Arg Leu Lys Ser Val His Phe Arg Arg Met Ile Val Ser Asp Leu
        115                 120                 125

Asp Leu Asp Val Leu Ala Lys Ala Arg Leu Asp Leu Glu Ala Leu
        130                 135                 140

Lys Leu Asp Lys Cys Ser Gly Phe Ser Thr Asp Gly Leu Phe Ser Ile
145                 150                 155                 160

Val Lys His Cys Arg Lys Met Lys Thr Leu Leu Met Glu Glu Ser Ser
                165                 170                 175

Phe Val Glu Lys Asp Gly Asn Trp Leu His Glu Leu Ala Leu His Asn
            180                 185                 190

Thr Ser Leu Glu Val Leu Asn Phe Tyr Met Thr Glu Phe Ala Lys Ile
        195                 200                 205

Asn Ala Lys Asp Leu Glu Ser Ile Ala Arg Asn Cys Arg Ser Leu Val
    210                 215                 220

Ser Val Lys Ile Gly Asp Phe Glu Met Leu Glu Leu Val Gly Phe Phe
225                 230                 235                 240

Lys Ala Ala Thr Asn Leu Glu Glu Phe Cys Gly Gly Ser Phe Asn Glu
                245                 250                 255

Glu Ile Gly Arg Pro Glu Lys Tyr Met Asn Leu Thr Phe Pro Pro Lys
```

```
                260                 265                 270
Leu Cys Cys Leu Gly Leu Ser Tyr Met Gly Pro Asn Glu Met Pro Ile
            275                 280                 285
Leu Phe Pro Phe Ala Ala Gln Ile Arg Lys Leu Asp Leu Ile Tyr Ala
            290                 295                 300
Leu Leu Ala Thr Glu Asp His Cys Thr Leu Ile Gln Lys Cys Pro Asn
305                 310                 315                 320
Leu Glu Val Leu Glu Thr Arg Asn Val Ile Gly Asp Arg Gly Leu Glu
                325                 330                 335
Val Leu Gly Gln Cys Cys Lys Lys Leu Lys Arg Leu Arg Ile Glu Arg
                340                 345                 350
Gly Glu Asp Glu Gln Gly Met Glu Asp Glu Glu Gly Leu Val Ser Gln
            355                 360                 365
Arg Gly Leu Val Ala Leu Ala Gln Gly Cys Gln Glu Leu Glu Tyr Met
            370                 375                 380
Val Val Tyr Val Ser Asp Ile Thr Asn Glu Ser Leu Glu Ser Ile Gly
385                 390                 395                 400
Thr Tyr Leu Lys Asn Leu Cys Asp Phe Arg Leu Val Leu Leu Asp Gln
                405                 410                 415
Glu Glu Arg Ile Thr Asp Leu Pro Leu Asp Asn Gly Val Arg Ser Leu
                420                 425                 430
Leu Ile Gly Cys Lys Lys Leu Arg Arg Phe Ala Phe Tyr Leu Arg Gln
            435                 440                 445
Gly Gly Leu Thr Asp Val Gly Leu Ser Tyr Ile Gly Gln Tyr Ser Pro
            450                 455                 460
Asn Val Arg Trp Met Leu Leu Gly Tyr Val Gly Glu Ser Asp Glu Gly
465                 470                 475                 480
Leu Met Glu Phe Ser Arg Gly Cys Pro Lys Leu Gln Lys Leu Glu Met
                485                 490                 495
Arg Gly Cys Cys Phe Ser Glu Arg Ala Ile Ala Ala Val Leu Lys
                500                 505                 510
Ile Pro Ser Leu Arg Tyr Leu Trp Val Gln Gly Tyr Arg Ala Ser Thr
            515                 520                 525
Thr Gly Gln Asp Leu Arg Leu Met Ser Arg Pro Tyr Trp Asn Ile Glu
            530                 535                 540
Leu Ile Pro Ala Arg Lys Val Pro Glu Val Asn Gln Leu Gly Glu Val
545                 550                 555                 560
Arg Glu Met Glu His Pro Ala His Ile Leu Ala Tyr Tyr Ser Leu Ala
                565                 570                 575
Gly Glu Arg Thr Asp Cys Pro Pro Thr Val Lys Val Leu Arg Glu Ala
            580                 585                 590

<210> SEQ ID NO 11
<211> LENGTH: 2084
<212> TYPE: DNA
<213> ORGANISM: Brassica oleracea

<400> SEQUENCE: 11
attattatta tcaacacttt tgattccttc ctccacacac actcacgcca cttcttcctc      60
ctctcctcac gctccaccta tcgtgattcc tatactcgat ttcgatttgt tatccgtttg     120
tttgatgacg atggaggatc cggatatcaa gaagtgcaga ttgagctccg tgacggtcga     180
tgacgtcatc gagcaggtca tgccttacat aaccgatccg aaagatcgag actccgcttc     240
cctcgtgtgc cggaggtggt tcgagatcga ctccgagacg agggagcacg tgaccatggc     300
```

-continued

```
actatgctac acctcgactc ctgaccgtct cagccgtagg tttccgaatc tgaggtcgat      360
taagctcaaa gggaagccga gagcagctat gttcaatctc atccccgaga actggggagg      420
gtttgttacc ccttgggtca acgaggtagc ttcatctctg ccaaggctca agtctgtgca      480
ttttaggcgg atgattgtca gcgatttgga tcttgatgtt ttggctaagg cgaggttgga      540
tgagctcgag gcgttgaagc tcgataagtg ctcaggtttc tctacggatg acttttcag      600
catcgttaag cactgcagga aaatgaaaac attgttaatg gaagagagtt cttttgttga      660
aaaggatggt aactggctgc atgaacttgc tctgcacaac acttctcttg aggttctaaa      720
tttctacatg actgagtttg caaaaatcaa tgccaaagac ttggaaagca agctagaaa      780
ttgccgctct ctggtttctg tgaagatcgg tgactttgag atgttggaac tagtcgggtt      840
cttaaagct gcaactaatc ttgaagaatt ttgtggcggc tccttcaatg aagaaattgg      900
aagaccggag aagtatatga atctgacttt ccctccaaaa ctatgttgtc ttggccttc      960
ttacatggga cctaatgaaa tgccaatact gtttccattc gctgcccaaa tccggaagct     1020
ggatctgatc tatgcattgc tcgcaactga ggatcattgt acacttattc aaaagtgtcc     1080
taatttggaa gttctcgaga caaggaatgt aattggagat aggggtctag aggttcttgg     1140
acagtgctgt aagaagttga agcggctgag gattgaacgg ggtgaagatg aacaaggaat     1200
ggaggatgaa gaaggcctag tatcacaaag aggattagtc gctttggctc agggctgcca     1260
ggagctagaa tacatggcgg tgtatgtctc agatataacc aacgagtctc tcgaaagcat     1320
aggcacatat ctgaaaaacc tctgtgactt ccgcctcgtc ttactcgacc aagaagagag     1380
aataacagat ctgccactag acaacggagt ccgatccctc ttgatcggat gcaagaaact     1440
cagacggttt gcattctatc tcagacaagg cggcttaaca gacgtggggt taagctacat     1500
cggacagtac agtccaaacg tgaggtggat gcttctcggt tacgttggtg aatcagacga     1560
aggcctaatg gagttctcaa gaggatgtcc gaaactacag aagctggaga tgagaggttg     1620
ttgcttcagc gagcgagcaa tagctgcagc ggtactgaaa atcccttcgc tgagatacct     1680
gtgggtacaa ggctacagag catcaacgac gggacaagac ctgaggctaa tgtctagacc     1740
gtactggaac atcgagctga ttccggcaag aaaagtccca gaagtgaatc agcttggaga     1800
ggtgagagag atggagcatc ctgctctata ctggcttac tactctctgg ctggtgagag     1860
aacagattgt ccaccaactg ttaaagtcct gagggaggca tgatgatgat gatgatgatg     1920
atgaaaagca ggtttgtaca taagatttg gttttgaggt ttccacgaac tgtcgaatgg     1980
attctatttt tctttattgg tgtattgtct gtagttttga gagattccat aaagactttt     2040
gagagattga ataagaaga gagaaaacta gtctattcag aaga                       2084
```

<210> SEQ ID NO 12
<211> LENGTH: 593
<212> TYPE: PRT
<213> ORGANISM: Theobroma cacao

<400> SEQUENCE: 12

```
Met Glu Glu Asn Asp Asn Lys Met Asn Lys Thr Met Thr Ser Pro Val
1               5                   10                  15

Gly Met Ser Asp Val Val Leu Gly Cys Val Met Pro Tyr Ile His Asp
            20                  25                  30

Pro Lys Asp Arg Asp Ala Val Ser Leu Val Cys Arg Arg Trp Tyr Glu
        35                  40                  45

Leu Asp Ala Leu Thr Arg Lys His Ile Thr Ile Ala Leu Cys Tyr Thr
```

```
                 50                  55                  60
Thr Ser Pro Asp Arg Leu Arg Arg Phe Gln His Leu Glu Ser Leu
 65                  70                  75                  80

Lys Leu Lys Gly Lys Pro Arg Ala Ala Met Phe Asn Leu Ile Pro Glu
                 85                  90                  95

Asp Trp Gly Gly Tyr Val Thr Pro Trp Val Asn Glu Ile Ala Glu Asn
                100                 105                 110

Phe Asn Cys Leu Lys Ser Leu His Phe Arg Arg Met Ile Val Lys Asp
                115                 120                 125

Ser Asp Leu Glu Val Leu Ala Arg Ser Arg Gly Lys Val Leu Gln Val
130                 135                 140

Leu Lys Leu Asp Lys Cys Ser Gly Phe Ser Thr Asp Gly Leu Leu His
145                 150                 155                 160

Val Gly Arg Ser Cys Arg Gln Leu Lys Thr Leu Phe Leu Glu Glu Ser
                165                 170                 175

Leu Ile Val Glu Lys Asp Gly Gln Trp Leu His Glu Leu Ala Val Asn
                180                 185                 190

Asn Ser Val Met Glu Thr Leu Asn Phe Tyr Met Thr Asp Leu Val Lys
                195                 200                 205

Val Ser Phe Glu Asp Leu Glu Leu Ile Ala Arg Asn Cys Arg Asn Leu
210                 215                 220

Ala Ser Val Lys Ile Ser Asp Cys Glu Ile Leu Asp Leu Val Gly Phe
225                 230                 235                 240

Phe Pro Ala Ala Ala Val Leu Glu Glu Phe Cys Gly Gly Ser Phe Asn
                245                 250                 255

Glu Gln Pro Asp Arg Tyr His Ala Val Ser Phe Pro Pro Lys Leu Cys
                260                 265                 270

Arg Leu Gly Leu Thr Tyr Met Gly Lys Asn Glu Met Pro Ile Val Phe
                275                 280                 285

Pro Phe Ala Ser Leu Leu Lys Lys Leu Asp Leu Leu Tyr Ala Leu Leu
                290                 295                 300

Asp Thr Glu Asp His Cys Leu Leu Ile Gln Arg Cys Pro Asn Leu Glu
305                 310                 315                 320

Val Leu Glu Thr Arg Asn Val Ile Gly Asp Arg Gly Leu Glu Val Leu
                325                 330                 335

Ala Arg Ser Cys Lys Arg Leu Lys Arg Leu Arg Ile Glu Arg Gly Ala
                340                 345                 350

Asp Glu Gln Gly Met Glu Asp Glu Gly Val Val Ser Gln Arg Gly
                355                 360                 365

Leu Met Ala Leu Ala Gln Gly Cys Leu Glu Leu Glu Tyr Leu Ala Val
370                 375                 380

Tyr Val Ser Asp Ile Thr Asn Ala Ser Leu Glu Tyr Ile Gly Thr Tyr
385                 390                 395                 400

Ser Lys Asn Leu Ser Asp Phe Arg Leu Val Leu Leu Asp Arg Glu Glu
                405                 410                 415

Arg Ile Thr Asp Leu Pro Leu Asp Asn Gly Val Arg Ala Leu Leu Arg
                420                 425                 430

Gly Cys Glu Lys Leu Arg Arg Phe Ala Leu Tyr Leu Arg Pro Gly Gly
                435                 440                 445

Leu Thr Asp Val Gly Leu Ser Tyr Ile Gly Gln Tyr Ser Pro Asn Val
                450                 455                 460

Arg Trp Met Leu Leu Gly Tyr Val Gly Glu Ser Asp Ala Gly Leu Leu
465                 470                 475                 480
```

```
Glu Phe Ser Lys Gly Cys Pro Ser Leu Gln Lys Leu Glu Met Arg Gly
                485                 490                 495

Cys Cys Phe Ser Glu His Ala Leu Ala Val Thr Val Met Gln Leu Thr
                500                 505                 510

Ser Leu Arg Tyr Leu Trp Val Gln Gly Tyr Arg Ala Ser Gln Ser Gly
                515                 520                 525

Arg Asp Leu Leu Ala Met Ala Arg Pro Phe Trp Asn Ile Glu Leu Ile
                530                 535                 540

Pro Ala Arg Arg Val Val Met Asn Asp Gln Val Gly Glu Ala Val Val
545                 550                 555                 560

Val Glu His Pro Ala His Ile Leu Ala Tyr Tyr Ser Leu Ala Gly Pro
                565                 570                 575

Arg Thr Asp Phe Pro Glu Thr Val Ile Pro Leu Asp Pro Leu Val Ala
                580                 585                 590

Ala

<210> SEQ ID NO 13
<211> LENGTH: 593
<212> TYPE: PRT
<213> ORGANISM: Theobroma cacao

<400> SEQUENCE: 13

Met Glu Glu Asn Asp Asn Lys Met Asn Lys Thr Met Thr Ser Pro Val
1               5                   10                  15

Gly Met Ser Asp Val Val Leu Gly Cys Val Met Pro Tyr Ile His Asp
                20                  25                  30

Pro Lys Asp Arg Asp Ala Val Ser Leu Val Cys Arg Arg Trp Tyr Glu
                35                  40                  45

Leu Asp Ala Leu Thr Arg Lys His Ile Thr Ile Ala Leu Cys Tyr Thr
            50                  55                  60

Thr Ser Pro Asp Arg Leu Arg Arg Arg Phe Gln His Leu Glu Ser Leu
65              70                  75                  80

Lys Leu Lys Gly Lys Pro Arg Ala Ala Met Phe Asn Leu Ile Pro Glu
                85                  90                  95

Asp Trp Gly Gly Tyr Val Thr Pro Trp Val Asn Glu Ile Ala Glu Asn
                100                 105                 110

Phe Asn Cys Leu Lys Ser Leu His Phe Arg Arg Met Ile Val Lys Asp
                115                 120                 125

Ser Asp Leu Glu Val Leu Ala Arg Ser Arg Gly Lys Val Leu Gln Val
                130                 135                 140

Leu Lys Leu Asp Lys Cys Ser Gly Phe Ser Thr Asp Gly Leu Leu His
145                 150                 155                 160

Val Gly Arg Ser Cys Arg Gln Leu Lys Thr Leu Phe Leu Glu Glu Ser
                165                 170                 175

Leu Ile Val Glu Lys Asp Gly Gln Trp Leu His Glu Leu Ala Val Asn
                180                 185                 190

Asn Ser Val Met Glu Thr Leu Asn Phe Tyr Met Thr Asp Leu Val Lys
                195                 200                 205

Val Ser Phe Glu Asp Leu Glu Leu Ile Ala Arg Asn Cys Arg Asn Leu
                210                 215                 220

Ala Ser Val Lys Ile Ser Asp Cys Glu Ile Leu Asp Leu Val Gly Phe
225                 230                 235                 240

Phe Pro Ala Ala Ala Val Leu Glu Glu Phe Cys Gly Gly Ser Phe Asn
                245                 250                 255
```

Glu Gln Pro Asp Arg Tyr His Ala Val Ser Phe Pro Pro Lys Leu Cys
              260                 265                 270

Arg Leu Gly Leu Thr Tyr Met Gly Lys Asn Glu Met Pro Ile Val Phe
              275                 280                 285

Pro Phe Ala Ser Leu Leu Lys Lys Leu Asp Leu Leu Tyr Ala Leu Leu
              290                 295                 300

Asp Thr Glu Asp His Cys Leu Leu Ile Gln Arg Cys Pro Asn Leu Glu
305                 310                 315                 320

Val Leu Glu Thr Arg Asn Val Ile Gly Asp Arg Gly Leu Glu Val Leu
              325                 330                 335

Ala Arg Ser Cys Lys Arg Leu Lys Arg Leu Arg Ile Glu Arg Gly Ala
              340                 345                 350

Asp Glu Gln Gly Met Glu Asp Glu Gly Val Val Ser Gln Arg Gly
              355                 360                 365

Leu Met Ala Leu Ala Gln Gly Cys Leu Glu Leu Glu Tyr Leu Val Val
              370                 375                 380

Tyr Val Ser Asp Ile Thr Asn Ala Ser Leu Glu Tyr Ile Gly Thr Tyr
385                 390                 395                 400

Ser Lys Asn Leu Ser Asp Phe Arg Leu Val Leu Asp Arg Glu Glu
              405                 410                 415

Arg Ile Thr Asp Leu Pro Leu Asp Asn Gly Val Arg Ala Leu Leu Arg
              420                 425                 430

Gly Cys Glu Lys Leu Arg Arg Phe Ala Leu Tyr Leu Arg Pro Gly Gly
              435                 440                 445

Leu Thr Asp Val Gly Leu Ser Tyr Ile Gly Gln Tyr Ser Pro Asn Val
              450                 455                 460

Arg Trp Met Leu Leu Gly Tyr Val Gly Glu Ser Asp Ala Gly Leu Leu
465                 470                 475                 480

Glu Phe Ser Lys Gly Cys Pro Ser Leu Gln Lys Leu Glu Met Arg Gly
              485                 490                 495

Cys Cys Phe Ser Glu His Ala Leu Ala Val Thr Val Met Gln Leu Thr
              500                 505                 510

Ser Leu Arg Tyr Leu Trp Val Gln Gly Tyr Arg Ala Ser Gln Ser Gly
              515                 520                 525

Arg Asp Leu Leu Ala Met Ala Arg Pro Phe Trp Asn Ile Glu Leu Ile
530                 535                 540

Pro Ala Arg Arg Val Val Met Asn Asp Gln Val Gly Glu Ala Val Val
545                 550                 555                 560

Val Glu His Pro Ala His Ile Leu Ala Tyr Tyr Ser Leu Ala Gly Pro
              565                 570                 575

Arg Thr Asp Phe Pro Glu Thr Val Ile Pro Leu Asp Pro Leu Val Ala
              580                 585                 590

Ala

<210> SEQ ID NO 14
<211> LENGTH: 2333
<212> TYPE: DNA
<213> ORGANISM: Theobroma cacao

<400> SEQUENCE: 14
aagtttcagc tctccttctc tgtttcacgt ttctgtgggc gctctctact ctgccatgcc      60
ttctctacac gacccatttt tgacccgatt cgtttagccc cggggggaaat ttgcttcgtt    120 tcagatccta ccgccgtttc gtttcttcca cttccgtaaa agagaagagt tccacgcccg    180

```
tttcttcttc ttcttcttct tcagatcagt cttttttttt ttttgccgtt tcgcgtttct      240
ggtttatttg ggctgaaaag atccgattcg attgtattga atggaggaaa atgataacaa      300
gatgaacaaa acgatgacgt caccagtcgg tatgtcggac gtcgttttag gctgcgtgat      360
gccgtacatc cacgacccga aagaccggga cgcagtttcg ctcgtgtgcc gacgttggta      420
cgagctcgac gcgttgacga ggaagcacat aacgatcgcg ctttgctaca cgacgagtcc      480
cgatcggttg cgacgtcgtt ccagcactt ggaatctttg aagttgaaag gcaagcctcg       540
ggcggcgatg ttcaatttga tacctgagga ttggggaggg tacgtgacgc cgtgggtgaa      600
tgagatagct gagaatttta attgcttgaa atctttgcat tttagaagga tgattgttaa      660
agattcggat ctggaagttt tggctcggtc tagagggaag gttttgcagg ttttgaagct      720
tgataaatgc tctggtttct ctactgatgg tctcttgcac gttggacgct cctgccggca      780
attaaaaacc ttgttcctgg aagagagctt aattgttgag aaagatggtc aatggcttca      840
tgagcttgca gtaaataact cagttatgga ctttgaaac ttttatatga cagatcttgt       900
caaagtgagt tttgaagacc ttgaacttat tgctagaaat tgtcgcaact tggcctctgt      960
gaaaattagc gattgtgaaa ttttggatct tgttggtttc tttcctgctg ctgctgtttt     1020
agaagaattt tgtggtggtt cttcaatga gcaaccggat aggtaccatg ctgtatcatt      1080 cccccccaaag ttatgccgtt tgggtttaac atacatgggg aagaatgaaa tgccaattgt    1140 gttcccttt gcatccttgc ttaaaaagtt ggatctcctc tatgcattac ttgacacaga      1200
agaccactgc ttgttaattc agatgcccc aacttagaa gttcttgaga caaggaatgt       1260
tattggagat agaggattag aagttcttgc tcgaagttgt aagagactaa agaggcttag     1320
aattgaaagg ggtgctgatg agcagggaat ggaggatgaa gaaggtgtgg tttcacaaag     1380
aggattaatg gctttagctc agggatgcct tgaattggaa tacttggctg tttatgtatc     1440
tgacatcacc aatgcatcat tggaatacat tgggacttac tcaaaaaatc tctctgattt     1500
tcgcctagtc ttgcttgacc gagaagaaag gataacagat ttgcctcttg ataatggagt     1560
ccgggctcta ttgaggggct gtgaaaagct tagaagattt gctctgtacc tccgacctgg     1620
tggtttgact gatgtaggcc tcagttatat tgggcaatac agtccgaatg taagatggat     1680
gcttctaggt tatgttgggg agtcggatgc cgggcttttg gagttctcta agggatgccc     1740
aagcctgcag aaaactagaaa tgaggggttg ttgcttcagt gagcatgcac ttgcagttac     1800
tgtgatgcaa ttaacttcct tgaggtattt gtgggtgcaa ggatatagag cgtcacaatc     1860
aggtcgtgat cttttagcaa tggctcgtcc attttggaat atcgagctaa ttcctgcaag     1920
acgagtagtt atgaatgatc aggttggaga ggctgttgtg gttgagcatc cggctcatat     1980
actcgcgtat tactccctag ctggaccaag aacagatttt ccagaaactg ttattccttt     2040
ggatccatta gttgctgcgt agagctgtaa atatgaccta tttttcgaag tgtccatttt     2100
tcccatccac gttctgtcta taagtttct gcacctttct cttttctctt ttcctttcct      2160
ttttgtttag agggtttcca atttgatatt tcattttcga ttttatttct agactttgtc     2220
ctgtaataag attgtgtttt cttctgtaat tttgaaagca cttgcactct tggtgggcta     2280 ctgttttgt cccttgtccc tggaaaaagt agtgaatgac tcttaacgga ata             2333
```

<210> SEQ ID NO 15
<211> LENGTH: 585
<212> TYPE: PRT
<213> ORGANISM: Prunus persica

<400> SEQUENCE: 15

```
Met Glu Asp Arg Asn Val Arg Ser Gly Met Ser Asp Val Ile Gly
1               5                   10                  15

Cys Val Met Pro Tyr Leu His Asp Ala Lys Asp Arg Asp Ala Val Ser
            20                  25                  30

Leu Val Cys Arg Arg Trp Tyr Glu Leu Asp Ala Leu Thr Arg Lys His
                35                  40                  45

Val Thr Ile Ala Leu Cys Tyr Thr Thr Ser Pro Asp Arg Leu Arg Arg
    50                  55                  60

Arg Phe Gln His Leu Glu Ser Leu Lys Leu Lys Gly Lys Pro Arg Ala
65                  70                  75                  80

Ala Met Phe Asn Leu Ile Pro Glu Asp Trp Gly Gly Phe Val Thr Pro
                85                  90                  95

Trp Val Lys Glu Ile Ala Glu Ser Phe Asn Arg Leu Lys Ser Leu His
                100                 105                 110

Phe Arg Arg Met Ile Val Lys Asp Ser Asp Leu Glu Leu Leu Ala Gln
                115                 120                 125

Ser Arg Gly Arg Val Leu Gln Ala Leu Lys Leu Asp Lys Cys Ser Gly
            130                 135                 140

Phe Ser Thr Asp Gly Leu Leu His Ile Gly Arg Ser Cys Arg Asn Leu
145                 150                 155                 160

Arg Thr Leu Phe Leu Glu Glu Ser Ser Ile Asp Glu Asn Asp Gly Gln
                165                 170                 175

Trp Leu His Glu Leu Ala Leu Asn Asn Ser Val Leu Glu Thr Leu Asn
                180                 185                 190

Phe Tyr Met Thr Asp Leu Ile Lys Val Lys Phe Glu Asp Leu Glu Leu
            195                 200                 205

Ile Ala Lys Asn Cys Arg Ser Leu Thr Ser Val Lys Thr Ser Asp Cys
210                 215                 220

Glu Ile Leu Glu Leu Val Gly Phe Phe Arg Ser Ala Ser Val Leu Glu
225                 230                 235                 240

Glu Phe Cys Gly Gly Phe Phe Asn Glu Gln Ser Glu Arg Tyr Ser Val
                245                 250                 255

Val Ser Leu Pro Gln Lys Leu Cys Arg Leu Gly Leu Thr Tyr Met Gly
            260                 265                 270

Lys Asn Glu Met Pro Ile Val Phe Pro Tyr Ala Thr Leu Leu Lys Lys
            275                 280                 285

Leu Asp Leu Leu Tyr Ala Leu Leu Asp Thr Glu Asp His Cys Thr Leu
            290                 295                 300

Ile Gln Arg Cys Pro Asn Leu Glu Val Leu Glu Thr Arg Asn Val Ile
305                 310                 315                 320

Gly Asp Arg Gly Leu Glu Val Leu Ala Arg Ser Cys Lys Arg Leu Arg
            325                 330                 335

Arg Leu Arg Ile Glu Arg Gly Ala Asp Glu Gln Gly Met Glu Asp Glu
                340                 345                 350

Glu Gly Val Val Ser Gln Arg Gly Leu Ile Ala Leu Ala Gln Gly Cys
            355                 360                 365

Leu Glu Leu Glu Tyr Leu Ala Val Tyr Val Ser Asp Ile Thr Asn Ala
    370                 375                 380

Ser Leu Glu Phe Ile Gly Thr Tyr Ser Lys Asn Leu Cys Asp Phe Arg
385                 390                 395                 400

Leu Val Leu Leu Asp Arg Glu Glu Thr Ile Thr Asp Leu Pro Leu Asp
                405                 410                 415
```

```
Asn Gly Val Arg Ala Leu Leu Arg Gly Cys Asp Lys Leu Arg Arg Phe
            420                 425                 430

Ala Leu Tyr Leu Arg Ala Gly Gly Leu Thr Asp Leu Gly Leu Ser Tyr
        435                 440                 445

Val Gly Gln Tyr Ser Gln Asn Val Arg Trp Met Leu Leu Gly Tyr Val
    450                 455                 460

Gly Glu Ser Asp Ala Gly Leu Leu Glu Phe Ser Lys Gly Cys Pro Ser
465                 470                 475                 480

Leu Gln Lys Leu Glu Met Arg Gly Cys Cys Phe Ser Glu Arg Ala Leu
                485                 490                 495

Ala Asp Ala Val Met Gln Leu Thr Ser Leu Arg Tyr Leu Trp Val Gln
            500                 505                 510

Gly Tyr Arg Gly Ser Ala Ser Gly Arg Asp Val Leu Ala Met Ala Arg
        515                 520                 525

Pro Tyr Trp Asn Ile Glu Leu Ile Pro Pro Arg Arg Val Val Asp Gln
    530                 535                 540

Gln Gly Glu Gly Val Val Met Glu His Pro Ala His Ile Leu Ala Tyr
545                 550                 555                 560

Tyr Ser Leu Ala Gly Gln Arg Thr Asp Tyr Pro Asn Thr Val Ile Pro
                565                 570                 575

Val Asp Pro Ala Ser Phe Ile Thr Ser
            580                 585

<210> SEQ ID NO 16
<211> LENGTH: 585
<212> TYPE: PRT
<213> ORGANISM: Prunus persica

<400> SEQUENCE: 16

Met Glu Asp Arg Asn Val Arg Ser Gly Met Ser Asp Val Val Ile Gly
1               5                   10                  15

Cys Val Met Pro Tyr Leu His Asp Ala Lys Asp Arg Asp Ala Val Ser
            20                  25                  30

Leu Val Cys Arg Arg Trp Tyr Glu Leu Asp Ala Leu Thr Arg Lys His
        35                  40                  45

Val Thr Ile Ala Leu Cys Tyr Thr Thr Ser Pro Asp Arg Leu Arg Arg
    50                  55                  60

Arg Phe Gln His Leu Glu Ser Leu Lys Leu Lys Gly Lys Pro Arg Ala
65                  70                  75                  80

Ala Met Phe Asn Leu Ile Pro Glu Asp Trp Gly Gly Phe Val Thr Pro
                85                  90                  95

Trp Val Lys Glu Ile Ala Glu Ser Phe Asn Arg Leu Lys Ser Leu His
            100                 105                 110

Phe Arg Arg Met Ile Val Lys Asp Ser Asp Leu Glu Leu Leu Ala Gln
        115                 120                 125

Ser Arg Gly Arg Val Leu Gln Ala Leu Lys Leu Asp Lys Cys Ser Gly
    130                 135                 140

Phe Ser Thr Asp Gly Leu Leu His Ile Gly Arg Ser Cys Arg Asn Leu
145                 150                 155                 160

Arg Thr Leu Phe Leu Glu Glu Ser Ile Asp Glu Asn Asp Gly Gln
                165                 170                 175

Trp Leu His Glu Leu Ala Leu Asn Asn Ser Val Leu Glu Thr Leu Asn
            180                 185                 190

Phe Tyr Met Thr Asp Leu Ile Lys Val Lys Phe Glu Asp Leu Glu Leu
```

-continued

```
            195                 200                 205
Ile Ala Lys Asn Cys Arg Ser Leu Thr Ser Val Lys Thr Ser Asp Cys
210                 215                 220

Glu Ile Leu Glu Leu Val Gly Phe Phe Arg Ser Ala Ser Val Leu Glu
225                 230                 235                 240

Glu Phe Cys Gly Gly Phe Phe Asn Glu Gln Ser Glu Arg Tyr Ser Val
                    245                 250                 255

Val Ser Leu Pro Gln Lys Leu Cys Arg Leu Gly Leu Thr Tyr Met Gly
                260                 265                 270

Lys Asn Glu Met Pro Ile Val Phe Pro Tyr Ala Thr Leu Leu Lys Lys
            275                 280                 285

Leu Asp Leu Leu Tyr Ala Leu Leu Asp Thr Glu Asp His Cys Thr Leu
290                 295                 300

Ile Gln Arg Cys Pro Asn Leu Glu Val Leu Glu Thr Arg Asn Val Ile
305                 310                 315                 320

Gly Asp Arg Gly Leu Glu Val Leu Ala Arg Ser Cys Lys Arg Leu Arg
                    325                 330                 335

Arg Leu Arg Ile Glu Arg Gly Ala Asp Glu Gln Gly Met Glu Asp Glu
                340                 345                 350

Glu Gly Val Val Ser Gln Arg Gly Leu Ile Ala Leu Ala Gln Gly Cys
            355                 360                 365

Leu Glu Leu Glu Tyr Leu Val Val Tyr Val Ser Asp Ile Thr Asn Ala
370                 375                 380

Ser Leu Glu Phe Ile Gly Thr Tyr Ser Lys Asn Leu Cys Asp Phe Arg
385                 390                 395                 400

Leu Val Leu Leu Asp Arg Glu Glu Thr Ile Thr Asp Leu Pro Leu Asp
                    405                 410                 415

Asn Gly Val Arg Ala Leu Leu Arg Gly Cys Asp Lys Leu Arg Arg Phe
                420                 425                 430

Ala Leu Tyr Leu Arg Ala Gly Gly Leu Thr Asp Leu Gly Leu Ser Tyr
            435                 440                 445

Val Gly Gln Tyr Ser Gln Asn Val Arg Trp Met Leu Leu Gly Tyr Val
450                 455                 460

Gly Glu Ser Asp Ala Gly Leu Leu Glu Phe Ser Lys Gly Cys Pro Ser
465                 470                 475                 480

Leu Gln Lys Leu Glu Met Arg Gly Cys Cys Phe Ser Glu Arg Ala Leu
                    485                 490                 495

Ala Asp Ala Val Met Gln Leu Thr Ser Leu Arg Tyr Leu Trp Val Gln
                500                 505                 510

Gly Tyr Arg Gly Ser Ala Ser Gly Arg Asp Val Leu Ala Met Ala Arg
            515                 520                 525

Pro Tyr Trp Asn Ile Glu Leu Ile Pro Pro Arg Arg Val Val Asp Gln
530                 535                 540

Gln Gly Glu Gly Val Val Met Glu His Pro Ala His Ile Leu Ala Tyr
545                 550                 555                 560

Tyr Ser Leu Ala Gly Gln Arg Thr Asp Tyr Pro Asn Thr Val Ile Pro
                    565                 570                 575

Val Asp Pro Ala Ser Phe Ile Thr Ser
                580                 585

<210> SEQ ID NO 17
<211> LENGTH: 1762
<212> TYPE: DNA
<213> ORGANISM: Prunus persica
```

<400> SEQUENCE: 17

```
atggaggatc gaaacgtgcg aagtggaatg tccgatgtgg tgataggctg cgtgatgccg      60
tatcttcacg acgctaagga ccgcgacgca gtgtcgttgg tgtgccggcg atggtacgag     120
ctcgacgctc tcacgcgcaa gcacgtgacc attgctctct gctacaccac gagcccccgat    180
cggttgcgga ggcgatttca gcacctcgag tccctgaagc tgaaagggaa gccgagagcg     240
gcgatgttca atctgatacc ggaggattgg ggaggctttg tgacgccgtg ggtgaaggag     300
atcgctgagt ccttcaatcg cttgaagtct ctgcactttc ggcgaatgat tgttaaggat     360
tcggacttgg agctcttggc tcagtcccgt gggcgcgtgc tacaggcgct caagcttgac     420
aagtgctctg gcttctccac cgatggcctt ttgcacatcg gccgctcctg caggaatttg     480
agaaccttgt ttttggaaga gagctccata gatgagaatg atggtcaatg ctacatgag     540
cttgctttga caactctgt gttggagact ttgaattttt atatgacaga tcttatcaaa     600
gtcaaatttg aagaccttga actcattgca aaaaactgtc gctccttaac ctctgtgaaa    660
actagcgatt gcgaaatctt ggaactcgtg gcttcttcc gttctgcaag cgtattagaa     720
gaattttgtg gcggttcctt caacgagcaa tcagagaggt actctgttgt atcgttaccc    780
caaaaattat gccgtttggg tctaacgtac atgggaaaga atgaaatgcc aatagtattc    840
ccatatgcaa cccttctcaa aaagctggat ctcctttatg cattgctcga cactgaggac    900
cattgcacac taattcaaag gtgccccaac ctggaagtgc ttgagacaag aatgttatt    960
ggagatagag gactagaagt tcttgctcgg agttgcaaga gattgaggag gctccgaatt   1020
gagcgaggtg cagatgagca aggcatggag gatgaagaag gtgttgtttc acaaaggggt   1080
ttgatagcat tggcacaggg ctgcctggaa cttgagtact tggctgtgta tgtgtcagat   1140
atcacaaacg catctctgga attcattggg acttactcta agaatctttg tgattttcga   1200
cttgtcttgc ttgaccgaga agagacgata acagatttac cacttgacaa tgggggttcga   1260
gctcttttga ggggctgtga taagctcaga aggtttgctc tgtatctccg tgctgggggc   1320
ttgaccgatt tgggacttag ttatgttggc cagtatagtc aaaatgtgag atggatgctt   1380
ctgggttatg ttggggaatc tgatgcaggg cttttggagt tctctaaagg ttgccctagc   1440
ctgcaaaaat tggaaatgag gggctgttgc ttcagtgagc gtgcactggc tgatgcagta   1500
atgcagctga cttcccttag gtacttgtgg gtgcaggggc acagaggatc tgcttcgggt   1560
cgtgatgttt tggcaatggc tcggccgtat tggaatattg agttaattcc cccgagacga   1620
gttgttgatc agcaggggga gggagtagtg atggagcatc agcccatat acttgcatac   1680
tactcacttg ctggacaaag aacagattat ccaaatactg ttatccccgt ggatccagca   1740
tcttttatta cctcctagag tt                                             1762
```

<210> SEQ ID NO 18
<211> LENGTH: 586
<212> TYPE: PRT
<213> ORGANISM: Malus domestica

<400> SEQUENCE: 18

```
Met Glu Asp Arg Ser Val Arg Cys Arg Ile Ser Asp Val Val Met Asp
1               5                  10                  15

Cys Val Met Pro Tyr Leu His Asp Pro Lys Asp Arg Asp Ala Val Ser
                20                  25                  30

Leu Val Cys Lys Arg Trp Tyr Glu Leu Asp Ala Leu Thr Arg Lys His
            35                  40                  45
```

```
Val Thr Ile Ala Leu Cys Tyr Thr Thr Thr Pro Asp Arg Leu Arg Gln
     50              55                  60

Arg Phe Gln His Leu Glu Ser Leu Lys Leu Lys Gly Lys Pro Arg Ala
 65              70              75                  80

Ala Met Phe Asn Leu Ile Pro Glu Asp Trp Gly Gly Phe Val Thr Pro
                 85              90                  95

Trp Val Met Glu Ile Ala Asn Ser Phe His Arg Leu Lys Cys Leu His
            100             105             110

Phe Arg Arg Met Ile Val Ser Asp Ser Asp Leu Glu Leu Leu Ala Asp
            115             120             125

Ser Arg Gly Arg Val Leu Gln Val Leu Lys Leu Asp Lys Cys Ser Gly
130             135             140

Phe Thr Thr Gly Gly Leu Leu His Ile Gly Arg Ser Cys Arg Asn Leu
145             150             155             160

Arg Thr Leu Phe Leu Glu Glu Ser Ser Ile Val Glu Glu Asp Gly Asp
                165             170             175

Trp Leu His Ala Leu Ala Val Asn Asn Thr Val Leu Glu Thr Leu Asn
                180             185             190

Phe Tyr Met Thr Asp Leu Ile Lys Val Lys Phe Glu Asp Leu Glu Leu
            195             200             205

Ile Ala Lys Asn Cys Arg Ser Leu Thr Ser Val Lys Ile Ser Asp Cys
210             215             220

Glu Ile Leu Glu Leu Val Gly Phe Phe Arg His Ala Ala Val Leu Glu
225             230             235             240

Glu Phe Cys Gly Gly Ser Phe Asn Asp Gln Ser Glu Ser Tyr Ser Val
                245             250             255

Val Thr Leu Pro Gln Lys Leu Cys Arg Leu Gly Leu Thr Tyr Met Gly
                260             265             270

Lys Asn Glu Met Gln Ile Val Phe Pro Phe Ala Thr Leu Leu Lys Lys
            275             280             285

Leu Asp Leu Leu Tyr Ala Leu Leu Asp Thr Glu Asp His Cys Thr Leu
290             295             300

Ile Gln Arg Cys Pro Asn Leu Glu Val Leu Glu Thr Arg Asn Val Ile
305             310             315             320

Gly Asp Arg Gly Leu Asp Val Leu Ala Arg Ser Cys Lys Arg Leu Arg
                325             330             335

Arg Leu Arg Ile Glu Arg Gly Ala Asp Glu Gly Met Glu Asp Glu Glu
            340             345             350

Gly Val Val Ser Gln Arg Gly Leu Met Ala Leu Ala Gln Gly Cys Leu
            355             360             365

Glu Leu Glu Tyr Leu Ala Val Tyr Val Ser Asp Ile Thr Asn Ala Ser
        370             375             380

Leu Glu Tyr Ile Gly Thr Tyr Ser Lys Asn Leu Ser Asp Phe Arg Leu
385             390             395             400

Val Leu Leu Asp Arg Glu Glu Thr Ile Thr Asp Leu Pro Leu Asp Asn
                405             410             415

Gly Val Arg Ala Leu Leu Arg Gly Cys His Lys Leu Arg Arg Phe Ala
            420             425             430

Leu Tyr Leu Arg Pro Gly Gly Leu Thr Asp Leu Gly Leu Ser Tyr Ile
        435             440             445

Gly Arg Tyr Ser Pro Asn Val Arg Trp Met Leu Leu Gly Tyr Val Gly
    450             455             460
```

Glu Ser Asp Ala Gly Leu Leu Glu Phe Ser Lys Gly Cys Pro Ser Leu
465                 470                 475                 480

Gln Lys Leu Glu Met Arg Gly Cys Cys Phe Ser Glu Arg Ala Leu Ala
            485                 490                 495

His Ala Val Met Gln Leu Thr Ser Leu Arg Tyr Leu Trp Val Gln Gly
            500                 505                 510

Tyr Arg Gly Ser Ala Thr Gly Arg Asp Leu Leu Ala Met Ala Arg Pro
            515                 520                 525

Phe Trp Asn Ile Glu Leu Ile Pro Pro Arg Arg Val Asp Val Pro Asp
        530                 535                 540

Gln His Gly Glu Ala Leu Ala Val Glu His Pro Ala His Ile Leu Ala
545                 550                 555                 560

Tyr Tyr Ser Leu Ala Gly Pro Arg Thr Asp Cys Pro Asp Thr Val Ile
                565                 570                 575

Pro Val Asp Pro Ala Ser Leu Leu Ile Ser
            580                 585

<210> SEQ ID NO 19
<211> LENGTH: 586
<212> TYPE: PRT
<213> ORGANISM: Malus domestica

<400> SEQUENCE: 19

Met Glu Asp Arg Ser Val Arg Cys Arg Ile Ser Asp Val Val Met Asp
1               5                   10                  15

Cys Val Met Pro Tyr Leu His Asp Pro Lys Asp Arg Asp Ala Val Ser
            20                  25                  30

Leu Val Cys Lys Arg Trp Tyr Glu Leu Asp Ala Leu Thr Arg Lys His
        35                  40                  45

Val Thr Ile Ala Leu Cys Tyr Thr Thr Thr Pro Asp Arg Leu Arg Gln
    50                  55                  60

Arg Phe Gln His Leu Glu Ser Leu Lys Leu Lys Gly Lys Pro Arg Ala
65                  70                  75                  80

Ala Met Phe Asn Leu Ile Pro Glu Asp Trp Gly Gly Phe Val Thr Pro
                85                  90                  95

Trp Val Met Glu Ile Ala Asn Ser Phe His Arg Leu Lys Cys Leu His
            100                 105                 110

Phe Arg Arg Met Ile Val Ser Asp Ser Asp Leu Glu Leu Leu Ala Asp
        115                 120                 125

Ser Arg Gly Arg Val Leu Gln Val Leu Lys Leu Asp Lys Cys Ser Gly
    130                 135                 140

Phe Thr Thr Gly Gly Leu Leu His Ile Gly Arg Ser Cys Arg Asn Leu
145                 150                 155                 160

Arg Thr Leu Phe Leu Glu Glu Ser Ser Ile Val Glu Glu Asp Gly Asp
                165                 170                 175

Trp Leu His Ala Leu Ala Val Asn Asn Thr Val Leu Glu Thr Leu Asn
            180                 185                 190

Phe Tyr Met Thr Asp Leu Ile Lys Val Lys Phe Glu Asp Leu Glu Leu
        195                 200                 205

Ile Ala Lys Asn Cys Arg Ser Leu Thr Ser Val Lys Ile Ser Asp Cys
    210                 215                 220

Glu Ile Leu Glu Leu Val Gly Phe Phe Arg His Ala Ala Val Leu Glu
225                 230                 235                 240

Glu Phe Cys Gly Gly Ser Phe Asn Asp Gln Ser Glu Ser Tyr Ser Val
                245                 250                 255

```
Val Thr Leu Pro Gln Lys Leu Cys Arg Leu Gly Leu Thr Tyr Met Gly
            260                 265                 270

Lys Asn Glu Met Gln Ile Val Phe Pro Phe Ala Thr Leu Leu Lys Lys
        275                 280                 285

Leu Asp Leu Leu Tyr Ala Leu Leu Asp Thr Glu Asp His Cys Thr Leu
    290                 295                 300

Ile Gln Arg Cys Pro Asn Leu Glu Val Leu Glu Thr Arg Asn Val Ile
305                 310                 315                 320

Gly Asp Arg Gly Leu Asp Val Leu Ala Arg Ser Cys Lys Arg Leu Arg
                325                 330                 335

Arg Leu Arg Ile Glu Arg Gly Ala Asp Glu Gly Met Glu Asp Glu Glu
            340                 345                 350

Gly Val Val Ser Gln Arg Gly Leu Met Ala Leu Ala Gln Gly Cys Leu
        355                 360                 365

Glu Leu Val Tyr Leu Ala Val Tyr Val Ser Asp Ile Thr Asn Ala Ser
    370                 375                 380

Leu Glu Tyr Ile Gly Thr Tyr Ser Lys Asn Leu Ser Asp Phe Arg Leu
385                 390                 395                 400

Val Leu Leu Asp Arg Glu Glu Thr Ile Thr Asp Leu Pro Leu Asp Asn
                405                 410                 415

Gly Val Arg Ala Leu Leu Arg Gly Cys His Lys Leu Arg Arg Phe Ala
            420                 425                 430

Leu Tyr Leu Arg Pro Gly Gly Leu Thr Asp Leu Gly Leu Ser Tyr Ile
        435                 440                 445

Gly Arg Tyr Ser Pro Asn Val Arg Trp Met Leu Leu Gly Tyr Val Gly
    450                 455                 460

Glu Ser Asp Ala Gly Leu Leu Glu Phe Ser Lys Gly Cys Pro Ser Leu
465                 470                 475                 480

Gln Lys Leu Glu Met Arg Gly Cys Cys Phe Ser Glu Arg Ala Leu Ala
                485                 490                 495

His Ala Val Met Gln Leu Thr Ser Leu Arg Tyr Leu Trp Val Gln Gly
            500                 505                 510

Tyr Arg Gly Ser Ala Thr Gly Arg Asp Leu Leu Ala Met Ala Arg Pro
        515                 520                 525

Phe Trp Asn Ile Glu Leu Ile Pro Pro Arg Arg Val Asp Val Pro Asp
    530                 535                 540

Gln His Gly Glu Ala Leu Ala Val Glu His Pro Ala His Ile Leu Ala
545                 550                 555                 560

Tyr Tyr Ser Leu Ala Gly Pro Arg Thr Asp Cys Pro Asp Thr Val Ile
                565                 570                 575

Pro Val Asp Pro Ala Ser Leu Leu Ile Ser
            580                 585

<210> SEQ ID NO 20
<211> LENGTH: 2563
<212> TYPE: DNA
<213> ORGANISM: Malus domestica

<400> SEQUENCE: 20
gcccgcttcc cttttcaatc cccctccct tatgtgtttg tgaggcgcat aattattctt    60
gaacaccact aataactgaa agtccgatcc aatagccgcc ggattcctcc ccggacgatc   120
cccaccgtac gtttcagatc cgtcttctca gaccatgtgc ttcgagtcca cgccgactcc   180
atgctccggc gctcctccac tggtcgccct gctccgccgt cttcgatccg attggtctgt   240
```

```
tttctgcgcg agcttctcgt agatcgtgct ttctagctcc tctctcttcc ctcttgttcc    300
tgctcgtttc ttgacacgtt gcggcgtttc tctgagattc tgattctgta aacgtcggtg    360
ccacggtgtc cttttagttc ttttttttga ttggatttgg aaatataaca gcttagggtt    420
ccgattttgg aaatccagtt tctatttctg gaaatatttg gagttgagga ttcggagctc    480
cgaaaacccg atcttgagag aattcgaatc tttttccact tttgactctg aaattttttt    540
gttagaaata gcagtagagt ttttcagtg agtatttca tcgccgacgt ttcttttag    600
cgatggagga tcgaagcgtg cggtgtagga tttccgacgt cgtaatggac tgcgtgatgc    660
cgtatctcca cgaccccaag gaccgtgacg ccgtgtcgtt ggtgtgcaag cggtggtacg    720
agctcgacgc gctcacgcgg aagcacgtga ccatcgcgct ctgctacacc acgaccccgg    780
atcggctgcg gcagcggttt cagcacctgg agtcgctgaa gctgaagggg aagccgaggg    840
cggcgatgtt caatctgatt cccgaggact ggggagggtt tgtaacgccg tgggtgatgg    900
agatcgccaa ctcgttccac cgcttgaagt gtctgcactt tcggcggatg attgttagtg    960
attcggacct ggagctcctg gctgactcac gtgggcgcgt gcttcaggtg cttaagctcg    1020
acaagtgctc agggtttacc accggtgggc ttttgcacat cggccgctcc tgcaggaatt    1080
tgaggacctt gttttggaa gagagctcca tagttgagga agatggcgac tggctacacg    1140
cgcttgctgt aaacaatact gtcctggaga ctctgaattt ttatatgacc gatcttatca    1200
aagtcaaatt cgaagacctt gaactgatag ccaaaaactg ccgctcctta acctctgtga    1260
aaattagtga ttgcgaaatc ttggaactgg ttggcttctt ccgtcatgca gctgtcttgg    1320
aagaattttg tgggggttcc ttcaacgatc aatccgagag ttactctgtt gtaacgttac    1380
cccaaaaact ttgccgtctc ggtctaacat acatgggaaa gaatgaaatg caaatagtgt    1440
tcccatttgc aacccttctc aaaaagctcg atctccttta tgcattgctg acactgagg    1500
accattgcac attaattcag aggtgcccca acctggaagt tctggagaca aggaatgtta    1560
ttggagatag aggactagat gttcttgctc ggagttgcaa gagactaagg aggctccgaa    1620
ttgagcgggg tgcagatgaa ggcatggagg acgaagaagg tgttgtttcc caacggggtc    1680
tgatggccct ggcgcaggga tgcctagagc tcgaatacct ggctgtttat gtatcggaca    1740
tcaccaatgc atctctggaa tacattggga cttactccaa aaatctctct gattttcgcc    1800
ttgtcttact tgaccgggaa gagacaataa cagatttgcc acttgacaat ggggttcgag    1860
cacttttgag gggatgccat aagcttcgaa ggtttgctct gtatctccgt cctgggggt    1920
tgactgacct cggactgagt tacattggcc ggtacagtcc gaatgtgaga tggatgcttc    1980
tgggttatgt tggggaatct gatgcagggc ttttggagtt ctcaaagggt tgccctagcc    2040
tgcaaaaatt ggaaatgagg ggttgctgct tcagcgagcg tgcactcgct catgcagtaa    2100
tgcaactgac ttcccttagg tacttgtggg tgcagggta cagaggatct gctactggtc    2160
gcgaccttt ggcaatggct cgcccgtttt ggaatattga gttgattcct cccagacgag    2220
ttgatgttcc tgatcagcat ggggaggcat tagcggtcga gcatccagcc catatacttg    2280
catactactc acttgctgga ccgagaacag attgtccaga tactgttatt cccgtggatc    2340
cggcatcttt actcatctcc tagagctgta catacaacct cttttttttct tccacaagca    2400
gtcatttct taccacgcct tgtttataaa ttcatgtaac ttttttactt ttggttaaga    2460
gggtttcgat ttcaagtttc aattatattt ctagacctta gttctgtaat aagtttgagt    2520
tacccctgtgt aatctgaaag cacttgcact ctttgatccg gaa               2563
```

<210> SEQ ID NO 21
<211> LENGTH: 590
<212> TYPE: PRT
<213> ORGANISM: Glycine max

<400> SEQUENCE: 21

```
Met Thr Glu Asp Arg Asn Val Arg Lys Thr Arg Val Val Asp Leu Val
1               5                   10                  15

Leu Asp Cys Val Ile Pro Tyr Ile Asp Pro Lys Asp Arg Asp Ala
            20                  25                  30

Val Ser Gln Val Cys Arg Arg Trp Tyr Glu Leu Asp Ser Leu Thr Arg
        35                  40                  45

Lys His Val Thr Ile Ala Leu Cys Tyr Thr Thr Pro Ala Arg Leu
    50                  55                  60

Arg Arg Arg Phe Pro His Leu Glu Ser Leu Lys Leu Lys Gly Lys Pro
65                  70                  75                  80

Arg Ala Ala Met Phe Asn Leu Ile Pro Glu Asp Trp Gly Gly His Val
                85                  90                  95

Thr Pro Trp Val Lys Glu Ile Ser Gln Tyr Phe Asp Cys Leu Lys Ser
            100                 105                 110

Leu His Phe Arg Arg Met Ile Val Lys Asp Ser Asp Leu Arg Asn Leu
        115                 120                 125

Ala Arg Asp Arg Gly His Val Leu His Ser Leu Lys Leu Asp Lys Cys
    130                 135                 140

Ser Gly Phe Thr Thr Asp Gly Leu Phe His Ile Gly Arg Phe Cys Lys
145                 150                 155                 160

Ser Leu Arg Val Leu Phe Leu Glu Glu Ser Ser Ile Val Glu Lys Asp
                165                 170                 175

Gly Glu Trp Leu His Glu Leu Ala Leu Asn Asn Thr Val Leu Glu Thr
            180                 185                 190

Leu Asn Phe Tyr Leu Thr Asp Ile Ala Val Val Lys Ile Gln Asp Leu
        195                 200                 205

Glu Leu Leu Ala Lys Asn Cys Pro Asn Leu Val Ser Val Lys Leu Thr
    210                 215                 220

Asp Ser Glu Ile Leu Asp Leu Val Asn Phe Phe Lys His Ala Ser Ala
225                 230                 235                 240

Leu Glu Glu Phe Cys Gly Gly Thr Tyr Asn Glu Glu Pro Glu Lys Tyr
                245                 250                 255

Ser Ala Ile Ser Leu Pro Ala Lys Leu Cys Arg Leu Gly Leu Thr Tyr
            260                 265                 270

Ile Gly Lys Asn Glu Leu Pro Ile Val Phe Met Phe Ala Ala Val Leu
        275                 280                 285

Lys Lys Leu Asp Leu Leu Tyr Ala Met Leu Asp Thr Glu Asp His Cys
    290                 295                 300

Met Leu Ile Gln Lys Cys Pro Asn Leu Glu Val Leu Glu Thr Arg Asn
305                 310                 315                 320

Val Ile Gly Asp Arg Gly Leu Glu Val Leu Gly Arg Cys Cys Lys Arg
                325                 330                 335

Leu Lys Arg Leu Arg Ile Glu Arg Gly Asp Asp Gln Gly Met Glu
            340                 345                 350

Asp Glu Glu Gly Thr Val Ser His Arg Gly Leu Ile Ala Leu Ser Gln
        355                 360                 365

Gly Cys Ser Glu Leu Glu Tyr Met Ala Val Tyr Val Ser Asp Ile Thr
    370                 375                 380
```

```
Asn Ala Ser Leu Glu His Ile Gly Thr His Leu Lys Asn Leu Cys Asp
385                 390                 395                 400

Phe Arg Leu Val Leu Leu Asp His Glu Glu Lys Ile Thr Asp Leu Pro
                405                 410                 415

Leu Asp Asn Gly Val Arg Ala Leu Leu Arg Gly Cys Asn Lys Leu Arg
            420                 425                 430

Arg Phe Ala Leu Tyr Leu Arg Arg Gly Gly Leu Thr Asp Val Gly Leu
        435                 440                 445

Gly Tyr Ile Gly Gln Tyr Ser Pro Asn Val Arg Trp Met Leu Leu Gly
    450                 455                 460

Tyr Val Gly Glu Ser Asp Ala Gly Leu Leu Glu Phe Ser Lys Gly Cys
465                 470                 475                 480

Pro Ser Leu Gln Lys Leu Glu Met Arg Gly Cys Ser Phe Phe Ser Glu
                485                 490                 495

Arg Ala Leu Ala Val Ala Ala Thr Gln Leu Thr Ser Leu Arg Tyr Leu
            500                 505                 510

Trp Val Gln Gly Tyr Gly Val Ser Pro Ser Gly Arg Asp Leu Leu Ala
        515                 520                 525

Met Ala Arg Pro Phe Trp Asn Ile Glu Leu Ile Pro Ser Arg Lys Val
    530                 535                 540

Ala Met Asn Thr Asn Ser Asp Glu Thr Val Val Val Glu His Pro Ala
545                 550                 555                 560

His Ile Leu Ala Tyr Tyr Ser Leu Ala Gly Gln Arg Ser Asp Phe Pro
                565                 570                 575

Asp Thr Val Val Pro Leu Asp Thr Ala Thr Cys Val Asp Thr
            580                 585                 590

<210> SEQ ID NO 22
<211> LENGTH: 590
<212> TYPE: PRT
<213> ORGANISM: Glycine max

<400> SEQUENCE: 22

Met Thr Glu Asp Arg Asn Val Arg Lys Thr Arg Val Val Asp Leu Val
1               5                   10                  15

Leu Asp Cys Val Ile Pro Tyr Ile Asp Asp Pro Lys Asp Arg Asp Ala
                20                  25                  30

Val Ser Gln Val Cys Arg Arg Trp Tyr Glu Leu Asp Ser Leu Thr Arg
            35                  40                  45

Lys His Val Thr Ile Ala Leu Cys Tyr Thr Thr Thr Pro Ala Arg Leu
        50                  55                  60

Arg Arg Arg Phe Pro His Leu Glu Ser Leu Lys Leu Gly Lys Pro
65                  70                  75                  80

Arg Ala Ala Met Phe Asn Leu Ile Pro Glu Asp Trp Gly Gly His Val
                85                  90                  95

Thr Pro Trp Val Lys Glu Ile Ser Gln Tyr Phe Asp Cys Leu Lys Ser
            100                 105                 110

Leu His Phe Arg Arg Met Ile Val Lys Asp Ser Asp Leu Arg Asn Leu
        115                 120                 125

Ala Arg Asp Arg Gly His Val Leu His Ser Leu Lys Leu Asp Lys Cys
    130                 135                 140

Ser Gly Phe Thr Thr Asp Gly Leu Phe His Ile Gly Arg Phe Cys Lys
145                 150                 155                 160

Ser Leu Arg Val Leu Phe Leu Glu Glu Ser Ser Ile Val Glu Lys Asp
```

```
            165                 170                 175
Gly Glu Trp Leu His Glu Leu Ala Leu Asn Asn Thr Val Leu Glu Thr
            180                 185                 190

Leu Asn Phe Tyr Leu Thr Asp Ile Ala Val Val Lys Ile Gln Asp Leu
        195                 200                 205

Glu Leu Leu Ala Lys Asn Cys Pro Asn Leu Val Ser Val Lys Leu Thr
    210                 215                 220

Asp Ser Glu Ile Leu Asp Leu Val Asn Phe Phe Lys His Ala Ser Ala
225                 230                 235                 240

Leu Glu Glu Phe Cys Gly Gly Thr Tyr Asn Glu Glu Pro Glu Lys Tyr
            245                 250                 255

Ser Ala Ile Ser Leu Pro Ala Lys Leu Cys Arg Leu Gly Leu Thr Tyr
        260                 265                 270

Ile Gly Lys Asn Glu Leu Pro Ile Val Phe Met Phe Ala Ala Val Leu
    275                 280                 285

Lys Lys Leu Asp Leu Leu Tyr Ala Met Leu Asp Thr Glu Asp His Cys
    290                 295                 300

Met Leu Ile Gln Lys Cys Pro Asn Leu Glu Val Leu Glu Thr Arg Asn
305                 310                 315                 320

Val Ile Gly Asp Arg Gly Leu Glu Val Leu Gly Arg Cys Cys Lys Arg
            325                 330                 335

Leu Lys Arg Leu Arg Ile Glu Arg Gly Asp Asp Asp Gln Gly Met Glu
        340                 345                 350

Asp Glu Glu Gly Thr Val Ser His Arg Gly Leu Ile Ala Leu Ser Gln
            355                 360                 365

Gly Cys Ser Glu Leu Glu Tyr Met Val Val Tyr Val Ser Asp Ile Thr
        370                 375                 380

Asn Ala Ser Leu Glu His Ile Gly Thr His Leu Lys Asn Leu Cys Asp
385                 390                 395                 400

Phe Arg Leu Val Leu Leu Asp His Glu Glu Lys Ile Thr Asp Leu Pro
            405                 410                 415

Leu Asp Asn Gly Val Arg Ala Leu Leu Arg Gly Cys Asn Lys Leu Arg
        420                 425                 430

Arg Phe Ala Leu Tyr Leu Arg Arg Gly Gly Leu Thr Asp Val Gly Leu
    435                 440                 445

Gly Tyr Ile Gly Gln Tyr Ser Pro Asn Val Arg Trp Met Leu Leu Gly
    450                 455                 460

Tyr Val Gly Glu Ser Asp Ala Gly Leu Leu Glu Phe Ser Lys Gly Cys
465                 470                 475                 480

Pro Ser Leu Gln Lys Leu Glu Met Arg Gly Cys Ser Phe Phe Ser Glu
            485                 490                 495

Arg Ala Leu Ala Val Ala Ala Thr Gln Leu Thr Ser Leu Arg Tyr Leu
        500                 505                 510

Trp Val Gln Gly Tyr Gly Val Ser Pro Ser Gly Arg Asp Leu Leu Ala
    515                 520                 525

Met Ala Arg Pro Phe Trp Asn Ile Glu Leu Ile Pro Ser Arg Lys Val
530                 535                 540

Ala Met Asn Thr Asn Ser Asp Glu Thr Val Val Glu His Pro Ala
545                 550                 555                 560

His Ile Leu Ala Tyr Tyr Ser Leu Ala Gly Gln Arg Ser Asp Phe Pro
            565                 570                 575

Asp Thr Val Val Pro Leu Asp Thr Ala Thr Cys Val Asp Thr
        580                 585                 590
```

<210> SEQ ID NO 23
<211> LENGTH: 1773
<212> TYPE: DNA
<213> ORGANISM: Glycine max

<400> SEQUENCE: 23

```
atgacggagg atcggaacgt gcggaagaca cgtgtggtcg acctggtcct cgactgtgtc      60
atcccttaca tcgacgaccc caaggaccgc gacgccgtct cacaggtctg ccgacgctgg     120
tacgaactcg actccctcac tcggaagcac gtcaccatcg cgctctgcta caccaccacg     180
ccggcgcgcc tccgccgccg cttcccgcac cttgagtcgc tcaagctcaa gggcaagccc     240
cgagcagcaa tgttcaactt gatacccgag gattggggag ccacgtcac cccatgggtc      300
aaggagattt ctcagtactt cgattgcctc aagagtctcc acttccgccg tatgattgtc     360
aaagattccg atcttcggaa tctcgctcgt gaccgcggcc acgtgcttca ctctctcaag     420
cttgacaagt gctccggttt caccaccgat ggtcttttcc atatcggtcg cttttgcaag     480
agtttaagag tcttgttttt ggaggaaagc tcaattgttg agaaggacgg agaatggtta     540
cacgagcttg ctttgaataa tacagttctt gagactctca atttttactt gacagatatt     600
gctgttgtga agattcagga ccttgaactt ttagctaaaa attgccccaa cttagtgtct     660
gtgaaactta ctgacagtga atactggat cttgtgaact tctttaagca tgcctctgca      720
ctggaagagt tttgtggagg cacctacaat gaagaaccag aaaaatactc tgctatatca     780
ttaccagcaa agttatgtcg attgggttta acatatattg gaagaatga gttgcccata      840
gtgttcatgt ttgcagccgt actaaaaaaa ttggatctcc tctatgcaat gctagacacg     900
gaggatcatt gcatgttaat ccaaaagtgt ccaaatctgg aagtccttga dcaaggaat      960
gtaattggag acagagggtt agaggttctt ggtcgttgtt gtaagaggct aaaaaggctt    1020
aggattgaaa gggtgatga tgatcaagga atggaggatg aagaaggtac tgtgtcccat     1080
agagggctaa tagccttgtc acagggctgt tcagagcttg aatacatggc tgtttatgtg    1140
tctgatatta caaatgcatc tctggaacat atcggaactc acttgaagaa cctctgcgat    1200
tttcgccttg tgttgcttga ccacgaagag aaaataactg atttgccact tgacaatggg    1260
gtgagggctc tactgagggg ctgtaacaag ctgaggagat tgctctcata tctcaggcgt    1320
ggcgggttga ccgatgtagg tcttggttac attggacagt acagtccaaa tgtgagatgg    1380
atgctgcttg gttatgtggg ggagtctgat gcagggcttt tggaattctc taaagggtgt    1440
cctagtcttc agaaactaga atgagaggg tgttcatttt tcagtgaacg tgcacttgct    1500
gtggctgcaa cacaattgac ttctcttagg tacttgtggg tgcaagggta tggtgtatct    1560
ccatctggac gtgatctttt ggcaatggct cgcccctttt ggaacattga gttaattcct    1620
tctagaaagg tggctatgaa taccaattca gatgagacgg tagttgttga gcatcctgct    1680
catattcttg catattattc tcttgcaggg cagagatcag attttccaga tactgttgtg    1740
cctttggaca ctgccacatg cgttgacacc tag                                 1773
```

<210> SEQ ID NO 24
<211> LENGTH: 603
<212> TYPE: PRT
<213> ORGANISM: Solanum lycopersicum

<400> SEQUENCE: 24

```
Met Glu Glu Arg Asn Ser Thr Arg Leu Ser Ser Ser Thr Asn Asp Thr
  1               5                  10                  15
```

```
Val Trp Glu Cys Val Ile Pro Tyr Ile Gln Glu Ser Arg Asp Arg Asp
             20                  25                  30

Ala Val Ser Leu Val Cys Lys Arg Trp Trp Gln Ile Asp Ala Ile Thr
         35                  40                  45

Arg Lys His Ile Thr Met Ala Leu Cys Tyr Thr Ala Lys Pro Glu Gln
     50                  55                  60

Leu Ser Arg Arg Phe Pro His Leu Glu Ser Val Lys Leu Lys Gly Lys
 65                  70                  75                  80

Pro Arg Ala Ala Met Phe Asn Leu Ile Pro Glu Asp Trp Gly Gly Tyr
                 85                  90                  95

Val Thr Pro Trp Val Met Glu Ile Thr Lys Ser Phe Ser Lys Leu Lys
             100                 105                 110

Ala Leu His Phe Arg Arg Met Ile Val Arg Asp Ser Asp Leu Glu Leu
         115                 120                 125

Leu Ala Asn Arg Arg Gly Arg Val Leu Gln Val Leu Lys Leu Asp Lys
130                 135                 140

Cys Ser Gly Phe Ser Thr Asp Gly Leu Leu His Ile Ser Arg Ser Cys
145                 150                 155                 160

Lys Asn Leu Arg Thr Leu Leu Met Glu Glu Ser Tyr Ile Ile Glu Lys
                165                 170                 175

Asp Gly Glu Trp Ala His Glu Leu Ala Leu Asn Asn Thr Val Leu Glu
             180                 185                 190

Asn Leu Asn Phe Tyr Met Thr Asp Leu Leu Gln Val Arg Ala Glu Asp
         195                 200                 205

Leu Glu Leu Ile Ala Arg Asn Cys Lys Ser Leu Val Ser Met Lys Ile
210                 215                 220

Ser Glu Cys Glu Ile Thr Asn Leu Leu Gly Phe Phe Arg Ala Ala Ala
225                 230                 235                 240

Ala Leu Glu Glu Phe Gly Gly Ala Phe Asn Asp Gln Pro Glu Leu
                245                 250                 255

Val Val Glu Asn Gly Tyr Asn Glu His Ser Gly Lys Tyr Ala Ala Leu
             260                 265                 270

Val Phe Pro Pro Arg Leu Cys Gln Leu Gly Leu Thr Tyr Leu Gly Arg
         275                 280                 285

Asn Glu Met Ser Ile Leu Phe Pro Ile Ala Ser Arg Leu Arg Lys Leu
290                 295                 300

Asp Leu Leu Tyr Ala Leu Leu Asp Thr Ala Ala His Cys Phe Leu Leu
305                 310                 315                 320

Gln Arg Cys Pro Asn Leu Glu Ile Leu Glu Thr Arg Asn Val Val Gly
                325                 330                 335

Asp Arg Gly Leu Glu Val Leu Gly Gln Tyr Cys Lys Arg Leu Lys Arg
             340                 345                 350

Leu Arg Ile Glu Arg Gly Ala Asp Asp Gln Glu Met Glu Asp Glu Glu
         355                 360                 365

Gly Ala Val Thr His Arg Gly Leu Ile Asp Leu Ala Lys Gly Cys Leu
             370                 375                 380

Glu Leu Glu Tyr Met Ala Val Tyr Val Ser Asp Ile Thr Asn Glu Ala
385                 390                 395                 400

Leu Glu Val Ile Gly Thr Tyr Leu Lys Asn Leu Ser Asp Phe Arg Leu
                405                 410                 415

Val Leu Leu Asp Arg Glu Glu Arg Ile Thr Asp Leu Pro Leu Asp Asn
             420                 425                 430
```

```
Gly Val Arg Ala Leu Leu Arg Gly Cys His Asn Leu Arg Phe Ala
            435                 440                 445

Leu Tyr Val Arg Pro Gly Gly Leu Thr Asp Val Gly Leu Ser Tyr Val
450                 455                 460

Gly Gln Tyr Ser Pro Asn Val Arg Trp Met Leu Leu Gly Tyr Val Gly
465                 470                 475                 480

Glu Ser Asp His Gly Leu Leu Glu Phe Ser Lys Gly Cys Pro Ser Leu
                485                 490                 495

Gln Lys Leu Glu Val Arg Gly Cys Cys Phe Ser Glu Arg Ala Leu Ala
            500                 505                 510

Leu Ala Thr Leu Gln Leu Lys Ser Leu Arg Tyr Leu Trp Val Gln Gly
            515                 520                 525

Tyr Arg Ala Ser Ser Ala Gly Arg Asp Leu Leu Ala Met Ala Arg Pro
530                 535                 540

Phe Trp Asn Ile Glu Leu Ile Pro Ala Arg Arg Val Ile Ala Asn Asp
545                 550                 555                 560

Gly Asn Asn Ala Glu Thr Val Val Ser Glu His Pro Ala His Ile Leu
                565                 570                 575

Ala Tyr Tyr Ser Leu Ala Gly Gln Arg Thr Asp Phe Pro Asp Thr Val
                580                 585                 590

Lys Pro Leu Asp Pro Thr Tyr Leu Leu Ala Glu
            595                 600

<210> SEQ ID NO 25
<211> LENGTH: 603
<212> TYPE: PRT
<213> ORGANISM: Solanum lycopersicum

<400> SEQUENCE: 25

Met Glu Glu Arg Asn Ser Thr Arg Leu Ser Ser Thr Asn Asp Thr
1               5                   10                  15

Val Trp Glu Cys Val Ile Pro Tyr Ile Gln Glu Ser Arg Asp Arg Asp
            20                  25                  30

Ala Val Ser Leu Val Cys Lys Arg Trp Trp Gln Ile Asp Ala Ile Thr
        35                  40                  45

Arg Lys His Ile Thr Met Ala Leu Cys Tyr Thr Ala Lys Pro Glu Gln
50                  55                  60

Leu Ser Arg Arg Phe Pro His Leu Glu Ser Val Lys Leu Lys Gly Lys
65                  70                  75                  80

Pro Arg Ala Ala Met Phe Asn Leu Ile Pro Glu Asp Trp Gly Gly Tyr
                85                  90                  95

Val Thr Pro Trp Val Met Glu Ile Thr Lys Ser Phe Ser Lys Leu Lys
            100                 105                 110

Ala Leu His Phe Arg Arg Met Ile Val Arg Asp Ser Asp Leu Glu Leu
        115                 120                 125

Leu Ala Asn Arg Arg Gly Arg Val Leu Gln Val Leu Lys Leu Asp Lys
130                 135                 140

Cys Ser Gly Phe Ser Thr Asp Gly Leu Leu His Ile Ser Arg Ser Cys
145                 150                 155                 160

Lys Asn Leu Arg Thr Leu Leu Met Glu Glu Ser Tyr Ile Ile Glu Lys
                165                 170                 175

Asp Gly Glu Trp Ala His Glu Leu Ala Leu Asn Asn Thr Val Leu Glu
            180                 185                 190

Asn Leu Asn Phe Tyr Met Thr Asp Leu Leu Gln Val Arg Ala Glu Asp
        195                 200                 205
```

Leu Glu Leu Ile Ala Arg Asn Cys Lys Ser Leu Val Ser Met Lys Ile
    210                 215                 220

Ser Glu Cys Glu Ile Thr Asn Leu Leu Gly Phe Phe Arg Ala Ala Ala
225                 230                 235                 240

Ala Leu Glu Glu Phe Gly Gly Ala Phe Asn Asp Gln Pro Glu Leu
                245                 250                 255

Val Val Glu Asn Gly Tyr Asn Glu His Ser Gly Lys Tyr Ala Ala Leu
            260                 265                 270

Val Phe Pro Pro Arg Leu Cys Gln Leu Gly Leu Thr Tyr Leu Gly Arg
            275                 280                 285

Asn Glu Met Ser Ile Leu Phe Pro Ile Ala Ser Arg Leu Arg Lys Leu
    290                 295                 300

Asp Leu Leu Tyr Ala Leu Leu Asp Thr Ala Ala His Cys Phe Leu Leu
305                 310                 315                 320

Gln Arg Cys Pro Asn Leu Glu Ile Leu Glu Thr Arg Asn Val Val Gly
                325                 330                 335

Asp Arg Gly Leu Glu Val Leu Gly Gln Tyr Cys Lys Arg Leu Lys Arg
            340                 345                 350

Leu Arg Ile Glu Arg Gly Ala Asp Asp Gln Glu Met Glu Asp Glu Glu
    355                 360                 365

Gly Ala Val Thr His Arg Gly Leu Ile Asp Leu Ala Lys Gly Cys Leu
370                 375                 380

Glu Leu Glu Tyr Met Val Val Tyr Val Ser Asp Ile Thr Asn Glu Ala
385                 390                 395                 400

Leu Glu Val Ile Gly Thr Tyr Leu Lys Asn Leu Ser Asp Phe Arg Leu
                405                 410                 415

Val Leu Leu Asp Arg Glu Glu Arg Ile Thr Asp Leu Pro Leu Asp Asn
            420                 425                 430

Gly Val Arg Ala Leu Leu Arg Gly Cys His Asn Leu Arg Arg Phe Ala
            435                 440                 445

Leu Tyr Val Arg Pro Gly Gly Leu Thr Asp Val Gly Leu Ser Tyr Val
    450                 455                 460

Gly Gln Tyr Ser Pro Asn Val Arg Trp Met Leu Leu Gly Tyr Val Gly
465                 470                 475                 480

Glu Ser Asp His Gly Leu Leu Glu Phe Ser Lys Gly Cys Pro Ser Leu
                485                 490                 495

Gln Lys Leu Glu Val Arg Gly Cys Cys Phe Ser Glu Arg Ala Leu Ala
            500                 505                 510

Leu Ala Thr Leu Gln Leu Lys Ser Leu Arg Tyr Leu Trp Val Gln Gly
            515                 520                 525

Tyr Arg Ala Ser Ser Ala Gly Arg Asp Leu Leu Ala Met Ala Arg Pro
    530                 535                 540

Phe Trp Asn Ile Glu Leu Ile Pro Ala Arg Arg Val Ile Ala Asn Asp
545                 550                 555                 560

Gly Asn Asn Ala Glu Thr Val Val Ser Glu His Pro Ala His Ile Leu
                565                 570                 575

Ala Tyr Tyr Ser Leu Ala Gly Gln Arg Thr Asp Phe Pro Asp Thr Val
            580                 585                 590

Lys Pro Leu Asp Pro Thr Tyr Leu Leu Ala Glu
            595                 600

<210> SEQ ID NO 26
<211> LENGTH: 2030

<212> TYPE: DNA
<213> ORGANISM: Solanum lycopersicum

<400> SEQUENCE: 26

```
ctctcctcca tcttcttcaa ctgtaacctc tcttccatta tcagtgtcaa gttgttgaag      60
ttttggtcat ggtcatggtg taatttgttg ttagtatttt gaagtatttg tgttttttgat    120
ttggttttgg ttttaatgga ggaacggaac tcaacgagat tgagtagctc aacaaacgat    180
acagtatggg agtgtgtgat tccgtatata caggaatcgc gtgatagaga cgcggtatcg    240
ttggtatgta agaggtggtg gcagatcgat gcgattacta gaaagcatat aactatggcg    300
ttgtgttata cagcgaaacc agagcagtta tctagaaggt ttccacatct tgaatcggtt    360
aaactgaaag ggaaaccaag agctgctatg tttaatttga taccggaaga ttggggagga    420
tatgttacac cttgggttat ggagataact aagtcgttta gtaaattgaa agcacttcat    480
tttcgtagaa tgattgttag agattcggat ctcgaattac ttgcgaatcg tcgtggaaga    540
gttcttcaag ttttgaagct ggataagtgt tctggatttt ctactgatgg tcttctgcat    600
atttctcgtt cctgcaagaa cttaagaact tgttaatgg aagagagtta tataattgag    660
aaagatggaa aatgggcaca tgaactagca ttgaacaaca ctgttcttga gaatttgaac    720
ttttacatga cagatcttct gcaagttagg gctgaagatc ttgaattgat agcaagaaat    780
tgtaaatctc tagtctctat gaaaattagc gagtgtgaaa ttacgaatct tcttggcttc    840
tttagagctg cggctgcatt ggaggagttt ggtggtggcg catttaatga ccaaccagaa    900
cttgttgttg aaaatggcta taatgagcat tccggaaaat atgccgcact agtcttccct    960
ccaagattat gtcaattggg cttgacatac ttagggagaa atgagatgtc cattctcttt   1020
cctattgcgt ctcgtctgag gaaattggat cttctttatg cacttcttga cacagcagcc   1080
cactgttttct tactgcaaag gtgtcccaac ttggaaaattc ttgagactag gaatgttgtt   1140
ggggatagag gattgaagt gcttggccag tactgtaaga ggttaaagcg gctcaggatt   1200
gagagaggag ctgatgatca ggagatggag gatgaagaag gtgcggttac acacagagga   1260
ttgattgatt tggcaaaggg atgtcttgaa ctagaataca tggctgttta tgtgtcagat   1320
attactaatg aagctttgga agttattggt acatatctga aaaatctgag tgattttcgg   1380
ctggttttgc ttgacagaga agaaagaata acagatctgc cacttgataa tggtgtgcgt   1440
gctttactaa gaggttgcca taatcttaga agatttgccc tctatgtccg gcctggggc    1500
cttactgatg taggtctcag ttatgtcggg caatacagcc caaacgtgag atggatgctt   1560
ctgggatacg ttggggaatc cgatcatggc cttctggagt tctctaaagg atgtccgagc   1620
ctgcaaaagc tagaagtgag aggctgctgt ttcagtgaac gtgcattagc cttggctacc   1680
ttgcagctaa aatcgttaag gtatctatgg gtacaaggat acagggcatc ttcagctggt   1740
cgtgatctct tagcgatggc tcgcccattc tggaatattg aattgattcc tgcaagacga   1800
gttattgcca acgatggaaa taatgcagaa actgtagtct cggagcatcc agcccatata   1860
cttgcctact attctcttgc cggacaaaga acagattttc cagacactgt caagcctttg   1920
gacccaactt accttctcgc tgaataggtt tgtaaatata acttttcctt gagtgaagtt   1980
gttcgaggtc tatttgcttc cttttttaggt gtcttgtcca tatgtatgcc               2030
```

<210> SEQ ID NO 27
<211> LENGTH: 599
<212> TYPE: PRT
<213> ORGANISM: Zea mays

```
<400> SEQUENCE: 27

Met Gly Gly Glu Ala Pro Glu Pro Arg Arg Leu Thr Arg Ala Leu Ser
1               5                   10                  15

Ile Gly Gly Asp Gly Gly Trp Val Pro Glu Met Leu Gln Leu
            20                  25                  30

Val Met Gly Phe Val Glu Asp Pro Arg Asp Arg Glu Ala Ala Ser Leu
        35                  40                  45

Val Cys His Arg Trp His Arg Val Asp Ala Leu Ser Arg Lys His Val
    50                  55                  60

Thr Val Pro Phe Cys Tyr Ala Val Ser Pro Ala Arg Leu Leu Ala Arg
65                  70                  75                  80

Phe Pro Arg Leu Glu Ser Leu Ala Val Lys Gly Lys Pro Arg Ala Ala
                85                  90                  95

Met Tyr Gly Leu Ile Pro Asp Asp Trp Gly Ala Tyr Ala Arg Pro Trp
            100                 105                 110

Ile Thr Glu Leu Ala Ala Pro Leu Glu Cys Leu Lys Ala Leu His Leu
        115                 120                 125

Arg Arg Met Val Val Thr Asp Asp Leu Ala Glu Leu Val Arg Ala
    130                 135                 140

Arg Gly His Met Leu Gln Glu Leu Lys Leu Asp Lys Cys Thr Gly Phe
145                 150                 155                 160

Ser Thr His Gly Leu Arg Leu Val Ala Arg Ser Cys Arg Ser Leu Arg
                165                 170                 175

Thr Leu Phe Leu Glu Glu Cys Gln Ile Asp Asp Lys Gly Ser Glu Trp
            180                 185                 190

Ile His Asp Leu Ala Val Cys Cys Pro Val Leu Thr Thr Leu Asn Phe
        195                 200                 205

His Met Thr Glu Leu Glu Val Met Pro Ala Asp Leu Lys Leu Leu Ala
    210                 215                 220

Lys Ser Cys Lys Ser Leu Ile Ser Leu Lys Ile Ser Asp Cys Asp Leu
225                 230                 235                 240

Ser Asp Leu Ile Glu Phe Phe Gln Phe Ala Thr Ala Leu Glu Glu Phe
                245                 250                 255

Ala Gly Gly Thr Phe Asn Glu Gln Gly Glu Leu Ser Lys Tyr Val Asn
            260                 265                 270

Val Lys Phe Pro Ser Arg Leu Cys Ser Leu Gly Leu Thr Tyr Met Gly
        275                 280                 285

Thr Asn Glu Met Pro Ile Met Phe Pro Phe Ser Ala Ile Leu Lys Lys
    290                 295                 300

Leu Asp Leu Gln Tyr Thr Phe Leu Thr Thr Glu Asp His Cys Gln Leu
305                 310                 315                 320

Ile Ala Lys Cys Pro Asn Leu Leu Val Leu Ala Val Arg Asn Val Ile
                325                 330                 335

Gly Asp Arg Gly Leu Gly Val Val Ala Asp Thr Cys Lys Lys Leu Gln
            340                 345                 350

Arg Leu Arg Ile Glu Arg Gly Asp Asp Glu Gly Gly Val Gln Glu Glu
        355                 360                 365

Gln Gly Gly Val Ser Val Gly Leu Thr Ala Ile Ala Val Gly Cys
    370                 375                 380

Arg Glu Leu Glu Tyr Ile Ala Ala Tyr Val Ser Asp Ile Thr Asn Gly
385                 390                 395                 400

Ala Leu Glu Ser Ile Gly Thr Phe Cys Lys Lys Leu Tyr Asp Phe Arg
                405                 410                 415
```

```
Leu Val Leu Leu Asp Arg Glu Arg Ile Thr Asp Leu Pro Leu Asp
            420                 425                 430

Asn Gly Val Arg Ala Leu Leu Arg Gly Cys Thr Lys Leu Arg Arg Phe
            435                 440                 445

Ala Leu Tyr Leu Arg Pro Gly Gly Leu Ser Asp Ala Gly Leu Gly Tyr
        450                 455                 460

Ile Gly Gln Cys Ser Gly Asn Ile Gln Tyr Met Leu Leu Gly Asn Val
465                 470                 475                 480

Gly Glu Thr Asp Asp Gly Leu Ile Ser Phe Ala Leu Gly Cys Val Asn
                485                 490                 495

Leu Arg Lys Leu Glu Leu Arg Ser Cys Cys Phe Ser Glu Arg Ala Leu
                500                 505                 510

Ala Leu Ala Ile Leu His Met Pro Ser Leu Arg Tyr Val Trp Val Gln
            515                 520                 525

Gly Tyr Lys Ala Ser Gln Thr Gly Arg Asp Leu Met Leu Met Ala Arg
        530                 535                 540

Pro Phe Trp Asn Ile Glu Phe Thr Pro Pro Asn Pro Lys Asn Gly Gly
545                 550                 555                 560

Trp Leu Met Glu Asp Gly Glu Pro Cys Val Asp Ser His Ala Gln Ile
                565                 570                 575

Leu Ala Tyr His Ser Leu Ala Gly Lys Arg Leu Asp Cys Pro Gln Ser
            580                 585                 590

Val Val Pro Leu Tyr Pro Ala
        595

<210> SEQ ID NO 28
<211> LENGTH: 599
<212> TYPE: PRT
<213> ORGANISM: Zea mays

<400> SEQUENCE: 28

Met Gly Gly Glu Ala Pro Glu Pro Arg Arg Leu Thr Arg Ala Leu Ser
1               5                   10                  15

Ile Gly Gly Asp Gly Gly Trp Val Pro Glu Glu Met Leu Gln Leu
            20                  25                  30

Val Met Gly Phe Val Glu Asp Pro Arg Asp Arg Glu Ala Ala Ser Leu
        35                  40                  45

Val Cys His Arg Trp His Arg Val Asp Ala Leu Ser Arg Lys His Val
    50                  55                  60

Thr Val Pro Phe Cys Tyr Ala Val Ser Pro Ala Arg Leu Leu Ala Arg
65              70                  75                  80

Phe Pro Arg Leu Glu Ser Leu Ala Val Lys Gly Lys Pro Arg Ala Ala
                85                  90                  95

Met Tyr Gly Leu Ile Pro Asp Asp Trp Gly Ala Tyr Ala Arg Pro Trp
            100                 105                 110

Ile Thr Glu Leu Ala Ala Pro Leu Glu Cys Leu Lys Ala Leu His Leu
        115                 120                 125

Arg Arg Met Val Val Thr Asp Asp Leu Ala Glu Leu Val Arg Ala
130                 135                 140

Arg Gly His Met Leu Gln Glu Leu Lys Leu Asp Lys Cys Thr Gly Phe
145                 150                 155                 160

Ser Thr His Gly Leu Arg Leu Val Ala Arg Ser Cys Arg Ser Leu Arg
                165                 170                 175

Thr Leu Phe Leu Glu Glu Cys Gln Ile Asp Asp Lys Gly Ser Glu Trp
```

-continued

```
            180                 185                 190
Ile His Asp Leu Ala Val Cys Cys Pro Val Leu Thr Thr Leu Asn Phe
            195                 200                 205
His Met Thr Glu Leu Glu Val Met Pro Ala Asp Leu Lys Leu Leu Ala
            210                 215                 220
Lys Ser Cys Lys Ser Leu Ile Ser Leu Lys Ile Ser Asp Cys Asp Leu
225                 230                 235                 240
Ser Asp Leu Ile Glu Phe Phe Gln Phe Ala Thr Ala Leu Glu Glu Phe
                    245                 250                 255
Ala Gly Gly Thr Phe Asn Glu Gln Gly Glu Leu Ser Lys Tyr Val Asn
                260                 265                 270
Val Lys Phe Pro Ser Arg Leu Cys Ser Leu Gly Leu Thr Tyr Met Gly
            275                 280                 285
Thr Asn Glu Met Pro Ile Met Phe Pro Phe Ser Ala Ile Leu Lys Lys
            290                 295                 300
Leu Asp Leu Gln Tyr Thr Phe Leu Thr Thr Glu Asp His Cys Gln Leu
305                 310                 315                 320
Ile Ala Lys Cys Pro Asn Leu Leu Val Leu Ala Val Arg Asn Val Ile
                    325                 330                 335
Gly Asp Arg Gly Leu Gly Val Val Ala Asp Thr Cys Lys Lys Leu Gln
                340                 345                 350
Arg Leu Arg Ile Glu Arg Gly Asp Asp Glu Gly Gly Val Gln Glu Glu
            355                 360                 365
Gln Gly Gly Val Ser Gln Val Gly Leu Thr Ala Ile Ala Val Gly Cys
            370                 375                 380
Arg Glu Leu Glu Tyr Ile Val Ala Tyr Val Ser Asp Ile Thr Asn Gly
385                 390                 395                 400
Ala Leu Glu Ser Ile Gly Thr Phe Cys Lys Lys Leu Tyr Asp Phe Arg
                    405                 410                 415
Leu Val Leu Leu Asp Arg Glu Glu Arg Ile Thr Asp Leu Pro Leu Asp
                420                 425                 430
Asn Gly Val Arg Ala Leu Leu Arg Gly Cys Thr Lys Leu Arg Arg Phe
            435                 440                 445
Ala Leu Tyr Leu Arg Pro Gly Gly Leu Ser Asp Ala Gly Leu Gly Tyr
            450                 455                 460
Ile Gly Gln Cys Ser Gly Asn Ile Gln Tyr Met Leu Leu Gly Asn Val
465                 470                 475                 480
Gly Glu Thr Asp Asp Gly Leu Ile Ser Phe Ala Leu Gly Cys Val Asn
                    485                 490                 495
Leu Arg Lys Leu Glu Leu Arg Ser Cys Cys Phe Ser Glu Arg Ala Leu
                500                 505                 510
Ala Leu Ala Ile Leu His Met Pro Ser Leu Arg Tyr Val Trp Val Gln
            515                 520                 525
Gly Tyr Lys Ala Ser Gln Thr Gly Arg Asp Leu Met Leu Met Ala Arg
            530                 535                 540
Pro Phe Trp Asn Ile Glu Phe Thr Pro Pro Asn Pro Lys Asn Gly Gly
545                 550                 555                 560
Trp Leu Met Glu Asp Gly Glu Pro Cys Val Asp Ser His Ala Gln Ile
                    565                 570                 575
Leu Ala Tyr His Ser Leu Ala Gly Lys Arg Leu Asp Cys Pro Gln Ser
                580                 585                 590
Val Val Pro Leu Tyr Pro Ala
            595
```

<210> SEQ ID NO 29
<211> LENGTH: 2169
<212> TYPE: DNA
<213> ORGANISM: Zea mays

<400> SEQUENCE: 29

| | | | | | |
|---|---|---|---|---|---|
| acccctgctt | gctgcagctt | caagcactac | cgaatcaggg | cgagtgggag | cagaggaggg | 60 |
| aatcccatgt | ctccgcccct | cgctggagca | gatcgttgtc | gagccgacgt | ggagctgctg | 120 |
| cggtagaaag | ctagcggagc | ctgcgagcta | gcctgatccg | tccgcagtcc | gatcgggatc | 180 |
| gatgggtggg | gaggcgccgg | agccgcggcg | gctgacccgg | gcgctgagca | tcggcggcgg | 240 |
| tgacggcggc | tgggttcccg | aggagatgct | gcaactcgtg | atggggttcg | tcgaggaccc | 300 |
| gcgcgaccgg | gaggccgcgt | cgctggtgtg | tcaccggtgg | caccgcgtcg | acgcgctctc | 360 |
| gcggaagcac | gtgacggtgc | ccttctgcta | cgccgtttcc | ccggcacgcc | tgctcgcgcg | 420 |
| gttcccgcgg | ctcgagtcgc | tcgcggtgaa | ggggaagccc | cgcgcggcca | tgtacgggct | 480 |
| cataccccgac | gactggggcg | cctacgcccg | cccgtggatc | accgagctcg | ccgcgccgct | 540 |
| cgagtgcctc | aaggcgctcc | acctccgacg | catggtcgtc | acagacgacg | acctcgccga | 600 |
| gctcgtccgt | gccaggggggc | acatgctgca | ggagctgaag | ctcgataagt | gcaccggctt | 660 |
| ctccactcat | ggactccgcc | tcgttgcccg | ctcctgcaga | tcactgagga | ctttatttt | 720 |
| ggaagaatgt | caaattgatg | ataagggcag | tgaatggatc | cacgatctcg | cagtctgctg | 780 |
| tcctgttctg | acaacattga | atttccacat | gactgagctt | gaagtgatgc | cagctgacct | 840 |
| aaagcttctt | gcaaagagct | gcaagtcact | gatttcattg | aagattagtg | actgcgatct | 900 |
| ttcagatttg | atagagttct | tccaatttgc | cacagcactg | gaagaatttg | ctggagggac | 960 |
| attcaatgag | caaggggaac | tcagcaagta | tgtgaatgtt | aaatttccat | caagactatg | 1020 |
| ctccttggga | cttacttaca | tgggaacaaa | tgaaatgccc | attatgttcc | ctttttctgc | 1080 |
| aatactaaag | aagctggatt | tgcaatacac | tttcctcacc | actgaggacc | attgccagct | 1140 |
| cattgcaaaa | tgcccgaact | tactagttct | cgcggtgagg | aatgtgattg | gagatagagg | 1200 |
| attaggagtt | gttgcggata | cgtgcaagaa | gctccaaagg | ctcagaatag | agcgaggaga | 1260 |
| tgatgaagga | ggtgtgcaag | aagagcaggg | aggggtctct | caagtgggct | tgacggctat | 1320 |
| agccgtaggt | tgccgtgagc | tggaatatat | agctgcctat | gtgtctgata | taaccaatgg | 1380 |
| ggccttggaa | tctatcggga | cattctgcaa | aaaactatac | gacttccggc | ttgttctact | 1440 |
| tgatagagaa | gagaggataa | cagacttgcc | actggacaat | ggtgtccgag | ctttgttgag | 1500 |
| gggctgcacc | aagcttcgga | ggtttgctct | gtacttgaga | ccaggagggc | tctcagatgc | 1560 |
| aggtctcggc | tacattggac | agtgcagcgg | aaacatccag | tacatgcttc | tcggtaatgt | 1620 |
| tggggaaact | gatgatggat | tgatcagctt | cgcattgggt | tgcgtaaacc | tgcgaaagct | 1680 |
| tgaactcagg | agttgctgct | tcagcgagcg | agcactggcc | cttgcaatac | tacatatgcc | 1740 |
| ttccctgagg | tacgtatggg | ttcagggcta | caaagcgtct | caaaccggcc | gagacctcat | 1800 |
| gctcatggca | aggcccttct | ggaacataga | gtttacacct | cccaatccta | agaacggagg | 1860 |
| ttggctgatg | aagatggggg | agccttgtgt | agatagtcac | gctcagatac | ttgcatacca | 1920 |
| ctccctcgcc | ggtaagaggc | tggactgccc | acaatccgtg | gttcctttgt | atcctgcgtg | 1980 |
| agtgtaaata | gactaagctg | gtgtctttcc | ttagcctcct | ggtcaacaag | aatggtgttg | 2040 |
| ataactcgat | atatgcggtt | attgtatgga | tctagatggc | tagctgctac | gtactgtaat | 2100 | aagctactag tagctgagag atgtcctgga ataagcccctt gctatttttg cctaaaaaaa    2160 aaaaaaaaa    2169

<210> SEQ ID NO 30
<211> LENGTH: 594
<212> TYPE: PRT
<213> ORGANISM: Triticum aestivum

<400> SEQUENCE: 30

```
Met Gly Gly Glu Val Pro Glu Pro Arg Arg Leu Ser Arg Ala Leu Ser
1               5                   10                  15

Phe Gly Val Pro Asp Glu Ala Leu His Leu Val Met Gly Tyr Val Asp
            20                  25                  30

Ala Pro Arg Asp Arg Glu Ala Ala Ser Leu Val Cys Arg Arg Trp His
        35                  40                  45

Arg Ile Asp Ala Leu Thr Arg Lys His Val Thr Val Ala Phe Cys Tyr
    50                  55                  60

Ala Ala Asp Pro Ser Arg Leu Leu Ala Arg Phe Pro Arg Leu Glu Ser
65                  70                  75                  80

Leu Ala Leu Lys Gly Arg Pro Arg Ala Ala Met Tyr Gly Leu Ile Ser
                85                  90                  95

Asp Asp Trp Gly Ala Tyr Ala Ala Pro Trp Val Ala Arg Leu Ala Ala
            100                 105                 110

Pro Leu Glu Cys Leu Lys Ala Leu His Leu Arg Arg Met Thr Val Thr
        115                 120                 125

Asp Asp Asp Val Ala Thr Leu Ile Arg Ser Arg Gly His Met Leu Gln
    130                 135                 140

Glu Leu Lys Leu Asp Lys Cys Ser Gly Phe Ser Thr Asp Ala Leu Arg
145                 150                 155                 160

Leu Val Ala Arg Ser Cys Arg Ser Leu Arg Thr Leu Phe Leu Glu Glu
                165                 170                 175

Cys Val Ile Thr Asp Glu Gly Gly Glu Trp Leu His Glu Leu Ala Val
            180                 185                 190

Asn Asn Ser Val Leu Val Thr Leu Asn Phe Tyr Met Thr Glu Leu Lys
        195                 200                 205

Val Val Pro Ala Asp Leu Glu Leu Leu Ala Lys Asn Cys Lys Ser Leu
    210                 215                 220

Leu Ser Leu Lys Ile Ser Glu Cys Asp Leu Ser Asp Leu Ile Gly Phe
225                 230                 235                 240

Phe Glu Ala Ala Asn Ala Leu Gln Asp Phe Ala Gly Gly Ser Phe Asn
                245                 250                 255

Glu Val Gly Glu Leu Thr Lys Tyr Glu Lys Val Lys Phe Pro Pro Arg
            260                 265                 270

Val Cys Phe Leu Gly Leu Thr Phe Met Gly Lys Asn Glu Met Pro Val
        275                 280                 285

Ile Phe Pro Phe Ser Ala Ser Leu Lys Lys Leu Asp Leu Gln Tyr Thr
    290                 295                 300

Phe Leu Thr Thr Glu Asp His Cys Gln Leu Ile Ser Lys Cys Pro Asn
305                 310                 315                 320

Leu Phe Val Leu Glu Val Arg Asn Val Ile Gly Asp Arg Gly Leu Glu
                325                 330                 335

Val Val Gly Asp Thr Cys Lys Lys Leu Arg Arg Leu Arg Ile Glu Arg
            340                 345                 350

Gly Asp Asp Asp Pro Gly Leu Gln Glu Glu Gln Gly Gly Val Ser Gln
```

```
                355                 360                 365
Leu Gly Leu Thr Ala Val Ala Val Gly Cys Arg Asp Leu Glu Tyr Ile
    370                 375                 380
Ala Ala Tyr Val Ser Asp Ile Thr Asn Gly Ala Leu Glu Ser Ile Gly
385                 390                 395                 400
Thr Phe Cys Lys Asn Leu Tyr Asp Phe Arg Leu Val Leu Leu Asp Arg
                405                 410                 415
Gln Lys Gln Val Thr Asp Leu Pro Leu Asp Asn Gly Val Arg Ala Leu
            420                 425                 430
Leu Arg Ser Cys Thr Lys Leu Arg Arg Phe Ala Leu Tyr Leu Arg Pro
            435                 440                 445
Gly Gly Leu Ser Asp Ile Gly Leu Asp Tyr Ile Gly Gln Tyr Ser Gly
        450                 455                 460
Asn Ile Gln Tyr Met Leu Leu Gly Asn Val Gly Glu Ser Asp His Gly
465                 470                 475                 480
Leu Ile Arg Phe Ala Ile Gly Cys Thr Asn Leu Arg Lys Leu Glu Leu
                485                 490                 495
Arg Ser Cys Cys Phe Ser Glu Gln Ala Leu Ser Leu Ala Val Leu His
            500                 505                 510
Met Pro Ser Leu Arg Tyr Ile Trp Val Gln Gly Tyr Lys Ala Ser Pro
            515                 520                 525
Ala Gly Leu Glu Leu Leu Leu Met Ala Arg Arg Phe Trp Asn Ile Glu
        530                 535                 540
Phe Thr Pro Pro Ser Pro Glu Gly Leu Phe Arg Met Thr Leu Glu Gly
545                 550                 555                 560
Glu Pro Cys Val Asp Lys Gln Ala Gln Val Leu Ala Tyr Tyr Ser Leu
                565                 570                 575
Ala Gly Gln Arg Gln Asp Cys Pro Asp Trp Val Thr Pro Leu His Pro
            580                 585                 590
Ala Ala

<210> SEQ ID NO 31
<211> LENGTH: 594
<212> TYPE: PRT
<213> ORGANISM: Triticum aestivum

<400> SEQUENCE: 31

Met Gly Gly Glu Val Pro Glu Pro Arg Arg Leu Ser Arg Ala Leu Ser
1               5                   10                  15
Phe Gly Val Pro Asp Glu Ala Leu His Leu Val Met Gly Tyr Val Asp
            20                  25                  30
Ala Pro Arg Asp Arg Glu Ala Ala Ser Leu Val Cys Arg Arg Trp His
        35                  40                  45
Arg Ile Asp Ala Leu Thr Arg Lys His Val Thr Val Ala Phe Cys Tyr
    50                  55                  60
Ala Ala Asp Pro Ser Arg Leu Leu Ala Arg Phe Pro Arg Leu Glu Ser
65                  70                  75                  80
Leu Ala Leu Lys Gly Arg Pro Arg Ala Ala Met Tyr Gly Leu Ile Ser
                85                  90                  95
Asp Asp Trp Gly Ala Tyr Ala Ala Pro Trp Val Ala Arg Leu Ala Ala
            100                 105                 110
Pro Leu Glu Cys Leu Lys Ala Leu His Leu Arg Arg Met Thr Val Thr
            115                 120                 125
Asp Asp Asp Val Ala Thr Leu Ile Arg Ser Arg Gly His Met Leu Gln
```

-continued

```
            130                 135                 140

Glu Leu Lys Leu Asp Lys Cys Ser Gly Phe Ser Thr Asp Ala Leu Arg
145                 150                 155                 160

Leu Val Ala Arg Ser Cys Arg Ser Leu Arg Thr Leu Phe Leu Glu Glu
                165                 170                 175

Cys Val Ile Thr Asp Glu Gly Gly Glu Trp Leu His Glu Leu Ala Val
            180                 185                 190

Asn Asn Ser Val Leu Val Thr Leu Asn Phe Tyr Met Thr Glu Leu Lys
                195                 200                 205

Val Val Pro Ala Asp Leu Glu Leu Leu Ala Lys Asn Cys Lys Ser Leu
            210                 215                 220

Leu Ser Leu Lys Ile Ser Glu Cys Asp Leu Ser Asp Leu Ile Gly Phe
225                 230                 235                 240

Phe Glu Ala Ala Asn Ala Leu Gln Asp Phe Ala Gly Gly Ser Phe Asn
                245                 250                 255

Glu Val Gly Glu Leu Thr Lys Tyr Glu Lys Val Lys Phe Pro Pro Arg
            260                 265                 270

Val Cys Phe Leu Gly Leu Thr Phe Met Gly Lys Asn Glu Met Pro Val
                275                 280                 285

Ile Phe Pro Phe Ser Ala Ser Leu Lys Lys Leu Asp Leu Gln Tyr Thr
            290                 295                 300

Phe Leu Thr Thr Glu Asp His Cys Gln Leu Ile Ser Lys Cys Pro Asn
305                 310                 315                 320

Leu Phe Val Leu Glu Val Arg Asn Val Ile Gly Asp Arg Gly Leu Glu
                325                 330                 335

Val Val Gly Asp Thr Cys Lys Lys Leu Arg Arg Leu Arg Ile Glu Arg
            340                 345                 350

Gly Asp Asp Pro Gly Leu Gln Glu Gln Gly Gly Val Ser Gln
                355                 360                 365

Leu Gly Leu Thr Ala Val Ala Val Gly Cys Arg Asp Leu Glu Tyr Ile
            370                 375                 380

Val Ala Tyr Val Ser Asp Ile Thr Asn Gly Ala Leu Glu Ser Ile Gly
385                 390                 395                 400

Thr Phe Cys Lys Asn Leu Tyr Asp Phe Arg Leu Val Leu Leu Asp Arg
                405                 410                 415

Gln Lys Gln Val Thr Asp Leu Pro Leu Asp Asn Gly Val Arg Ala Leu
            420                 425                 430

Leu Arg Ser Cys Thr Lys Leu Arg Arg Phe Ala Leu Tyr Leu Arg Pro
                435                 440                 445

Gly Gly Leu Ser Asp Ile Gly Leu Asp Tyr Ile Gly Gln Tyr Ser Gly
            450                 455                 460

Asn Ile Gln Tyr Met Leu Leu Gly Asn Val Gly Glu Ser Asp His Gly
465                 470                 475                 480

Leu Ile Arg Phe Ala Ile Gly Cys Thr Asn Leu Arg Lys Leu Glu Leu
                485                 490                 495

Arg Ser Cys Cys Phe Ser Glu Gln Ala Leu Ser Leu Ala Val Leu His
            500                 505                 510

Met Pro Ser Leu Arg Tyr Ile Trp Val Gln Gly Tyr Lys Ala Ser Pro
            515                 520                 525

Ala Gly Leu Glu Leu Leu Leu Met Ala Arg Arg Phe Trp Asn Ile Glu
            530                 535                 540

Phe Thr Pro Pro Ser Pro Glu Gly Leu Phe Arg Met Thr Leu Glu Gly
545                 550                 555                 560
```

```
Glu Pro Cys Val Asp Lys Gln Ala Gln Val Leu Ala Tyr Tyr Ser Leu
                565                 570                 575

Ala Gly Gln Arg Gln Asp Cys Pro Asp Trp Val Thr Pro Leu His Pro
            580                 585                 590

Ala Ala

<210> SEQ ID NO 32
<211> LENGTH: 592
<212> TYPE: PRT
<213> ORGANISM: Triticum aestivum

<400> SEQUENCE: 32

Met Gly Gly Glu Ala Pro Glu Pro Arg Arg Leu Ser Arg Ala Leu Ser
1               5                   10                  15

Leu Asp Gly Gly Val Pro Glu Glu Ala Leu His Leu Val Leu Gly
            20                  25                  30

Tyr Val Asp Asp Pro Arg Asp Arg Glu Ala Ala Ser Leu Ala Cys Arg
            35                  40                  45

Arg Trp His His Ile Asp Ala Leu Thr Arg Lys His Val Thr Val Pro
    50                  55                  60

Phe Cys Tyr Ala Val Ser Pro Ala Arg Leu Leu Ala Arg Phe Pro Arg
65                  70                  75                  80

Leu Glu Ser Leu Gly Val Lys Gly Lys Pro Arg Ala Ala Met Tyr Gly
                85                  90                  95

Leu Ile Pro Asp Asp Trp Gly Ala Tyr Ala Arg Pro Trp Val Ala Glu
            100                 105                 110

Leu Ala Ala Pro Leu Glu Cys Leu Lys Ala Leu His Leu Arg Arg Met
        115                 120                 125

Val Val Thr Asp Asp Leu Ala Ala Leu Val Arg Ala Arg Gly His
    130                 135                 140

Met Leu Gln Glu Leu Lys Leu Asp Lys Cys Ser Gly Phe Ser Thr Asp
145                 150                 155                 160

Ala Leu Arg Leu Val Ala Arg Ser Cys Arg Ser Leu Arg Thr Leu Phe
                165                 170                 175

Leu Glu Glu Cys Thr Ile Thr Asp Asn Gly Thr Glu Trp Leu His Asp
            180                 185                 190

Leu Ala Ala Asn Asn Pro Val Leu Val Thr Leu Asn Phe Tyr Leu Thr
        195                 200                 205

Tyr Leu Arg Val Glu Pro Ala Asp Leu Glu Leu Leu Ala Lys Asn Cys
    210                 215                 220

Lys Ser Leu Ile Ser Leu Lys Ile Ser Asp Cys Asp Leu Ser Asp Leu
225                 230                 235                 240

Ile Gly Phe Phe Gln Ile Ala Thr Ser Leu Gln Glu Phe Ala Gly Ala
                245                 250                 255

Glu Ile Ser Glu Gln Lys Tyr Gly Asn Val Lys Leu Pro Ser Lys Leu
            260                 265                 270

Cys Ser Phe Gly Leu Thr Phe Met Gly Thr Asn Glu Met His Ile Ile
        275                 280                 285

Phe Pro Phe Ser Ala Val Leu Lys Lys Leu Asp Leu Gln Tyr Ser Phe
    290                 295                 300

Leu Thr Thr Glu Asp His Cys Gln Leu Ile Ala Lys Cys Pro Asn Leu
305                 310                 315                 320

Leu Val Leu Ala Val Arg Asn Val Ile Gly Asp Arg Gly Leu Gly Val
                325                 330                 335
```

```
Val Gly Asp Thr Cys Lys Lys Leu Gln Arg Leu Arg Val Glu Arg Gly
            340                 345                 350

Glu Asp Asp Pro Gly Met Gln Glu Glu Gly Gly Val Ser Gln Val
        355                 360                 365

Gly Leu Thr Ala Ile Ala Val Gly Cys Arg Glu Leu Glu Asn Ile Ala
    370                 375                 380

Ala Tyr Val Ser Asp Ile Thr Asn Gly Ala Leu Glu Ser Ile Gly Thr
385                 390                 395                 400

Phe Cys Lys Asn Leu His Asp Phe Arg Leu Val Leu Asp Lys Gln
            405                 410                 415

Glu Thr Ile Thr Asp Leu Pro Leu Asp Asn Gly Ala Arg Ala Leu Leu
            420                 425                 430

Arg Gly Cys Thr Lys Leu Arg Arg Phe Ala Leu Tyr Leu Arg Pro Gly
            435                 440                 445

Gly Leu Ser Asp Val Gly Leu Gly Tyr Ile Gly Gln His Ser Gly Thr
        450                 455                 460

Ile Gln Tyr Met Leu Leu Gly Asn Val Gly Gln Thr Asp Gly Gly Leu
465                 470                 475                 480

Ile Ser Phe Ala Ala Gly Cys Arg Asn Leu Arg Lys Leu Glu Leu Arg
                485                 490                 495

Ser Cys Cys Phe Ser Glu Arg Ala Leu Ala Leu Ala Ile Arg Gln Met
            500                 505                 510

Pro Ser Leu Arg Tyr Val Trp Val Gln Gly Tyr Arg Ala Ser Gln Thr
            515                 520                 525

Gly Arg Asp Leu Met Leu Met Ala Arg Pro Phe Trp Asn Ile Glu Phe
            530                 535                 540

Thr Pro Pro Ser Thr Glu Thr Ala Gly Arg Leu Met Glu Asp Gly Glu
545                 550                 555                 560

Pro Cys Val Asp Arg Gln Ala Gln Val Leu Ala Tyr Tyr Ser Leu Ser
                565                 570                 575

Gly Lys Arg Ser Asp Tyr Pro Gln Ser Val Val Pro Leu Tyr Pro Ala
            580                 585                 590

<210> SEQ ID NO 33
<211> LENGTH: 592
<212> TYPE: PRT
<213> ORGANISM: Triticum aestivum

<400> SEQUENCE: 33

Met Gly Gly Glu Ala Pro Glu Pro Arg Arg Leu Ser Arg Ala Leu Ser
1               5                   10                  15

Leu Asp Gly Gly Gly Val Pro Glu Glu Ala Leu His Leu Val Leu Gly
            20                  25                  30

Tyr Val Asp Asp Pro Arg Asp Arg Glu Ala Ala Ser Leu Ala Cys Arg
        35                  40                  45

Arg Trp His His Ile Asp Ala Leu Thr Arg Lys His Val Thr Val Pro
    50                  55                  60

Phe Cys Tyr Ala Val Ser Pro Ala Arg Leu Leu Ala Arg Phe Pro Arg
65              70                  75                  80

Leu Glu Ser Leu Gly Val Lys Gly Lys Pro Arg Ala Ala Met Tyr Gly
                85                  90                  95

Leu Ile Pro Asp Asp Trp Gly Ala Tyr Ala Arg Pro Trp Val Ala Glu
            100                 105                 110

Leu Ala Ala Pro Leu Glu Cys Leu Lys Ala Leu His Leu Arg Arg Met
```

```
            115                 120                 125
Val Val Thr Asp Asp Leu Ala Ala Leu Val Arg Ala Arg Gly His
    130                 135                 140

Met Leu Gln Glu Leu Lys Leu Asp Lys Cys Ser Gly Phe Ser Thr Asp
145                 150                 155                 160

Ala Leu Arg Leu Val Ala Arg Ser Cys Arg Ser Leu Arg Thr Leu Phe
                165                 170                 175

Leu Glu Glu Cys Thr Ile Thr Asp Asn Gly Thr Glu Trp Leu His Asp
                180                 185                 190

Leu Ala Ala Asn Asn Pro Val Leu Val Thr Leu Asn Phe Tyr Leu Thr
                195                 200                 205

Tyr Leu Arg Val Glu Pro Ala Asp Leu Glu Leu Leu Ala Lys Asn Cys
    210                 215                 220

Lys Ser Leu Ile Ser Leu Lys Ile Ser Asp Cys Asp Leu Ser Asp Leu
225                 230                 235                 240

Ile Gly Phe Phe Gln Ile Ala Thr Ser Leu Gln Glu Phe Ala Gly Ala
                245                 250                 255

Glu Ile Ser Glu Gln Lys Tyr Gly Asn Val Lys Leu Pro Ser Lys Leu
                260                 265                 270

Cys Ser Phe Gly Leu Thr Phe Met Gly Thr Asn Glu Met His Ile Ile
                275                 280                 285

Phe Pro Phe Ser Ala Val Leu Lys Lys Leu Asp Leu Gln Tyr Ser Phe
290                 295                 300

Leu Thr Thr Glu Asp His Cys Gln Leu Ile Ala Lys Cys Pro Asn Leu
305                 310                 315                 320

Leu Val Leu Ala Val Arg Asn Val Ile Gly Asp Arg Gly Leu Gly Val
                325                 330                 335

Val Gly Asp Thr Cys Lys Lys Leu Gln Arg Leu Arg Val Glu Arg Gly
                340                 345                 350

Glu Asp Asp Pro Gly Met Gln Glu Glu Gly Gly Val Ser Gln Val
                355                 360                 365

Gly Leu Thr Ala Ile Ala Val Gly Cys Arg Glu Leu Glu Asn Ile Val
    370                 375                 380

Ala Tyr Val Ser Asp Ile Thr Asn Gly Ala Leu Glu Ser Ile Gly Thr
385                 390                 395                 400

Phe Cys Lys Asn Leu His Asp Phe Arg Leu Val Leu Leu Asp Lys Gln
                405                 410                 415

Glu Thr Ile Thr Asp Leu Pro Leu Asp Asn Gly Ala Arg Ala Leu Leu
                420                 425                 430

Arg Gly Cys Thr Lys Leu Arg Arg Phe Ala Leu Tyr Leu Arg Pro Gly
    435                 440                 445

Gly Leu Ser Asp Val Gly Leu Gly Tyr Ile Gly Gln His Ser Gly Thr
    450                 455                 460

Ile Gln Tyr Met Leu Leu Gly Asn Val Gly Gln Thr Asp Gly Gly Leu
465                 470                 475                 480

Ile Ser Phe Ala Ala Gly Cys Arg Asn Leu Arg Lys Leu Glu Leu Arg
                485                 490                 495

Ser Cys Cys Phe Ser Glu Arg Ala Leu Ala Leu Ala Ile Arg Gln Met
                500                 505                 510

Pro Ser Leu Arg Tyr Val Trp Val Gln Gly Tyr Arg Ala Ser Gln Thr
                515                 520                 525

Gly Arg Asp Leu Met Leu Met Ala Arg Pro Phe Trp Asn Ile Glu Phe
530                 535                 540
```

```
Thr Pro Pro Ser Thr Glu Thr Ala Gly Arg Leu Met Glu Asp Gly Glu
545                 550                 555                 560

Pro Cys Val Asp Arg Gln Ala Gln Val Leu Ala Tyr Tyr Ser Leu Ser
            565                 570                 575

Gly Lys Arg Ser Asp Tyr Pro Gln Ser Val Val Pro Leu Tyr Pro Ala
            580                 585                 590

<210> SEQ ID NO 34
<211> LENGTH: 2167
<212> TYPE: DNA
<213> ORGANISM: Triticum aestivum

<400> SEQUENCE: 34
```

| | | | | | |
|---|---|---|---|---|---|
| acgagcacca | ccatcggaga | agggccagcg | ggaagggggg | aaatcaatcc | ccatgccccc | 60 |
| acccctcgcc | ggaccagatc | cccggcgggc | cggcgcggag | ccttaggcgg | ggatgggcgg | 120 |
| ggaggccccg | gagccgcggc | ggctgagccg | cgcgctcagc | ctggacggcg | gcggcgtccc | 180 |
| ggaggaggcg | ctgcacctgg | tgctcggcta | cgtggacgac | ccgcgcgacc | gcgaggcggc | 240 |
| ctcgctggcg | tgccgccgct | ggcaccacat | cgacgcgctc | acgcggaagc | acgtcaccgt | 300 |
| gcccttctgc | tacgccgtgt | ccccggcgcg | cctgctcgcg | cgcttcccgc | gcctcgagtc | 360 |
| gctcggggtc | aagggcaagc | cccgcgccgc | catgtacggc | ctcatccccg | acgactgggg | 420 |
| cgcctacgcc | cggccctggg | tcgccgagct | cgccgccccg | ctcgagtgcc | tcaaggcgct | 480 |
| ccacctgcgc | cgcatggtcg | tcaccgacga | cgacctcgcc | gccctcgtcc | gcgcccgcgg | 540 |
| ccacatgctg | caggagctca | agctcgacaa | gtgctccggc | ttctccaccg | acgccctccg | 600 |
| cctcgtcgcc | cgctcctgca | gatcactgag | aactttgttt | ctggaagaat | gtacaattac | 660 |
| tgataatggc | actgaatggc | tccatgacct | tgctgccaac | aatcctgttc | tggtgacctt | 720 |
| gaacttctac | ttgacttacc | tcagagtgga | gccagctgac | ctcgagcttc | tcgccaagaa | 780 |
| ttgcaagtca | ctaatttcgt | tgaagattag | cgactgcgac | ctttcagatt | tgattggatt | 840 |
| tttccaaata | gctacatctt | tgcaagaatt | tgctggagcg | gaaatcagtg | agcaaaagta | 900 |
| tggaaatgtt | aagcttcctt | caaagctttg | ctccttcgga | cttaccttca | tggggacaaa | 960 |
| tgagatgcac | ataatctttc | cttttctgc | tgtactcaag | aagctggatt | tgcagtacag | 1020 |
| tttctcacc | actgaagatc | attgccagct | cattgcaaaa | tgtccaaact | tactagtcct | 1080 |
| tgcggtgagg | aatgtgattg | gggatagagg | actgggggtt | gtcggagaca | catgcaagaa | 1140 |
| gctacaaagg | ctcagagttg | agcgagggga | agatgaccct | ggcatgcaag | aagaggaagg | 1200 |
| cggagtttct | caagtaggcc | taacagccat | agccgtaggt | tgccgtgaac | tggaaaacat | 1260 |
| agctgcctat | gtgtctgata | tcacaaatgg | ggccctggaa | tccatcggaa | cgttctgcaa | 1320 |
| aaatctccat | gactttcgcc | ttgtcctgct | tgacaaaaca | gagacgataa | cagatttgcc | 1380 |
| gctggacaac | ggtgcccgcg | cgctgctcag | gggctgcacc | aagcttcgga | ggttcgctct | 1440 |
| atacctgaga | ccaggggggc | tttcagatgt | aggcctcggc | tacatcgggc | agcacagtgg | 1500 |
| aaccatccag | tacatgcttc | tgggtaacgt | cgggcagacg | gatggtggat | tgatcagttt | 1560 |
| cgcagccggg | tgccggaacc | tgcggaagct | tgaactgagg | agctgttgct | tcagcgagcg | 1620 |
| ggctctggcc | ctcgccatac | ggcaaatgcc | ttccctgagg | tatgtgtggg | tgcagggcta | 1680 |
| cagggcctct | cagaccggcc | gcgacctcat | gctcatggcg | cggccttct | ggaacatcga | 1740 |
| gtttacgcct | cccagcacgg | agaccgcggg | ccggctgatg | gaagatgggg | agccctgcgt | 1800 |
| tgataggcaa | gctcaggtgc | tggcgtacta | ctcccttct | gggaagaggt | ccgactaccc | 1860 |

```
gcagtctgtt gttcctctgt atcctgcgtg actgtaaata cattaagccg gtatggtgtc    1920
tctctgggac ggcccctggc tggccctctg cgcttctcgg gcaataagga tgtttgtatg    1980
tgggtattgt atggatctgg tagattttct agctgctgtg tactggaata agcgcattgg    2040 tattttttgcc tggtactcct atctaatctt aggaagatgt atactaaagt aacattgtgc    2100
gagtgaactg tgacactatt gcgcttgctt cgcaggcata agcttgtctg gtttccgcgg    2160
cctgccc                                                              2167
```

<210> SEQ ID NO 35
<211> LENGTH: 573
<212> TYPE: PRT
<213> ORGANISM: Populus trichocarpa

<400> SEQUENCE: 35

```
Met Pro Tyr Ile Asn Asp Pro Arg Asp Arg Asp Ala Val Ser Leu Val
1               5                   10                  15

Cys Arg Arg Trp Tyr Glu Leu Asp Ala Leu Thr Arg Lys Asn Val Thr
            20                  25                  30

Ile Ala Phe Cys Tyr Ser Thr Ser Pro Asp Arg Leu Arg Arg Arg Phe
        35                  40                  45

Asn Asp Ile Glu Ser Leu Lys Leu Lys Gly Lys Pro Arg Ala Ala Met
    50                  55                  60

Phe Phe Asn Leu Ile Pro Glu Asp Trp Gly Phe Val Thr Pro Trp
65                  70                  75                  80

Val Asn Glu Ile Ala Glu Ser Phe Asn Cys Leu Lys Ser Leu His Phe
                85                  90                  95

Arg Arg Met Ile Val Lys Asp Ser Asp Leu Glu Leu Leu Ala Arg Ser
            100                 105                 110

Arg Gly Arg Leu Leu Gln Val Leu Lys Leu Asp Lys Cys Ser Gly Phe
        115                 120                 125

Ser Thr Asp Gly Leu Ser His Ile Gly Arg Ser Cys Arg Gln Leu Arg
    130                 135                 140

Thr Leu Phe Leu Glu Glu Ser Ala Ile Val Glu Arg Asp Gly Asp Trp
145                 150                 155                 160

Leu His Glu Leu Ala Thr Asn Asn Thr Val Leu Glu Thr Leu Asn Phe
                165                 170                 175

Tyr Met Thr Glu Leu Thr Arg Val Arg Ser Glu Asp Leu Glu Leu Leu
            180                 185                 190

Ala Arg Asn Cys Arg Ser Leu Val Ser Val Lys Val Ser Asp Cys Glu
        195                 200                 205

Ile Leu Asp Leu Val Gly Phe Phe His Ala Ala Ser Ala Leu Glu Glu
    210                 215                 220

Phe Cys Gly Gly Ser Phe Asn Glu Pro Asp Glu Pro Asp Lys Tyr Ser
225                 230                 235                 240

Ala Val Lys Phe Pro Pro Lys Leu Cys Cys Leu Gly Leu Ser Tyr Met
                245                 250                 255

Glu Lys Asn Val Met Ser Ile Val Phe Pro Phe Ala Ser Leu Leu Lys
            260                 265                 270

Lys Leu Asp Leu Leu Tyr Ala Phe Leu Gly Thr Glu Asp His Cys Val
        275                 280                 285

Leu Val Gln Arg Cys Pro Asn Leu Glu Val Leu Glu Thr Arg Asn Val
    290                 295                 300

Ile Gly Asp Arg Gly Leu Glu Ala Leu Ala Gln Ser Cys Lys Leu Leu
```

Lys Arg Leu Arg Ile Glu Arg Gly Ala Asp Glu Gln Gly Met Glu Asp
305                 310                 315                 320

Val Asp Gly Arg Val Ser His Arg Gly Leu Ile Ala Leu Ala Gln Gly
        325                 330                 335

Cys Leu Glu Leu Glu Tyr Ile Ala Val Tyr Val Ser Asp Ile Thr Asn
            340                 345                 350

Ala Ala Leu Glu His Met Gly Thr Tyr Ser Lys Asn Leu Asn Asp Phe
355                 360                 365

Arg Leu Val Leu Leu Gln Glu Gly Arg Ile Thr Asp Leu Pro Leu
370                 375                 380

Asp Asn Gly Val Arg Ala Leu Leu Arg Gly Cys Glu Lys Leu Gln Arg
385                 390                 395                 400

Phe Gly Leu Tyr Leu Arg Pro Gly Gly Leu Thr Asp Val Gly Leu Gly
            405                 410                 415

Tyr Ile Gly Gln Tyr Ser Arg Arg Val Arg Trp Met Ile Leu Gly Ser
        420                 425                 430

Val Gly Glu Ser Asp Glu Gly Leu Leu Ala Phe Ser Arg Gly Cys Pro
            435                 440                 445

Ser Leu Gln Lys Leu Glu Met Arg Ala Cys Cys Phe Ser Glu Ser Ala
450                 455                 460

Leu Ala Arg Ala Ala Leu Gln Leu Thr Ser Leu Arg Tyr Leu Trp Val
465                 470                 475                 480

His Gly Tyr Arg Glu Thr Ser Thr Gly His Arg Asp Leu Leu Thr Met
            485                 490                 495

Val Arg Pro Phe Trp Asn Ile Glu Leu Ile Pro Ser Arg Lys Val Glu
        500                 505                 510

Ser Val Asn Glu Ala Gly Glu Asn Ile Val Ser Glu Asn Pro Ala His
            515                 520                 525

Ile Leu Ala Tyr Tyr Ser Leu Ala Gly Pro Arg Thr Asp Phe Pro Asp
530                 535                 540

Thr Val Arg Pro Leu Asp Pro Ala Asn Ile Val Ala Ala
545                 550                 555                 560

565                 570

<210> SEQ ID NO 36
<211> LENGTH: 573
<212> TYPE: PRT
<213> ORGANISM: Populus trichocarpa

<400> SEQUENCE: 36

Met Pro Tyr Ile Asn Asp Pro Arg Asp Arg Asp Ala Val Ser Leu Val
1               5                   10                  15

Cys Arg Arg Trp Tyr Glu Leu Asp Ala Leu Thr Arg Lys Asn Val Thr
            20                  25                  30

Ile Ala Phe Cys Tyr Ser Thr Ser Pro Asp Arg Leu Arg Arg Phe
        35                  40                  45

Asn Asp Ile Glu Ser Leu Lys Leu Lys Gly Lys Pro Arg Ala Ala Met
    50                  55                  60

Phe Phe Asn Leu Ile Pro Glu Asp Trp Gly Gly Phe Val Thr Pro Trp
65                  70                  75                  80

Val Asn Glu Ile Ala Glu Ser Phe Asn Cys Leu Lys Ser Leu His Phe
                85                  90                  95

Arg Arg Met Ile Val Lys Asp Ser Asp Leu Glu Leu Leu Ala Arg Ser
            100                 105                 110

-continued

```
Arg Gly Arg Leu Leu Gln Val Leu Lys Leu Asp Lys Cys Ser Gly Phe
            115                 120                 125

Ser Thr Asp Gly Leu Ser His Ile Gly Arg Ser Cys Arg Gln Leu Arg
    130                 135                 140

Thr Leu Phe Leu Glu Glu Ser Ala Ile Val Glu Arg Asp Gly Asp Trp
145                 150                 155                 160

Leu His Glu Leu Ala Thr Asn Asn Thr Val Leu Glu Thr Leu Asn Phe
                165                 170                 175

Tyr Met Thr Glu Leu Thr Arg Val Arg Ser Glu Asp Leu Glu Leu Leu
                180                 185                 190

Ala Arg Asn Cys Arg Ser Leu Val Ser Val Lys Val Ser Asp Cys Glu
            195                 200                 205

Ile Leu Asp Leu Val Gly Phe Phe His Ala Ala Ser Ala Leu Glu Glu
        210                 215                 220

Phe Cys Gly Gly Ser Phe Asn Glu Pro Asp Glu Pro Asp Lys Tyr Ser
225                 230                 235                 240

Ala Val Lys Phe Pro Pro Lys Leu Cys Cys Leu Gly Leu Ser Tyr Met
                245                 250                 255

Glu Lys Asn Val Met Ser Ile Val Phe Pro Phe Ala Ser Leu Leu Lys
            260                 265                 270

Lys Leu Asp Leu Leu Tyr Ala Phe Leu Gly Thr Glu Asp His Cys Val
        275                 280                 285

Leu Val Gln Arg Cys Pro Asn Leu Glu Val Leu Glu Thr Arg Asn Val
    290                 295                 300

Ile Gly Asp Arg Gly Leu Glu Ala Leu Ala Gln Ser Cys Lys Leu Leu
305                 310                 315                 320

Lys Arg Leu Arg Ile Glu Arg Gly Ala Asp Glu Gln Gly Met Glu Asp
                325                 330                 335

Val Asp Gly Arg Val Ser His Arg Gly Leu Ile Ala Leu Ala Gln Gly
            340                 345                 350

Cys Leu Glu Leu Glu Tyr Ile Val Val Tyr Val Ser Asp Ile Thr Asn
        355                 360                 365

Ala Ala Leu Glu His Met Gly Thr Tyr Ser Lys Asn Leu Asn Asp Phe
    370                 375                 380

Arg Leu Val Leu Leu Glu Gln Glu Glu Arg Ile Thr Asp Leu Pro Leu
385                 390                 395                 400

Asp Asn Gly Val Arg Ala Leu Leu Arg Gly Cys Glu Lys Leu Gln Arg
                405                 410                 415

Phe Gly Leu Tyr Leu Arg Pro Gly Gly Leu Thr Asp Val Gly Leu Gly
            420                 425                 430

Tyr Ile Gly Gln Tyr Ser Arg Arg Val Arg Trp Met Ile Leu Gly Ser
        435                 440                 445

Val Gly Glu Ser Asp Glu Gly Leu Leu Ala Phe Ser Arg Gly Cys Pro
    450                 455                 460

Ser Leu Gln Lys Leu Glu Met Arg Ala Cys Cys Phe Ser Glu Ser Ala
465                 470                 475                 480

Leu Ala Arg Ala Ala Leu Gln Leu Thr Ser Leu Arg Tyr Leu Trp Val
                485                 490                 495

His Gly Tyr Arg Glu Thr Ser Thr Gly His Arg Asp Leu Leu Thr Met
            500                 505                 510

Val Arg Pro Phe Trp Asn Ile Glu Leu Ile Pro Ser Arg Lys Val Glu
        515                 520                 525

Ser Val Asn Glu Ala Gly Glu Asn Ile Val Ser Glu Asn Pro Ala His
```

```
                530             535             540
Ile Leu Ala Tyr Tyr Ser Leu Ala Gly Pro Arg Thr Asp Phe Pro Asp
545                 550             555             560

Thr Val Arg Pro Leu Asp Pro Ala Asn Ile Val Ala Ala
                565             570
```

<210> SEQ ID NO 37
<211> LENGTH: 2040
<212> TYPE: DNA
<213> ORGANISM: Populus trichocarpa

<400> SEQUENCE: 37

```
atgccgtaca taaacgaccc gcgggaccgc gacgccgttt cgttagtttg ccggagatgg    60
tacgagctag atgcgttaac acggaagaac gtgactatag cttttgtta cagtacaagt    120 ccagatcgat tacgacgtcg ttttaatgac attgaatcat taaagctaaa agggaaaccc   180
cgggctgcta tgtttttaa tttgataccg gaggattggg gagggtttgt gactccatgg    240
gttaatgaaa tagcggagag ttttaattgc ttgaaatcgc ttcattttag aaggatgatt    300
gttaaagatt cggatctgga gttacttgct aggtccagag ggagactttt gcaggttttg    360
aagcttgata agtgctctgg gttttccacg atggcctttt cgcacatcgg tcgctcttgc    420
aggcaattga gaacattatt cttggaagag agtgcaattg ttgagagaga tggtgactgg    480
ctccatgagc ttgctacgaa caatacagtt ctcgagactc taaattttta catgacagaa    540
cttaccagag tcagatcgga agaccttgag cttcttgcca ggaactgtcg ttcattagtc    600
tctgtaaagg ttagcgactg tgaaatcttg gatcttgttg gtttctttca tgctgcatct    660
gctttagagg aattttgtgg aggttccttc aatgagccag atgaaccaga caaatactct    720
gctgtcaaat tcccccccaaa attatgctgt ttgggtctta gctatatgga agaacgta    780 atgtcaatag tgtttccttt tgcatccctg ctcaaaaagc tggatctcct ctacgctttt    840
cttggcacgg aagatcattg tgttttagtc caaaggtgcc ccaacttaga agttctcgag    900
acaagaaatg ttattggaga tagagggttg gaagcccttg cccagagttg taagctacta    960
aagaggcttc gaatagagcg tggtgccgat gagcagggaa tggaggatgt ggatggccga   1020
gtttcacata gaggattaat tgccttggct caaggctgct agaactcga gtacatcgcc    1080 gtttatgttt ctgatattac caatgcagct ctagaacata tgggcacata tcaaagaac    1140 ctcaatgatt tccgcctggt cttgcttgag caagaagaga ggataaccga cctgcccctt   1200
gacaatggag ttcgagctct attaagggc tgtgaaaagc tccaaaggtt cggtctgtat    1260
ctccgaccag ggggtttgac tgatgtgggt cttggatata ttggacagta cagcagacga   1320
gtaagatgga tgattctagg tagtgttggg gagtctgatg aagggctttt ggcgttttct    1380
agaggctgtc ctagcctgca aaaacttgaa atgagggcct gttgcttcag tgagagtgca   1440
ctggctagag ctgccttgca actgacttct ctgaggtact tgtgggtgca tggttataga   1500
gagacctcta ctggtcatcg tgatctctta acaatggttc gcccattttg gaacatcgaa   1560
ttgattcctt ctaggaaggt tgagtcggtt aatgaagctg agaaaatat tgtttccgag    1620 aatccagccc acattcttgc atattactcc cttgctggac caagaacaga ctttccagat    1680
actgtgagac cactggatcc agcgaacata gttgctgcgt agagctgtat atgaagttga    1740
tgtcatgttc tttttattgc cacgccctgt ttatagattt atccatcttt ttatcatttg    1800
ggtaagagtg tttcggttta attttaaatt tctattttac ttagaccgtt gtcctgtaat    1860
aagtctacgt tctctgctgt aatttagcac ttccgctcta ggtacactac tgtcttttct    1920
```
gtcgtctgtg gcagttagct taaccttttg gtgactttgt atttcatctg cttcaatgtt    1980
ggaaatgttg ctagaatttt ggctgctttt tattgataaa tacacagatt ttcacttgca    2040

<210> SEQ ID NO 38
<211> LENGTH: 265
<212> TYPE: PRT
<213> ORGANISM: Arachis hypogaeal

<400> SEQUENCE: 38

Arg His Cys Lys Lys Leu Gln Arg Leu Trp Ile Met Asp Ser Ile Gly
1               5                   10                  15

Asp Lys Gly Leu Gly Val Val Ala Asn Thr Cys Lys Glu Leu Gln Glu
            20                  25                  30

Leu Arg Val Phe Pro Ser Asp Asn Ile Gly Gln His Ala Ala Val Thr
        35                  40                  45

Glu Lys Gly Leu Val Ala Ile Ser Met Gly Cys Pro Lys Leu His Ser
    50                  55                  60

Leu Leu Tyr Phe Cys His Gln Met Thr Asn Ala Ala Leu Ile Thr Val
65                  70                  75                  80

Ala Lys Asn Cys Pro Asn Phe Ile Arg Phe Arg Leu Ala Ile Leu Asp
                85                  90                  95

Ala Thr Lys Pro Asp Pro Asp Thr Asn Gln Pro Leu Asp Glu Gly Phe
            100                 105                 110

Gly Ala Ile Val Gln Ser Cys Arg Arg Leu Arg Arg Leu Ser Leu Ser
        115                 120                 125

Gly Gln Leu Thr Asp Lys Val Phe Leu Tyr Ile Gly Met Tyr Ala Glu
    130                 135                 140

Gln Leu Glu Met Leu Ser Ile Ala Phe Ala Gly Glu Ser Asp Lys Gly
145                 150                 155                 160

Met Leu Tyr Val Leu Asn Gly Cys Lys Lys Leu Arg Lys Leu Glu Ile
                165                 170                 175

Arg Asp Cys Pro Phe Gly Asn Thr Ala Leu Leu Thr Asp Val Gly Lys
            180                 185                 190

Tyr Glu Thr Met Arg Ser Leu Trp Met Ser Ser Cys Glu Val Thr Val
        195                 200                 205

Gly Ala Cys Lys Val Leu Ala Met Lys Met Pro Arg Leu Asn Val Glu
    210                 215                 220

Ile Phe Asn Glu Asn Glu Pro Ala Asp Cys Glu Pro Asp Asp Val Gln
225                 230                 235                 240

Lys Val Glu Lys Met Tyr Leu Tyr Arg Thr Leu Ala Gly Lys Arg Lys
                245                 250                 255

Asp Ala Pro Glu Tyr Val Trp Thr Leu
            260                 265

<210> SEQ ID NO 39
<211> LENGTH: 265
<212> TYPE: PRT
<213> ORGANISM: Arachis hypogaeal

<400> SEQUENCE: 39

Arg His Cys Lys Lys Leu Gln Arg Leu Trp Ile Met Asp Ser Ile Gly
1               5                   10                  15

Asp Lys Gly Leu Gly Val Val Ala Asn Thr Cys Lys Glu Leu Gln Glu
            20                  25                  30

Leu Arg Val Phe Pro Ser Asp Asn Ile Gly Gln His Ala Ala Val Thr

```
              35                  40                  45
Glu Lys Gly Leu Val Ala Ile Ser Met Gly Cys Pro Lys Leu His Ser
 50                  55                  60

Leu Val Tyr Phe Cys His Gln Met Thr Asn Ala Ala Leu Ile Thr Val
 65                  70                  75                  80

Ala Lys Asn Cys Pro Asn Phe Ile Arg Phe Leu Ala Ile Leu Asp
                 85                  90                  95

Ala Thr Lys Pro Asp Pro Asp Thr Asn Gln Pro Leu Asp Glu Gly Phe
                100                 105                 110

Gly Ala Ile Val Gln Ser Cys Arg Arg Leu Arg Arg Leu Ser Leu Ser
            115                 120                 125

Gly Gln Leu Thr Asp Lys Val Phe Leu Tyr Ile Gly Met Tyr Ala Glu
130                 135                 140

Gln Leu Glu Met Leu Ser Ile Ala Phe Ala Gly Glu Ser Asp Lys Gly
145                 150                 155                 160

Met Leu Tyr Val Leu Asn Gly Cys Lys Lys Leu Arg Lys Leu Glu Ile
                165                 170                 175

Arg Asp Cys Pro Phe Gly Asn Thr Ala Leu Leu Thr Asp Val Gly Lys
                180                 185                 190

Tyr Glu Thr Met Arg Ser Leu Trp Met Ser Ser Cys Glu Val Thr Val
            195                 200                 205

Gly Ala Cys Lys Val Leu Ala Met Lys Met Pro Arg Leu Asn Val Glu
210                 215                 220

Ile Phe Asn Glu Asn Glu Pro Ala Asp Cys Glu Pro Asp Asp Val Gln
225                 230                 235                 240

Lys Val Glu Lys Met Tyr Leu Tyr Arg Thr Leu Ala Gly Lys Arg Lys
                245                 250                 255

Asp Ala Pro Glu Tyr Val Trp Thr Leu
                260                 265

<210> SEQ ID NO 40
<211> LENGTH: 900
<212> TYPE: DNA
<213> ORGANISM: Arachis hypogaeal

<400> SEQUENCE: 40
cgtcactgca agaaacttca gcgcttatgg ataatggatt ccattggaga taaagggcta      60
ggtgttgtag ctaacacatg taaggaattg caagaattga gggttttttcc ttccgacaac    120 attggtcagc atgcggctgt cacagagaag ggattggttg cgatatctat gggctgcccg    180
aaacttcact cattgctcta cttctgccac cagatgacaa atgctgccct aataactgtg    240
gccaagaact gcccgaattt tatccgcttt aggttggcca tccttgacgc aacaaaaccc    300
gaccccgaca caaatcagcc actggatgaa ggttttgggg cgattgtgca atcttgcagg    360
cgtcttaggc ggctttccct ctctggccag ctgactgata aggtattcct ctacatcgga    420
atgtatgctg agcagcttga gatgttgtcc attgcctttg ccggggagag cgacaagggg    480
atgctctatg ttctgaacgg atgcaagaag ctccgcaagc ttgagatcag ggactgccct    540
ttcggcaaca cggcacttct gacagacgta gggaagtatg aaacaatgcg atcccttttgg   600 atgtcgtcgt gcgaagtaac cgtcggagca tgcaaggtgc tagcaatgaa gatgccgagg    660
ctaaatgttg agatcttcaa cgagaatgag ccagccgact gcgagccgga tgatgtgcag    720
aaggtggaga gatgtacttt gtaccggaca ttggctggga gaggaaaga tgcaccggaa     780 tatgtatgga cccctttaggt gcattttttag gtcaattttta attttattgt tattattgag  840
```

```
cagtttgtac gttaggctga cttattaatg caattttagc cttgtgtagt ggttggtttg      900
```

<210> SEQ ID NO 41
<211> LENGTH: 591
<212> TYPE: PRT
<213> ORGANISM: Physcomitrella patens

<400> SEQUENCE: 41

| Met | Gly | Arg | Glu | Lys | Arg | Pro | Ser | Gly | Ser | Gly | Thr | Gly | Leu | Ser | Asp |
|---|---|---|---|---|---|---|---|---|---|---|---|---|---|---|---|
| 1 | | | | 5 | | | | | 10 | | | | | 15 | |

| Glu | Thr | Leu | Ala | Cys | Val | Leu | Lys | Tyr | Val | Glu | Ser | Ala | Glu | Asp | Arg |
|---|---|---|---|---|---|---|---|---|---|---|---|---|---|---|---|
| | | | 20 | | | | | 25 | | | | | 30 | | |

| Ala | Ser | Val | Ser | Leu | Val | Cys | Lys | Gln | Trp | Arg | Leu | Val | Asp | Gly | Ala |
|---|---|---|---|---|---|---|---|---|---|---|---|---|---|---|---|
| | | | | 35 | | | | | 40 | | | | | 45 | |

| Thr | Arg | Lys | Phe | Val | Thr | Ile | Ala | Tyr | Met | Tyr | Ser | Thr | Ser | Pro | Glu |
|---|---|---|---|---|---|---|---|---|---|---|---|---|---|---|---|
| | 50 | | | | | 55 | | | | | 60 | | | | |

| Met | Leu | Thr | Arg | Arg | Phe | Lys | Arg | Leu | Glu | Gly | Leu | Lys | Leu | Lys | Gly |
|---|---|---|---|---|---|---|---|---|---|---|---|---|---|---|---|
| 65 | | | | | 70 | | | | | 75 | | | | | 80 |

| Lys | Pro | Arg | Ala | Ala | Glu | Tyr | Asp | Leu | Leu | Val | Pro | Asp | Trp | Gly | Gly |
|---|---|---|---|---|---|---|---|---|---|---|---|---|---|---|---|
| | | | | 85 | | | | | 90 | | | | | 95 | |

| Tyr | Ala | Glu | Pro | Trp | Ile | Arg | Asp | Leu | Gly | Arg | Ala | Tyr | Thr | Ser | Leu |
|---|---|---|---|---|---|---|---|---|---|---|---|---|---|---|---|
| | | | 100 | | | | | 105 | | | | | 110 | | |

| Gln | Thr | Leu | Gln | Leu | Arg | Arg | Cys | Gln | Val | Ser | Asn | Ala | Asp | Leu | Thr |
|---|---|---|---|---|---|---|---|---|---|---|---|---|---|---|---|
| | | | 115 | | | | | 120 | | | | | 125 | | |

| Leu | Ile | Ala | Ser | Ser | Pro | Cys | Gln | Ala | Ser | Leu | Gln | Val | Leu | Tyr | Leu |
|---|---|---|---|---|---|---|---|---|---|---|---|---|---|---|---|
| | 130 | | | | | 135 | | | | | 140 | | | | |

| His | Lys | Cys | Ala | Gly | Phe | Ser | Thr | Ala | Gly | Leu | Leu | Pro | Val | Ala | Lys |
|---|---|---|---|---|---|---|---|---|---|---|---|---|---|---|---|
| 145 | | | | | 150 | | | | | 155 | | | | | 160 |

| Ser | Cys | Arg | Ser | Leu | Lys | Ser | Leu | Ser | Val | Glu | Asp | Ser | Asp | Val | Thr |
|---|---|---|---|---|---|---|---|---|---|---|---|---|---|---|---|
| | | | | 165 | | | | | 170 | | | | | 175 | |

| Asp | Glu | Gly | Gly | Glu | Trp | Leu | Phe | Glu | Leu | Ala | Arg | Asn | Asn | Ser | Val |
|---|---|---|---|---|---|---|---|---|---|---|---|---|---|---|---|
| | | | 180 | | | | | 185 | | | | | 190 | | |

| Leu | Glu | Val | Leu | Asn | Phe | Ala | Val | Leu | Gly | Leu | Glu | Asp | Val | Asp | Ala |
|---|---|---|---|---|---|---|---|---|---|---|---|---|---|---|---|
| | | | 195 | | | | | 200 | | | | | 205 | | |

| Ala | Asp | Leu | Val | Leu | Leu | Val | Glu | Arg | Cys | Lys | Ser | Leu | Val | Ser | Leu |
|---|---|---|---|---|---|---|---|---|---|---|---|---|---|---|---|
| | 210 | | | | | 215 | | | | | 220 | | | | |

| Lys | Val | Gly | Glu | Val | Glu | Met | Val | Asp | Met | Ile | Ser | Ala | Ile | Ser | Arg |
|---|---|---|---|---|---|---|---|---|---|---|---|---|---|---|---|
| 225 | | | | | 230 | | | | | 235 | | | | | 240 |

| Ala | Ser | Ser | Leu | Thr | Glu | Phe | Gly | Thr | Gly | Ser | Cys | Asn | Phe | Phe | Gly |
|---|---|---|---|---|---|---|---|---|---|---|---|---|---|---|---|
| | | | | 245 | | | | | 250 | | | | | 255 | |

| Asp | Glu | Asp | Ser | Arg | Thr | His | Val | Ser | Ile | Ser | Leu | Pro | Ser | Ser | Leu |
|---|---|---|---|---|---|---|---|---|---|---|---|---|---|---|---|
| | | | 260 | | | | | 265 | | | | | 270 | | |

| Thr | Gly | Leu | Ser | Gly | Leu | Trp | Ala | Met | Ser | Asp | Pro | Gly | Leu | Ala | Met |
|---|---|---|---|---|---|---|---|---|---|---|---|---|---|---|---|
| | | 275 | | | | | 280 | | | | | 285 | | | |

| Val | Leu | Pro | Ile | Ala | Pro | Asn | Leu | Arg | Lys | Leu | Asp | Leu | Lys | Phe | Thr |
|---|---|---|---|---|---|---|---|---|---|---|---|---|---|---|---|
| | 290 | | | | | 295 | | | | | 300 | | | | |

| Leu | Leu | Ser | Arg | Lys | Ala | Tyr | Cys | Gln | Leu | Phe | Ser | Gln | Cys | His | Ala |
|---|---|---|---|---|---|---|---|---|---|---|---|---|---|---|---|
| 305 | | | | | 310 | | | | | 315 | | | | | 320 |

| Leu | Glu | Glu | Leu | Gln | Val | Arg | Asn | Ala | Val | Gly | Asp | Glu | Gly | Met | Glu |
|---|---|---|---|---|---|---|---|---|---|---|---|---|---|---|---|
| | | | | 325 | | | | | 330 | | | | | 335 | |

| Val | Ile | Gly | Lys | Thr | Cys | Lys | Ser | Leu | Arg | Arg | Leu | Arg | Val | Glu | His |
|---|---|---|---|---|---|---|---|---|---|---|---|---|---|---|---|
| | | | 340 | | | | | 345 | | | | | 350 | | |

| Asp | Asn | Ala | Gly | Ala | Ile | Thr | Gln | Arg | Gly | Val | Val | Ala | Val | Ala | Gln |
|---|---|---|---|---|---|---|---|---|---|---|---|---|---|---|---|
| | | | 355 | | | | | 360 | | | | | 365 | | |

```
Gly Cys Ala Arg Met Gln Gln Leu Ile Val Tyr Val Ser Asp Ile Thr
        370                 375                 380

Asn Ala Ala Leu Ala Met Leu Gly Gln Cys Cys Ala Gln Leu Thr Asp
385                 390                 395                 400

Phe Arg Leu Val Leu Glu Thr Ala Ala Arg Arg Val Val Asp Leu Pro
                405                 410                 415

Leu Asp Asp Gly Ile Lys Leu Leu Lys Gly Cys Arg Lys Ile Ser
                420                 425                 430

Lys Leu Ala Val Tyr Leu Arg His Gly Gly Leu Thr Asp Arg Gly Met
            435                 440                 445

Gly Tyr Ile Gly Glu Phe Gly Thr Asn Leu Lys Trp Leu Leu Leu Gly
        450                 455                 460

Cys Thr Gly Glu Ser Asp Ile Gly Leu Ala Ser Leu Ala Tyr Lys Ala
465                 470                 475                 480

Gln Arg Ile Glu Arg Leu Glu Cys Arg Asp Cys Pro Phe Gly Glu Ala
                485                 490                 495

Gly Leu Ala Ala Ala Val Val Ala Met Ser Ser Leu Lys Phe Ile Trp
            500                 505                 510

Ile Gln Gly Tyr Arg Ala Pro Trp Ala Gly Glu His Leu Leu Ala Leu
        515                 520                 525

Ser Arg Pro Tyr Leu Asn Ile Glu Val Ile Ser Ser Thr Asp Thr Gln
530                 535                 540

Pro Gly Gln Leu Ile Ala His Tyr Thr Thr Val Gly Pro Arg Thr Asp
545                 550                 555                 560

Asn Pro Leu Glu Val Lys Gln Leu Thr Leu Asn Pro Asp Asp His Leu
                565                 570                 575

Gln Glu Met Arg Pro Ser Leu His Ser Pro Gly Ser Thr Arg His
            580                 585                 590

<210> SEQ ID NO 42
<211> LENGTH: 591
<212> TYPE: PRT
<213> ORGANISM: Physcomitrella patens

<400> SEQUENCE: 42

Met Gly Arg Glu Lys Arg Pro Ser Gly Ser Gly Thr Gly Leu Ser Asp
1               5                   10                  15

Glu Thr Leu Ala Cys Val Leu Lys Tyr Val Glu Ser Ala Glu Asp Arg
                20                  25                  30

Ala Ser Val Ser Leu Val Cys Lys Gln Trp Arg Leu Val Asp Gly Ala
            35                  40                  45

Thr Arg Lys Phe Val Thr Ile Ala Tyr Met Tyr Ser Thr Ser Pro Glu
        50                  55                  60

Met Leu Thr Arg Arg Phe Lys Arg Leu Glu Gly Leu Lys Leu Lys Gly
65                  70                  75                  80

Lys Pro Arg Ala Ala Glu Tyr Asp Leu Leu Val Pro Asp Trp Gly Gly
                85                  90                  95

Tyr Ala Glu Pro Trp Ile Arg Asp Leu Gly Arg Ala Tyr Thr Ser Leu
            100                 105                 110

Gln Thr Leu Gln Leu Arg Arg Cys Gln Val Ser Asn Ala Asp Leu Thr
        115                 120                 125

Leu Ile Ala Ser Ser Pro Cys Gln Ala Ser Leu Gln Val Leu Tyr Leu
    130                 135                 140

His Lys Cys Ala Gly Phe Ser Thr Ala Gly Leu Leu Pro Val Ala Lys
```

-continued

```
            145                 150                 155                 160
        Ser Cys Arg Ser Leu Lys Ser Leu Ser Val Glu Asp Ser Asp Val Thr
                        165                 170                 175

Asp Glu Gly Gly Glu Trp Leu Phe Glu Leu Ala Arg Asn Asn Ser Val
                        180                 185                 190

Leu Glu Val Leu Asn Phe Ala Val Leu Gly Leu Glu Asp Val Asp Ala
                        195                 200                 205

Ala Asp Leu Val Leu Leu Val Glu Arg Cys Lys Ser Leu Val Ser Leu
        210                 215                 220

Lys Val Gly Glu Val Glu Met Val Asp Met Ile Ser Ala Ile Ser Arg
        225                 230                 235                 240

Ala Ser Ser Leu Thr Glu Phe Gly Thr Gly Ser Cys Asn Phe Phe Gly
                        245                 250                 255

Asp Glu Asp Ser Arg Thr His Val Ser Ile Ser Leu Pro Ser Ser Leu
                        260                 265                 270

Thr Gly Leu Ser Gly Leu Trp Ala Met Ser Asp Pro Gly Leu Ala Met
                        275                 280                 285

Val Leu Pro Ile Ala Pro Asn Leu Arg Lys Leu Asp Leu Lys Phe Thr
        290                 295                 300

Leu Leu Ser Arg Lys Ala Tyr Cys Gln Leu Phe Ser Gln Cys His Ala
        305                 310                 315                 320

Leu Glu Glu Leu Gln Val Arg Asn Ala Val Gly Asp Glu Gly Met Glu
                        325                 330                 335

Val Ile Gly Lys Thr Cys Lys Ser Leu Arg Arg Leu Arg Val Glu His
                        340                 345                 350

Asp Asn Ala Gly Ala Ile Thr Gln Arg Gly Val Val Ala Val Ala Gln
                        355                 360                 365

Gly Cys Ala Arg Met Gln Gln Leu Val Val Tyr Val Ser Asp Ile Thr
                        370                 375                 380

Asn Ala Ala Leu Ala Met Leu Gly Gln Cys Cys Ala Gln Leu Thr Asp
        385                 390                 395                 400

Phe Arg Leu Val Leu Glu Thr Ala Ala Arg Arg Val Val Asp Leu Pro
                        405                 410                 415

Leu Asp Asp Gly Ile Lys Leu Leu Lys Gly Cys Arg Lys Ile Ser
                        420                 425                 430

Lys Leu Ala Val Tyr Leu Arg His Gly Gly Leu Thr Asp Arg Gly Met
                        435                 440                 445

Gly Tyr Ile Gly Glu Phe Gly Thr Asn Leu Lys Trp Leu Leu Leu Gly
                        450                 455                 460

Cys Thr Gly Glu Ser Asp Ile Gly Leu Ala Ser Leu Ala Tyr Lys Ala
        465                 470                 475                 480

Gln Arg Ile Glu Arg Leu Glu Cys Arg Asp Cys Pro Phe Gly Glu Ala
                        485                 490                 495

Gly Leu Ala Ala Ala Val Val Ala Met Ser Ser Leu Lys Phe Ile Trp
                        500                 505                 510

Ile Gln Gly Tyr Arg Ala Pro Trp Ala Gly Glu His Leu Leu Ala Leu
                        515                 520                 525

Ser Arg Pro Tyr Leu Asn Ile Glu Val Ile Ser Ser Thr Asp Thr Gln
                        530                 535                 540

Pro Gly Gln Leu Ile Ala His Tyr Thr Thr Val Gly Pro Arg Thr Asp
        545                 550                 555                 560

Asn Pro Leu Glu Val Lys Gln Leu Thr Leu Asn Pro Asp Asp His Leu
                        565                 570                 575
```

Gln Glu Met Arg Pro Ser Leu His Ser Pro Gly Ser Thr Arg His
         580                 585                 590

<210> SEQ ID NO 43
<211> LENGTH: 2194
<212> TYPE: DNA
<213> ORGANISM: Physcomitrella patens

<400> SEQUENCE: 43

| | | | | | |
|---|---|---|---|---|---|
| atggggcgag | agaagagacc | atcaggatct | gggacgggct | tatccgacga | gaccctggcg | 60 |
| tgtgtgttga | agtatgtgga | gagtgcggag | gatagagcgt | cagtctccct | ggtgtgcaag | 120 |
| caatggcgac | tcgtggatgg | tgccacgagg | aagtttgtaa | cgatagctta | catgtactcc | 180 |
| actagccctg | agatgctcac | ccgacgcttc | aagcgcctgg | aagggcttaa | gctgaagggg | 240 |
| aagcctcgcg | ctgcggaata | tgatttacta | gtacccgatt | ggggtggata | tgctgagccc | 300 |
| tggattcggg | atctggggcg | cgcatataca | agtctgcaaa | cgctgcaact | gcgtcggtgc | 360 |
| caggtttcta | atgcggattt | gaccttaatt | gcgtcttctc | cctgtcaagc | gtctctgcaa | 420 |
| gttttgtatt | tacataaatg | cgctgggttt | ccaccgctg | gcctcctccc | tgttgctaag | 480 |
| tcctgccggt | ctctgaagtc | tttgagcgta | gaggacagcg | atgtaactga | tgaaggtgga | 540 |
| gagtggctat | tcgagctggc | ccgcaacaat | tccgtgttgg | aggtcctgaa | ttttgctgta | 600 |
| cttggtcttg | aggatgttga | tgcagctgac | ttggtgttgc | tagtggagag | gtgcaaatca | 660 |
| ctggtttctc | taaaagttgg | tgaagttgaa | atggtggaca | tgataagtgc | cattagcaga | 720 |
| gcgtcttctt | tgactgaatt | cggcacaggc | tcttgcaatt | tcttcgggga | cgaggacagc | 780 |
| aggacacatg | tatctatatc | tttaccttca | agcttgacgg | gtttgtcagg | tttgtgggcc | 840 |
| atgtccgacc | ctggattggc | tatggttctt | cccatagcac | caaacttgag | aaaactggac | 900 |
| ctgaagttca | cgcttttgag | cagaaaagct | tactgccaac | ttttcagtca | gtgccatgct | 960 |
| ttggaagagc | ttcaggttcg | caacgcagtt | ggggacgagg | gcatggaagt | tatcggcaag | 1020 |
| acatgcaaga | gcctcaggcg | attacgcgtg | gagcacgata | atgcaggagc | tatcactcaa | 1080 |
| cgaggcgttg | ttgctgttgc | ccaagggtgt | gcacgaatgc | agcagttgat | cgtgtacgtg | 1140 |
| tccgacatca | ccaacgccgc | gctggcgatg | ctgggacaat | gctgcgcaca | gctgacggac | 1200 |
| ttccgtctcg | tgctggagac | cgctgcaaga | gcgtcgtcg | acctgccgtt | ggacgatgga | 1260 |
| atcaagctcc | tgctcaaagg | ctgccgaaaa | atatccaagc | ttgctgtata | tcttcggcac | 1320 |
| gggggcttga | cagacagagg | aatgggttac | atcggggagt | ttggcacgaa | tttgaaatgg | 1380 |
| ttattgttgg | gatgcacagg | cgaatccgac | attggattgg | ccagtttggc | atacaaagcg | 1440 |
| cagcgcattg | aaaggttaga | gtgtcgggat | tgtccgtttg | ggaggcagg | tcttgcggca | 1500 |
| gcagtagtgg | cgatgagctc | gctcaagttt | atatggattc | aaggctatag | ggctccatgg | 1560 |
| gcaggagagc | atctactggc | cttatcacga | ccgtatctga | acatagaagt | tatctcctca | 1620 |
| acagacaccc | aaccaggcca | gctcatagcc | cactatacca | ctgtcgggcc | tcgcactgat | 1680 |
| aacccttttgg | aggtaaagca | gctgacgtta | aacccggacg | atcacctgca | ggaaatgcga | 1740 |
| ccgagtttac | actcacctgg | atctacgcgg | cactaagcag | agattaggcc | aagcgtcatt | 1800 |
| gctttcaggc | cctctattga | tttctgtctt | ctagccgcgg | atggtcgcag | tgcgccgttg | 1860 |
| gataccctac | cagaagcgtg | gctattaata | ctaatgagtg | tttgccagaa | cggcccttga | 1920 |
| ttgtggtctg | tggtggacgt | ttactgacag | caggaggtgt | acgagagatt | gccctcatt | 1980 |
| gtaaaatctg | tattaggaca | gctaggctac | caatgctgct | gtttcaagtc | cttgaaacag | 2040 |

```
tgaagatgtt gcatgcgtac gaggactgcc tactactgta taagtgtagt gcaatgtgaa    2100
agtgtaatgt agtgtattga aattgggcaa ggagttatgg gaaaggctat gtagctgaca    2160
cagttgaatg tacctattgt gcattttgga gaaa                                2194
```

```
<210> SEQ ID NO 44
<211> LENGTH: 597
<212> TYPE: PRT
<213> ORGANISM: Oryza sativa

<400> SEQUENCE: 44

Met Gly Gly Glu Ala Pro Glu Ala Arg Arg Leu Asp Arg Ala Met Ser
1               5                   10                  15

Phe Gly Gly Ala Gly Ser Ile Pro Glu Glu Ala Leu His Leu Val Leu
            20                  25                  30

Gly Tyr Val Asp Asp Pro Arg Asp Arg Glu Ala Val Ser Leu Val Cys
        35                  40                  45

Arg Arg Trp His Arg Ile Asp Ala Leu Thr Arg Lys His Val Thr Val
    50                  55                  60

Pro Phe Cys Tyr Ala Ala Ser Pro Ala His Leu Leu Ala Arg Phe Pro
65                  70                  75                  80

Arg Leu Glu Ser Leu Ala Val Lys Gly Lys Pro Arg Ala Ala Met Tyr
                85                  90                  95

Gly Leu Ile Pro Glu Asp Trp Gly Ala Tyr Ala Arg Pro Trp Val Ala
            100                 105                 110

Glu Leu Ala Ala Pro Leu Glu Cys Leu Lys Ala Leu His Leu Arg Arg
        115                 120                 125

Met Val Val Thr Asp Asp Leu Ala Ala Leu Val Arg Ala Arg Gly
    130                 135                 140

His Met Leu Gln Glu Leu Lys Leu Asp Lys Cys Ser Gly Phe Ser Thr
145                 150                 155                 160

Asp Ala Leu Arg Leu Val Ala Arg Ser Cys Arg Ser Leu Arg Thr Leu
                165                 170                 175

Phe Leu Glu Glu Cys Ser Ile Ala Asp Asn Gly Thr Glu Trp Leu His
            180                 185                 190

Asp Leu Ala Val Asn Asn Pro Val Leu Glu Thr Leu Asn Phe His Met
        195                 200                 205

Thr Glu Leu Thr Val Val Pro Ala Asp Leu Glu Leu Leu Ala Lys Lys
    210                 215                 220

Cys Lys Ser Leu Ile Ser Leu Lys Ile Ser Asp Cys Asp Phe Ser Asp
225                 230                 235                 240

Leu Ile Gly Phe Phe Arg Met Ala Ala Ser Leu Gln Glu Phe Ala Gly
                245                 250                 255

Gly Ala Phe Ile Glu Gln Gly Glu Leu Thr Lys Tyr Gly Asn Val Lys
            260                 265                 270

Phe Pro Ser Arg Leu Cys Ser Leu Gly Leu Thr Tyr Met Gly Thr Asn
        275                 280                 285

Glu Met Pro Ile Ile Phe Pro Phe Ser Ala Leu Leu Lys Lys Leu Asp
    290                 295                 300

Leu Gln Tyr Thr Phe Leu Thr Thr Glu Asp His Cys Gln Leu Ile Ala
305                 310                 315                 320

Lys Cys Pro Asn Leu Leu Val Leu Ala Val Arg Asn Val Ile Gly Asp
                325                 330                 335

Arg Gly Leu Gly Val Val Ala Asp Thr Cys Lys Lys Leu Gln Arg Leu
```

```
                   340                 345                 350
Arg Val Glu Arg Gly Asp Asp Pro Gly Leu Gln Glu Glu Gln Gly
            355                 360                 365
Gly Val Ser Gln Val Gly Leu Thr Thr Val Ala Val Gly Cys Arg Glu
        370                 375                 380
Leu Glu Tyr Ile Ala Ala Tyr Val Ser Asp Ile Thr Asn Gly Ala Leu
385                 390                 395                 400
Glu Ser Ile Gly Thr Phe Cys Lys Asn Leu Cys Asp Phe Arg Leu Val
                405                 410                 415
Leu Leu Asp Arg Glu Glu Arg Ile Thr Asp Leu Pro Leu Asp Asn Gly
            420                 425                 430
Val Arg Ala Leu Leu Arg Gly Cys Thr Lys Leu Arg Arg Phe Ala Leu
        435                 440                 445
Tyr Leu Arg Pro Gly Gly Leu Ser Asp Thr Gly Leu Gly Tyr Ile Gly
            450                 455                 460
Gln Tyr Ser Gly Ile Ile Gln Tyr Met Leu Leu Gly Asn Val Gly Glu
465                 470                 475                 480
Thr Asp Asp Gly Leu Ile Arg Phe Ala Leu Gly Cys Glu Asn Leu Arg
                485                 490                 495
Lys Leu Glu Leu Arg Ser Cys Cys Phe Ser Glu Gln Ala Leu Ala Arg
            500                 505                 510
Ala Ile Arg Ser Met Pro Ser Leu Arg Tyr Val Trp Val Gln Gly Tyr
        515                 520                 525
Lys Ala Ser Lys Thr Gly His Asp Leu Met Leu Met Ala Arg Pro Phe
            530                 535                 540
Trp Asn Ile Glu Phe Thr Pro Pro Ser Ser Glu Asn Ala Asn Arg Met
545                 550                 555                 560
Arg Glu Asp Gly Glu Pro Cys Val Asp Ser Gln Ala Gln Ile Leu Ala
                565                 570                 575
Tyr Tyr Ser Leu Ala Gly Lys Arg Ser Asp Cys Pro Arg Ser Val Val
            580                 585                 590
Pro Leu Tyr Pro Ala
        595

<210> SEQ ID NO 45
<211> LENGTH: 597
<212> TYPE: PRT
<213> ORGANISM: Oryza sativa

<400> SEQUENCE: 45

Met Gly Gly Glu Ala Pro Glu Ala Arg Arg Leu Asp Arg Ala Met Ser
1               5                   10                  15
Phe Gly Gly Ala Gly Ser Ile Pro Glu Glu Ala Leu His Leu Val Leu
            20                  25                  30
Gly Tyr Val Asp Asp Pro Arg Asp Arg Glu Ala Val Ser Leu Val Cys
        35                  40                  45
Arg Arg Trp His Arg Ile Asp Ala Leu Thr Arg Lys His Val Thr Val
    50                  55                  60
Pro Phe Cys Tyr Ala Ala Ser Pro Ala His Leu Leu Ala Arg Phe Pro
65                  70                  75                  80
Arg Leu Glu Ser Leu Ala Val Lys Gly Lys Pro Arg Ala Ala Met Tyr
                85                  90                  95
Gly Leu Ile Pro Glu Asp Trp Gly Ala Tyr Ala Arg Pro Trp Val Ala
            100                 105                 110
```

```
Glu Leu Ala Ala Pro Leu Glu Cys Leu Lys Ala Leu His Leu Arg Arg
            115                 120                 125

Met Val Val Thr Asp Asp Leu Ala Ala Leu Val Arg Ala Arg Gly
130                 135                 140

His Met Leu Gln Glu Leu Lys Leu Asp Lys Cys Ser Gly Phe Ser Thr
145                 150                 155                 160

Asp Ala Leu Arg Leu Val Ala Arg Ser Cys Arg Ser Leu Arg Thr Leu
                165                 170                 175

Phe Leu Glu Glu Cys Ser Ile Ala Asp Asn Gly Thr Glu Trp Leu His
                180                 185                 190

Asp Leu Ala Val Asn Asn Pro Val Leu Glu Thr Leu Asn Phe His Met
            195                 200                 205

Thr Glu Leu Thr Val Val Pro Ala Asp Leu Glu Leu Leu Ala Lys Lys
210                 215                 220

Cys Lys Ser Leu Ile Ser Leu Lys Ile Ser Asp Cys Asp Phe Ser Asp
225                 230                 235                 240

Leu Ile Gly Phe Phe Arg Met Ala Ala Ser Leu Gln Glu Phe Ala Gly
                245                 250                 255

Gly Ala Phe Ile Glu Gln Gly Glu Leu Thr Lys Tyr Gly Asn Val Lys
                260                 265                 270

Phe Pro Ser Arg Leu Cys Ser Leu Gly Leu Thr Tyr Met Gly Thr Asn
            275                 280                 285

Glu Met Pro Ile Ile Phe Pro Phe Ser Ala Leu Leu Lys Lys Leu Asp
290                 295                 300

Leu Gln Tyr Thr Phe Leu Thr Thr Glu Asp His Cys Gln Leu Ile Ala
305                 310                 315                 320

Lys Cys Pro Asn Leu Leu Val Leu Ala Val Arg Asn Val Ile Gly Asp
                325                 330                 335

Arg Gly Leu Gly Val Val Ala Asp Thr Cys Lys Lys Leu Gln Arg Leu
                340                 345                 350

Arg Val Glu Arg Gly Asp Asp Pro Gly Leu Gln Glu Gln Gly
            355                 360                 365

Gly Val Ser Gln Val Gly Leu Thr Thr Val Ala Val Gly Cys Arg Glu
370                 375                 380

Leu Glu Tyr Ile Val Ala Tyr Val Ser Asp Ile Thr Asn Gly Ala Leu
385                 390                 395                 400

Glu Ser Ile Gly Thr Phe Cys Lys Asn Leu Cys Asp Phe Arg Leu Val
                405                 410                 415

Leu Leu Asp Arg Glu Glu Arg Ile Thr Asp Leu Pro Leu Asp Asn Gly
            420                 425                 430

Val Arg Ala Leu Leu Arg Gly Cys Thr Lys Leu Arg Arg Phe Ala Leu
435                 440                 445

Tyr Leu Arg Pro Gly Gly Leu Ser Asp Thr Gly Leu Gly Tyr Ile Gly
450                 455                 460

Gln Tyr Ser Gly Ile Ile Gln Tyr Met Leu Leu Gly Asn Val Gly Glu
465                 470                 475                 480

Thr Asp Asp Gly Leu Ile Arg Phe Ala Leu Gly Cys Glu Asn Leu Arg
                485                 490                 495

Lys Leu Glu Leu Arg Ser Cys Cys Phe Ser Glu Gln Ala Leu Ala Arg
            500                 505                 510

Ala Ile Arg Ser Met Pro Ser Leu Arg Tyr Val Trp Val Gln Gly Tyr
            515                 520                 525

Lys Ala Ser Lys Thr Gly His Asp Leu Met Leu Met Ala Arg Pro Phe
```

```
                530                 535                 540
Trp Asn Ile Glu Phe Thr Pro Pro Ser Ser Glu Asn Ala Asn Arg Met
545                 550                 555                 560

Arg Glu Asp Gly Glu Pro Cys Val Asp Ser Gln Ala Gln Ile Leu Ala
                565                 570                 575

Tyr Tyr Ser Leu Ala Gly Lys Arg Ser Asp Cys Pro Arg Ser Val Val
                580                 585                 590

Pro Leu Tyr Pro Ala
        595

<210> SEQ ID NO 46
<211> LENGTH: 2495
<212> TYPE: DNA
<213> ORGANISM: Oryza sativa

<400> SEQUENCE: 46
ctgcgattgc catcccggcc acctccaaag ctttagccg gcgggggaca aagggcggcc        60 cacccctgc gtgcgccaag caatttggcc gcctgacccc gtgccgacgt ggcccggcat       120 ccctagctg atcccgcag aagtaaacgc ccgcctcctc ccccaatccc catctcctct        180
ccactcttct tctccctcca ataattctct ccctctcct cctcttcacc accaccaca        240 ccaccagcag cagcagagag caccatctcc atccaataat cccatgctt gcgcaccact       300 cccggccaca tcccgcgcga ggaggaggag gaggaggag gtgtgcttga tccgcgctcc       360
cgcctggttg gtggtggtgg ggtgagggggg gagggatggg aggggaggca ccggaggcgc     420
ggcggttgga ccgcgcgatg agcttcggcg gcgcgggcag catcccggag gaggcgctgc      480
acctggtgct ggggtacgtg gacgacccgc gggacaggga ggcggtgtcg ctcgtgtgcc      540
gccgctggca ccgcatcgac gcgctcacgc ggaagcacgt caccgtgccc ttctgctacg     600
ccgcgtcgcc cgcgcacctg ctcgcgcggt tccgcggct ggagtcgctc gcggtcaagg       660
ggaagccgcg cgccgccatg tacgggctca tcccggagga ctggggcgcc tacgcgcgcc     720
cctgggtcgc cgagctcgcc gcgccgctcg agtgcctcaa ggcgctccac ctgcgccgca      780
tggtcgtcac cgacgacgac ctcgccgcgc tcgtccgcgc ccgcggccac atgctgcagg     840
agctcaagct cgacaagtgc tccggcttct ccaccgacgc tctccgcctc gtcgccgct      900 cctgcagatc actgagaaca ttatttctgg aggaatgctc aattgctgat aatggtactg     960
aatggctcca cgaccttgct gtcaacaatc ctgttctgga cattgaac ttccacatga      1020 ccgaactcac agtggtgcca gctgacctgg agcttctcgc aaagaagtgc aagtcactaa    1080
tttcattgaa gatcagtgac tgtgactttt cagatttaat tggatttttc cggatggctg    1140
catcattgca agagtttgcg ggaggggcat tcattgagca aggggagctc actaagtatg    1200
gaaatgttaa attcccttca agactgtgct ccttaggact tacgtacatg gggacaaacg    1260
agatgcccat tatcttccct ttctctgcat tactcaagaa gctggacttg cagtacactt     1320
ttctcaccac tgaagatcac tgccaactca ttgcaaaatg tcccaactta ctagttcttg    1380
cggtgaggaa tgtgattgga gatagaggat taggggttgt tgcagacaca tgcaagaagc    1440
tacaaagact cagagttgag cgaggagatg atgatccagg tttgcaagaa gaacaaggag    1500
gagtctctca agtcgggttg acaactgtag ccgtaggatg ccgtgaactg gaatacatag    1560
ctgcctatgt gtctgatatc acaaatgggg ccctggagtc tattgggact ttctgcaaaa   1620
atctttgcga cttccgtctt gtcctactcg atagagaaga gaggataaca gatttgccct    1680
tagacaatgg tgtccgtgca ctgctgaggg gctgcacgaa acttcggagg tttgctctat    1740
```

-continued

```
acttgagacc aggggggactt tcagatacag gccttggcta tattggacag tacagtggaa    1800
ttatccaata catgcttctg ggtaatgttg gggaaacaga tgatggtctg atccggtttg    1860
cattggggtg tgagaacctg cggaagcttg agctaaggag ttgttgcttc agtgagcaag    1920
ctttagcccg cgctatacgg agtatgcctt ccctgagata cgtgtgggta cagggctaca    1980
aggcttctaa gactggtcac gatctcatgc tcatggccag gcccttctgg aacatagagt    2040
ttacacctcc cagttctgag aatgcaaatc gaatgagaga agatggtgaa ccttgtgtag    2100
atagtcaagc tcagatactt gcatactact cccttgccgg gaagaggtcg gactgcccac    2160
gatctgtggt tcctttgtat cctgcgtgac tgtaaatacc gatatggtat ctctctgctt    2220
cgttcttgcc tcttgccttt tttgggtgat atgttgatat gtggttattg tatgggtcta    2280
gaactctaga tggctagctg ctatgtaccg taataagcta ctggtagctg agatgtactg    2340
gaataagcac ttctatttcc cactctacta ctatctaatc ctaggaagat gtatactaag    2400
gaacactctg tgccactact ccttgcttgt tcatgctccc gtcctggttt gttaccattg    2460
gaggtataag aatacctggt tttggcagtc cttaa                              2495
```

<210> SEQ ID NO 47
<211> LENGTH: 599
<212> TYPE: PRT
<213> ORGANISM: Sorghum bicolor

<400> SEQUENCE: 47

```
Met Gly Gly Glu Ala Pro Glu Pro Arg Arg Leu Thr Arg Ala Leu Ser
1               5                   10                  15

Ile Gly Gly Gly Asp Gly Gly Trp Val Pro Glu Met Leu His Leu
            20                  25                  30

Val Met Gly Phe Val Glu Asp Pro Arg Asp Arg Glu Ala Ala Ser Leu
        35                  40                  45

Val Cys Arg Arg Trp His Arg Val Asp Ala Leu Ser Arg Lys His Val
    50                  55                  60

Thr Val Pro Phe Cys Tyr Ala Val Ser Pro Ala Arg Leu Leu Ala Arg
65                  70                  75                  80

Phe Pro Arg Leu Glu Ser Leu Ala Ile Lys Gly Lys Pro Arg Ala Ala
                85                  90                  95

Met Tyr Gly Leu Ile Pro Asp Asp Trp Gly Ala Tyr Ala Arg Pro Trp
            100                 105                 110

Val Ala Glu Leu Ala Ala Pro Leu Glu Cys Leu Lys Ala Leu His Leu
        115                 120                 125

Arg Arg Met Val Val Thr Asp Asp Leu Ala Glu Leu Val Arg Ala
    130                 135                 140

Arg Gly His Met Leu Gln Glu Leu Lys Leu Asp Lys Cys Thr Gly Phe
145                 150                 155                 160

Ser Thr Asp Gly Leu Arg Leu Val Ala Arg Ser Cys Arg Ser Leu Arg
                165                 170                 175

Thr Leu Phe Leu Glu Glu Cys Gln Ile Asn Asp Lys Gly Ser Glu Trp
            180                 185                 190

Ile His Asp Leu Ala Asp Gly Cys Pro Val Leu Thr Thr Leu Asn Phe
        195                 200                 205

His Met Thr Glu Leu Gln Val Met Pro Ala Asp Leu Glu Phe Leu Ala
    210                 215                 220

Arg Ser Cys Lys Ser Leu Ile Ser Leu Lys Ile Ser Asp Cys Asp Val
225                 230                 235                 240
```

```
Ser Asp Leu Ile Gly Phe Phe Gln Phe Ala Thr Ala Leu Glu Glu Phe
            245                 250                 255

Ala Gly Gly Thr Phe Asn Glu Gln Gly Glu Leu Thr Met Tyr Gly Asn
        260                 265                 270

Val Arg Phe Pro Ser Arg Leu Cys Ser Leu Gly Leu Thr Phe Met Gly
    275                 280                 285

Thr Asn Glu Met Pro Ile Ile Phe Pro Phe Ser Ala Ile Leu Lys Lys
290                 295                 300

Leu Asp Leu Gln Tyr Thr Val Leu Thr Thr Glu Asp His Cys Gln Leu
305                 310                 315                 320

Ile Ala Lys Cys Pro Asn Leu Val Leu Ala Val Arg Asn Val Ile
                325                 330                 335

Gly Asp Arg Gly Leu Gly Val Val Ala Asp Thr Cys Lys Lys Leu Gln
                340                 345                 350

Arg Leu Arg Ile Glu Arg Gly Asp Asp Glu Gly Gly Val Gln Glu Glu
            355                 360                 365

Gln Gly Gly Val Ser Gln Val Gly Leu Thr Ala Ile Ala Val Gly Cys
            370                 375                 380

Arg Glu Leu Glu Tyr Ile Ala Ala Tyr Val Ser Asp Ile Thr Asn Gly
385                 390                 395                 400

Ala Leu Glu Ser Ile Gly Thr Phe Cys Lys Lys Leu Tyr Asp Phe Arg
                405                 410                 415

Leu Val Leu Leu Asp Arg Glu Glu Arg Ile Thr Glu Leu Pro Leu Asp
                420                 425                 430

Asn Gly Val Arg Ala Leu Leu Arg Gly Cys Thr Lys Leu Arg Arg Phe
                435                 440                 445

Ala Leu Tyr Leu Arg Pro Gly Gly Leu Ser Asp Ala Gly Leu Gly Tyr
            450                 455                 460

Ile Gly Gln Cys Ser Gly Asn Ile Gln Tyr Met Leu Leu Gly Asn Val
465                 470                 475                 480

Gly Glu Thr Asp Asp Gly Leu Phe Ser Phe Ala Leu Gly Cys Val Asn
                485                 490                 495

Leu Arg Lys Leu Glu Leu Arg Ser Cys Cys Phe Ser Glu Arg Ala Leu
                500                 505                 510

Ala Leu Ala Ile Leu Arg Met Pro Ser Leu Arg Tyr Val Trp Val Gln
            515                 520                 525

Gly Tyr Lys Ala Ser Gln Thr Gly Arg Asp Leu Met Leu Met Ala Arg
        530                 535                 540

Pro Phe Trp Asn Ile Glu Phe Thr Pro Pro Ser Ser Glu Asn Ala Gly
545                 550                 555                 560

Arg Leu Met Glu Asp Gly Glu Pro Cys Val Asp Ser His Ala Gln Ile
                565                 570                 575

Leu Ala Tyr His Ser Leu Ala Gly Lys Arg Leu Asp Cys Pro Gln Ser
                580                 585                 590

Val Val Pro Leu Tyr Pro Ala
        595
```

<210> SEQ ID NO 48
<211> LENGTH: 599
<212> TYPE: PRT
<213> ORGANISM: Sorghum bicolor

<400> SEQUENCE: 48

Met Gly Gly Glu Ala Pro Glu Pro Arg Arg Leu Thr Arg Ala Leu Ser

```
  1               5                  10                 15
Ile Gly Gly Gly Asp Gly Gly Trp Val Pro Glu Glu Met Leu His Leu
                  20                 25                 30

Val Met Gly Phe Val Glu Asp Pro Arg Asp Arg Glu Ala Ala Ser Leu
            35                 40                 45

Val Cys Arg Arg Trp His Arg Val Asp Ala Leu Ser Arg Lys His Val
 50                      55                 60

Thr Val Pro Phe Cys Tyr Ala Val Ser Pro Ala Arg Leu Leu Ala Arg
 65                 70                 75                 80

Phe Pro Arg Leu Glu Ser Leu Ala Ile Lys Gly Lys Pro Arg Ala Ala
                 85                 90                 95

Met Tyr Gly Leu Ile Pro Asp Asp Trp Gly Ala Tyr Ala Arg Pro Trp
                 100                105                110

Val Ala Glu Leu Ala Ala Pro Leu Glu Cys Leu Lys Ala Leu His Leu
                 115                120                125

Arg Arg Met Val Val Thr Asp Asp Leu Ala Glu Leu Val Arg Ala
 130                135                140

Arg Gly His Met Leu Gln Glu Leu Lys Leu Asp Lys Cys Thr Gly Phe
145                 150                155                160

Ser Thr Asp Gly Leu Arg Leu Val Ala Arg Ser Cys Arg Ser Leu Arg
                165                170                175

Thr Leu Phe Leu Glu Glu Cys Gln Ile Asn Asp Lys Gly Ser Glu Trp
                180                185                190

Ile His Asp Leu Ala Asp Gly Cys Pro Val Leu Thr Thr Leu Asn Phe
                195                200                205

His Met Thr Glu Leu Gln Val Met Pro Ala Asp Leu Glu Phe Leu Ala
210                 215                220

Arg Ser Cys Lys Ser Leu Ile Ser Leu Lys Ile Ser Asp Cys Asp Val
225                 230                235                240

Ser Asp Leu Ile Gly Phe Phe Gln Phe Ala Thr Ala Leu Glu Glu Phe
                245                250                255

Ala Gly Gly Thr Phe Asn Glu Gln Gly Glu Leu Thr Met Tyr Gly Asn
                260                265                270

Val Arg Phe Pro Ser Arg Leu Cys Ser Leu Gly Leu Thr Phe Met Gly
                275                280                285

Thr Asn Glu Met Pro Ile Ile Phe Pro Phe Ser Ala Ile Leu Lys Lys
                290                295                300

Leu Asp Leu Gln Tyr Thr Val Leu Thr Thr Glu Asp His Cys Gln Leu
305                 310                315                320

Ile Ala Lys Cys Pro Asn Leu Leu Val Leu Ala Val Arg Asn Val Ile
                325                330                335

Gly Asp Arg Gly Leu Gly Val Val Ala Asp Thr Cys Lys Lys Leu Gln
                340                345                350

Arg Leu Arg Ile Glu Arg Gly Asp Asp Glu Gly Gly Val Gln Glu Glu
                355                360                365

Gln Gly Gly Val Ser Gln Val Gly Leu Thr Ala Ile Ala Val Gly Cys
                370                375                380

Arg Glu Leu Glu Tyr Ile Val Ala Tyr Val Ser Asp Ile Thr Asn Gly
385                 390                395                400

Ala Leu Glu Ser Ile Gly Thr Phe Cys Lys Lys Leu Tyr Asp Phe Arg
                405                410                415

Leu Val Leu Leu Asp Arg Glu Glu Arg Ile Thr Glu Leu Pro Leu Asp
                420                425                430
```

```
Asn Gly Val Arg Ala Leu Leu Arg Gly Cys Thr Lys Leu Arg Arg Phe
            435                 440                 445

Ala Leu Tyr Leu Arg Pro Gly Gly Leu Ser Asp Ala Gly Leu Gly Tyr
450                 455                 460

Ile Gly Gln Cys Ser Gly Asn Ile Gln Tyr Met Leu Leu Gly Asn Val
465                 470                 475                 480

Gly Glu Thr Asp Asp Gly Leu Phe Ser Phe Ala Leu Gly Cys Val Asn
                485                 490                 495

Leu Arg Lys Leu Glu Leu Arg Ser Cys Cys Phe Ser Glu Arg Ala Leu
            500                 505                 510

Ala Leu Ala Ile Leu Arg Met Pro Ser Leu Arg Tyr Val Trp Val Gln
        515                 520                 525

Gly Tyr Lys Ala Ser Gln Thr Gly Arg Asp Leu Met Leu Met Ala Arg
    530                 535                 540

Pro Phe Trp Asn Ile Glu Phe Thr Pro Pro Ser Ser Glu Asn Ala Gly
545                 550                 555                 560

Arg Leu Met Glu Asp Gly Glu Pro Cys Val Asp Ser His Ala Gln Ile
                565                 570                 575

Leu Ala Tyr His Ser Leu Ala Gly Lys Arg Leu Asp Cys Pro Gln Ser
            580                 585                 590

Val Val Pro Leu Tyr Pro Ala
            595
```

<210> SEQ ID NO 49
<211> LENGTH: 2401
<212> TYPE: DNA
<213> ORGANISM: Sorghum bicolor

<400> SEQUENCE: 49

```
ctcgtccgtc ctcctctcca ctctctcttc tccctccaat aattctctcc tctctctctg    60
cactctgctt gctccacctc caagcaccac cgaatcaggg ccagtgggag cagcagcagc   120
agcgagtggg agcagaggag ggcagagaat cccatgtctc cgcccctcgc tagagcagat   180
cctcggcgag ccgggcgtgg agctgcttcg gtagaaaagc gagccaactg agcctgcgag   240
cgcctgatcc gcccgcggcc cgatcgggat cgatgggcgg tgaggcgccg gagcccggc    300
ggctgacccg cgcgctgagc atcggcggcg gcgacggcgg ctgggtcccc gaggagatgc   360
tgcacctggt gatggggttc gtcgaggacc cgcgcgaccg ggaggccgcg tcgctggtgt   420
gccgccggtg gcaccgcgtc gacgcgctgt cgcggaagca cgtcacggtg cccttctgct   480
acgccgtgtc cccggcgcgc ctgctcgcgc ggttcccgcg gctcgagtcg ctggccatca   540
aggggaagcc ccgcgcggcc atgtacggcc tcataccgga cgactggggc gcctacgccc   600
gcccctgggt cgccgagctc gccgcgccgc tcgagtgcct caaggcgctc cacctccgac   660
gcatggtcgt cacggacgac gacctcgccg agtcgtccg tgccagggga cacatgctgc    720
aggagctcaa gctcgacaag tgcaccggct tctccacgga tggactccgc ctcgttgcgc    780
gctcctgcag atcactgaga actttgtttc tggaagaatg tcaaattaat gataaaggca   840
gtgaatggat ccacgatctt gcagacggtt gtcctgttct gacaacattg aatttccaca   900
tgactgagct tcaagtgatg ccagctgacc tagagtttct tgcaaggagc tgcaagtcac   960
tgatttcctt gaagattagc gactgtgatg tttcagattt gatagggttc ttccaatttg  1020
ccacagcact ggaagaattt gctggaggga cattcaatga gcaggggaa ctcaccatgt   1080
atgggaatgt cagatttcca tcaagactat gctccttggg acttactttc atgggaacaa  1140
```

```
atgaaatgcc tattatattt ccttttctg caatactgaa gaagctggat ttgcagtaca    1200
ctgtcctcac cactgaagac cattgccagc ttattgcaaa atgtccgaac ttactagttc    1260
tcgcggtgag gaatgtgatt ggagatagag gattaggagt tgttgcagat acatgcaaga    1320
agctccaaag gctcagaatt gagcgaggag acgatgaagg aggtgtgcaa gaagagcagg    1380
gaggggtctc tcaagtgggc ttgacggcta tagccgtcgg ttgccgtgaa ctggaataca    1440
tagctgccta tgtgtctgat ataaccaatg gggccctgga atctatcggg acattctgca    1500
aaaaactcta tgacttccgg cttgttctgc ttgatagaga agagaggata acagaattgc    1560
cactggacaa tggtgtccga gctttgttga ggggctgcac caaacttcgg aggttttgctc    1620 tgtacttgag accaggaggg ctctcagatg caggtctcgg ctacattgga cagtgcagtg    1680
gaaacatcca atacatgctt ctcggtaatg ttggggaaac tgatgatgga ttgttcagtt    1740
tcgcattggg atgcgtaaac ctgcggaagc ttgaactcag gagttgttgc ttcagcgagc    1800
gagctctggc cctcgccata ctacgcatgc cttccctgag gtacgtatgg gttcagggct    1860
acaaagcgtc tcaaaccggc cgagacctca tgctcatggc gaggcccttc tggaacatag    1920
agtttacacc tcccagttcc gagaacgcag gtcggttgat ggaagatggg gaaccttgtg    1980
tagatagtca tgctcagata ctcgcatacc actccctcgc cggtaagagg ttggactgcc    2040
cacaatccgt ggtccctttg tatcctgcct gagtgtaaat agactaagct ggtgttttc    2100 tccctcatcc ctgcttcctt agcctcctgg tcaacaagaa cgatgttgat gacttgatat    2160
gtggttattg tatggatcta gatggctagc tgctacgtac tgtaataagc tactagtagc    2220
tgagatgtcc tggaataagc ccttgctatt ttcgcctgta ctgctatcta atcctaggaa    2280
gatgtatact actaagtaac ggtggaagat gtgagtcttg cttgctcgcc ctgatttgta    2340
ctattggagg tataagaata cctgggtttt tgccgcctac tttgagcatt gagatgtgtc    2400
t                                                                   2401

<210> SEQ ID NO 50
<211> LENGTH: 24
<212> TYPE: DNA
<213> ORGANISM: Artificial Sequence
<220> FEATURE:
<223> OTHER INFORMATION: A synthetic oligonucleotide primer

<400> SEQUENCE: 50
cgaataaatc acacagctta ttgg                                           24

<210> SEQ ID NO 51
<211> LENGTH: 24
<212> TYPE: DNA
<213> ORGANISM: Artificial Sequence
<220> FEATURE:
<223> OTHER INFORMATION: A synthetic oligonucleotide primer

<400> SEQUENCE: 51
gatatggttc tttgtacaac gacg                                           24

<210> SEQ ID NO 52
<211> LENGTH: 19
<212> TYPE: DNA
<213> ORGANISM: Artificial Sequence
<220> FEATURE:
<223> OTHER INFORMATION: A synthetic oligonucleotide primer

<400> SEQUENCE: 52
attttgccga tttcggaac                                                 19
```

<210> SEQ ID NO 53
<211> LENGTH: 21
<212> TYPE: DNA
<213> ORGANISM: Artificial Sequence
<220> FEATURE:
<223> OTHER INFORMATION: A synthetic oligonucleotide primer

<400> SEQUENCE: 53
ctgcagtgtg taacgatgct c                                     21

<210> SEQ ID NO 54
<211> LENGTH: 22
<212> TYPE: DNA
<213> ORGANISM: Artificial Sequence
<220> FEATURE:
<223> OTHER INFORMATION: A synthetic oligonucleotide primer

<400> SEQUENCE: 54
ggttacaaga caaggttcac tc                                    22

<210> SEQ ID NO 55
<211> LENGTH: 22
<212> TYPE: DNA
<213> ORGANISM: Artificial Sequence
<220> FEATURE:
<223> OTHER INFORMATION: A synthetic oligonucleotide primer

<400> SEQUENCE: 55
cattcaggac caaactcttc ag                                    22

<210> SEQ ID NO 56
<211> LENGTH: 21
<212> TYPE: DNA
<213> ORGANISM: Artificial Sequence
<220> FEATURE:
<223> OTHER INFORMATION: A synthetic oligonucleotide primer

<400> SEQUENCE: 56
atgaggttaa cgatgatgct g                                     21

<210> SEQ ID NO 57
<211> LENGTH: 20
<212> TYPE: DNA
<213> ORGANISM: Artificial Sequence
<220> FEATURE:
<223> OTHER INFORMATION: A synthetic oligonucleotide primer

<400> SEQUENCE: 57
cttagcctcc tggaaatctg                                       20

<210> SEQ ID NO 58
<211> LENGTH: 20
<212> TYPE: DNA
<213> ORGANISM: Artificial Sequence
<220> FEATURE:
<223> OTHER INFORMATION: A synthetic oligonucleotide primer

<400> SEQUENCE: 58
ggctaactac aactacgctg                                       20

<210> SEQ ID NO 59
<211> LENGTH: 21
<212> TYPE: DNA
<213> ORGANISM: Artificial Sequence
<220> FEATURE:
<223> OTHER INFORMATION: A synthetic oligonucleotide primer

```
<400> SEQUENCE: 59
tctcgttcac ataattccca c                                             21

<210> SEQ ID NO 60
<211> LENGTH: 25
<212> TYPE: DNA
<213> ORGANISM: Artificial Sequence
<220> FEATURE:
<223> OTHER INFORMATION: A synthetic oligonucleotide primer

<400> SEQUENCE: 60
acttactaac cagtccgaaa gacga                                         25

<210> SEQ ID NO 61
<211> LENGTH: 25
<212> TYPE: DNA
<213> ORGANISM: Artificial Sequence
<220> FEATURE:
<223> OTHER INFORMATION: A synthetic oligonucleotide primer

<400> SEQUENCE: 61
acaacaactc tgtcacatat accgt                                         25
```

STRUCTURALLY MODIFIED COI1

This application claims benefit of priority to the filing date of U.S. Provisional Application Ser. No. 62/413,850, filed Oct. 27, 2016, the contents of which are specifically incorporated herein by reference in their entity.

GOVERNMENT FUNDING

This invention was made with government support under AI060761 awarded by the National Institutes of Health, and under DE-FG02-91ER20021 awarded by the U.S. Department of Energy. The government has certain rights in the invention.

BACKGROUND

The protection of crops from weeds and other vegetation which inhibit crop growth is a constantly recurring problem in agriculture. To help combat this problem, researchers in the field of synthetic chemistry have produced an extensive variety of chemicals and chemical formulations effective in the control of such unwanted growth. Secondary metabolites produced by microbes have in some instances been used for weed and pest control in agricultural applications.

Plants are capable of activating a large array of defense mechanisms in response to pathogen attack, some of which are preexisting and others are inducible. In the past few years it has become apparent that jasmonic acid (JA) and salicylic acid (SA) signaling can play an important role in regulation of pathogen defenses. SA signaling and JA signaling pathways are interconnected in complicated ways. For example, some studies have shown that SA signaling and JA signaling are mutually inhibitory (Creelman et al., *Annu. Rev. Plant Physiol. Plant Mol. Biol.*, 48:355 (1997); Gupta et al., Molec Plant-Microbe Interact 13(5): 503-511 (2000).

Pathogen infections and weeds can cause significant crop losses worldwide. Pathogens can also lead to disturbances in natural ecosystems. An understanding how plants control infections and respond to herbicides, for example via expression of defense mechanisms, can lead to new and beneficial ways to handle plant pathogens and control weed problems.

SUMMARY

Modified polypeptides, expression cassettes, modified plants, and modified seeds are described herein that are resistant to plant pathogens, including highly evolved plant pathogens and pests such as bacteria and insects. In addition, the modified polypeptides, expression cassettes, modified plants, and modified seeds described herein are resistant to herbicides.

Described herein are modified CORONATINE INSENSITIVE 1 (COI1) proteins that have amino acid sequences with at least one amino acid substitution within a jasmonate binding pocket of the modified COI1 protein relative to a native (wild type) COI1 protein amino acid sequence, wherein the at least one amino acid substitution reduces complex formation between the modified COI1 protein, coronatine, and a JAZ repressor protein as compared to the native (wild types) COI1 protein.

Expression cassettes and expression cassettes that encode and can express such modified COI1 proteins are also described herein. Cells and plants that have been modified to express such modified COI1 proteins are also described herein. The modified cells and plants can express heterologous modified COI1 proteins or the endogenous COI1 gene can be modified so that the modified COI1 protein is expressed.

Methods of making modified cells and modified plants are also described herein.

Methods are also described that involve applying an herbicide to a series of plants, to an agricultural field, or to any area where weed control is desired, where the series of plants, the agricultural field, or the area includes a modified plant that can express the modified COI1 plant. Such methods can reduce the growth, root length, and/or survival of undesired plants (e.g., weeds), while in comparison the modified plant has longer roots and grows well (better than the undesired plants or weeds).

DESCRIPTION OF THE FIGURES

FIG. 1A-1B illustrate the effects of CORONATINE INSENSITIVE 1 (COI1) alanine substitutions on COI1-JAZ9 interactions as measured by Y2H assays of protein-protein interaction, when the assays included 10 μM coronatine (COR; a JA-mimicking toxin). FIG. 1A shows interactions between JAZ9 and thirty-two different alanine-substitution COI1 mutants selected on the basis of the TIR1 crystal structure. Darker (blue) colonies indicate positive interactions, while lighter (light green) colonies indicate that COI1-JAZ9 were disrupted. As illustrated, JAZ9 interactions were reduced when COI1 had alanine substitution at M88, F89, L91, R121, E173, R348, R351, D354, G357, Y386, D407, R409, L410, V411, L412, L413, R415, R440, F443, L469, L470, Y472, Q491, K492, R496, and R516. FIG. 1B shows interactions between JAZ9 and ten additional alanine-substitution COI1 mutants selected on the basis of the COI1 crystal structure. As illustrated, JAZ9 interactions were reduced with COI1 Y302, R326, and Y444 alanine substitution mutants.

FIG. 2A shows liquid Y2H results of JAZ9 interaction with COI1 mutants in which each of seven selected JA-Ile-contacting residues within COI1 was substituted with alanine. FIG. 2B shows liquid Y2H results of JAZ9 interaction with COI1 mutants in which each of three additional JA-Ile-interacting residues was substituted with alanine. FIG. 2C shows liquid Y2H results of JAZ9 and seven additional COI1 mutants with substitutions at the A384 position. FIG. 2D shows a Western blot for COI1 A384 substitution mutant expression in yeast, showing that A384V and other A384 substitution mutants are expressed and stable in yeast. Anti-LexA antibody was used for detection of COI1 proteins expressed from a pGilda vector and anti-HA antibody was used for detection of JAZ9 expression from pB42AD vector. RLU indicates the degree of interaction between COI1 mutants and JAZ9 in the presence of either 1 μM COR, 10 μM JA-Ile (or 30 μM JA-Ile), or 1% DMSO treatment. Different letters above columns indicate significant differences (P<0.05) between different treatments (i.e., DMSO, JAIle, or COR) for the same set of interacting proteins. For those interacting proteins that do not have letter labels above columns, no significant differences were detected between treatments. Two-way ANOVA with Bonferroni posttest was used. Data were presented as mean±SEM (A: n=2; B and C: n=3). FIG. 2E shows an alignment of amino acids of COI1 orthologs involved in ligand-receptor interaction in the ligand binding pocket where the species of the orthologs are recited at the right. The position of A86 with respect to JA-Ile and COR bound in COI1 ligand binding pocket is also shown. Fourteen amino acids involved in JA-Ile interaction in the *Arabidopsis* COI1 protein are shown with the corresponding amino acids in six representative plant species. Green dots below the alignment indicate amino acids contacting with JA-Ile/COR; blue dots indicate amino acids that also make contact with JAZ1; and red dots indicate amino acids that make contact with InsP5. Abbreviations: *Arabidopsis thaliana* (At), *Solanum lycopersicum* (Sl), *Populus trichocarpa* (Pt), *Brachypodium distachyon* (Bd), *Picea abies* (Pa), *Selaginella moellendorffii* (Sm), *Physcomitrella patlens* (Pp).

FIG. 4A illustrates liquid Y2H assay results of JAZ9 interaction with mutant COI1 proteins containing amino acid substitutions at position 86 or 384 in the presence of 1 μM COR or 30 μM JA-Ile. FIG. 4B illustrates liquid Y2H results of COI1-JAZ9 interaction in the presence of different concentrations of JA-Ile and COR. Relative light units (RLU) indicated the degree of interaction between COI1 mutants and JAZ9. One-percent DMSO treatment was used as mock treatment. Different letters of the same type above columns indicate significant differences (P<0.05) between different treatments (i.e., DMSO, JA-Ile, or COR) for the same set of interacting proteins (n=3, error bars, SEM). For bar graphs that do not have letter labels above their columns, no significant differences were detected for the interacting proteins in those treatments. Two-way ANOVA with Bonferroni posttest was used for FIG. 4A. One-way ANOVA with Tukey's multiple comparison test was used for FIG. 4B. FIG. 4C illustrates results of co-receptor pull-down assays. Pulldown assays were performed with protein extracts from pCOI1:COI1WT/A384V-4×c-Myc plants and recombinant E. coli-expressed MBP-JAZ9-8×His in the presence of COR or JA-Ile at the indicated concentrations. Proteins bound to MBP-JAZ9-8×His were analyzed by immunoblotting. Anti-c-Myc antibody was used for detection of COI1WT/A384V-4×c-Myc protein. The Coomassie blue-stained gel shows the amounts of MBP-JAZ9-8×His pulled down by the Ni affinity resin.

FIG. 5A shows an image illustrating restoration of male fertility in transgenic COI1/COI1WT and COI1/COI1A384V plants. FIG. 5B illustrates COI1 protein levels in pCOI1:COI1WT-4×c-Myc and pCOI1:COI1A384V-4×c-Myc transgenic plants. Coomassie blue-stained ribulose-1,5-bisphosphate carboxylase/oxygenase (RuBisCo) protein was used as loading control. FIG. 5C illustrates the quantity (percentage) of root growth in an assay in the presence of 10 μM MeJA or 0.2 μM COR. Relative root length was compared with mock treatment (0.1% DMSO). Different letters of the same type above columns indicate significant differences (P<0.05) between different plant genotypes with the same treatment (MeJA or COR) (n=15, error bars, SEM, except for COI1-30, n=7), as determined by two-way ANOVA with Bonferroni posttest. * indicates P<0.001 significant differences between two ligand treatments of the same plant genotype (while ns: not significant). FIG. 5D illustrates the fold-changes of JAZ9 gene expression in Col-0, transgenic COI1WT, COI1A384V, and COI1-30 plants after 10 μM MeJA or 0.2 μM COR induction, relative to those in COI1-30-null plants with 10 μM MeJA. The internal control employed was the PROTEIN PHOSPHATASE 2A SUBUNIT A3 gene (PP2AA3, AT1G13320). Different letters of the same type above columns indicate significant differences (P<0.05) of gene expression between different plant genotypes with the same ligand treatment (MeJA or COR) (n=4, error bars, SEM), by two-way ANOVA with Bonferroni posttest. P<0.01 and ***P<0.001 indicate significant differences between two different ligand treatments of the same plant genotype (ns, not significant). FIG. 5E graphically illustrates expression of the salicylic acid (SA)-responsive gene, PR1, in Col-0, COI1WT and COI1A384V plants. FIG. 5F graphically illustrates expression of the SA-responsive gene SID2 in Col-0, COI1WT, and COI1A384V plants. For the experiments providing the results in FIG. 5E-5F, PP2AA3 was used as an internal control gene, and a one-way ANOVA with Dunnett test was used (n=4, error bars, SEM). No significant difference (P<0.05) was detected in the expression levels shown in FIGS. 5E-5F.

FIG. 6A illustrates the disease symptoms of Col-0, COI1-30, COI1WT and COI1A384V leaves 3 days after dip-inoculation with 1×10$^8$ cfu/mL Pst DC3000. FIG. 6B illustrates the quantity of bacterial populations on Col-0, COI1-30, COI1WT and COI1A384V 3 days after dip-inoculation with 1×10$^8$ cfu/mL Psi DC3000. For FIGS. 6A-6B, *P<0.001 indicates significant difference between mutant lines and wild-type Col-0 by one-way ANOVA with Dunnett test (n=4, error bars, SEM). FIG. 6C illustrates the disease symptoms of Col-0, COI1-30, COI1WT and COI1A384V leaves 3 days after dip-inoculation with 1×10$^8$ cfu/mL Pseudomonas syringae pv maculicola (Psm) ES4326. FIG. 6D graphically illustrates the quantity of bacterial populations 3 days after dip-inoculation with 1×10$^8$ cfu/mL Psm ES4326. For FIGS. 6C-6D, P<0.01 and ***P<0.001 indicate significant difference between mutant lines and Col-0 wild-type by One way ANOVA with Dunnett test (n=4, error bars, SEM). FIG. 6E graphically illustrates the quantity of bacterial populations 4 days after infection by syringe-infiltration with 1×10$^6$ cfu/mL of COR-deficient P. syringae mutant Pst DC3118. FIG. 6F graphically illustrates the quantity of bacterial populations 4 days after infection by syringe-infiltration with 1×10$^6$ cfu/mL of COR-deficient P. syringae mutant DB29. No significant difference (P<0.05) was detected between plant genotypes by One-way ANOVA with Dunnett test (n=4, error bars, SEM) for the data shown in FIGS. 6E-6F.

FIG. 7A graphically illustrates the average weights of 12-day-old Spodoptera exigua larvae fed on Col-0, COI1-30, COI1WT or COI1A384V plants. The symbol *** indicates a significant difference at P<0.001 in comparisons to Col-0 using One-way ANOVA with Dunnett test (n=10, error bars, SEM). No significant difference was detected in the weight of larvae reared on Col-0, COI1WT and COI1A384V L1 plants. FIG. 7B shows images of representative larvae 12 days after feeding as described for FIG. 7A. FIG. 7C shows images of *Arabidopsis* plants after *Spodoptera exigla* larvae exposure.

DETAILED DESCRIPTION

Figure 2A:
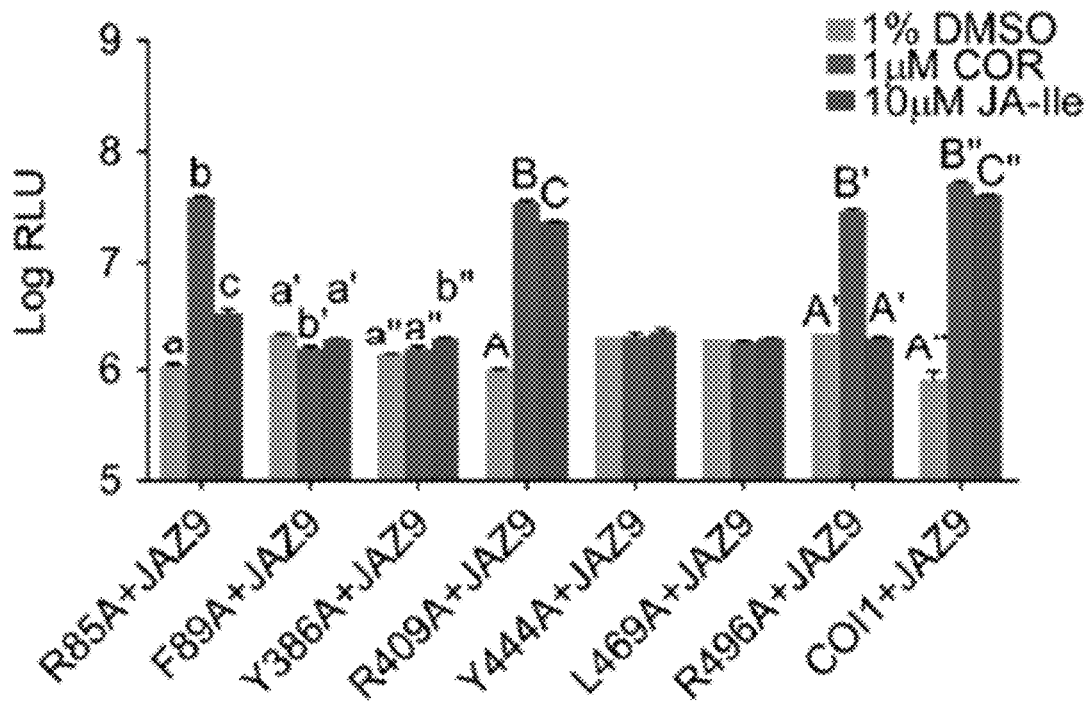
FIG. 2A-2E illustrate interactions between COI1 substitution mutants and JAZ9 under various conditions.

The invention relates to plants, plant cells, and seeds that express modified CORONATINE INSENSITIVE 1 (COI1) proteins. Expression of such modified COI proteins in plants provides near-normal defense responses to pathogens and pests. Additionally, the modified COI1 proteins provide resistance to the phytotoxin coronatine, which several pathogens produce as a virulence factor. Plants expressing the modified COI1 are thus rendered resistant to coronatine (COR) and to the pathogens that use coronatine as a virulence factor. As illustrated herein, coronatine can reduce plant growth and act as an herbicide, but plants expressing the modified COI1 proteins are not susceptible to reduced plant growth. Hence, described herein are plants expressing modified COI1 proteins, as well as methods of reducing growth of plants that do not express such modified COI1 proteins while cultivating plants that do express the types of modified COI1 proteins.

COI1 is an F-box protein that can mediate jasmonate signaling by promoting hormone-dependent ubiquitination and degradation of transcriptional repressor JASMONATE ZIM DOMAIN (JAZ) proteins. JAZ proteins are repressors of the jasmonic acid signaling pathway. COI1 proteins can form a co-receptor with one or more JAZ transcriptional repressor protein that can bind jasmonate. Formation, or lack of formation, of jasmonate/COI1/JAZ complexes can regulate the sophisticated, multilayered immune signaling network present in plants.

The stress hormone jasmonate (JA) plays a central role in regulating plant defenses against a variety of chewing insects and necrotrophic pathogens. Salicylic acid (SA) is another plant hormone that can be employed for plant defense against biotrophic or hemibiotrophic pathogens. During host-pathogen coevolution, however, many successful plant pathogens developed mechanisms to attack or hijack components of the plant immune signaling network as part of their pathogenesis strategies. As a result, the plant immune system, although powerful, is often fallible in the face of highly evolved pathogens.

Jasmonate is one of the common targets of virulence factors from highly evolved biotrophic/hemibiotrophic pathogens. Strains of the bacterial pathogen *Pseudomonas syringae*, for example, produce proteinaceous effectors, as well as a JA-mimicking toxin, coronatine (COR), to activate JA signaling and promote disease susceptibility. Higher plants synthesize different forms of JA, including the most bioactive form, jasmonoyl-L-isoleucine (JA-Ile). By way of example, structures of (3R,7S) JA-Ile and the JA-mimicking toxin, coronatine (COR), are shown below:

(3R,7S)-JA-L-Ile            coronatine

A plant's perception of JA-Ile (or COR) occurs through the COI1-JAZ co-receptor. Guided by the crystal structure of the JA receptor and evolutionary clues, the inventors have modified the JA receptor (COI1) to allow for sufficient endogenous JA signaling but greatly reduced sensitivity to COR. As illustrated herein, transgenic *Arabidopsis* expressing this modified COI1-containing receptor are not only fertile and maintain a high level of defense against insects, but also have the ability to resist COR-producing pathogens *Pseudomonas syringae* pv tomato and *P. syringae* pv maculicola.

In addition, the modified COI1 proteins do not form a complex with herbicide compounds as readily as do wild type, unmodified COI1 proteins. Accordingly, expression of the modified COI1 proteins described herein can confer herbicide resistance to plants. Hence, growth of weeds and undesired plants that do not express the modified COI1 proteins can be inhibited by application of herbicides, but plants that express the modified COI1 proteins described herein are resistant to the herbicides and grow well despite exposure to herbicides.

Ligands that Bind COI1

A variety of molecules can bind to COI1 protein. Jasmonic acid and variants thereof are the natural ligands of COI1. Higher plants synthesize different forms of jasmonic acid, including the most bioactive form jasmonoyl-L-isoleucine (JA-Ile). As described herein the modified COI1 polypeptides preferentially bind ligands such as jasmonic acid and JA-Ile, rather than a structurally related molecule, coronatine (COR), which is produced by several strains of *Pseudomonas syringae*. The differences in binding affinities between jasmonic acid variants and coronatine, mean that coronatine can be an effective herbicide for plants that do not express the modified COI1 polypeptides described herein. Only by expressing these modified COI1 proteins can plants grow well and resist infection by various pests when exposed to coronatine and other herbicides.

The types of molecules that can act as herbicides of plants that do not express the modified COI1 proteins include compounds of formula I:

I wherein:

$R_1$ can be a three to six carbon ($C_3$ to $C_6$) alkyl that can have one double bond, or $R_1$ can be a $C_3$ to $C_6$ alkylene that can have one double bond and that links to $R_2$ to form a cycloalkyl ring;

$R_2$ can be a $CH_2$ or a CH;

A is a cyclopentyl ring;

B can be a $C_3$ to $C_6$ cycloalkyl ring or a heterocycloalkyl ring; and $R_3$ can be a $C_1$ to $C_3$ alkyl; and $R_4$ can be hydrogen or $C_1$ to $C_3$ alkyl.

The compounds of formula I bind with good affinity to wild type, unmodified COI1 proteins. Some researchers have reported that the highest biological activity in terms of JA-responses was observed with coronatine (COR) (Feys et al, Plant Cell 6: 751-59 (1994)). This high activity may be due in part to the (3R,7S)-configuration at the cyclopentanone ring of coronatine (COR). Structures for coronatine (COR) and different isomers of jasmonate-Ile are shown below.

[Chemical structures shown:
(+)-7-iso-JA-L-Ile
COR
(−)-JA-L-Ile
(+)-JA-L-Ile]

In addition, various herbicides can bind to COI1 proteins, especially wild type COIL proteins. See Irvine et al. *Pest Manag Sci* 64: 891-899 (2008). For example, the structures of herbicides cinnacidin 1, and cinnacidin analogs 2 and 11 that can bind to COI1 proteins are shown below (id.).

[Chemical structures:
1
2, R = H
11, R = CH₂Ph]

COI1 Modifications

Plants, plant cells, and seeds described herein can express at least one type of modified COI1 protein. The modified COI1 proteins do not bind coronatine and herbicide ligands at the concentrations that wild type (or parental unmodified) COI1 proteins bind coronatine and herbicide ligands. Instead, much higher concentrations of coronatine and herbicide ligands are needed for formation of a complex with the modified COI1 proteins described herein. Hence, expression of the modified COI1 proteins in plants can protect the plants against bacterial infection and herbicides without compromising the plants' natural resistance to insects. Hence, at least 2-fold, at least 3-fold, at least 4-fold, at least 5-fold, at least 7-fold, at least 10-fold, at least 15-fold, at least 20-fold, at least 25-fold, at least 50-fold, at least 75-fold, at least 90-fold, at least 100-fold higher concentrations of coronatine and/or herbicide compounds are needed for formation of a complex with the modified COI1 proteins than are needed for formation of a complex with wild type or unmodified COI1 proteins.

The modified COI1 proteins can be expressed in plants, plant cells, and/or seeds from an expression cassette, transgene, or modified endogenous nucleic acid that encodes the modified COI1 protein.

Plants, plant cells, and seeds described herein can optionally have one or more genomic deletions, insertions, or substitutions in at least part of an endogenous COI1 gene. Such deletions, insertions, or substitutions can either alter the endogenous COI1 gene so that the endogenous gene encodes a modified COI1 protein, or the deletions, insertions, or substitutions can reduce/eliminate endogenous COI1 expression so that COI1 function can be replaced by a transgene encoding a modified COI1 protein. Rather than expression a native (e.g., endogenous, wild type) COI1 protein, the plants, plant cells, and seeds described herein can therefore express a modified COI1 protein. Expression of the modified COI1 protein can therefore be from a modified COI1 transgene, from a modified endogenous COI1 gene, or from a modified COI1 transgene that replaces an endogenous COI1 gene.

Deletions, insertions, or substitutions of endogenous COI1 genomic sequences can be generated site-specific recombination-mediated methods. Non-limiting examples of methods of introducing a modification into the genome of a plant cell can include microinjection, viral delivery, recombinase technologies, homologous recombination, TALENS, CRISPR, and/or ZFN, see, e.g. Clark and Whitelaw Nature Reviews Genetics 4:825-833 (2003); which is incorporated by reference herein in its entirety.

The mutations can range in size from one or two nucleotides to thousands of nucleotides (or any value therebetween). Deletions, insertions, and/or substitutions are created at a desired location in the genome. For example, borders (end points) of the deletions, insertions, or substitutions can be at defined locations to control the size of the deletions, insertions, or substitutions.

In some cases at least one amino acid is replaced with a hydrophobic amino acid. Examples of hydrophobic amino acids include valine, leucine, isoleucine, methionine, glycine, proline, or phenylalanine. In some cases the amino acid that is replaced can be an alanine. Hence, in many cases the amino acid that replaces the native, wild type, or parental COI1 protein is not an alanine. In other words, even though alanine may be a hydrophobic amino acid, in many cases no amino acid is replaced by alanine to generate a modified COI1 protein.

The mutation(s) can reduce or eliminate expression of endogenous COI1 genes within plant cells, plants, and seeds (e.g., so that a mutant COI1 transgene can provide expression of the modified COI1 protein). Alternatively, the mutations can modify the sequence of the endogenous COI1 gene(s) so that a modified COI1 protein is expressed.

For example, in some cases the mutations can eliminate transcription and/or translation of from an endogenous COI1 gene so that it can be replaced by a modified COI1 transgene. In some cases, the mutations can also eliminate transcription and/or translation of from genes related to a COI1 gene so that it can be replaced by a modified COI1 transgene.

For example, in some cases endogenous native (e.g., wild type) transcription and/or translation can be reduced by at least 40%, or at least 50%, or at least 60%, or at least 70%, or at least 80%, or at least 90%, or at least 95%, or at least 97%, or at least 99% compared to parental or wild type plant cells, plants, and seeds of the same species (that do not have the COI1 mutation(s)).

Mutation(s) that modify the sequence of a COI protein (expressed from a modified endogenous COI1 gene or from a transgene that encodes a modified COI1 protein) can reduce or eliminate interaction of the COI1 protein with one or more jasmonic acid-mimicking toxins. For example, the mutation(s) can reduce or eliminate COI1 protein interaction with a coronatine (COR), cinnacidin, or combinations thereof. For example, interaction between a COI1 protein and one or more jasmonic acid-mimicking toxins can be reduced by at least 40%, or at least 50%, or at least 60%, or at least 70%, or at least 80%, or at least 90%, or at least 95%, or at least 97%, or at least 99% compared to a native (e.g., unmodified, wild type) COI1 protein (that does not have the COI1 mutation(s)).

COI1 Sequences

As an example, an *Arabidopsis thaliana* COI1 protein with a sequence provided by the NCBI database as accession number O04197.1 (GI:59797640), is shown below as SEQ ID NO:1.

```
  1 MEDPDIKRCK LSCVATVDDV IEQVMTYITD PKDRDSASLV
 41 CRRWFKIDSE TREHVTMALC YTATPDRLSR RFPNLRSLKL
 81 KGKPRAAMFN LIPENWGGYV TPWVTEISNN LRQLKSVHFR
121 RMIVSDLDLD RLAKARADDL ETLKLDKCSG FTTDGLLSIV
161 THCRKIKTLL MEESSFSEKD GKWLHELAQH NTSLEVLNFY
201 MTEFAKISPK DLETIARNCR SLVSVKVGDF EILELVGFFK
241 AAANLEEFCG GSLNEDIGMP EKYMNLVFPR KLCRLGLSYM
281 GPNEMPILFP FAAQIRKLDL LYALLETEDH CTLIQKCPNL
321 EVLETRNVIG DRGLEVLAQY CKOLKRLRIE RGADEQGMED
361 EEGLVSQRGL IALAQGCQEL EYMAVYVSDI TNESLESIGT
401 YLKNLCDFRL VLLDREERIT DLPLDNGVRS LLIGCKKLRR
441 FAFYLRQGGL TDLGLSYIGQ YSPNVRWMLL GYVGESDEGL
481 MEFSRGCPNL QKLEMRGCCF SERAIAAAVT KLPSLRYLWV
521 QGYRASMTGQ DLMQMARPYW NIELIPSRRV PEVNQQGEIR
561 EMEHPAHILA YYSLAGQRTD CPTTVRVLKE PI
```

The jasmonate binding pocket can include amino acids within about three amino acid positions of positions 85, 86, 88, 89, 355, 386, 409, 440, 444, 445, 446, 467, 469, and 496 (e.g., identified in bold and with underlining in the SEQ ID NO:1 sequence shown above). For example, in the *Arabidopsis thaliana* COI1 protein shown as SEQ ID NO:1 above, the jasmonate binding pocket can include amino acids within about three positions of R85, A86, M88, F89, E355, Y386, R409, R440, Y444, L445, R446, W467, L469, and R496.

In some embodiments, the modified COI1 protein have an amino acid substitution, replacement, deletion, or insertion at an amino acid position that directly contacts the jasmonate or coronatine ligand (e.g., a modification of any of positions 85, 86, 88, 89, 355, 386, 409, 440, 444, 445, 446, 467, 469, and 496 in the SEQ ID NO:1 sequence). However, in other embodiments, the modified COI1 protein have an amino acid substitution, replacement, deletion, or insertion at an amino acid position that does not directly contacts the ligand (e.g., a modification that is not at any of positions 85, 86, 88, 89, 355, 386, 409, 440, 444, 445, 446, 467, 469, and 496 in the SEQ ID NO:1 sequence).

For example, as described in more detail in the Examples, an alanine at position 384 of a COI1 protein was replaced with a valine to generate a modified COI1 protein with reduced COR binding and enhanced resistance to bacterial infection, but plants that express such a modified COI1 protein are fertile and normal levels of insect defense. A sequence for the modified *Arabidopsis thaliana* COI1 protein with valine at position 384 is shown below as SEQ ID NO:2.

```
  1 MEDPDIKRCK LSCVATVDDV IEQVMTYITD PKDRDSASLV
 41 CRRWFKIDSE TREHVTMALC YTATPDRLSR RFPNLRSLKL
```

```
 81 KGKPRAAMFN LIPENWGGYV TPWVTEISNN LRQLKSVHFR

121 RMIVSDLDLD RLAKARADDL ETLKLDKCSG FTTDGLLSIV

161 THCRKIKTLL MEESSFSEKD GKWLHELAQH NTSLEVLNFY

201 MTEFAKISPK DLETIARNCR SLVSVKVGDF EILELVGFFK

241 AAANLEEFCG GSLNEDIGMP EKYMNLVFPR KLCRLGLSYM

281 GPNEMPILFP FAAQIRKLDL LYALLETEDH CTLIQKCPNL

321 EVLETRNVIG DRGLEVLAQY CKQLKRLRIE RGADEQGMED

361 EEGLVSQRGL IALAQGCQEL EYMVVYVSDI TNESLESIGT

401 YLKNLCDFRL VLLDREERIT DLPLDNGVRS LLIGCKKLRR

441 FAFYLRQGGL TDLGLSYIGO YSPNVRWMLL GYVGESDEGL

481 MEFSRGCPNL QKLEMRGCCF SERAIAAAVT KLPSLRYLWV

521 QGYRASMTGQ DLMQMARPYW NIELIPSRRV PEVNQQGEIR

561 EMEHPAHILA YYSLAGQRTD CPTTVRVLKE PI
```

An example of a nucleotide (cDNA) sequence that encodes the SEQ ID NO:1 COI1 protein (NCBI accession number NM_129552.4 (GI:1063702813)) is shown below as SEQ ID NO:3.

```
   1 GCAAAATGA AAAGAAAAAC ATAGAAGTAG AGAGAAGATC

41 GCATCTCGAC CGTCAACTTC AGTGTATGAA ATAATGATCG

81 TCCCACTTGA TCCTCAAAAA TATTATTAAC CAAACAAAAT

121 TTGATTCCAT CGTCCCACTT TCTTCTTCTT CCTCCCAATC

161 CGCCTCTTCT TCCTACGCGT GTCTTCTTCT CCCTCACTCT

201 CTCAATCTCT AGTCTTCTCC GATTCACCGG ATCTTTCCTT

241 TCTTACTTCT TTCTTCTCAC TCTGGTGGTT ATGTGTGGAT

281 CTGCGACCTC GATTTCAATT CGAAGTCGTC GGTTTCTTCT

321 CTAAATCGAA TCTTTCCAGG ATTCGTTTGT TTTTTTCTTT

361 TGTTTTTTTT TCGATCCGAT GGAGGATCCT GATATCAAGA

401 GGTGTAAATT GAGCTGCGTC GCGACGGTTG ATGATGTCAT

441 CGAGCAAGTC ATGACCTATA TAACTGACCC GAAAGATCGC

481 GATTCGGCTT CTTTGGTGTG TCGGAGATGG TTCAAGATTG

521 ATTCCGAGAC GAGAGAGCAT GTGACTATGG CGCTTTGCTA

561 CACTGCGACG CCTGATCGTC TTAGCCGTCG ATTCCCGAAC

601 TTGAGGTCGC TCAAGCTTAA AGGCAAGCCT AGAGCAGCTA

641 TGTTTAATCT GATCCCTGAG AACTGGGGAG GTTATGTTAC

681 TCCTTGGGTT ACTGAGATTT CTAACAACCT TAGGCAGCTC

721 AAATCGGTGC ACTTCCGACG GATGATTGTC AGTGACTTAG

761 ATCTAGATCG TTTAGCTAAA GCTAGAGCAG ATGATCTTGA

801 GACTTTGAAG CTAGACAAGT GTTCTGGTTT TACTACTGAT

841 GGACTTTTGA GCATCGTTAC ACACTGCAGG AAAATAAAAA

881 CTTTGTTAAT GGAAGAGAGT TCTTTTAGTG AAAAGGATGG

921 TAAGTGGCTT CATGAGCTTG CTCAGCACAA CACATCTCTT

961 GAGGTTTTAA ACTTCTACAT GACGGAGTTT GCCAAAATCA

1001 GTCCCAAAGA CTTGGAAACC ATAGCTAGAA ATTGCCGCTC

1041 TCTGGTATCT GTGAAGGTCG GTGACTTTGA GATTTTGGAA

1081 CTAGTTGGGT TCTTTAAGGC TGCAGCTAAT CTTGAAGAAT

1121 TTTGTGGTGG CTCCTTGAAT GAGGATATTG GAATGCCTGA

1161 GAAGTACATG AATCTGGTTT TCCCCGAAA ACTATGTCGG

1201 CTTGGTCTCT CTTACATGGG ACCTAATGAA ATGCCAATAC

1241 TATTTCCATT CGCGGCCCAA ATCCGAAAGC TGGATTTGCT

1281 TTATGCATTG CTAGAAACTG AAGACCATTG TACGCTTATC

1321 CAAAAGTGTC CTAATTTGGA AGTTCTCGAG ACAAGGAATG

1361 TAATCGGAGA TAGGGGTCTA GAGGTCCTTG CACAGTACTG

1401 TAAGCAGTTG AAGCGGCTGA GGATTGAACG CGGTGCAGAT

1441 GAACAAGGAA TGGAGGACGA AGAAGGCTTA GTCTCACAAA

1481 GAGGATTAAT CGCTTTGGCT CAGGGCTGCC AGGAGCTAGA

1521 ATACATGGCG GTGTATGTCT CAGATATAAC TAACGAATCT

1561 CTTGAAAGCA TAGGCACATA TCTGAAAAAC CTCTGTGACT

1601 TCCGCCTTGT CTTACTCGAC CGGGAAGAAA GGATTACAGA

1641 TCTGCCACTG GACAACGGAG TCCGATCTCT TTTGATTGGA

1681 TGCAAGAAAC TCAGACGATT TGCATTCTAT CTGAGACAAG

1721 GCGGCTTAAC CGACTTGGGC TTAAGCTACA TCGGACAGTA

1761 CAGTCCAAAC GTGAGATGGA TGCTGCTGGG TTACGTAGGT

1801 GAATCAGATG AAGGTTTAAT GGAATTCTCA AGAGGCTGTC

1841 CAAATCTACA GAAGCTAGAG ATGAGAGGTT GTTGCTTCAG

1881 TGAGCGAGCA ATCGCTGCAG CGGTTACAAA ATTGCCTTCA

1921 CTGAGATACT TGTGGGTACA AGGTTACAGA GCATCGATGA

1961 CGGGACAAGA TCTAATGCAG ATGGCTAGAC CGTACTGGAA

2001 CATCGAGCTG ATTCCATCAA GAAGAGTCCC GGAAGTGAAT

2041 CAACAAGGAG AGATAAGAGA GATGGAGCAT CCGGCTCATA

2081 TATTGGCTTA CTACTCTCTG GCTGGCCAGA GAACAGATTG

2121 TCCAACAACT GTTAGAGTCC TGAAGGAGCC AATATGATAT

2161 GACCCAAAAA ACAGGTTTGT ATATAAAGAT TTTTAGTCTC

2201 GAGTTTTGGG GTTTCCACAA ACTGTGTACT ATACTACTTT

2241 GGTTCTTTTT TTGTTTCATG TTGTGTCGTC GATGTTTTTG

2281 GGAGATTACA TAGAGTCAGT CTTGTTTGTT GTATGGTCAT

2321 TACTTCTTTA TTTTTCCTCA GGGGTCTGTT TACTTTAATT

2361 TCTTTAATAA AACCCCGAAG ATTTTGAGAG ATTTCTTTAT

2401 CGTCCATGGT GTTGACTTCT GAGAGCTATA TTTGTTTGGA

2441 TTGGCATCTG AAACTTTATT TGTGGTTGTG ATTGTTTTGA

2481 TAACATTAGT AAAAAGGCAA ATAATAGAGT AC
```

An example of a COI1 protein from *Brassica rapa* (turnip) with NCBI accession number XP_009133392.1 (GI:685284974) has the following sequence (SEQ ID NO:4).

```
  1 MEDPDIKKCR LSSVTVDDVI EQVMPYITDP KDRDSASLVC

41 RRWFEIDSET REHVTMALCY TSTPDRLSRR FPNLRSIKLK

81 GKPRAAMFNL IPENWGGFVT PWVNEIASSL RRLKSVHFRR
```

A comparison of the *Arabidopsis thaliana* COI1 SEQ ID NO:1 sequence and the *Brassica rapa* COI SEQ ID NO:4 sequence is shown below, illustrating that the two proteins have at least 90% sequence identity. In addition, the location of the alanine at position 384 that can be replaced, for example with a valine, to generate a modified COI1 protein is also identified in bold and with underlining. As illustrated, this alanine is at about position 383 in the *Brassica rapa* COI1 SEQ ID NO:4 sequence.

```
89.8% identity in 590 residues overlap; Score: 2792.0; Gap frequency: 0.2%
Seq1   1 MEDPDIKRCKLSCVATVDDVIEQVMTYITDPKDRDSASLVCRRWFKIDSETREHVTMALC
Seq4   1 MEDPDIKKCRLSSV-TVDDVIEQVMPYITDPKDRDSASLVCRRWFEIDSETREHVTMALC
         ******* ** * ********* ***************** **************

Seq1  61 YTATPDRLSRRFPNLRSLKLKGKPRAAMFNLIPENWGGYVTPWVTEISNNLRQLKSVHFR
Seq4  60 YTSTPDRLSRRFPNLRSIKLKGKPRAAMFNLIPENWGGFVTPWVNEIASSLRRLKSVHFR
         ** ************** ******************** **** **   ** *******

Seq1 121 RMIVSDLDLDRLAKARADDLETLKLDKCSGFTTDGLLSIVTHCRKIKTLLMEESSFSEKD
Seq4 120 RMIVSDLDLDVLAKARLDELEALKLDKCSGFSTDGLFSIVKHCRKMKTLLMEESSFVEKD
         ********** ***** * ** ********* **** *** *** **********  ***

Seq1 181 GKWLHELAQHNTSLEVLNKYMTEFAKISPKDLETIARNCRSLVSVKVGDFEILELVGFFK
Seq4 180 GNWLHELALHNTSLEVLNFYMTEFAKINAKDLESIARNCRSLVSVKIGDFEMLELVGFFK
         * ****** ********* ********  **** ************ **** ********

Seq1 241 AAANLEEFCGGSLNEDIGMPEKYMNLVFPRKLCRLGLSYMGPNEMPILFPFAAQIRKLDL
Seq4 240 AATNLEEFCGGSLNEEIGRPEKYMNLIFPPKLCCLGLSYMGPNEMPILFPFAAQIRKLDL
         ** ************ ** ****** ** *** ***************************

Seq1 301 LYALLETEDHCTLIQKCPNLEVLETRNVIGDRGLEVLAQYCKQLKRLRIERGADEQGMED
Seq4 300 IYALLATEDHCTLIQKCPNLEVLETRNVIGDRGLEVLGQCCKKLKRLRIERGEDEQGMED
         **** ******************************** * ** ********* *******

Seq1 361 EEGLVSQRGLIALAQGCQELEYMAVYVSDITNESLESIGTYLKNLCDFRLVLLDREERIT
Seq4 360 EEGLVSQRGLVALAQGCQELEYMAVYVSDITNESLESIGTYLKNLCDFRLVLLDQEERIT
         ********** ********************************************* *****

Seq1 421 DLPLDNGVRSLLIGCKKLRRFAFYLRQGGLTDLGLSYIGQYSPNVRWMLLGYVGESDEGL
Seq4 420 DLPLDNGVRSLLIGCKKLRRFAFYLRQGGLTDVGLSYIGQYSPNVRWMLLGYVGESDEGL
         ******************************* ****************************

Seq1 481 MEFSRGCPNLQKLEMRGCCFSERAIAAAVTKLPSLRYLWVQGYRASMTGQLMQMARPYW
Seq4 480 MEFSRGCPKLQKLEMRGCCFSERAIAAAVLKIPSLRYLWVQGYRASTTGQDLRLMSRPYW
         ******** ******************** * ************* ****  *  ****

Seq1 541 NIELIPSRRVPEVNQQGEIREMEHPAHILAYYSLAGQRTDCPTTVRVLKE
Seq4 540 NIELIPARKVPEVNQLGEVREMEHPAHILAYYSLAGERTDCPPTVKVLRE
         ******  * ******  ** ****************** *** ** * 
```

```
                    -continued
121 MIVSDLDLDV LAKARLDELE ALKLDKCSGF STDGLFSIVK

161 HCRKMKTLLM EESSFVEKDG NWLHELALHN TSLEVLNFYM

201 TEFAKINAKD LESIARNCRS LVSVKIGDFE MLELVGFFKA

241 ATNLEEFCGG SLNEEIGRPE KYMNLTFPPK LCCLGLSYMG

281 PNEMPILFPF AAQIRKLDLI YALLATEDHC TLIQKCPNLE

321 VLETRNVIGD RGLEVLGQCC KKLKRLRIER GEDEQGMEDE

361 EGLVSQRGLV ALAQGCQELE YMAVYVSDIT NESLESIGTY

401 LKNLCDFRLV LLDQEERITD LPLDNGVRSL LIGCKKLRRF

441 AFYLRQGGLT DVGLSYIGQY SPNVRWMLLG YVGESDEGLM

481 EFSRGCPKLQ KLEMRGCCFS ERAIAAAVLK IPSLRYLWVQ

521 GYRASTTGQD LRLMSRPYWN IELIPARKVP EVNQLGEVRE

561 MEHPAHILAY YSLAGERTDC PPTVKVLREA
```

An example of a modified COI1 protein from *Brassica rapa* (turnip) with a valine instead of the alanine at position 383 (as shown in SEQ ID NO:4) can have the following sequence (SEQ ID NO:5).

```
  1 MEDPDIKKCR LSSVTVDDVI EQVMPYITDP KDRDSASLVC

41 RRWFEIDSET REHVTMALCY TSTPDRLSRR FPNLRSIKLK

81 GKPRAAMFNL IPENWGGFVT PWVNEIASSL RRLKSVHFRR

121 MIVSDLDLDV LAKARLDELE ALKLDKCSGF STDGLFSIVK

161 HCRKMKTLLM EESSFVEKDG NWLHELALHN TSLEVLNFYM

201 TEFAKINAKD LESIARNCRS LVSVKIGDFE MLELVGFFKA

241 ATNLEEFCGG SLNEEIGRPE KYMNLTFPPK LCCLGLSYMG

281 PNEMPILFPF AAQIRKLDLI YALLATEDHC TLIQKCPNLE

321 VLETRNVIGD RGLEVLGQCC KKLKRLRIER GEDEQGMEDE

361 EGLVSQRGLV ALAQGCQELE YMVVYVSDIT NESLESIGTY
```

```
401 LKNLCDFRLV LLDQEERITD LPLDNGVRSL LIGCKKLRRF

441 AFYLRQGGLT DVGLSYIGQY SPNVRWMLLG YVGESDEGLM

481 EFSRGCPKLQ KLEMRGCCFS ERAIAAAVLK IPSLRYLWVQ

521 GYRASTTGQD LRLMSRPYWN IELIPARKVP EVNQLGEVRE

561 MEHPAHILAY YSLAGERTDC PPTVKVLREA
```

An example of a nucleotide (cDNA) sequence that encodes the SEQ ID NO:4 *Brassica rapa* (turnip) COI protein (NCBI cDNA accession number XM_009135144.1 (GI:685284973)) is shown below as SEQ ID NO:6.

```
   1 GCCACTTCTT CCTCCTCTCC TCACGCTCCA CGTCCCCTGC

41 TAGCATCCCT CCCGCTTCCT CCTCCGATCT CTGCTCGTCT

81 TATCTTCACT CTCTACTGTA TTACTTTGGA TCTGCGAGAG

121 ATTCGTGTAA TTGAAATCGA TCTCGTCCCT CAGCTGGTAT

161 TCGAATTTGT TGATTGTTTT GGTTTGTTTT AGATTCGATT

201 TCGATTTGTT ACATGGAGGA TCCGGATATC AAGAAGTGCA

241 GATTGAGCTC CGTGACGGTC GATGACGTCA TCGAGCAGGT

281 CATGCCTTAC ATAACCGATC CGAAAGATCG AGACTCCGCT

321 TCCCTCGTGT GCCGGAGGTG GTTCGAGATC GACTCCGAGA

361 CGAGGGAGCA CGTGACCATG GCCTTGTGCT ACACCTCGAC

401 GCCCGATCGT CTCAGCCGTA GGTTTCCCAA TCTGAGGTCG

441 ATCAAGCTCA AAGGGAAGCC GAGAGCAGCT ATGTTCAATC

481 TCATCCCCGA GAACTGGGGA GGGTTTGTTA CCCCTTGGGT

521 CAACGAGATA GCTTCGTCGC TGCGAAGGCT CAAGTCTGTG

561 CATTTTAGGC GGATGATTGT GAGCGATTTG GATCTGGATG

601 TTTTGGCTAA GGCGAGGTTG GATGAGCTCG AGGCGTTGAA

641 GCTTGATAAG TGCTCGGGTT TCTCTACGGA TGGACTTTTC

681 AGCATCGTTA AGCACTGCAG GAAAATGAAA ACATTGTTAA

721 TGGAAGAGAG TTCTTTTGTT GAAAAGGATG GTAACTGGCT

761 TCATGAACTT GCTCTGCACA ACACTTCTCT CGAGGTTCTA

801 AATTTCTACA TGACTGAGTT TGCAAAAATC AATGCCAAAG

841 ACTTGGAAAG CATAGCTAGA AATTGCCGCT CTCTGGTTTC

881 TGTGAAGATC GGTGACTTTG AGATGTTGGA ACTAGTCGGG

921 TTCTTTAAAG CTGCAACTAA TCTTGAAGAA TTTTGTGGTG

961 GCTCCTTAAA TGAAGAAATT GGAAGACCGG AGAAGTATAT

1001 GAATCTGACT TTCCCTCCAA AACTATGTTG TCTGGGCCTT

1041 TCTTACATGG GACCTAATGA AATGCCAATA CTGTTTCCAT

1081 TCGCTGCCCA AATCCGGAAG CTGGATCTGA TCTATGCATT

1121 GCTCGCAACT GAGGATCATT GTACACTTAT TCAAAAGTGT

1161 CCTAATTTGG AAGTTCTCGA GACAAGGAAT GTAATTGGAG

1201 ATAGGGGTCT AGAGGTTCTT GGACAGTGCT GTAAGAAGTT

1241 GAAGCGGCTG AGGATTGAAC GGGGTGAAGA TGAACAAGGA

1281 ATGGAGGATG AAGAAGGCTT AGTCTCACAA AGAGGATTAG

1321 TCGCTTTGGC TCAGGGCTGC CAGGAGCTAG AATACATGGC

1361 GGTGTATGTC TCAGATATAA CCAACGAGTC TCTCGAAAGC

1401 ATAGGCACAT ATCTGAAAAA CCTCTGTGAC TTCCGCCTCG

1441 TCTTACTCGA CCAAGAAGAG AGAATAACAG ATCTGCCACT

1481 GGACAACGGA GTCAGATCCC TCTTGATCGG ATGCAAAAAA

1521 CTCAGACGGT TTGCATTCTA TCTCAGACAA GGCGGCTTAA

1561 CAGACGTGGG GTTAAGCTAC ATCGGACAGT ACAGTCCAAA

1601 CGTGAGGTGG ATGCTTCTCG GTTACGTTGG TGAATCAGAC

1641 GAAGGCCTAA TGGAATTCTC AAGAGGATGT CCGAAACTAC

1681 AGAAGCTGGA GATGAGAGGT TGTTGCTTCA GCGAGCGAGC

1721 AATAGCTGCA GCGGTACTGA AAATCCCTTC GCTGAGATAC

1761 CTGTGGGTAC AAGGCTATAG AGCATCGACG ACGGGACAAG

1801 ACCTGAGGCT AATGTCTAGA CCGTACTGGA ACATCGAGCT

1841 GATTCCGGCA AGAAAAGTCC CGGAAGTGAA TCAGCTTGGA

1881 GAGGTGAGAG AGATGGAGCA TCCTGCTCAT ATACTGGCTT

1921 ACTACTCTCT GGCTGGTGAG AGAACAGATT GTCCACCAAC

1961 GGTTAAAGTC CTGAGGGAGG CATGATGATG ATGATGAAAA

2001 GCAGGTTTGT ACATAAAGAT TTGGTTTTGA GGTTTCCACG

2041 AACTGTCGAA TGGATTCTAT TTTTTCTTTA TTGGTGTATT

2081 GTCTGTAGTT TTGAGAGATT CCATAAAGAC TTTTGAGAGA

2121 TTGAAATAAG AAGAGAGAAA ACTAGTCTTT CAGAAGA
```

An example of a COI1 protein from *Brassica napus* (rapeseed) with NCBI accession number CDY60996.1 (GI: 674872982) has the following sequence (SEQ ID NO:7).

```
   1 MLQRIFWMFF FSFNMLTRYF IKTPPGYFCR LARCAAYATR

41 LTKQTDSIAS SPPSIYIKNN NYPLCPLDPK LLLLLSTLLI

81 PSFTHTYATS SSSPHAPQIR VIEIDLIRFR FVTMEDPDIK

121 KCRLSSVTVD DVIEQVMPYI TDPKDRDSAS LVCRRWFEID

161 SETREHVTMA LCYTSTPDRL SRRFPNLRSI KLKGKPRAAM

201 FNLIPENWGG FVTPWVNEIA SSLRRLKSVH FRRMIVSDLD

241 LDVLAKARLD ELEALKLDKC SGFSTDGLFS IVKHCRKMKT

281 LLMEESSFVE KDGNWLHELA LHNTSLEVLN FYMTEFAKIN

321 AKDLESIARN CRSLVSVKIG DFEMLELVGF FKAATNLEEF

361 CGGSLNEEIG RPEKYMNLTF PPKLCCLGLS YMGPNEMPIL

401 FPFAAQIRKL DLIYALLATE DHCTLIQKCP NLEVLETRNV

441 IGDRGLEVLG QCCKKLKRLR IERGEDEQGM EDEEGLVSQR

481 GLVALAQGCQ ELEYMAVYVS DITNESLESI GTYLKNLCDF

521 RLVLLDQEER ITDLPLDNGV RSLLIGCKKL RRFAFYLRQS

561 GLTDVGLSYI GQYSPNVRWM LLGYVGESDE GLMEFSRGCP

601 KLQKLEMRGC CFSERAIAAA VLKIPSLRYL WVQGYRASTT
```

```
641 GQDLRLMSRP YWNIELIPAR KVPEVNQLGE VREMEHPAHI

681 LAYYSLAGER TDCPPTVKVL REA
```

A comparison of the *Arabidopsis thaliana* COI1 SEQ ID NO:1 sequence and the *Brassica napus* COI SEQ ID NO:7 sequence is shown below, illustrating that the two proteins have at least 90% sequence identity. In addition, the location of the alanine at position 384 (of SEQ ID NO:1) that can be replaced, for example with a valine, to generate a modified COI1 protein is also identified in bold and with underlining. As illustrated, this alanine is at about position 496 in the *Brassica napus* COI1 SEQ ID NO:7 sequence.

```
321 AKDLESIARN CRSLVSVKIG DFEMLELVGF FKAATNLEEF

361 CGGSLNEEIG RPEKYMNLTF PPKLCCLGLS YMGPNEMPIL

401 FPFAAQIRKL DLIYALLATE DHCTLIQKCP NLEVLETRNV

441 IGDRGLEVLG QCCKKLKRLR IERGEDEQGM EDEEGLVSQR

481 GLVALAQGCQ ELEYMVVYVS DITNESLESI GTYLKNLCDF

521 RLVLLDQEER ITDLPLDNGV RSLLIGCKKL RRFAFYLRQS

561 GLTDVGLSYI GQYSPNVRWM LLGYVGESDE GLMEFSRGCP
```

```
89.7% identity in 590 residues overlap; Score: 2786.0; Gap frequency:
0.2%
Seq1     1 MEDPDIKRCKLSCVATVDDVIEQVMTYITDPKDRDSASLVCRRWFKIDSETREHVTMALC
Seq7   114 MEDPDIKKCRLSSV-TVDDVIEQVMPYITDPKDRDSASLVCRRWFEIDSETREHVTMALC
             ******* * ** * ********** ********************* ***********

Seq1    61 YTATPDRLSRRFPNLRSLKLKGKPRAAMFNLIPENWGGYVTPWVTEISNNLRQLKSVHFR
Seq7   173 YTSTPDRLSRRFPNLRSIKLKGKPRAAMFNLIPENWGGFVTPWVNEIASSLRRLKSVHFR
           ** ************** ******************** ***** **   ** *******

Seq1   121 RMIVSDLDLDRLAKARADDLETLKLDKCSGFTTDGLLSIVTHCRKIKTLLMEESSFSEKD
Seq7   233 RMIVSDLDLDVLAKARLDELEALKLDKCSGFSTDGLFSIVKHCRKMKTLLMEESSFVEKD
           ********** ***** *  ** ********  ****  *** *** ***********  ***

Seq1   181 GKWLHELAQHNTSLEVLNFYMTEFAKISPKDLETIARNCRSLVSVKVGDFEILELVGFFK
Seq7   293 GNWLHELALHNTSLEVLNFYMTEFAKINAKDLESIARNCRSLVSVKIGDFEMLELVGFFK
           * ****** ****************** * ****  ************* *** ********

Seq1   241 AAANLEEFCGGSLNEDIGMPEKYMNLVFPRKLCRLGLSYMGPNEMPILFPFAAQIRKLDL
Seq7   353 AATNLEEFCGGSLNEEIGRPEKYMNLTFPPKLCCLGLSYMGPNEMPILFPFAAQIRKLDL
           ** ************ ** ******** * *** ****************************

Seq1   301 LYALLETEDHCTLIQKCPNLEVLETRNVIGDRGLEVLAQYCKQLKRLRIERGADEQGMED
Seq7   413 IYALLATEDHCTLIQKCPNLEVLETPNVIGDRGLEVLGQCCKKLKRLRIERGEDEQGMED
            **** ******************* ********** *  ** ********* *******

Seq1   361 EEGLVSQRGLIALAQGCQELEYMAVYVSDITNESLESIGTYLKNLCDFRLVLLDREERIT
Seq7   473 EEGLVSQRGLVALAQGCQELEYMAVYVSDITNESLESIGTYIKNLCDFRLVLLDQEERIT
           ********** ****************************** *********** *****

Seq1   421 DLPLPLDNGVRSLLIGCKKLRRFAFYLRQGGLTDLGLSYIGQYSPNVRWMLLGYVGESDEGL
Seq7   533 DLPLPLDNGVRSLLIGCKKLRRFAFYLRQSGLTDVGLSYIGQYSPNVRWMLLGYVGESDEGL
           ****************************   **** ****************************

Seq1   481 MEFSRGCPNLQKLEMRGCCFSERAIAAAVTKLPSLRYLWVQGYRASMTGQDLMQMARPYW
Seq7   593 MEFSRGCPKLQKLEMRGCCFSERAIAAAVLKIPSLRYLWVQGYRASTTGQDLRLMSRPYW
           ******** ********************* * ************* ***** *  ****

Seq1   541 NIELIPSRRVPEVNQQGEIREMEHPAHILAYYSLAGQRTDCPTTVRVLKE
Seq7   653 NIELIPARKVPEVNQLGEVREMEHPAHILAYYSLAGERTDCPPTVKVLRE
           ****** * ****** ** ***************** ***** ** **  *
```

An example of a modified COI1 *Brassica napus* (rapeseed) protein with a valine at position 496 instead of an alanine has the following sequence (SEQ ID NO:8).

```
  1 MLQRIFWMFF FSFNMLTRYF IKTPPGYFCR LARCAAYATR

41 LTKQTDSIAS SPPSIYIKNN NYPLCPLDPK LLLLLSTLLI

81 PSFTHTYATS SSSPHAPQIR VIEIDLIRFR FVTMEDPDIK

121 KCRLSSVTVD DVIEQVMPYI TDPKDRDSAS LVCRRWFEID

161 SETREHVTMA LCYTSTPDRL SRRFPNLRSI KLKGKPRAAM

201 FNLIPENWGG FVTPWVNEIA SSLRRLKSVH FRRMIVSDLD

241 LDVLAKARLD ELEALKLDKC SGFSTDGLFS IVKHCRKMKT

281 LLMEESSFVE KDGNWHELA LHNTSLEVLN FYMTEFAKIN
```

```
601 KLQKLEMRGC CFSERAIAAA VLKIPSLRYL WVQGYRASTT

641 GQDLRLMSRP YWNIELIPAR KVPEVNQLGE VREMEHPAHI

681 LAYYSLAGER TDCPPTVKVL REA
```

An example of a COI1 protein from *Brassica oleracea* (cabbage, Brussel sprouts, kale, cauliflower, etc.) with NCBI accession number XP_013628733.1 (GI:922451771) has the following sequence (SEQ ID NO:9).

```
  1 MTMEDPDIKK CRLSSVTVDD VIEQVMPYIT DPKDRDSASL

41 VCRRWFEIDS ETREHVTMAL CYTSTPDRLS RRFPNLRSIK

81 LKGKPRAAMF NLIPENWGGF VTPWVNEVAS SLPRLKSVHF
```

```
                         -continued
121 RRMIVSDLDL DVLAKARLDE LEALKLDKCS GFSTDGLFSI

161 VKHCRKMKTL LMEESSFVEK DGNWLHELAL HNTSLEVLNF

201 YMTEFAKINA KDLESIARNC RSLVSVKIGD FEMLELVGFF

241 KAATNLEEFC GGSFNEEIGR PEKYMNLTFP PKLCCLGLSY

281 MGPNEMPILF PFAAQIRKLD LIYALLATED HCTLIQKCPN

321 LEVLETRNVI GDRGLEVLGQ CCKKLKRLRI ERGEDEQGME

361 DEEGLVSQRG LVALAQGCQE LEYMAVYVSD ITNESLESIG

401 TYLKNLCDFR LVLLDQEERI TDLPLDNGVR SLLIGCKKLR

441 RFAFYLRQGG LTDVGLSYIG QYSPNVRWML LGYVGESDEG

481 LMEFSRGCPK LQKLEMRGCC FSERAIAAAV LKIPSLRYLW

521 VQGYRASTTG QDLRLMSRPY WNIELIPARK VPEVNQLGEV

561 REMEHPAHIL AYYSLAGERT DCPPTVKVLR EA
```

A comparison of the *Arabidopsis thaliana* COI1 SEQ ID NO:1 sequence and the *Brassica oleracea* COI1 SEQ ID NO:9 sequence is shown below, illustrating that the two proteins have at least 89% sequence identity. In addition, the location of the alanine at position 384 that can be replaced, for example with a valine, to generate a modified COI1 protein is also identified in bold and with underlining. As illustrated, this alanine is at about position 385 in the *Brassica oleracea* COI1 SEQ ID NO:9 sequence.

An example of a modified *Brassica oleracea* COI1 protein with a valine instead of an alanine at position 385 has the following sequence (SEQ ID NO:10).

1 MTMEDPDIKK CRLSSVTVDD VIEQVMPYIT DPKDRDSASL

41 VCRRWFEIDS ETREHVTMAL CYTSTPDRLS RRFPNLRSIK

81 LKGKPRAAMF NLIPENWGGF VTPWVNEVAS SLPRLKSVHF

121 RRMIVSDLDL DVLAKARLDE LEALKLDKCS GFSTDGLFSI

161 VKHCRKMKTL LMEESSFVEK DGNWLHELAL HNTSLEVLNF

201 YMTEFAKINA KDLESIARNC RSLVSVKIGD FEMLELVGFF

241 KAATNLEEFC GGSFNEEIGR PEKYMNLTFP PKLCCLGLSY

281 MGPNEMPILF PFAAQIRKLD LIYALLATED HCTLIQKCPN

321 LEVLETRNVI GDRGLEVLGQ CCKKLKRLRI ERGEDEQGME

361 DEEGLVSQRG LVALAQGCQE LEYMVVYVSD ITNESLESIG

401 TYLKNLCDFR LVLLDQEERI TDLPLDNGVR SLLIGCKKLR

441 RFAFYLRQGG LTDVGLSYIG QYSPNVRWML LGYVGESDEG

481 LMEFSRGCPK LQKLEMRGCC FSERAIAAAV LKIPSLRYLW

521 VQGYRASTTG QDLRLMSRPY WNIELIPARK VPEVNQLGEV

561 REMEHPAHIL AYYSLAGERT DCPPTVKVLR EA

An example of a nucleotide (cDNA) sequence that encodes the *Brassica oleracea* SEQ ID NO:9 COI1 protein

```
89.3% identity in 590 residues overlap; Score: 2780.0; Gap frequency:
0.2%
Seq1    1 MEDPDIKRCKLSCVATVDDVIEQVMTYITDPKDRDSASLVCRRWFKIDSETREHVTMALC
Seq9    3 MEDPDIKKCRLSSV-TVDDVIEQVMPYITDPKDRDSASLVCRRWFEIDSETREHVTMALC
          ******* * ** * ********** ******************* **************

Seq1   61 YTATPDRLSRRFPNLRSLKLKGKPRAAMFNLIPENWGGYVTPWVTEISNNLRQLKSVHFR
Seq9   62 YTSTPDRLSRRFPNLRSIKLKGKPRAAMFNLIPENWGGEVTPWVNEVASSLPRLKSVHFR
          ** ************** ******************** ***** *    *  *******

Seq1  121 RMIVSDLDLDRLAKARADDLETLKLDKCSGFTTDGLLSIVTHCRKIKTLLMEESSFSEKD
Seq9  122 RMIVSDLDLDVLAKARLDELEALKLDKCSGFSTDGLFSIVKHCRKMKTLLMEESSFVEKD
          ********** ***** * ** ********* **** *** **** ********** ***

Seq1  181 GKWLHELAQHNTSLEVLNFYMTEFAKISPKDLETIAPNCRSLVSVKVGDFEILELVGFFK
Seq9  182 GNWLHELALHNTSLEVLNFYMTEFAKINAKDLESIARNCRSLVEVKIGDFEMLELVGFFK
          * ****** ******************  **** ************ **** ********

Seq1  241 AAANLEEFCGGSLNEDIGMPEKYMNLVFPRKLCRLGLSYMGPNEMPILFPFAAQIRYLDL
Seq9  242 AATNLEEFCGGSFNEEIGRPEKYMNLTFPPKLCCLGLSYMGPNEMPILFPFAAQIRKLDL
          ** ********* ** ** ******* ** *** *************************

Seq1  301 LYALLETEDHCTLIQKCPNLEVLETRNVIGDRGLEVLACYCKQLKRLRIERGADEQGMED
Seq9  302 IYALLATEDHCTLIQKCPNLEVLETRNVIGDRGLEVLGQCCKKLKRLRIERGEDEQGMED
           **** ***************************** * ** ********* *******

Seq1  361 EEGLVSQRGLIALAQGCQELEYMAVYVSDITNESLESIGTYLKNLCDFRLVLLDREERIT
Seq9  362 EEGLVSQRGLVALAQGCQELEYMAVYVSDITNESLESIGTYLKNLCDFRLVLLDQEERIT
          ********** ********************************************* *****

Seq1  421 DLPLDNGVRSLLIGCKKLRRFAFYLRQGGLTDLGLSYIGQYSPNVRWMLLGYVGESDEGL
Seq9  422 DLPLDNGVRSLLIGCKKLRRFAFYLRQGGLTDVGLSYIGQYSPNVRWMLLGYVGESDEGL
          ******************************** ***************************

Seq1  481 MEFSRGCPNLQKLEMRGCCFSERAIAAAVTKLPSLRYLWVQGYRASMTGQDLMQMARPYW
Seq9  482 MEFSRGCPKLQKLEMRGCCFSERAIAAAVLKIPSLRYLWVQGYRASTTGQDLRLMSRPYW
          ******** ******************** * ************** *****  * ****

Seq1  541 NIELIPSRRVPEVNQQEIREMEHPAHILAYYSLAGQRTDCPTTVRVLKE
Seq9  542 NIELIPARKVPEVNQLGEVREMEHPAHILAYYSLAGERTDCPPTVKVLRE
          ****** * ****** ** **************** ***** ** ** *
```

(NCBI cDNA accession number XM_013773279.1 (GI: 922451770)) is shown below as SEQ ID NO:11.

```
   1 ATTATTATTA TCAACACTTT TGATTCCTTC CTCCACACAC
  41 ACTCACGCCA CTTCTTCCTC CTCTCCTCAC GCTCCACCTA
  81 TCGTGATTCC TATACTCGAT TTCGATTTGT TATCCGTTTG
 121 TTTGATGACG ATGGAGGATC CGGATATCAA GAAGTGCAGA
 161 TTGAGCTCCG TGACGGTCGA TGACGTCATC GAGCAGGTCA
 201 TGCCTTACAT AACCGATCCG AAAGATCGAG ACTCCGCTTC
 241 CCTCGTGTGC CGGAGGTGGT TCGAGATCGA CTCCGAGACG
 281 AGGGAGCACG TGACCATGGC ACTATGCTAC ACCTCGACTC
 321 CTGACCGTCT CAGCCGTAGG TTTCCGAATC TGAGGTCGAT
 361 TAAGCTCAAA GGGAAGCCGA GAGCAGCTAT GTTCAATCTC
 401 ATCCCCGAGA ACTGGGGAGG GTTTGTTACC CCTTGGGTCA
 441 ACGAGGTAGC TTCATCTCTG CCAAGGCTCA AGTCTGTGCA
 481 TTTTAGGCGG ATGATTGTCA GCGATTTGGA TCTTGATGTT
 521 TTGGCTAAGG CGAGGTTGGA TGAGCTCGAG GCGTTGAAGC
 561 TCGATAAGTG CTCAGGTTTC TCTACGGATG GACTTTTCAG
 601 CATCGTTAAG CACTGCAGGA AAATGAAAAC ATTGTTAATG
 641 GAAGAGAGTT CTTTTGTTGA AAAGGATGGT AACTGGCTGC
 681 ATGAACTTGC TCTGCACAAC ACTTCTCTTG AGGTTCTAAA
 721 TTTCTACATG ACTGAGTTTG CAAAAATCAA TGCCAAAGAC
 761 TTGGAAAGCA TAGCTAGAAA TTGCCGCTCT CTGGTTTCTG
 801 TGAAGATCGG TGACTTTGAG ATGTTGGAAC TAGTCGGGTT
 841 CTTTAAAGCT GCAACTAATC TTGAAGAATT TTGTGGCGGC
 881 TCCTTCAATG AAGAAATTGG AAGACCGGAG AAGTATATGA
 921 ATCTGACTTT CCCTCCAAAA CTATGTTGTC TTGGCCTTTC
 961 TTACATGGGA CCTAATGAAA TGCCAATACT GTTTCCATTC
1001 GCTGCCCAAA TCCGGAAGCT GGATCTGATC TATGCATTGC
1041 TCGCAACTGA GGATCATTGT ACACTTATTC AAAGTGTCC
1081 TAATTTGGAA GTTCTCGAGA CAAGGAATGT AATTGGAGAT
1121 AGGGGTCTAG AGGTTCTTGG ACAGTGCTGT AAGAAGTTGA
1161 AGCGGCTGAG GATTGAACGG GGTGAAGATG AACAAGGAAT
1201 GGAGGATGAA GAAGGCCTAG TATCACAAAG AGGATTAGTC
1241 GCTTTGGCTC AGGGCTGCCA GGAGCTAGAA TACATGGCGG
1281 TGTATGTCTC AGATATAACC AACGAGTCTC TCGAAAGCAT
1321 AGGCACATAT CTGAAAAACC TCTGTGACTT CCGCCTCGTC
1361 TTACTCGACC AAGAAGAGAG AATAACAGAT CTGCCACTAG
1401 ACAACGGAGT CCGATCCCTC TTGATCGGAT GCAAGAAACT
1441 CAGACGGTTT GCATTCTATC TCAGACAAGG CGGCTTAACA
1481 GACGTGGGGT TAAGCTACAT CGGACAGTAC AGTCCAAACG
1521 TGAGGTGGAT GCTTCTCGGT TACGTTGGTG AATCAGACGA
1561 AGGCCTAATG GAGTTCTCAA GAGGATGTCC GAAACTACAG
1601 AAGCTGGAGA TGAGAGGTTG TTGCTTCAGC GAGCGAGCAA
1641 TAGCTGCAGC GGTACTGAAA ATCCCTTCGC TGAGATACCT
1681 GTGGGTACAA GGCTACAGAG CATCAACGAC GGGACAAGAC
1721 CTGAGGCTAA TGTCTAGACC GTACTGGAAC ATCGAGCTGA
1761 TTCCGGCAAG AAAAGTCCCA GAAGTGAATC AGCTTGGAGA
1801 GGTGAGAGAG ATGGAGCATC CTGCTCATAT ACTGGCTTAC
1841 TACTCTCTGG CTGGTGAGAG AACAGATTGT CCACCAACTG
1881 TTAAAGTCCT GAGGGAGGCA TGATGATGAT GATGATGATG
1921 ATGAAAAGCA GGTTTGTACA TAAAGATTTG GTTTTGAGGT
1961 TTCCACGAAC TGTCGAATGG ATTCTATTTT TCTTTATTGG
2001 TGTATTGTCT GTAGTTTTGA GAGATTCCAT AAAGACTTTT
2041 GAGAGATTGA AATAAGAAGA GAGAAAACTA GTCTATTCAG
2081 AAGA
```

An example of a COI1 protein from *Theobroma cacao* (cocoa) with NCBI accession number XP_007009091.2 (GI:1063526274) has the following sequence (SEQ ID NO:12).

```
  1 MEENDNKMNK TMTSPVGMSD VVLGCVMPYI HDPKDRDAVS
 41 LVCRRWYELD ALTRKHITIA LCYTTSPDRL RRRFQHLESL
 81 KLKGKPRAAM FNLIPEDWGG YVTPWVNEIA ENFNCLKSLH
121 FRRMIVKDSD LEVLARSRGK VLQVLKLDKC SGFSTDGLLH
161 VGRSCRQLKT LFLEESLIVE KDGQWLHELA VNNSVMETLN
201 FYMTDLVKVS FEDLELIARN CRNLASVKIS DCEILDLVGF
241 FPAAAVLEEF CGGSFNEQPD RYHAVSFPPK LCRLGLTYMG
281 KNEMPIVFPF ASLLKKLDLL YALLDTEDHC LLIQRCPNLE
321 VLETRNVIGD RGLEVLARSC KRLKRLRIER GADEQGMEDE
361 EGVVSQRGLM ALAQGCLELE YLAVYVSDIT NASLEYIGTY
401 SKNLSDFRLV LLDREERITD LPLDNGVRAL LRGCEKLRRF
441 ALYLRPGGLT DVGLSYIGQY SPNVRWMLLG YVGESDAGLL
481 EFSKGCPSLQ KLEMRGCCFS EHALAVTVMQ LTSLRYLWVQ
521 GYRASQSGRD LLAMARPFWN IELIPARRVV MNDQVGEAVV
561 VEHPAHILAY YSLAGPRTDF PETVIPLDPL VAA
```

A comparison of the *Arabidopsis thaliana* COI1 SEQ ID NO:1 sequence and the *Theobroma cacao* COI1 SEQ ID NO:12 sequence is shown below, illustrating that the two proteins have at least 73% sequence identity. In addition, the location of the alanine at position 384 that can be replaced, for example with a valine, to generate a modified COI1 protein is also identified in bold and with underlining. As illustrated, this alanine is at about position 383 in the *Theobroma cacao* COI1 SEQ ID NO:12 sequence.

73.1% identity in 583 residues overlap; Score: 2221.0; Gap frequency: 0.5%

```
Seq1    3 DPDIKRCKLSCVATVDDVIEQVMTYITDPKDRDSASLVCRRWFKIDSETREHVTMALCYT
Seq12   5 DNKMNKTMTSPVGMSDVVLGCVMPYIHDPKDRDAVSLVCRRWYELDALTRKHITIALCYT
          *       *  *   *  ** ** ****** *******   *  ** *  * *****

Seq1   63 ATPDRLSRRFPNLRSLKLKGKPRAAMFTLIPENWGGYVTPWVTEISNNLRQLKSVHFRRM
Seq12  65 TSPDRLRRRFQHLESLKLKGKPRAAMFNLIPEDWGGYVTPWVNEIAENFNCLKSLHFRRM
           **** *** * ******************* **** ** **  *  ** *** *****

Seq1  123 IVSDLDLDRLAKARADDLETLKLDKCSGFTTDGLLSIVTHCRKIKTLLMEESSFSEKDGK
Seq12 125 IVKDSDLEVLARSRGKVLQVLKLDKCSGFSTDGLLHVGRSCRQLKTLFLEESLIVEKDGQ
         ** **  **  *   *  * ********* ***** *  **  ***  *** * ****

Seq1  183 WLHELAQHNTSLEVLNFYMTEFAKISPKDLETIARNCRSLVSVKVGDFEILELVGFFKAA
Seq12 185 WLHELAVNNSVMETLNFYMTDLVKVSFEDLELIARNCRNLASVKISDCEILDLVGFFPAA
         ******  *  * * ***** * * * *** *******  *** *  *** ***** **

Seq1  243 ANLEEFCGGSLNEDIGMPEKYMNLVFPRKLCRLGLSYMGPNEMPILFPPAAQIRKLDLLY
Seq12 245 AVLEFFCGGSFNEQ---PDRYHAVSFPPKLCRLGLTYMGKNEMPIVFPFASLLKKLDLLY
         * ******** **    *  *   *** ****** *** ***** **  *  ******

Seq1  303 ALLETEDHCTLIQKCPNLEVLETRNVIGDRGLEVLAQYCKQLKRLRIERGADEQGMEDEE
Seq12 302 ALLDTEDHCLLIQRCPNLEVLETRNVIGDRGLEVLARSCKRLKRLRIERGADEQGMEDEE
         *** ***** *** ********************** ** ********************

Seq1  363 GLVSQRGLIALAQGCQELEYMAVYVSDITNESLESIGTYLKNLCDFRLVLLDREERITDL
Seq12 362 GVVSQRGLMALAQGCLELEYLAVYVSDITNASLEYIGTYSKNLSDFRLVLLDREERITDL
         * ****** ****** ****  ********  **  ****  ***  *************

Seq1  423 PLDNGVRSLLIGCKKLRRFAFYLKGGLTDLGLSYIGQYSPNVRWMLLGYVGESDEGLME
Seq12 422 PLDNGVRALLRGCEKLRRFALYLRPGGLTDVGLSYIGQYSPNVRWMLLGYVGESDAGLLE
         ******* ** ** ****** ***  ***** ************************ *

Seq1  483 FSRGCPNLQKLEMRGCCFSERAIAAAVTKLPSLRYLWVQGYRABMTGQDLMQMARPYWNI
Seq12 482 FSKGCPSLQKLEMRGCCFSEHALAVTVMQLTSLRYLWVQGYRASQSGRDLLAMARPFWNI
         ** *** ************* * *  *  * * ************  * * **** ***

Seq1  543 ELIPSRRVPEVNQQGEIREMEHPAHILAYYSLAGQRTDCPTTV
Seq12 542 ELIPARRVVMNDQVGEAVVVEHPAHILAYYSLAGPRTDFPETV
         **** ***  * **  *  ***************** *** *
```

A modified COI1 *Theobroma cacao* (cocoa) protein with a valine instead of the alanine at position 383 (of SEQ ID NO: 12) has the following sequence (SEQ ID NO:13).

```
  1 MEENDNKMNK TMTSPVGMSD VVLGCVMPYI HDPKDRDAVS
 41 LVCRRWYELD ALTRKHITIA LCYTTSPDRL RRRFQHLESL
 81 KLKGKPRAAM FNLIPEDWGG YVTPWVNEIA ENFNCLKSLH
121 FRRMIVKDSD LEVLARSRGK VLQVLKLDKC SGFSTDGLLH
161 VGRSCRQLKT LFLEESLIVE KDGQWLHELA VNNSVMETLN
201 FYMTDLVKVS FEDLELIARN CRNLASVKIS DCEILDLVGF
241 FPAAAVLEEF CGGSFNEQPD RYHAVSFPPK LCRLGLTYMG
281 KNEMPIVPF  ASLLKKLDLL YALLDTEDHC LLIQRCPNLE
321 VLETRNVIGD RGLEVLARSC KRLKRLRIER GADEQGMEDE
361 EGVVSQRGLM ALAQGCLELE YLVVYVSDIT NASLEYIGTY
401 SKNLSDFRLV LLDREERITD LPLDNGVRAL LRGCEKLRRF
441 ALYLRPGGLT DVGLSYIGQY SPNVRWMLLG YVGESDAGLL
481 EFSKGCPSLQ KLEMRGCCFS EHALAVTVMQ LTSLRYLWVQ
521 GYRASQSGRD LLAMARPFWN IELIPARRVV MNDQVGEAVV
561 VEHPAHILAY YSLAGPRTDF PETVIPLDPL VAA
```

An example of a nucleotide (cDNA) sequence that encodes the *Theobroma cacao* SEQ ID NO: 12 COI1 protein (NCBI cDNA accession number XM_007009029.2 (GI: 1063526273) is shown below as SEQ ID NO:14.

```
  1 AAGTTTCAGC TCTCCTTCTC TGTTTCACGT TTCTGTGGGC
 41 GCTCTCTACT CTGCCATGCC TTCTCTACAC GACCCATTTT
 81 TGACCCGATT CGTTTAGCCC CGGGGGAAAT TTGCTTCGTT
121 TCAGATCCTA CCGCCGTTTC GTTCTTCCA  CTTCCGTAAA
161 AGAGAAGAGT TCCACGCCCG TTTCTTCTTC TTCTTCTTCT
201 TCAGATCAGT CTTTTTTTTT TTTTGCCGTT TCGCGTTTCT
241 GGTTTATTTG GGCTGAAAAG ATCCGATTCG ATTGTATTGA
281 ATGGAGGAAA ATGATAACAA GATGAACAAA ACGATGACGT
321 CACCAGTCGG TATGTCGGAC GTCGTTTTAG GCTGCGTGAT
361 GCCGTACATC CACGACCCGA AAGACCGGGA CGCAGTTTCG
401 CTCGTGTGCC GACGTTGGTA CGAGCTCGAC GCGTTGACGA
441 GGAAGCACAT AACGATCGCG CTTTGCTACA CGACGAGTCC
481 CGATCGGTTG CGACGTCGTT TCCAGCACTT GGAATCTTTG
521 AAGTTGAAAG GCAAGCCTCG GGCGGCGATG TTCAATTTGA
561 TACCTGAGGA TTGGGGAGGG TACGTGACGC CGTGGGTGAA
601 TGAGATAGCT GAGAATTTTA ATTGCTTGAA ATCTTTGCAT
641 TTTAGAAGGA TGATTGTTAA AGATTCGGAT CTGGAAGTTT
```

-continued

```
 681 TGGCTCGGTC TAGAGGGAAG GTTTTGCAGG TTTTGAAGCT
 721 TGATAAATGC TCTGGTTTCT CTACTGATGG TCTCTTGCAC
 761 GTTGGACGCT CCTGCCGGCA ATTAAAAACC TTGTTCCTGG
 801 AAGAGAGCTT AATTGTTGAG AAAGATGGTC AATGGCTTCA
 841 TGAGCTTGCA GTAAATAACT CAGTTATGGA GACTTTGAAC
 881 TTTTATATGA CAGATCTTGT CAAAGTGAGT TTTGAAGACC
 921 TTGAACTTAT TGCTAGAAAT TGTCGCAACT TGGCCTCTGT
 961 GAAAATTAGC GATTGTGAAA TTTTGGATCT TGTTGGTTTC
1001 TTTCCTGCTG CTGCTGTTTT AGAAGAATTT GTGGTGGTT
1041 CTTTCAATGA GCAACCGGAT AGGTACCATG CTGTATCATT
1081 CCCCCCAAAG TTATGCCGTT TGGGTTTAAC ATACATGGGG
1121 AAGAATGAAA TGCCAATTGT GTTCCCTTTT GCATCCTTGC
1161 TTAAAAAGTT GGATCTCCTC TATGCATTAC TTGACACAGA
1201 AGACCACTGC TTGTTAATTC AGAGATGCCC CAACTTAGAA
1241 GTTCTTGAGA CAAGGAATGT TATTGGAGAT AGAGGATTAG
1281 AAGTTCTTGC TCGAAGTTGT AAGAGACTAA AGAGGCTTAG
1321 AATTGAAAGG GGTGCTGATG AGCAGGGAAT GGAGGATGAA
1361 GAAGGTGTGG TTTCACAAAG AGGATTAATG GCTTTAGCTC
1401 AGGGATGCCT TGAATTGGAA TACTTGGCTG TTTATGTATC
1441 TGACATCACC AATGCATCAT TGGAATACAT TGGGACTTAC
1481 TCAAAAAATC TCTCTGATTT TCGCCTAGTC TTGCTTGACC
1521 GAGAAGAAAG GATAACAGAT TTGCCTCTTG ATAATGGAGT
1561 CCGGGCTCTA TTGAGGGGCT GTGAAAAGCT TAGAAGATTT
1601 GCTCTGTACC TCCGACCTGG TGGTTTGACT GATGTAGGCC
1641 TCAGTTATAT TGGGCAATAC AGTCCGAATG TAAGATGGAT
1681 GCTTCTAGGT TATGTTGGGG AGTCGGATGC CGGGCTTTTG
1721 GAGTTCTCTA AGGGATGCCC AAGCCTGCAG AAACTAGAAA
1761 TGAGGGGTTG TTGCTTCAGT GAGCATGCAC TTGCAGTTAC
1801 TGTGATGCAA TTAACTTCCT TGAGGTATTT GTGGGTGCAA
1841 GGATATAGAG CGTCACAATC AGGTCGTGAT CTTTTAGCAA
1881 TGGCTCGTCC ATTTTGGAAT ATCGAGCTAA TTCCTGCAAG
1921 ACGAGTAGTT ATGAATGATC AGGTTGGAGA GGCTGTTGTG
1961 GTTGAGCATC CGGCTCATAT ACTCGCGTAT TACTCCCTAG
2001 CTGGACCAAG AACAGATTTT CCAGAAACTG TTATTCCTTT
2041 GGATCCATTA GTTGCTGCGT AGAGCTGTAA ATATGACCTA
2081 TTTTTCGAAG TGTCCATTTT TCCCATCCAC GTTCTGTCTA
2121 TAAAGTTTCT GCACCTTTCT CTTTTCTCTT TTCCTTTCCT
2161 TTTTGTTTAG AGGGTTTCCA ATTTGATATT TCATTTTCGA
2201 TTTTATTTCT AGACTTTGTC CTGTAATAAG ATTGTGTTTT
2241 CTTCTGTAAT TTTGAAAGCA CTTGCACTCT TGGTGGGCTA
2281 CTGTTTTTGT CCCTTGTCCC TGGAAAAAGT AGTGAATGAC
2321 TCTTAACGGA ATA
```

An example of a COI1 protein from *Prunus persica* (peach) with NCBI accession number XP_007220435.1 (GI:596048914) has the following sequence (SEQ ID NO:15).

```
  1 MEDRNVRSGM SDVVIGCVMP YLHDAKDRDA VSLVCRRWYE
 41 LDALTRKHVT IALCYTTSPD RLRRRFQHLE SLKLKGKPRA
 81 AMFNLIPEDW GGFVTPWVKE IAESFNRLKS LHFRRMIVKD
121 SDLELLAQSR GRVLQALKLD KCSGFSTDGL LHIGRSCRNL
161 RTLFLEESSI DENDGQWLHE LALNNSVLET LNFYMTDLIK
201 VKFEDLELIA KNCRSLTSVK TSDCEILELV GFFRSASVLE
241 EFCGGFFNEQ SERYSVVSLP QKLCRLGLTY MGKNEMPIVF
281 PYATLLKKLD LLYALLDTED HCTLIQRCPN LEVLETRNVI
321 GDRGLEVLAR SCKRLRRLRI ERGADEQGME DEEGVVSQRG
361 LIALAQGCLE LEYLAVYVSD ITNASLEFIG TYSKNLCDFR
401 LVLLDREETI TDLPLDNGVR ALLRGCDKLR RFALYLRAGG
441 LTDLGLSYVG QYSQNVRWML LGYVGESDAG LLEFSKGCPS
481 LQKLEMRGCC FSERALADAV MQLTSLRYLW VQGYRGSASG
521 RDVLAMARPY WNIELIPPRR VVDQQGEGVV MEHPAHILAY
561 YSLAGQRTDY PNTVIPVDPA SFITS
```

A comparison of the *Arabidopsis thaliana* COI1 SEQ ID NO:1 sequence and the *Prunus persica* COI1 SEQ ID NO:15 sequence is shown below, illustrating that the two proteins have at least 73% sequence identity. In addition, the location of the alanine at position 384 that can be replaced, for example with a valine, to generate a modified COI1 protein is also identified in bold and with underlining. As illustrated, this alanine is at about position 375 in the *Prunus persica* COI1 SEQ ID NO:15 sequence.

```
74.3% identity in 568 residues overlap; Score: 2187.0; Gap frequency:
0.9%
Seq1   18 DDVIEQVMTYITDPKDRDSASLVCRRWFKIDSETREHVTMALCYTATPDRLSRRFPNLRS
Seq15  12 DVVIGCVMPYLHDAKDRDAVSLVCRRWYELDALTRKHVTIALCYTTSPDRLRPRFQHLES
              * **  ** *  * ****  *******    *  ** *** *****  **** ***  * *

Seq1   78 LKLKGKPRAAMFNLIPENWGGYVTPWVTEISNNLRQLKSVHFRRMIVSDLDLDRLAKARA
Seq15  72 LKLKGKPRAAMFNLIPEDWGGEVTPWVKEIAESFNRLKSLHFRRMIVKDSDLELLAQSRG
          *****************  ***  ***** **    ***  *******  *  ** **  *
```

```
Seq1   138 DDLETLKLDKCSGFTTDGLLSIVTHCRKIKTLLMEESSFSEKDGKWLHELAQHNTSLEVL
Seq15  132 RVLQALKLDKCSGFSTDGLLHIGRSCRNLRTLFLEESSIDENDGQWLHELALNNSVLETL
           * ********  *****  *   **    **   **** * ** ****** *  ** *

Seq1   198 NFYMTEFAKISPKDLETIARNCRSLVSVKVGDFEILELVGFFKAAANLEEFCGGSLNEDI
Seq15  192 NFYMTDLIKVKFEDLELIAKNCRSLTSVKTSDCEILELVGFFRSASVLEEFCGGFFNEQ-
           *****  *    ***  ***** ***     ********* *    *******  **

Seq1   258 GMPEKYMNVFPRKLCRLGLSYMGPNEMPILFPPAAQIRKLDLLYALLETEDHCTLIQKC
Seq15  251 -SERYSVVSLPQKLCRLGLTYMGKNEMPIVFPYATLLKKLDLLYALLDTEDHCTLIQRC
            *  *   *  ******* **** ***** **  *  ********* *********  *

Seq1   318 PNLEVLETRNVIGDRGLEVLAQYCKQLKRLRIERGADEQGMEDEEGLVSQRGLIALAQGC
Seq15  309 PNLEVLETRNVIGDRGLEVLARSCKRLRRLRIERGADEQGMEDEEGVVSQRGLIALAQGC
           ********************  ** *  *  ************** *************

Seq1   378 QELEYM<u>A</u>VYVSDITNESLESIGTYLKNLCDFRLVLLDREERITDLPLDNGVRSLLIGCKK
Seq15  369 LELEYL<u>A</u>VYVSDITNASLEFIGTYSKNLCDFRLVLLDREETITDLPLDNGVRALLRGCDK
            ****  ********  *** ****  *************** ************   **  **

Seq1   438 LRRFAFYLRQGGLTDLGLSYIGQYSPNVRWMLLGYVGESDEGLMEFSRGCPNLQKLEMRG
Seq15  429 LRRFALYLRAGGLTDLGLSYVGQYSQNVRWMLLGYVGESDAGLLEFSKGCPSLQKLEMRG
           ***** *** **********  **** ************ ** *** *** *******

Seq1   498 CCFSERAIAAAVTKLPSLRYLWVQGYRASMTGQDLMQMARPYWNIELIPSRRVPEVNQQG
Seq15  489 CCFSERALADAVMQLTSLRYLWVQGYRGSASGRDVLAMARPYWNIELIPPRRV--VDQQG
           *******    **  * ********* *  *   *  ************* ***  * ***

Seq1   558 EIREMEHPAHILAYYSLAGQRTDCPTTV
Seq15  547 EGVVMEHPAHILAYYSLAGQRTDYPNTV
            *  ********************  * **
```

An example of a modified COI1 *Prunus persica* (peach) protein with a valine instead of an alanine at position 375 has the following sequence (SEQ ID NO:16).

```
  1 MEDRNVRSGM SDVVIGCVMP YLHDAKDRDA VSLVCRRWYE
 41 LDALTRKHVT IALCYTTSPD RLRRRFQHLE SLKLKGKPRA
 81 AMFNLIPEDW GGFVTPWVKE IAESFNRLKS LHFRRMIVKD
121 SDLELLAQSR GRVLQALKLD KCSGFSTDGL LHIGRSCRNL
161 RTLFLEESSI DENDGQWLHE LALNNSVLET LNFYMTDLIK
201 VKFEDLELIA KNCRSLTSVK TSDCEILELV GFFRSASVLE
241 EFCGGFFNEQ SERYSVVSLP QKLCRLGLTY MGKNEMPIVF
281 PYATLLKKLD LLYALLDTED HCTLIQRCPN LEVLETRNVI
321 GDRGLEVLAR SCKRLRRLRI ERGADEQGME DEEGVVSQRG
361 LIALAQGCLE LEYL<u>V</u>VYVSD ITNASLEFIG TYSKNLCDFR
401 LVLLDREETI TDLPLDNGVR ALLRGCDKLR RFALYLRAGG
441 LTDLGLSYVG QYSQNVRWML LGYVGESDAG LLEFSKGCPS
481 LQKLEMRGCC FSERALADAV MQLTSLRYLW VQGYRGSASG
521 RDVLAMARPY WNIELIPPRR VVDQQGEGVV MEHPAHILAY
561 YSLAGQRTDY PNTVIPVDPA SFITS
```

An example of a nucleotide (cDNA) sequence that encodes the *Prunus persica* SEQ ID NO:15 COI1 protein (NCBI cDNA accession number XM_007220373.1 (GI: 596048913)) is shown below as SEQ ID NO:17.

```
   1 ATGGAGGATC GAAACGTGCG AAGTGGAATG TCCGATGTGG
  41 TGATAGGCTG CGTGATGCCA TATCTTCACG ACGCTAAGGA
  81 CCGCGACGCA GTGTCGTTGG TGTGCCGGCG ATGGTACGAG
 121 CTCGACGCTC TCACGCGCAA GCACGTGACC ATTGCTCTCT
 161 GCTACACCAC GAGCCCCGAT CGGTTGCGGA GGCGATTTCA
 201 GCACCTCGAG TCCCTGAAGC TGAAAGGGAA GCCGAGAGCG
 241 GCGATGTTCA ATCTGATACC GGAGGATTGG GGAGGCTTTG
 281 TGACGCCGTG GGTGAAGGAG ATCGCTGAGT CCTTCAATCG
 321 CTTGAAGTCT CTGCACTTTC GGCGAATGAT TGTTAAGGAT
 361 TCGGACTTGG AGCTCTTGGC TCAGTCCCGT GGGCGCGTGC
 401 TACAGGCGCT CAAGCTTGAC AAGTGCTCTG GCTTCTCCAC
 441 CGATGGCCTT TTGCACATCG GCCGCTCCTG CAGGAATTTG
 481 AGAACCTTGT TTTTGGAAGA GAGCTCCATA GATGAGAATG
 521 ATGGTCAATG GCTACATGAG CTTGCTTTGA ACAACTCTGT
 561 GTTGGAGACT TTGAATTTTT ATATGACAGA TCTTATCAAA
 601 GTCAAATTTG AAGACCTTGA ACTCATTGCA AAAAACTGTC
 641 GCTCCTTAAC CTCTGTGAAA ACTAGCGATT GCGAAATCTT
 681 GGAACTCGTG GGCTTCTTCC GTTCTGCAAG CGTATTAGAA
 721 GAATTTTGTG GCGGTTTCTT CAACGAGCAA TCAGAGAGGT
 761 ACTCTGTTGT ATCGTTACCC CAAAAATTAT GCCGTTTGGG
 801 TCTAACGTAC ATGGGAAAGA ATGAAATGCC AATAGTATTC
 841 CCATATGCAA CCCTTCTCAA AAAGCTGGAT CTCCTTTATG
 881 CATTGCTCGA CACTGAGGAC CATTGCACAC TAATTCAAAG
 921 GTGCCCCAAC CTGGAAGTGC TTGAGACAAG GAATGTTATT
 961 GGAGATAGAG GACTAGAAGT TCTTGCTCGG AGTTGCAAGA
1001 GATTGAGGAG GCTCCGAATT GAGCGAGGTG CAGATGAGCA
```

```
1041 AGGCATGGAG GATGAAGAAG GTGTTGTTTC ACAAAGGGGT
1081 TTGATAGCAT TGGCACAGGG CTGCCTGGAA CTTGAGTACT
1121 TGGCTGTGTA TGTGTCAGAT ATCACAAACG CATCTCTGGA
1161 ATTCATTGGG ACTTACTCTA AGAATCTTTG TGATTTTCGA
1201 CTTGTCTTGC TTGACCGAGA AGAGACGATA ACAGATTTAC
1241 CACTTGACAA TGGGGTTCGA GCTCTTTTGA GGGGCTGTGA
1281 TAAGCTCAGA AGGTTTGCTC TGTATCTCCG TGCTGGGGGC
1321 TTGACCGATT TGGGACTTAG TTATGTTGGC CAGTATAGTC
1361 AAAATGTGAG ATGGATGCTT CTGGGTTATG TTGGGGAATC
1401 TGATGCAGGG CTTTTGGAGT TCTCTAAAGG TTGCCCTAGC
1441 CTGCAAAAAT TGGAAATGAG GGGCTGTTGC TTCAGTGAGC
1481 GTGCACTGGC TGATGCAGTA ATGCAGCTGA CTTCCCTTAG
1521 GTACTTGTGG GTGCAGGGGT ACAGAGGATC TGCTTCGGGT
1561 CGTGATGTTT TGGCAATGGC TCCGCCGTAT TGGAATATTG
1601 AGTTAATTCC CCCGAGACGA GTTGTTGATC AGCAGGGGGA
1641 GGGAGTAGTG ATGGAGCATC CAGCCCATAT ACTTGCATAC
1681 TACTCACTTG CTGGACAAAG AACAGATTAT CCAAATACTG
1721 TTATCCCCGT GGATCCAGCA TCTTTTATTA CCTCCTAGAG
1761 TT
```

An example of a COI1 protein from *Malus domestica* (apple) with NCBI accession number XP_008392915.1 (GI: 658000912) has the following sequence (SEQ ID NO:18).

```
  1 MEDRSVRCRI SDVVMDCVMP YLHDPKDRDA VSLVCKRWYE
 41 LDALTRKHVT IALCYTTTPD RLRQRFQHLE SLKLKGKPRA
 81 AMFNLIPEDW GGFVTPWVME IANSFHRLKC LHFRRMIVSD
121 SDLELLADSR GRVLQVLKLD KCSGFTTGGL LHIGRSCRNL
161 RTLFLEESSI VEEDGDWLHA LAVNNTVLET LNFYMTDLIK
201 VKFEDLELIA KNCRSLTSVK ISDCEILELV GFFRHAAVLE
241 EFCGGSFNDQ SESYSVVTLP QKLCRLGLTY MGKNEMQIVF
281 PFATLLKKLD LLYALLDTED HCTLIQRCPN LEVLETRNVI
321 GDRGLDVLAR SCKRLRRLRI ERGADEGMED EEGVVSQRGL
361 MALAQGCLEL EYLAVYVSDI TNASLEYIGT YSKNLSDFRL
401 VLLDREETIT DLPLDNGVRA LLRGCHKLRR FALYLRPGGL
441 TDLGLSYIGR YSPNVRWMLL GYVGESDAGL LEFSKGCPSL
481 QKLEMRGCCF SERALAHAVM QLTSLRYLWV QGYRGSATGR
521 DLLAMARPFW NIELIPPRRV DVPDQHGEAL AVEHPAHILA
561 YYSLAGPRTD CPDTVIPVDP ASLLIS
```

A comparison of the *Arabidopsis thaliana* COI1 SEQ ID NO:1 sequence and the *Malus domestica* (apple) COI1 SEQ ID NO:18 sequence is shown below, illustrating that the two proteins have at least 72% sequence identity. In addition, the location of the alanine at position 384 that can be replaced, for example with a valine, to generate a modified COI1 protein is also identified in bold and with underlining. As illustrated, this alanine is at about position 374 in the *Malus domestica* COI1 SEQ ID NO:18 sequence.

```
73.6% identity in 568 residues overlap; Score: 2171.0;
Gap frequency: 0.7%
Seq1   18 DDVIEQVMTYITDPKDRDSASLVCRRWFKIDSETREHVTMALCYTATPDRLSRRFPNLRS
Seq18  12 DVVMDCVMPYLHDPKDRDAVSLVCKRWYELDALTRKHVTIALGYTTTPDRLRQRFQHLES
          *  *    ** *  ****** **** ** *   * ** *** ***** *****   *  * *

Seq1   78 LKLKGKPRAAMFNLIPENWGGYVTPWVTEISNNLRQLKSVHFRRMIVSDLDLDRLAKARA
Seq18  72 LKLKGKPRAAMFNLIPEDWGGFVTPWVMEIANSFHRLKCLHFRRMIVSDSDLELLADSRG
          ***************** *** ***** **  *  ** * ********* **  **  *

Seq1  138 DDLETLKLDKCSGFTTDGLLSIVTHCRKIKTLLMEESSFSEKDGKWLHELAQHNTSLEVL
Seq18 132 RVLQVLKLDKCSGFTTGGLLHIGRSCRNLRTLFLEESSIVEEDGDWLHALAVNNTVLETL
             * **********  *** *   ** ** ****  * *** ***  ** **  *

Seq1  198 NFYMTEFAKISPKDLETIARNCRSLVSVKVGDFEILELVGFFKAAANLEEFCGGSLNEDI
Seq18 192 NFYMTDLIKVKFEDLELIAKNCRSLTSVKISDCEILELVGFFRHAAVLEEFCGGSFNDQ-
          *****   *   *  *** ** *** *** * ********   ** ********  *

Seq1  258 GMPEKYMNLVFPRKLCRLGLSYMGPNEMPILFPFAAQIRKLDLLYALLETEDHCTLIQKC
Seq18 251 --SESYSVVTLPQKLCRLGLTYMGKNEMQIVFPFATLLKKLDLLYALLDTEDHCTLIQRC
            *  *       ******** *** *** *  ****   ******** ********  *

Seq1  318 PNLEVLETRNVIGDRGLEVLAQYCKQLKRLRIERGADEQGMEDEEGLVSQRGLIALAQGC
Seq18 309 PNLEVLETRNVIGDRGLDVLARSCKRLRRLRIERGADE-GMEDEEGVVSQGLMALAQGC
          *****************  *** *  ** ** ******* ******  *** *******

Seq1  378 QELEYMAVYVSDITNESLESIGTYLKMLCDFRLVLLDREERITDLPLDNGVRSLLIGCKK
Seq18 368 LELEYLAVYVSDITNASLEYIGTYSKMLSDFRLVLLDREETITDLPLDNGVRALLRGCHK
           ****  ******** ***  ****   ***  ********  ***********  **  **

Seq1  438 LRRFAFYLRQGGLTDLGLSYIGQYSPNVRWMLLGYVGESDEGLMEFSRGCPNLQKLEMRG
Seq18 428 LRRFALYLRPGGLTDLGLSYIGRYSPNVRWMLLGYVGESDAGLLEFSKGCPSLQKLEMRG
          ***** *** ************ **************** ** *** *** ********

Seq1  498 CCFSERAIAAAVTKLPSLRYLWVQGYRASMTGQDLMQMARPYWNIELIPSRRVPEVNQOG
Seq18 488 CCFSERALAHAVMQLTSLRYLWVQGYRGSATGRDLLAMARPFWNIELIPPRRVDVPDQHG
          *******   **   * ******** * * ** ** * ****  *********  *  *
```

```
Seq1   658 EIREMEHPAHILAYYSLAGQRTDCPTTV
Seq18  548 EALAVEHPAHILAYYSLAGPRTDCPDTV
            *   ************** ***** **
```

An example of a modified *Malus domestica* (apple) COI1 protein with a valine instead of a glutamic acid at about position 374 has the following sequence (SEQ ID NO:19).

```
  1 MEDRSVRCRI SDVVMDCVMP YLHDPKDRDA VSLVCKRWYE

41 LDALTRKHVT IALCYTTTPD RLRQRFQHLE SLKLKGKPRA

81 AMFNLIPEDW GGFVTPWVME IANSFHRLKC LHFRRMIVSD

121 SDLELLADSR GRVLQVLKLD KCSGFTTGGL LHIGRSCRNL

161 RTLFLEESSI VEEDGDWLHA LAVNNTVLET LNFYMTDLIK

201 VKFEDLELIA KNCRSLTSVK ISDCEILELV GFFRHAAVLE

241 EFCGGSFNDQ SESYSVVTLP QKLCRLGLTY MGKNEMQIVF

281 PFATLLKKLD LLYALLDTED HCTLIQRCPN LEVLETRNVI

321 GDRGLDVLAR SCKRLRRLRI ERGADEGMED EEGVVSQRGL

361 MALAQGCLEL VYLAVYVSDI TNASLEYIGT YSKNLSDFRL

401 VLLDREETIT DLPLDNGVRA LLRGCHKLRR FALYLRPGGL

441 TDLGLSYIGR YSPNVRWMLL GYVGESDAGL LEFSKGCPSL

481 QKLEMRGCCF SERALAHAVM QLTSLRYLWV QGYRGSATGR

521 DLLAMARPFW NIELIPPRRV DVPDQHGEAL AVEHPAHILA

561 YYSLAGPRTD CPDTVIPVDP ASLLIS
```

An example of a nucleotide (cDNA) sequence that encodes the *Malts domestica* SEQ ID NO:18 COI1 protein (NCBI cDNA accession number XM_008394693.2 (GI: 1039847064)) is shown below as SEQ ID NO:20.

```
   1 GCCCGCTTCC CTTTTCAATC CCCCCTCCCT TATGTGTTTG
  41 TGAGGCGCAT AATTATTCTT GAACACCACT AATAACTGAA
  81 AGTCCGATCC AATAGCCGCC GGATTCCTCC CCGGACGATC
 121 CCCACCGTAC GTTTCAGATC CGTCTTCTCA GACCATGTGC
 161 TTCGAGTCCA CGCCGACTCC ATGCTCCGGC GCTCCTCCAC
 201 TGGTCGCCCT GCTCCGCCGT CTTCGATCCG ATTGGTCTGT
 241 TTTCTGCGCG AGCTTCTCGT AGATCGTGCT TTCTAGCTCC
 281 TCTCTCTTCC CTCTTGTTCC TGCTCGTTTC TTGACACGTT
 321 GCGGCGTTTC TCTGAGATTC TGATTCTGTA AACGTCGGTG
 361 CCACGGTGTC CTTTTAGTTC TTTTTTTTGA TTGGATTTGG
 401 AAATATAACA GCTTAGGGTT CCGATTTTGG AAATCCAGTT
 441 TCTATTTCTG GAAATATTTG GAGTTGAGGA TTCGGAGCTC
 481 CGAAACCCG ATCTTGAGAG AATTCGAATC TTTTTCCACT
 521 TTTGACTCTG AAATTTTTTT GTTAGAAATA GCAGTAGAGT
 561 TTTTTCAGTG AGTATTTTCA TCGCCGACGT TTCTTTTTAG
 601 CGATGGAGGA TCGAAGCGTG CGGTGTAGGA TTTCCGACGT
 641 CGTAATGGAC TGCGTGATGC CGTATCTCCA CGACCCCAAG
 681 GACCGTGACG CCGTGTCGTT GGTGTGCAAG CGGTGGTACG
 721 AGCTCGACGC GCTCACGCGG AAGCACGTGA CCATCGCGCT
 761 CTGCTACACC ACGACCCCGG ATCGGCTGCG GCAGCGGTTT
 801 CAGCACCTGG AGTCGCTGAA GCTGAAGGGG AAGCCGAGGG
 841 CGGCGATGTT CAATCTGATT CCCGAGGACT GGGGAGGGTT
 881 TGTAACGCCG TGGGTGATGG AGATCGCCAA CTCGTTCCAC
 921 CGCTTGAAGT GTCTGCACTT TCGGCGGATG ATTGTTAGTG
 961 ATTCGGACCT GGAGCTCCTG GCTGACTCAC GTGGGCGCGT
1001 GCTTCAGGTG CTTAAGCTCG ACAAGTGCTC AGGGTTTACC
1041 ACCGGTGGGC TTTTGCACAT CGGCCGCTCC TGCAGGAATT
1081 TGAGGACCTT GTTTTTGGAA GAGAGCTCCA TAGTTGAGGA
1121 AGATGGCGAC TGGCTACACG CGCTTGCTGT AAACAATACT
1161 GTCCTGGAGA CTCTGAATTT TTATATGACC GATCTTATCA
1201 AAGTCAAATT CGAAGACCTT GAACTGATAG CCAAAAACTG
1241 CCGCTCCTTA ACCTCTGTGA AAATTAGTGA TTGCGAAATC
1281 TTGGAACTGG TTGGCTTCTT CCGTCATGCA GCTGTCTTGG
1321 AAGAATTTTG TGGGGGTTCC TTCAACGATC AATCCGAGAG
1361 TTACTCTGTT GTAACGTTAC CCCAAAAACT TTGCCGTCTC
1401 GGTCTAACAT ACATGGGAAA GAATGAAATG CAAATAGTGT
1441 TCCCATTTGC AACCCTTCTC AAAAAGCTCG ATCTCCTTTA
1481 TGCATTGCTG GACACTGAGG ACCATTGCAC ATTAATTCAG
1521 AGGTGCCCCA ACCTGGAAGT TCTGGAGACA AGGAATGTTA
1561 TTGGAGATAG AGGACTAGAT GTTCTTGCTC GGAGTTGCAA
1601 GAGACTAAGG AGGCTCCGAA TTGAGCGGGG TGCAGATGAA
1641 GGCATGGAGG ACGAAGAAGG TGTTGTTTCC CAACGGGGTC
1681 TGATGGCCCT GGCGCAGGGA TGCCTAGAGC TCGAATACCT
1721 GGCTGTTTAT GTATCGGACA TCACCAATGC ATCTCTGGAA
1761 TACATTGGGA CTTACTCCAA AAATCTCTCT GATTTTCGCC
1801 TTGTCTTACT TGACCGGGAA GAGACAATAA CAGATTTGCC
1841 ACTTGACAAT GGGGTTCGAG CACTTTTGAG GGGATGCCAT
1881 AAGCTTCGAA GGTTTGCTCT GTATCTCCGT CCTGGGGGT
1921 TGACTGACCT CGGACTGAGT TACATTGGCC GGTACAGTCC
1961 GAATGTGAGA TGGATGCTTC TGGGTTATGT TGGGGAATCT
2001 GATGCAGGGC TTTTGGAGTT CTCAAAGGGT TGCCCTAGCC
2041 TGCAAAAATT GGAAATGAGG GGTTGCTGCT TCAGCGAGCG
2081 TGCACTCGCT CATGCAGTAA TGCAACTGAC TTCCCTTAGG
2121 TACTTGTGGG TGCAGGGGTA CAGAGGATCT GCTACTGGTC
```

-continued

```
2161 GCGACCTTTT GGCAATGGCT CGCCCGTTTT GGAATATTGA
2201 GTTGATTCCT CCCAGACGAG TTGATGTTCC TGATCAGCAT
2241 GGGGAGGCAT TAGCGGTCGA GCATCCAGCC CATATACTTG
2281 CATACTACTC ACTTGCTGGA CCGAGAACAG ATTGTCCAGA
2321 TACTGTTATT CCCGTGGATC CGGCATCTTT ACTCATCTCC
2361 TAGAGCTGTA CATACAACCT CTTTTTTTCT TCCACAAGCA
2401 GTCATTTTCT TACCACGCCT TGTTTATAAA TTCATGTAAC

2441 TTTTTACTT TTGGTTAAGA GGGTTTCGAT TTCAAGTTTC

2481 AATTATATTT CTAGACCTTA GTTCTGTAAT AAGTTTGAGT
2521 TACCCTGTGT AATCTGAAAG CACTTGCACT CTTTGATCCG
2561 GAA
```

An example of a COI1 protein from *Glycine max* (soybean) with NCBI accession number NP_001238590.1 (GI: 351724347) has the following sequence (SEQ ID NO:21).

```
  1 MTEDRNVRKT RVVDLVLDCV IPYIDDPKDR DAVSQVCRRW

41 YELDSLTRKH VTIALCYTTT PARLRRRFPH LESLKLKGKP

81 RAAMFNLIPE DWGGHVTPWV KEISQYFDCL KSLHFRRMIV
```

-continued

```
121 KDSDLRNLAR DRGHVLHSLK LDKCSGFTTD GLFHIGRFCK
161 SLRVLFLEES SIVEKDGEWL HELALNNTVL ETLNFYLTDI
201 AVVKIQDLEL LAKNCPNLVS VKLTDSEILD LVNFFKHASA
241 LEEFCGGTYN EEPEKYSAIS LPAKLCRLGL TYIGKNELPI
281 VFMFAAVLKK LDLLYAMLDT EDHCMLIQKC PNLEVLETRN
321 VIGDRGLEVL GRCCKRLKRL RIERGDDDQG MEDEEGTVSH
361 RGLIALSQGC SELEYMAVYV SDITNASLEH IGTHLKNLCD
401 FRLVLLDHEE KITDLPLDNG VRALLRGCNK LRRFALYLRR
441 GGLTDVGLGY IGQYSPNVRW MLLGYVGESD AGLLEFSKGC
481 PSLQKLEMRG CSFFSERALA VAATQLTSLR YLWVQGYGVS
521 PSGRDLLAMA RPFWNIELIP SRKVAMNTNS DETVVVEHPA
561 HILAYYSLAG QRSDFPDTVV PLDTATCVDT
```

A comparison of the *Arabidopsis thaliana* COI1 SEQ ID NO:1 sequence and the *Glycine max* COI1 SEQ ID NO:21 sequence is shown below, illustrating that the two proteins have at least 70% sequence identity. In addition, the location of the alanine at position 384 that can be replaced, for example with a valine, to generate a modified COI1 protein is also identified in bold and with underlining. As illustrated, this alanine is at about position 377 in the *Glycine max* COI1 SEQ ID NO:21 sequence.

```
71.8% identity in 570 residues overlap; Score: 2115.0;
Gap frequency: 0.7%
Seq1    17 VDDVIEQVMTYITDPKDRDSASLVCRRWFKIDSETREHVTMALCYTATPDRLSRRFPNLR
Seq21   13 VDLVLDVIPYIDDPKDRDAVSQNCRRWYELDSLTRKHVTIALCYTTTPARLRRRFPHLE
           ** *   **  ** ****  * *****   ** ** *** ***** ** ** **** *

Seq1    77 SLKLKGKPRAAMFNLIPENWGGYVTPWVTEISNNLRQLKSVHFRRMIVSDLDLDRLAKAR
Seq21   73 SLKLKGKPRAAMFNLIPEDWGGHVTPWVKEISQYFDCLKSLHFRRMIVKDSDLRNLARDR
           ****************** *** ***** *** ***     ******* * **   **   *

Seq1   137 ADDLETLKLDKCSGFTTDGLLSIVTHCRKIKTLLMEESSFSEKDGKWLHELAQHNTSLEV
Seq21  133 GHVLHSLKLDKCSGFTTDGLFHIGRFCKSLRVLFLEESSIVEKDGEWLHELALNNTVLET
              *  **************  *    *      *  ****  **** ******   ** **

Seq1   197 LNFYMTEFAKISPKDLETIARNCRSLVSVKVGDFEILELVGFFKAAANLEEFCGGSLNED
Seq21  193 LNFYLTDIAVVKIQDLELLAKNCPNLVSVKLTDSEILDLVNFFKHASALEEFCGGTYNEE
           **** *  *      ***  * **  *****  * *** ** *** *  *******   **

Seq1   257 IGMPEKYMNLVFPRKLCRLGLSYMGPNEMPILFPFAAQIRKLDLLYALLETEDHCTLIQK
Seq21  253 ---PEKYSAISLPAKLCRLGLTYIGKNELPIVFMFAAVLKKLDLLYAMLDTEDHCMLIQK
              ****      * ******* * * ** ** * ***    ******* * ***** ****

Seq1   317 CPNLEVLETRNVIGDRGLEVLAQYCKQLKRLRIERGADEQGMEDEEGLVSQRGLIALAQG
Seq21  310 CPNLEVLETRNVIGDRGLEVLGRCCKRLKRLRIERGDDDQGMEDEEGTVSHRGLIALSQG
           *********************    ** ********* * ******** ** ****** **

Seq1   377 CQELEYMAVYVSDITNESLESIGTYLKYLCDFRLVLLDREERITDLPLDNGVRSLLIGCK
Seq21  370 CSELEYMAVYVSDITNASLEHIGTHLKNLCDFRLVLLDHEEKITDLPLDNGVRALLRGCN
           * ************** *** *** ************* ** *********** ** **

Seq1   437 KLRRFAFYLRQGGLTDLGLSYIGQYSPNVRWMLLGYVGESDEGLMEFSRGCPNLQKLEMR
Seq21  430 KLRRFALYLRRGGLTDVGLGYIGQYSPNVRWMLLGYVGESDAGLLEFSKGCPSLQKLEMR
           ****** *** ***** ** ********************* ** *** *** *******

Seq1   497 GCCF-SERAIAAAVTKLPSLRYLWVQGYRASMTGQDLMQMARPYWNIELIPSRRVPEVNQ
Seq21  490 GCSFFSERALAVAATQLTSLRYLWVQGYGVSPSGRDLLAMARPFWNIELIPSRKVAMNTN
           ** * **** * * * * *********  *   * **   **** ********* *

Seq1   556 QGEIREMEHPAHILAYYSLAGQRTDCPTTV
Seq21  550 SDETVVVEHPAHILAYYSLAGQRSDFPDTV
            *    **************** * * **
```

(In the alignment, the alanine A at Seq1 position 384 and Seq21 position 377 is printed in bold and underlined.)

An example of a modified *Glycine max* (soybean) COI1 protein with a valine instead an alanine at about position 377 has the following sequence (SEQ ID NO:22).

```
  1 MTEDRNVRKT RVVDLVLDCV IPYIDDPKDR DAVSQVCRRW
 41 YELDSLTRKH VTIALCYTTT PARLRRRFPH LESLKLKGKP
 81 RAAMFNLIPE DWGGHVTPWV KEISQYFDCL KSLHFRRMIV
121 KDSDLRNLAR DRGHVLHSLK LDKCSGFTTD GLFHIGRFCK
161 SLRVLFLEES SIVEKDGEWL HELALNNTVL ETLNFYLTDI
201 AVVKIQDLEL LAKNCPNLVS VKLTDSEILD LVNFFKHASA
241 LEEFCGGTYN EEPEKYSAIS LPAKLCRLGL TYIGKNELPI
281 VFMFAAVLKK LDLLYAMLDT EDHCMLIQKC PNLEVLETRN
321 VIGDRGLEVL GRCCKRLKRL RIERGDDDQG MEDEEGTVSH
361 RGLIALSQGC SELEYMVVYV SDITNASLEH IGTHLKNLCD
401 FRLVLLDHEE KITDLPLDNG VRALLRGCNK LRRFALYLRR
441 GGLTDVGLGY IGQYSPNVRW MLLGYVGESD AGLLEFSKGC
481 PSLQKLEMRG CSFFSERALA VAATQLTSLR YLWVQGYGVS
521 PSGRDLLAMA RPFWNIELIP SRKVAMNTNS DETVVVEHPA
561 HILAYYSLAG QRSDFPDTVV PLDTATCVDT
```

An example of a nucleotide (cDNA) sequence that encodes the *Glycine max* SEQ ID NO:21 COI1 protein (NCBI cDNA accession number NM_001251661.1 (GI: 351724346)) is shown below as SEQ ID NO:23.

```
   1 ATGACGGAGG ATCGGAACGT GCGGAAGACA CGTGTGGTCG
  41 ACCTGGTCCT CGACTGTGTC ATCCCTTACA TCGACGACCC
  81 CAAGGACCGC GACGCCGTCT CACAGGTCTG CCGACGCTGG
 121 TACGAACTCG ACTCCCTCAC TCGGAAGCAC GTCACCATCG
 161 CGCTCTGCTA CACCACCACG CCGGCGCGCC TCCGCCGCCG
 201 CTTCCCGCAC CTTGAGTCGC TCAAGCTCAA GGGCAAGCCC
 241 CGAGCAGCAA TGTTCAACTT GATACCCGAG GATTGGGGAG
 281 GCCACGTCAC CCCATGGGTC AAGGAGATTT CTCAGTACTT
 321 CGATTGCCTC AAGAGTCTCC ACTTCCGCCG TATGATTGTC
 361 AAAGATTCCG ATCTTCGGAA TCTCGCTCGT GACCGCGGCC
 401 ACGTGCTTCA CTCTCTCAAG CTTGACAAGT GCTCCGGTTT
 441 CACCACCGAT GGTCTTTTCC ATATCGGTCG CTTTTGCAAG
 481 AGTTTAAGAG TCTTGTTTTT GGAGGAAAGC TCAATTGTTG
 521 AGAAGGACGG AGAATGGTTA CACGAGCTTG CTTTGAATAA
 561 TACAGTTCTT GAGACTCTCA ATTTTTACTT GACAGATATT
 601 GCTGTTGTGA AGATTCAGGA CCTTGAACTT TTAGCTAAAA
 641 ATTGCCCCAA CTTAGTGTCT GTGAAACTTA CTGACAGTGA
 681 AATACTGGAT CTTGTGAACT TCTTTAAGCA TGCCTCTGCA
 721 CTGGAAGAGT TTTGTGGAGG CACCTACAAT GAAGAACCAG
 761 AAAAATACTC TGCTATATCA TTACCAGCAA AGTTATGTCG
 801 ATTGGGTTTA ACATATATTG GAAAGAATGA GTTGCCCATA
 841 GTGTTCATGT TTGCAGCCGT ACTAAAAAAA TTGGATCTCC
 881 TCTATGCAAT GCTAGACACG GAGGATCATT GCATGTTAAT
 921 CCAAAAGTGT CCAAATCTGG AAGTCCTTGA GACAAGGAAT
 961 GTAATTGGAG ACAGAGGGTT AGAGGTTCTT GGTCGTTGTT
1001 GTAAGAGGCT AAAAAGGCTT AGGATTGAAA GGGGTGATGA
1041 TGATCAAGGA ATGGAGGATG AAGAAGGTAC TGTGTCCCAT
1081 AGAGGGCTAA TAGCCTTGTC ACAGGGCTGT TCAGAGCTTG
1121 AATACATGGC TGTTTATGTG TCTGATATTA CAAATGCATC
1161 TCTGGAACAT ATCGGAACTC ACTTGAAGAA CCTCTGCGAT
1201 TTTCGCCTTG TGTTGCTTGA CCACGAAGAG AAAATAACTG
1241 ATTTGCCACT TGACAATGGG GTGAGGGCTC TACTGAGGGG
1281 CTGTAACAAG CTGAGGAGAT TTGCTCTATA TCTCAGGCGT
1321 GGCGGGTTGA CCGATGTAGG TCTTGGTTAC ATTGGACAGT
1361 ACAGTCCAAA TGTGAGATGG ATGCTGCTTG GTTATGTGGG
1401 GGAGTCTGAT GCAGGGCTTT TGGAATTCTC TAAAGGGTGT
1441 CCTAGTCTTC AGAAACTAGA AATGAGAGGG TGTTCATTTT
1481 TCAGTGAACG TGCACTTGCT GTGGCTGCAA CACAATTGAC
1521 TTCTCTTAGG TACTTGTGGG TGCAAGGGTA TGGTGTATCT
1561 CCATCTGGAC GTGATCTTTT GGCAATGGCT CGCCCCTTTT
1601 GGAACATTGA GTTAATTCCT TCTAGAAAGG TGGCTATGAA
1641 TACCAATTCA GATGAGACGG TAGTTGTTGA GCATCCTGCT
1681 CATATTCTTG CATATTATTC TCTTGCAGGG CAGAGATCAG
1721 ATTTTCCAGA TACTGTTGTG CCTTTGGACA CTGCCACATG
1761 CGTTGACACC TAG
```

An example of a COI1 protein from *Solanum lycopersicum* (tomato) with NCBI accession number NP_001234464.1 (GI:350535701) has the following sequence (SEQ ID NO:24).

```
  1 MEERNSTRLS SSTNDTVWEC VIPYIQESRD RDAVSLVCKR
 41 WWQIDAITRK HITMALCYTA KPEQLSRRFP HLESVKLKGK
 81 PRAAMFNLIP EDWGGYVTPW VMEITKSFSK LKALHFRRMI
121 VRDSDLELLA NRRGRVLQVL KLDKCSGFST DGLLHISRSC
161 KNLRTLLMEE SYIIEKDGEW AHELALNNTV LENLNFYMTD
201 LLQVRAEDLE LIARNCKSLV SMKISECEIT NLLGFFRAAA
241 ALEEFGGGAF NDQPELVVEN GYNEHSGKYA ALVFPPRLCQ
281 LGLTYLGRNE MSILFPIASR LRKLDLLYAL LDTAAHCFLL
321 QRCPNLEILE TRNVVGDRGL EVLGQYCKRL KRLRIERGAD
361 DQEMEDEEGA VTHRGLIDLA KGCLELEYMA VYVSDITNEA
401 LEVIGTYLKN LSDFRLVLLD REERITDLPL DNGVRALLRG
441 CHNLRRFALY VRPGGLTDVG LSYVGQYSPN VRWMLLGYVG
```

```
-continued
481 ESDHGLLEFS KGCPSLQKLE VRGCCFSERA LALATLQLKS

521 LRYLWVQGYR ASSAGRDLLA MARPFWNIEL IPARRVIAND

561 GNNAETVVSE HPAHILAYYS LAGQRTDFPD TVKPLDPTYL

601 LAE
```

A comparison of the *Arabidopsis thaliana* COI1 SEQ ID NO:1 sequence and the *Solanum lycopersicum* COI SEQ ID NO:24 sequence is shown below, illustrating that the two proteins have at least 69% sequence identity. In addition, the location of the alanine at position 384 that can be replaced, for example with a valine, to generate a modified COI1 protein is also identified in bold and with underlining. As illustrated, this alanine is at about position 390 in the *Solanum lycopersicum* COI1 SEQ ID NO:24 sequence.

```
69.3% identity in 584 residues overlap; Score: 2071.0;
Gap frequency: 1.7%
Seq1    15 ATVDDVIEQVMTYITDPKDRDSASLVCRRWFKIDSETREHVTMALCYTATPDRLSRRFPN
Seq24   12 STNDTVWECVIPYIQESRDRDAVSLVCKRWWQIDAITRKHITMALCYTAKPEQLSRREPH
              *  *  *  **     *** ****  **   **  *   ********    *   ******

Seq1    75 LRSLKLKGKPRAAMFNLIPENWGGYVTPWVTEISNNLRQLKSVHFRRMIVSDLDLDRLAK
Seq24   72 LESVKLKGKPRAAMFNLIPEDWGGYVTPWVMEITKSFSKLKALHFRRMIVRDSDLELLAN
            * *  ****************  ********* **      **   ******  **  ** **

Seq1   135 ARADDLETLKLDKCSGETTDGLLSIVTHCRKIKTLLMEESSFSEKDGKWLHELAQHNTSL
Seq24  132 RRGRVLQVLKLDKCSGFSTDGLLHISRSCKNLRTLLMEESYIIEKDGEWAHELALNNTVL
              *   *  ********* *****    *  *  *******    ****  ****   ** *

Seq1   195 EVLNFYMTEFAKISPKDLETIARNCRSLVSVKVGDFEILELVGFFKAAANLEEFCGGSLN
Seq24  192 ENLNFYMTDLLQVRAEDLELIARNCKSLVSMKISECEITNLLGFFRAAAALEEFGGGAFN
            * ******     *** ***** **** *  * ** *   ***  *** **** ***   *

Seq1   255 E------DIGMPE---KYMNLVFPRKLCRLGLSYMGPNEMPILFPFAAQIRKLDLLYALL
Seq24  252 DQPELVVENGYNEHSGKYAALVEPPRLCQLGLTYLGRNEMSILFPIASRLRKLIDLLYALL
              *    *  **   ****  *  *** **** * * ***  * *** *  *   **********

Seq1   306 ETEDHCTLIQKCPNLEVLETPNVIGDRGLEVLAQYCKQLKRLRIERGADEQGMEDEEGLV
Seq24  312 DTAAHCELLQRCPNLEILETRNVVGDRGLEVLGQYCKRLKRLRIERGADDQEMEDEEGAV
              *  **  *  ***** ***  ** ********  ****  ************   * ****** *

Seq1   366 SQRGLIALAQGCQELEYMAVYVSDITNESLESIGTYLKNLCDFRLVLLDREERITDLPLD
Seq24  372 THRGLIDLAKGCLELEYMAVYVSDITNEALEVIGTYLKNLSDFRLVLLDREERITDLPLD
              ****  **  ** *********************  **  ****************   ******************

Seq1   426 NGVRSLLIGCKKLRRFAFYLRQGGLTDLGLSYIGQYSPNVRWMLLGYVGESDEGLMEFSR
Seq24  432 NGVRALLRGCHNLRRFALYVRPGGLTDVGLSYVGQYSPNVRWMLLGYVGESDHGLLEFSK
            ****  **    ******  *  ***** *****  *******************  **   ***

Seq1   486 GCPNLQKLEMRGCCFSERAIAAAVTKLPSLRYLWVQGYRASMTGQDLMQMARPYWNIELI
Seq24  492 GCPSLQKLEVRGCCFSERALALATLQLKSLRYLWVQGYRASSAGRDLLAMARPFWNIELI
            ***  ***** ********     *  * *  *************     *  **   ****   ******

Seq1   546 PSRRV-PEVNQQGEIREMEHPAHILAYYSLAGQRTDCPTTVRVL
Seq24  552 PARRVIANDGNNAETVVSEHPAHILAYYSLAGQRTDFPDTVKPL
              * ***      *             ****************** *  **   *
```

An example of a modified COI1 *Solanum lycopersicum* (tomato) protein with a valine alanine at about position 390 has the following sequence (SEQ ID NO:25).

```
  1 MEERNSTRLS SSTNDTVWEC VIPYIQESRD RDAVSLVCKR

41 WWQIDAITRK HITMALCYTA KPEQLSRRFP HLESVKLKGK

81 PRAAMFNLIP EDWGGYVTPW VMEITKSFSK LKALHFRRMI

121 VRDSDLELLA NRRGRVLQVL KLDKCSGFST DGLLHISRSC

161 KNLRTLLMEE SYIIEKDGEW AHELALNNTV LENLNFYMTD

201 LLQVRAEDLE LIARNCKSLV SMKISECEIT NLLGFFRAAA
```

```
-continued
241 ALEEFGGGAF NDQPELVVEN GYNEHSGKYA ALVFPPRLCQ

281 LGLTYLGRNE MSILFPIASR LRKLDLLYAL LDTAAHCFLL

321 QRCPNLEILE TRNVVGDRGL EVLGQYCKRL KRLRIERGAD

361 DQEMEDEEGA VTHRGLIDLA KGCLELEYMV VYVSDITNEA

401 LEVIGTYLKN LSDFRLVLLD REERITDLPL DKGVRALLRG

441 CHNLRRFALY VRPGGLTDVG LSYVGQYSPN VRWMLLGYVG

481 ESDHGLLEFS KGCPSLQKLE VRGCCFSERA LALATLQLKS

521 LRYLWVQGYR ASSAGRDLLA MARPFWNIEL IPARRVIAND

561 GNNAETVVSE HPAHILAYYS LAGQRTDFPD TVKPLDPTYL

601 LAE
```

An example of a nucleotide (cDNA) sequence that encodes the *Solanum lycopersicum* SEQ ID NO:24 COI1 protein (with NCBI cDNA accession number NM_001247535.1 (GI:350535700)) is shown below as SEQ ID NO:26.

```
  1   CTCTCCTCCA TCTTCTTCAA CTGTAACCTC TCTTCCATTA

41   TCAGTGTCAA GTTGTTGAAG TTTTGGTCAT GGTCATGGTG
```

-continued

```
  81 TAATTTGTTG TTAGTATTTT GAAGTATTTG TGTTTTTGAT
 121 TTGGTTTTGG TTTTAATGGA GGAACGGAAC TCAACGAGAT
 161 TGAGTAGCTC AACAAACGAT ACAGTATGGG AGTGTGTGAT
 201 TCCGTATATA CAGGAATCGC GTGATAGAGA CGCGGTATCG
 241 TTGGTATGTA AGAGGTGGTG GCAGATCGAT GCGATTACTA
 281 GAAAGCATAT AACTATGGCG TTGTGTTATA CAGCGAAACC
 321 AGAGCAGTTA TCTAGAAGGT TTCCACATCT TGAATCGGTT
 361 AAACTGAAAG GGAAACCAAG AGCTGCTATG TTTAATTTGA
 401 TACCGGAAGA TTGGGGAGGA TATGTTACAC CTTGGGTTAT
 441 GGAGATAACT AAGTCGTTTA GTAAATTGAA AGCACTTCAT
 481 TTTCGTAGAA TGATTGTTAG AGATTCGGAT CTCGAATTAC
 521 TTGCGAATCG TCGTGGAAGA GTTCTTCAAG TTTTGAAGCT
 561 GGATAAGTGT TCTGGATTTT CTACTGATGG TCTTCTGCAT
 601 ATTTCTCGTT CCTGCAAGAA CTTAAGAACT TTGTTAATGG
 641 AAGAGAGTTA TATAATTGAG AAAGATGGAG AATGGGCACA
 681 TGAACTAGCA TTGAACAACA CTGTTCTTGA GAATTTGAAC
 721 TTTTACATGA CAGATCTTCT GCAAGTTAGG GCTGAAGATC
 761 TTGAATTGAT AGCAAGAAAT TGTAAATCTC TAGTCTCTAT
 801 GAAAATTAGC GAGTGTGAAA TTACGAATCT TCTTGGCTTC
 841 TTTAGAGCTG CGGCTGCATT GGAGGAGTTT GGTGGTGGCG
 881 CATTTAATGA CCAACCAGAA CTTGTTGTTG AAAATGGCTA
 921 TAATGAGCAT TCCGGAAAAT ATGCCGCACT AGTCTTCCCT
 961 CCAAGATTAT GTCAATGGG CTTGACATAC TTAGGGAGAA
1001 ATGAGATGTC CATTCTCTTT CCTATTGCGT CTCGTCTGAG
1041 GAAATTGGAT CTTCTTTATG CACTTCTTGA CACAGCAGCC
1081 CACTGTTTCT TACTGCAAAG GTGTCCCAAC TTGGAAATTC
1121 TTGAGACTAG GAATGTTGTT GGGGATAGAG GATTGGAAGT
1161 GCTTGGCCAG TACTGTAAGA GGTTAAAGCG GCTCAGGATT
1201 GAGAGAGGAG CTGATGATCA GGAGATGGAG GATGAAGAAG
1241 GTGCGGTTAC ACACAGAGGA TTGATTGATT TGGGAAAGGG
1281 ATGTCTTGAA CTAGAATACA TGGCTGTTTA TGTGTCAGAT
1321 ATTACTAATG AAGCTTTGGA AGTTATTGGT ACATATCTGA
1361 AAAATCTGAG TGATTTTCGG CTGGTTTTGC TTGACAGAGA
1401 AGAAAGAATA ACAGATCTGC CACTTGATAA TGGTGTGCGT
1441 GCTTTACTAA GAGGTTGCCA TAATCTTAGA AGATTTGCCC
1481 TCTATGTCCG GCCTGGGGGC CTTACTGATG TAGGTCTCAG
1521 TTATGTCGGG CAATACAGCC CAAACGTGAG ATGGATGCTT
1561 CTGGGATACG TTGGGGAATC CGATCATGGC CTTCTGGAGT
1601 TCTCTAAAGG ATGTCCGAGC CTGCAAAAGC TAGAAGTGAG
1641 AGGCTGCTGT TTCAGTGAAC GTGCATTAGC CTTGGCTACC
1681 TTGCAGCTAA AATCGTTAAG GTATCTATGG GTACAAGGAT
1721 ACAGGGCATC TTCAGCTGGT CGTGATCTCT TAGCGATGGC
1761 TCGCCCATTC TGGAATATTG AATTGATTCC TGCAAGACGA
1801 GTTATTGCCA ACGATGGAAA TAATGCAGAA ACTGTAGTCT
1841 CGGAGCATCC AGCCCATATA CTTGCCTACT ATTCTCTTGC
1861 CGGACAAAGA ACAGATTTTC CAGACACTGT CAAGCCTTTG
1921 GACCCAACTT ACCTTCTCGC TGAATAGGTT TGTAAATATA
1961 ACTTTTCCTT GAGTGAAGTT GTTCGAGGTC TATTTGCTTC
2001 CTTTTTAGGT GTCTTGTCCA TATGTATGCC
```

An example of a COI1 protein from *Zea mays* (corn) with NCBI accession number NP_001150429.1 (GI:226503785) has the following sequence (SEQ ID NO:27).

```
  1 MGGEAPEPRR LTRALSIGGG DGGWVPEEML QLVMGFVEDP
 41 RDREAASLVC HRWHRVDALS RKHVTVPFCY AVSPARLLAR
 81 FPRLESLAVK GKPRAAMYGL IPDDWGAYAR PWITELAAPL
121 ECLKALHLRR MVVTDDDLAE LVRARGHMLQ ELKLDKCTGF
161 STHGLRLVAR SCRSLRTLFL EECQIDDKGS EWIHDLAVCC
201 PVLTTLNFHM TELEVMPADL KLLAKSCKSL ISLKISDCDL
241 SDLIEFFQFA TALEEFAGGT FNEQGELSKY VNVKFPSRLC
281 SLGLTYMGTN EMPIMFPFSA ILKKLDLQYT FLTTEDHCQL
321 IAKCPNLLVL AVRNVIGDRG LGVVADTCKK LQRLRIERGD
361 DEGGVQEEQG GVSQVGLTAI AVGCRELEYI AAYVSDITNG
401 ALESIGTFCK KLYDFRLVLL DREERITDLP LDNGVRALLR
441 GCTKLRRFAL YLRPGGLSDA GLGYIGQCSG NIQYMLLGNV
481 GETDDGLISF ALGCVNLRKL ELRSCCFSER ALALAILHMP
521 SLRYVWVQGY KASQTGRDLM LMARPFWNIE FTPPNPKNGG
561 WLMEDGEPCV DSHAQILAYH SLAGKRLDCP QSVVPLYPA
```

A comparison of the *Arabidopsis thaliana* COI1 SEQ ID NO:1 sequence and the *Zea mays* COI1 SEQ ID NO:27 sequence is shown below, illustrating that the two proteins have at least 58% sequence identity. In addition, the location of the alanine at position 384 that can be replaced, for example with a valine, to generate a modified COI1 protein is also identified in bold and with underlining. As illustrated, this alanine is at about position 391 in the *Zea mays* COI1 SEQ ID NO:27 sequence.

```
57.9% identity in 570 residues overlap; Score: 1722.0;
Gap frequency: 0.9%
Seq1    18 DDVIEQVMTYITDPKDRDSASLVCRRWFKIDSETREHVTMALCYTATPDRLSRRFPNLRS
Seq27   27 EEMLQLVMGFVEDPRDPEAASLVCHRWHRVDALSRKHVTVPFCYAVSPARLLARFPPLES
                 **    ** **  ***** **   *   * ***   **   * **  *** * *
```

-continued

```
Seq1   78 LKLKGKPRAAMFNLIPENWGGYVTPWVTEISNNLRQLKSVHFRRMIVSDLDLDRLAKARA
Seq27  87 LAVKGKPRAAMYGLIPDDWGAYARPWITELAAPLECLKALHLRRMVVTDDDLAELVRARG
          * ******** *** ** * ** **     * ** * *** ** * **   *   **

Seq1  138 DDLETLKLDKCSGFTTDGLLSIVTHCRKIKTLLMEESSFSEKDGKWLHELAQHNTSLEVL
Seq27 147 HMLQELKLDKCTGFSTHGLRLVARSCRSLRTLFLEECQIDDKGSEWIHDLAVCCPVLTTL
             * ****** ** * **       **    ** **   ** *  *   * * *   *

Seq1  198 NFYMTEFAKISPKDLETIARNCRSLVSVKVGDFEILELVGFFKAAANLEEFCGGSLNEDI
Seq27 207 NFHMTEL-EVMPADLKLLAKSCKSLISLKISDCDLSDLIEFFQFATALEEFAGGTFNEQ-
          ** ***     * **    *   * *  *   *       * ** *  **** **  **

Seq1  258 GMPEKYMNLVFPRKLCRLGLSYMGPNEMPILFPFAAQIRKLDLLYALLETEDHCTLIQKC
Seq27 265 GELSKYVNVKFPSRLCSLGLTYMGTNEMPIMFPFSAILKKLDLQYTFLTTEDHCQLIAKC
          *   ** *  ** *** *** *** ***** *** *  ****     * ***** ** **

Seq1  318 PNLEVLETRNVIGDRGLEVLAQYCKQLKRLRIERGADEQGMEDEEGLVSQRGLIALAQGC
Seq27 325 PNLLVLAVPNVIGDRGLGVVADTCKKLQRLRIERGDDEGGVQEEQGVSQVGLTAIAVGC
          *** **    ********* * ** ** ********* *  * *  *** **  ** **

Seq1  378 QELEYMAVYVSDITNESLESIGTYLKNLCDFRLVLLDREERITDLPLDNGVRSLLIGCKK
Seq27 385 RELEYIAAYVSDITNGALESIGTFCKKLYDFRLVLLDREERITDLPLDNGVRALLRGCTK
           **** * ******* ****** * *  *************************  **  *

Seq1  438 LRRFAFYLRQGGLTDLGLSYIGQYSPNVRWMLLGYVGESDEGLMEFSRGCPNLQKLEMRG
Seq27 445 LRRFALYLRPGGLSDAGLGYIGQCSGNIQYMLLGNVGETDDGLISFALGCVNLRKLELRS
          ***** *** *** * ** **** * *   ***** ***  *** *  ** ** *** *

Seq1  498 CCFSERAIAAAVTKLPSLRYLWVQGYRASMTGQDLMQMARPYWNIELIPS--RRVPEVNQ
Seq27 505 CCFSERALALAILHMPSLRYVWVQGYKASQTGRDLMLMARPFWNIEFTPPNPKNGGWLME
          ******* *  *    **** ***** *  ** *** **** ****  *

Seq1  556 QGEIREMEHPAHILAYYSLAGQRTDCPTTV
Seq27 565 DGEPCVDSH-AQILAYHSLAGKRLDCPQSV
           **    *    ***** **** * *** **
```

An example of a modified COI1 *Zea mays* (corn) protein with a valine instead of an alanine at position 391 has the following sequence (SEQ ID NO:28).

```
  1 MGGEAPEPRR LTRALSIGGG DGGWVPEEML QLVMGFVEDP
 41 RDREAASLVC HRWHRVDALS RKHVTVPFCY AVSPARLLAR
 81 FPRLESLAVK GKPRAAMYGL IPDDWGAYAR PWITELAAPL
121 ECLKALHLRR MVVTDDDLAE LVRARGHMLQ ELKLDKCTGF
161 STHGLRLVAR SCRSLRTLFL EECQIDDKGS EWIHDLAVCC
201 PVLTTLNFHM TELEVMPADL KLLAKSCKSL ISLKISDCDL
241 SDLIEFFQFA TALEEFAGGT FNEQGELSKY VNVKFPSRLC
281 SLGLTYMGTN EMPIMFPFSA ILKKLDLQYT FLTTEDHCQL
321 IAKCPNLLVL AVRNVIGDRG LGVVADTCKK LQRLRIERGD
361 DEGGVQEEQG GVSQVGLTAI AVGCRELEYI VAYVSDITNG
401 ALESIGTFCK KLYDFRLVLL DREERITDLP LDNGVRALLR
441 GCTKLRRFAL YLRPGGLSDA GLGYIGQCSG NIQYMLLGNV
481 GETDDGLISF ALGCVNLRKL ELRSCCFSER ALALAILHMP
521 SLRYVWVQGY KASQTGRDLM LMARPFWNIE FTPPNPKNGG
561 WLMEDGEPCV DSHAQILAYH SLAGKRLDCP QSVVPLYPA
```

An example of a nucleotide (cDNA) sequence that encodes the *Zea mays* SEQ ID NO:27 COI1 protein (with NCBI cDNA accession number NM_001156957.1 (GI: 226503784)) is shown below as SEQ ID NO:29.

```
  1 ACCCCTGCTT GCTGCAGCTT CAAGCACTAC CGAATCAGGG
 41 CGAGTGGGAG CAGAGGAGGG AATCCCATGT CTCCGCCCCT
 81 CGCTGGAGCA GATCGTTGTC GAGCCGACGT GGAGCTGCTG
121 CGGTAGAAAG CTAGCGGAGC CTGCGAGCTA GCCTGATCCG
161 TCCGCAGTCC GATCGGGATC GATGGGTGGG GAGGCGCCGG
201 AGCCGCGGCG GCTGACCCGG GCGCTGAGCA TCGGCGGCGG
241 TGACGGCGGC TGGGTTCCCG AGGAGATGCT GCAACTCGTG
281 ATGGGGTTCG TCGAGGACCC GCGCGACCGG GAGGCCGCGT
321 CGCTGGTGTG TCACCGGTGG CACCGCGTCG ACGCGCTCTC
361 GCGGAAGCAC GTGACGGTGC CCTTCTGCTA CGCCGTTTCC
401 CCGGCACGCC TGCTCGCGCG GTTCCCGCGG CTCGAGTCGC
441 TCGCGGTGAA GGGGAAGCCC CGCGCGGCCA TGTACGGGCT
481 CATACCCGAC GACTGGGGCG CCTACGCCCG CCCGTGGATC
521 ACCGAGCTCG CCGCGCCGCT CGAGTGCCTC AAGGCGCTCC
561 ACCTCCGACG CATGGTCGTC ACAGACGACG ACCTCGCCGA
601 GCTCGTCCGT GCCAGGGGGC ACATGCTGCA GGAGCTGAAG
641 CTCGATAAGT GCACCGGCTT CTCCACTCAT GGACTCCGCC
681 TCGTTGCCCG CTCCTGCAGA TCACTGAGGA CTTTATTTTT
721 GGAAGAATGT CAAATTGATG ATAAGGGCAG TGAATGGATC
761 CACGATCTCG CAGTCTGCTG TCCTGTTCTG CAACATTGA
801 ATTTCCACAT GACTGAGCTT GAAGTGATGC CAGCTGACCT
841 AAAGCTTCTT GCAAAGAGCT GCAAGTCACT GATTTCATTG
881 AAGATTAGTG ACTGCGATCT TTCAGATTTG ATAGAGTTCT
921 TCCAATTTGC CACAGCACTG GAAGAATTTG CTGGAGGGAC
```

-continued

```
 961 ATTCAATGAG CAAGGGGAAC TCAGCAAGTA TGTGAATGTT
1001 AAATTTCCAT CAAGACTATG CTCCTTGGGA CTTACTTACA
1041 TGGGAACAAA TGAAATGCCC ATTATGTTCC CTTTTTCTGC
1081 AATACTAAAG AAGCTGGATT TGCAATACAC TTTCCTCACC
1121 ACTGAGGACC ATTGCCAGCT CATTGCAAAA TGCCCGAACT
1161 TACTAGTTCT CGCGGTGAGG AATGTGATTG GAGATAGAGG

1201 ATTAGGAGTT GTTGCGGATA CGTGCAAGAA GCTCCAAAGG

1241 CTCAGAATAG AGCGAGGAGA TGATGAAGGA GGTGTGCAAG
1281 AAGAGCAGGG AGGGGTCTCT CAAGTGGGCT TGACGGCTAT
1321 AGCCGTAGGT TGCCGTGAGC TGGAATATAT AGCTGCCTAT
1361 GTGTCTGATA TAACCAATGG GGCCTTGGAA TCTATCGGGA
1401 CATTCTGCAA AAAACTATAC GACTTCCGGC TTGTTCTACT
1441 TGATAGAGAA GAGAGGATAA CAGACTTGCC ACTGGACAAT
1481 GGTGTCCGAG CTTTGTTGAG GGGCTGCACC AAGCTTCGGA
1521 GGTTTGCTCT GTACTTGAGA CCAGGAGGGC TCTCAGATGC
1561 AGGTCTCGGC TACATTGGAC AGTGCAGCGG AAACATCCAG
1601 TACATGCTTC TCGGTAATGT TGGGGAAACT GATGATGGAT
1641 TGATCAGCTT CGCATTGGGT TGCGTAAACC TGCGAAAGCT
1681 TGAACTCAGG AGTTGCTGCT TCAGCGAGCG AGCACTGGCC
1721 CTTGCAATAC TACATATGCC TTCCCTGAGG TACGTATGGG
1761 TTCAGGGCTA CAAAGCGTCT CAAACCGGCC GAGACCTCAT
1801 GCTCATGGCA AGGCCCTTCT GGAACATAGA GTTTACACCT
1841 CCCAATCCTA AGAACGGAGG TTGGCTGATG GAAGATGGGG
1881 AGCCTTGTGT AGATAGTCAC GCTCAGATAC TTGCATACCA
1921 CTCCCTCGCC GGTAAGAGGC TGGACTGCCC ACAATCCGTG
1961 GTTCCTTTGT ATCCTGCGTG AGTGTAAATA GACTAAGCTG
2001 GTGTCTTTCC TTAGCCTCCT GGTCAACAAG AATGGTGTTG
```

-continued

```
2041 ATAACTCGAT ATATGCGGTT ATTGTATGGA TCTAGATGGC
2081 TAGCTGCTAC GTACTGTAAT AAGCTACTAG TAGCTGAGAG
2121 ATGTCCTGGA ATAAGCCCTT GCTATTTTTG CCTAAAAAAA
2161 AAAAAAAAA
```

An example of a COI1 protein from *Triticum aestivum* (wheat) with NCBI accession number ADK66974.1 (GI: 301318118) has the following sequence (SEQ ID NO:30).

1 MGGEVPEPRR LSRALSFGVP DEALHLVMGY VDAPRDREAA

41 SLVCRRWHRI DALTRKHVTV AFCYAADPSR LLARFPRLES

81 LALKGRPRAA MYGLISDDWG AYAAPWVARL AAPLECLKAL

121 HLRRMTVTDD DVATLIRSRG HMLQELKLDK CSGFSTDALR
161 LVARSCRSLR TLFLEECVIT DEGGEWLHEL AVNNSVLVTL
201 NFYMTELKVV PADLELLAKN CKSLLSLKIS ECDLSDLIGF
241 FEAANALQDF AGGSFNEVGE LTKYEKVKFP PRVCFLGLTF
281 MGKNEMPVIF PFSASLKKLD LQYTFLTTED HCQLISKCPN
321 LFVLEVRNVI GDRGLEVVGD TCKKLRRLRI ERGDDDPGLQ
361 EEQGGVSQLG LTAVAVGCRD LEYIAAYVSD ITNGALESIG
401 TFCKNLYDFR LVLLDRQKQV TDLPLDNGVR ALLRSCTKLR
441 RFALYLRPGG LSDIGLDYIG QYSGNIQYML LGNVGESDHG
481 LIRFAIGCTN LRKLELRSCC FSEQALSLAV LHMPSLRYIW
521 VQGYKASPAG LELLLMARRF WNIEFTPPSP EGLFRMTLEG
561 EPCVDKQAQV LAYYSLAGQR QDCPDWVTPL HPAA

A comparison of the *Arabidopsis thaliana* COI1 SEQ ID NO:1 sequence and the *Triticum aestivum* COI1 SEQ ID NO:30 sequence is shown below, illustrating that the two proteins have at least 58% sequence identity. In addition, the location of the alanine at position 384 that can be replaced, for example with a valine, to generate a modified COI1 protein is also identified in bold and with underlining. As illustrated, this alanine is at about position 385 in the *Triticum aestivum* COI1 SEQ ID NO:30 sequence.

```
57.3% identity in 572 residues overlap; Score: 1724.0; Gap frequency:
0.5%
Seq1     18DDVIEVMTYITDPKDPDSASLVCRRWFKIDSETREHVTMALCYTATPDRLSRRFPNLRS
Seq30    21DEALHLVMGYVDAPRDREAASLVCRRWHRIDALTRKHVTVAFCYAADPSRLLARFPRLES
           *     ** *   * **  ********  **  ** *** * ** * * **  *** * *

Seq1     78LKLKGEPRAAMFNLIPENWGGYVTPWVTEISNNLRQLKSVHFRRMIVSDLDLDRLAKARA
Seq30    81LALKGRPRAAMYGLISDDWGAYAAPWVARLAAPLECLKALHLRRMTVTDDDVATLIRSRG
           * *** *****  **   ** *  ***      *  **  * *** * * *   *   *

Seq1    138DDLETLKLDKCSGFTTDGLLSIVTHCRKIKTLLMEESSFSEKDGKWLHELAQHNTSLEVL
Seq30   141HMLQELKLDKCSGFSTDALRLVARSCRSLRTLFLEECVITDEGGEWLHELAMNNSVLVTL
             *  ********* ** *      **   **  **       * ******  *  *  *

Seq1    198NFYMTEFAKISPKDLETIARNCRSLVSVKVGDFEILELVGFFKAAANLEEFCGGSLNEDI
Seq30   201NFYMTEL-KVVPADLELLAKNCKSLLSLKISECDLSDLIGFFEAANALLQDFAGGSFNE-V
           ******  *  * ***  * ** ** * *        * *** **  *  * *** **

Seq1    258GMPEKYMNLVFPRKLCRLGLSYMGPNEMPILFPFAAQIRKLDLLYALLETEDHCTLIQKC
Seq30   259GELTKYEKVKFPPRVCFLGLTFMGKNEMPVIFPFSASLKKLDLQYTFLTTEDHCQLISKC
           *   **    **   * ***  ** ****  *** *   **** *  * ***** ** **
```

```
                         -continued
Seq1    318 PNLEVLETRNVIGDRGLEVLAQYCKQLKRLRIERGADEQGMEDEEGLVSQRGLIALAQGC
Seq30   319 PNLFVLEVRNVIGDRGLEVVGDTCKKLRRLRIERGDDDPGLQEEQGGVSQLGLTAVAVGC
            *** *** **********   ** * *******  *  *  * * *** ** * * **

Seq1    378 QELEYMAVYVSDITNESLESIGTYLKNLCDFRLVLLDREERITDLPLDNGVRSLLIGCKK
Seq30   379 RDLEYIAAYVSDITNGALESIGTFCKNLYDFRLVLLDRQKQVTDLPLDNGVRALLRSCTK
            *** * *******  ****** ***   *** *********          ** * *

Seq1    438 LRRFAFYLRQGGLTDLGLSYIGQYSPNVRWMLLGYVGESDEGLMEFSRGCPNLQKLEMRG
Seq30   439 LRRFALYLRPGGLSDIGLDYIGQYSGNIQYMLLGNVGESDHGLIRFAIGCTNLRKLELRS
            ***** *** *** * ** ****** *  **** ***** **  *  ** *** ***  *

Seq1    498 CCFSERAIAAAVTKLPSLRYLWVQGYRASMTGQDLMQMARPYWNIELIPSRRVPEVNQQG
Seq30   499 CCFSEQALSLAVLHMPSLRYIWVQGYKASPAGLELLLMARRFWNIEFTPPSPEGLFRMTL
            *****  *   ** ***** ***** **     *   *** ****   **  *

Seq1    558 EIRE-MEHPAHILAYYSLAGQRTDCPTTVRVL
Seq30   559 EGEPCVDKQAQVLAYYSLAGQRQDCPDWVTPL
            *      *   * ********** *** *  *
```

An example of a modified *Triticum aestivum* (wheat) COI1 protein with a valine instead of an alanine at position 385 has the following sequence (SEQ ID NO:31).

```
  1 MGGEVPEPRR LSRALSFGVP DEALHLVMGY VDAPRDREAA
 41 SLVCRRWHRI DALTRKHVTV AFCYAADPSR LLARFPRLES
 81 LALKGRPRAA MYGLISDDWG AYAAPWVARL AAPLECLKAL
121 HLRRMTVTDD DVATLIRSRG HMLQELKLDK CSGFSTDALR
161 LVARSCRSLR TLFLEECVIT DEGGEWLHEL AVNNSVLVTL
201 NFYMTELKVV PADLELLAKN CKSLLSLKIS ECDLSDLIGF
241 FEAANALQDF AGGSFNEVGE LTKYEKVKFP PRVCFLGLTF
281 MGKNEMPVIF PFSASLKKLD LQYTFLTTED HCQLISKCPN
321 LFVLEVRNVI GDRGLEVVGD TCKKLRRLRI ERGDDDPGLQ
361 EEQGGVSQLG LTAVAVGCRD LEYIVAYVSD ITNGALESIG
401 TFCKNLYDFR LVLLDRQKQV TDLPLDNGVR ALLRSCTKLR
441 RFALYLRPGG LSDIGLDYIG QYSGNIQYML LGNVGESDHG
481 LIRFAIGCTN LRKLELRSCC FSEQALSLAV LHMPSLRYIW
521 VQGYKASPAG LELLLMARRF WNIEFTPPSP EGLFRMTLEG
561 EPCVDKQAQV LAYYSLAGQR QDCPDWVTPL HPAA
```

Another example of a COI1 protein from *Triticum aestivum* (wheat) with NCBI accession number ADK66973.1 (GI:301318116) has the following sequence (SEQ ID NO:32).

```
  1 MGGEAPEPRR LSRALSLDGG GVPEEALHLV LGYVDDPRDR
 41 EAASLACRRW HHIDALTRKH VTVPFCYAVS PARLLARFPR
 81 LESLGVKGKP RAAMYGLIPD DWGAYARPWV AELAAPLECL
121 KALHLRRMVV TDDDLAALVR ARGHMLQELK LDKCSGFSTD
161 ALRLVARSCR SLRTLFLEEC TITDNGTEWL HDLAANNPVL
201 VTLNFYLTYL RVEPADLELL AKNCKSLISL KISDCDLSDL
241 IGFFQIATSL QEFAGAEISE QKYGNVKLPS KLCSFGLTFM
281 GTNEMHIIFP FSAVLKKLDL QYSFLTTEDH CQLIAKCPNL
321 LVLAVRNVIG DRGLGVVGDT CKKLQRLRVE RGEDDPGMQE
361 EEGGVSQVGL TAIAVGCREL ENIAAYVSDI TNGALESIGT
401 FCKNLHDFRL VLLDKQETIT DLPLDNGARA LLRGCTKLRR
441 FALYLRPGGL SDVGLGYIGQ HSGTIQYMLL GNVGQTDGGL
481 ISFAAGCRNL RKLELRSCCF SERALALAIR QMPSLRYVWV
521 QGYRASQTGR DLMLMARPFW NIEFTPPSTE TAGRLMEDGE
561 PCVDRQAQVL AYYSLSGKRS DYPQSVVPLY PA
```

A comparison of the *Arabidopsis thaliana* COI1 SEQ ID NO:1 sequence and the *Triticum aestivum* COI1 SEQ ID NO:32 sequence is shown below, illustrating that the two proteins have at least 56% sequence identity. In addition, the location of the alanine at position 384 that can be replaced, for example with a valine, to generate a modified COI1 protein is also identified in bold and with underlining. As illustrated, this alanine is at about position 384 in the *Triticum aestivum* COI1 SEQ ID NO:32 sequence.

```
56.1% identity in 569 residues overlap; Score: 1679.0; Gap frequency:
1.2%
Seq1    18 DDVIEQVMTYITDPKDRDSASLVCRRWFKIDSETREHVTMALCYTATPDRLSRRFPNLRS
Seq32   24 EEALHLVLGYVDDPRDREAASLACRRWHHIDALTRKHVTVPFCYAVSPARLLARFPRLES
                 *  *  ** **  *** ****  **  ** ***   **   * **  *** * *

Seq1    78 LKLKGKPRAAMFNLIPENWGGYVTPWVTEISNNLRLKSVHFRRMIVSDLDLDRLAKARA
Seq32   84 LGVKGKPRAAMYGLIPDDWGAYARPWVAELAAPLECLKALHLRRMVVTDDDLAALVRARG
           *  ********  ***  ** *  *** *    *  **  * *** * * **  *  **

Seq1   138 DDLETLKLDKCSGFTTDGLLSIVTHCRKIKTLLMEESSFSEKDGKWLHELAQHNTSLEVL
Seq32  144 HMLQLKLDKCSGFSTDALRLVARSCRSLRTLFLEECTITDNGTEWLHDLAANNPVLVTL
             *  ********* ** *      **   **  **         *** **  *  *  *
```

-continued

```
Seq1   198 NFYMTEFAKISPKIDLETIARNCRSLVSVKVGDFEILELVGFFKAAANLEEFCGGSLNEDI
Seq32  204 NFYLT-YLRVEPADLELLAKNCKSLISLKISDCDLSDLIGFFQIATSLQFAGAEISE--
           ***  *       * ***  *   ** ** *     *     * *** *   * **  *

Seq1   258 GMPEKYMNLVFPPPKLCRLGLSYMGPNEMPILFPFAAQIRKLDLLYALLETEDHCTLIQKC
Seq32  261 ---QKYGNVKLPSKLCSFGLTFMGTNEMHIIFPFSAVLKKLIDLQSFLTTEDHCQLIAKC
              **    *  ***  **  **  ***  ***** *  ****  *  *  ***** ** **

Seq1   318 PNLEVLETRNVIGDRGLEVIAQYCKQLKRLRIERGADEQGMEDEEGLVSQRGLIALAQGC
Seq32  318 PNLLVLAVPNVIGDRGLGVVGDTCKKLQRLRVERGEDDPGMQEEGGVSQVGLTAIAVGC
           *** **  ********* *   ** **** *****  *** *** *** **  ** **

Seq1   378 QELEYMAVYVSDITNESLESIGTYLKNLCDFRLVLLDREERITDLPLDNGVRSLLIGCKK
Seq32  378 RELENIAAYVSDITNGALESIGTFCKNLHDFRLVLLDKQETITDLPLIDNGARALLRGCTK
            *** *  ******* ******* **** ********  * ****** *** *  ** * *

Seq1   438 LRRFAFYLKGGLTDLGLSYIGQYSPNVRWMLLGYVGESDEGLMEFSRGCPNLQKLEMRG
Seq32  438 LRRFALYLRPGGLSDVGLGYIGQHSGTIQYMLLGNVGQTDGGLISFAAGCRNLRKLELRS
           ***** *** *** * ** ****  *   *** *** * **  ** * ** ** ** **

Seq1   498 CCFSERAIAAAVTKLPSLRYLWVQGYRASMTGQDLMQMARPYWNIELIP-SRRVPEVNQQ
Seq32  498 CCFSERALALAIRQMPSLRYVWVQGYRASQTGRDLMLMARPFWNIEFTPPSTETAGRLME
           *******  *  *  ***** ******** ** *** **** **** *  *   *

Seq1   557 GEIREMEHPAHILAYYSLAGQRTDCPTTV
Seq32  558 DGEPCVDRQAQVLAYYSLSGKRSDYPQSV
            *  ******  *****  *  *
```

A modified COI1 *Triticum aestivum* (wheat) protein with a valine instead of an alanine has the following sequence (SEQ ID NO:33).

```
  1 MGGEAPEPRR LSRALSLDGG GVPEEALHLV LGYVDDPRDR
 41 EAASLACRRW HHIDALTRKH VTVPFCYAVS PARLLARFPR
 81 LESLGVKGKP RAAMYGLIPD DWGAYARPWV AELAAPLECL
121 KALHLRRMVV TDDDLAALVR ARGHMLQELK LDKCSGFSTD
161 ALRLVARSCR SLRTLFLEEC TITDNGTEWL HDLAANNPVL
201 VTLNFYLTYL RVEPADLELL AKNCKSLISL KISDCDLSDL
241 IGFFQIATSL QEFAGAEISE QKYGNVKLPS KLCSFGLTFM
281 GTNEMHIIFP FSAVLKKLDL QYSFLTTEDH CQLIAKCPNL
321 LVLAVRNVIG DRGLGVVGDT CKKLQRLRVE RGEDDPGMQE
361 EEGGVSQVGL TAIAVGCREL ENIVAYVSDI TNGALESIGT
401 FCKNLHDFRL VLLDKQETIT DLPLDNGARA LLRGCTKLRR
441 FALYLRPGGL SDVGLGYIGQ HSGTIQYMLL GNVGQTDGGL
481 ISFAAGCRNL RKLELRSCCF SERALALAIR QMPSLRYVWV
521 QGYRASQTGR DLMLMARPFW NIEFTPPSTE TAGRLMEDGE
561 PCVDRQAQVL AYYSLSGKRS DYPQSVVPLY PA
```

An example of a nucleotide (cDNA) sequence that encodes the *Triticum aestivum* SEQ ID NO:32 COI1 protein (NCBI cDNA accession number HM447645.1 (GI: 301318115)) is shown below as SEQ ID NO:34.

```
   1 ACGAGCACCA CCATCGGAGA AGGGCCAGCG GGAAGGGGGG
  41 AAATCAATCC CCATGCCCCC ACCCCTCGCC GGACCAGATC
  81 CCCGGCGGGC CGGCGCGGAG CCTTAGGCGG GGATGGGCGG
 121 GGAGGCCCCG GAGCCGCGGC GGCTGAGCCG CGCGCTCAGC
 161 CTGGACGGCG GCGGCGTCCC GGAGGAGGCG CTGCACCTGG
 201 TGCTCGGCTA CGTGGACGAC CCGCGCGACC GCGAGGCGGC
 241 CTCGCTGGCG TGCCGCCGCT GGCACCACAT CGACGCGCTC
 281 ACGCGGAAGC ACGTCACCGT GCCCTTCTGC TACGCCGTGT
 321 CCCCGGCGCG CCTGCTCGCG CGCTTCCCGC GCCTCGAGTC
 361 GCTCGGGGTC AAGGGCAAGC CCCGCGCCGC CATGTACGGC
 401 CTCATCCCCG ACGACTGGGG CGCCTACGCC CGGCCCTGGG
 441 TCGCCGAGCT CGCCGCCCCG CTCGAGTGCC TCAAGGCGCT
 481 CCACCTGCGC CGCATGGTCG TCACCGACGA CGACCTCGCC
 521 GCCCTCGTCC GCGCCCGCGG CCACATGCTG CAGGAGCTCA
 561 AGCTCGACAA GTGCTCCGGC TTCTCCACCG ACGCCCTCCG
 601 CCTCGTCGCC CGCTCCTGCA GATCACTGAG AACTTTGTTT
 641 CTGGAAGAAT GTACAATTAC TGATAATGGC ACTGAATGGC
 681 TCCATGACCT TGCTGCCAAC AATCCTGTTC TGGTGACCTT
 721 GAACTTCTAC TTGACTTACC TCAGAGTGGA GCCAGCTGAC
 761 CTCGAGCTTC TCGCCAAGAA TTGCAAGTCA CTAATTTCGT
 801 TGAAGATTAG CGACTGCGAC CTTTCAGATT TGATTGGATT
 841 TTTCCAAATA GCTACATCTT TGCAAGAATT TGCTGGAGCG
 881 GAAATCAGTG AGCAAAAGTA TGGAAATGTT AAGCTTCCTT
 921 CAAAGCTTTG CTCCTTCGGA CTTACCTTCA TGGGGACAAA
 961 TGAGATGCAC ATAATCTTTC CTTTTTCTGC TGTACTCAAG
1001 AAGCTGGATT TGCAGTACAG TTTTCTCACC ACTGAAGATC
1041 ATTGCCAGCT CATTGCAAAA TGTCCAAACT TACTAGTCCT
1081 TGCGGTGAGG AATGTGATTG GGGATAGAGG ACTGGGGGTT
1121 GTCGGAGACA CATGCAAGAA GCTACAAAGG CTCAGAGTTG
1161 AGCGAGGGGA AGATGACCCT GGCATGCAAG AAGAGGAAGG
```

```
1201 CGGAGTTTCT CAAGTAGGCC TAACAGCCAT AGCCGTAGGT
1241 TGCCGTGAAC TGGAAAACAT AGCTGCCTAT GTGTCTGATA
1281 TCACAAATGG GGCCCTGGAA TCCATCGGAA CGTTCTGCAA
1321 AAATCTCCAT GACTTTCGCC TTGTCCTGCT TGACAAACAA
1361 GAGACGATAA CAGATTTGCC GCTGGACAAC GGTGCCCGCG
1401 CGCTGCTCAG GGGCTGCACC AAGCTTCGGA GGTTCGCTCT
1441 ATACCTGAGA CCAGGGGGGC TTTCAGATGT AGGCCTCGGC
1481 TACATCGGGC AGCACAGTGG AACCATCCAG TACATGCTTC
1521 TGGGTAACGT CGGGCAGACG GATGGTGGAT TGATCAGTTT
1561 CGCAGCCGGG TGCCGGAACC TGCGGAAGCT TGAACTGAGG
1601 AGCTGTTGCT TCAGCGAGCG GGCTCTGGCC CTCGCCATAC
1641 GGCAAATGCC TTCCCTGAGG TATGTGTGGG TGCAGGGCTA
1681 CAGGGCCTCT CAGACCGGCC GCGACCTCAT GCTCATGGCG
1721 CGGCCCTTCT GGAACATCGA GTTTACGCCT CCCAGCACGG
1761 AGACCGCGGG CCGGCTGATG GAAGATGGGG AGCCCTGCGT
1801 TGATAGGCAA GCTCAGGTGC TGGCGTACTA CTCCCTTTCT
1841 GGGAAGAGGT CCGACTACCC GCAGTCTGTT GTTCCTCTGT
1881 ATCCTGCGTG ACTGTAAATA CATTAAGCCG GTATGGTGTC
1921 TCTCTGGGAC GGCCCCTGGC TGGCCCTCTG CGCTTCTCGG
1961 GCAATAAGGA TGTTTGTATG TGGGTATTGT ATGGATCTGG
2001 TAGATTTTCT AGCTGCTGTG TACTGGAATA AGCGCATTGG
2041 TATTTTTGCC TGGTACTCCT ATCTAATCTT AGGAAGATGT
2081 ATACTAAAGT AACATTGTGC GAGTGAACTG TGACACTATT
2121 GCGCTTGCTT CGCAGGCATA AGCTTGTCTG GTTTCCGCGG
2161 CCTGCCC
```

An example of a COI1 protein from *Populus trichocarpa* (black cottonwood, western balsam-poplar or California poplar) with NCBI accession number XP_002312140.1 (GI: 224101095) has the following sequence (SEQ ID NO:35).

```
  1 MPYINDPRDR DAVSLVCRRW YELDALTRKN VTIAFCYSTS
 41 PDRLRRRFND IESLKLKGKP RAAMFFNLIP EDWGGFVTPW
 81 VNEIAESFNC LKSLHFRRMI VKDSDLELLA RSRGRLLQVL
121 KLDKCSGFST DGLSHIGRSC RQLRTLFLEE SAIVERDGDW
161 LHELATNNTV LETLNFYMTE LTRVRSEDLF LLARNCRSLV
201 SVKVSDCEIL DLVGFFHAAS ALEEFCGGSF NEPDEPDKYS
241 AVKFPPKLCC LGLSYMEKNV MSIVFPFASL LKKLDLLYAF
281 LGTEDHCVLV QRCPNLEVLE TRNVIGDRGL EALAQSCKLL
321 KRLRIERGAD EQGMEDVDGR VSHRGLIALA QGCLELEYIA
361 VYVSDITNAA LEHMGTYSKN LNDFRLVLLE QEERITDLPL
401 DNGVRALLRG CEKLQRFGLY LRPGGLTDVG LGYIGQYSRR
441 VRWMILGSVG ESDEGLLAFS RGCPSLQKLE MRACCFSESA
481 LARAALQLTS LRYLWVHGYR ETSTGHRDLL TMVRPFWNIE
521 LIPSRKVESV NEAGENIVSE NPAHILAYYS LAGPRTDFPD
561 TVRPLDPANI VAA
```

A comparison of the *Arabidopsis thaliana* COI1 SEQ ID NO:1 sequence and the *Populus trichocarpa* COI1 SEQ ID NO:35 sequence is shown below, illustrating that the two proteins have at least 70% sequence identity. In addition, the location of the alanine at position 384 that can be replaced, for example with a valine, to generate a modified COI1 protein is also identified in bold and with underlining. As illustrated, this alanine is at about position 360 in the *Populus trichocarpa* COI1 SEQ ID NO:35 sequence.

```
70.0% identity in 566 residues overlap; Score: 2037.0; Gap frequency: 0.5%
Seq1   25 MTYITDPKDRDSASLVCRRWFKIDSETREHVTMALCYTATPDRLSRRFPNLRSLKLKGKP
Seq35   1 MPYINDPRDRDAVSLVCRRWYELDALTRKNVTIAFCYSTSPDRLRRRFNDIESLKLKGKP
           * ** ** ***  *******    *  **  ** * **    ****  ***  ********

Seq1   85 RAAMF-NLIPENWGGYVTPWVTEISNNLRQLKSVHFRRMIVSDLDLDRLAKARADDLETL
Seq35  61 RAAMFFNLIPEDWGGFVTPWVNEIAESFNCLKSLHFRRMIVKDSDLELLARSRGRLLQVL
          *****  *****  ***  *****  **   ***  *******  *  **  **    *  *

Seq1  144 KLDKCSGFTTDGLLSIVTHCRKIKTLLMEESSFSEKDGEWLHELAQHNTSLEVLNFYMTE
Seq35 121 KLDKCSGFSTDGLSHIGRSCKLRTLFLEESAIVERDGDWLHELATNNTVLETLNFYMTE
          ********  ****  *    **   ** **    * **   ******   **  ** *******

Seq1  204 FAKISPKDLETIARNCRSLVSVKVGDFEILELVGFFKAAANLEEFCGGSLNEDIGMPEKY
Seq35 181 LTRVRSEDLELLARNCRSLVSVKVSDCEILDINGFFHAASALEEFCGGSFNEP-DEPDKY
           *** ************ *  *** ***  ********  **  * **

Seq1  264 MNLVFPRKLCRLGLSYMGPNEMPILFPPAKIRKLDLLYALLETEDHCTLIQKCPNLEVL
Seq35 240 SAVKFPPKLCCLGLSYMEKNVMSIVFPFASLLKKLDLLYAFLGTEDHCVLVQRCPNLEVL
          ** *** ******    * * ****  *******  * *****  * *  *  *******

Seq1  324 ETRNVIGDRGLEVLAQYCKQLKRLRIERGADEQGMEDEEGLVSQRGLIALAQGCQELEYM
Seq35 300 ETRNVIGDRGLEALAQSCKLLKRLRIERGADEQGMEDVDGRVSHRGLIALAQGCLELEYI
          ************ ***  **  ****************     *  ** **********  ****
```

```
Seq1   384 AVYVSDITNESLESIGTYLKNLCDFRLVLLDREERITIDLPLDNGVRSLLIGCKKLRRFAF
Seq35  360 AVYVSDITNAALEHMGTYSKNLNDFRLVLLEQEERITDLPLDNGVRALLRGCEKLQRFGL
           ********* **  *** *** ******  ************** ** ** ** **

Seq1   444 YLRQGGLTDLGLSYIGQYSPNVRWMLLGYVGESDEGLMEFSRGCPNLQKLEMRGCCFSER
Seq35  420 YLRPGGLTDVGLGYIGQYSRRVRWMILGSVGESDEGLLAFSRGCPSLQKLEMRACCFSES
           *** ***** ** ******   **** ** ******    ****** ******* ****

Seq1   504 AIAAAVTKLPSLRYLWVQGYRASMTG-QDLMQMARPYWNIELIPSRRVPEVNQQGEIREM
Seq35  480 ALARAALQLTSLRYLWVHGYRETSTGHRDLLTMVRPFWNIELIPSRKVESVNEAGENIVS
           *  *    * ******* ***    ***   ** * ** *********  **   **

Seq1   563 EHPAHILAYYSLAGQRTDCPTTVRVL
Seq35  540 ENPAHILAYYSLAGPRTDFPDTVRPL
           * ************ *** * *** *
```

An example of a modified *Populus trichocarpa* COI1 protein with a valine instead of an alanine has the following sequence (SEQ ID NO:36).

```
  1 MPYINDPRDR DAVSLVCRRW YELDALTRKN VTIAFCYSTS
 41 PDRLRRRFND IESLKLKGKP RAAMFFNLIP EDWGGFVTPW
 81 VNEIAESFNC LKSLHFRRMI VKDSDLELLA RSRGRLLQVL
121 KLDKCSGFST DGLSHIGRSC RQLRTLFLEE SATVERDGDW
161 LHELATNNTV LETLNFYMTE LTRVRSEDLE LLARNCRSLV
201 SVKVSDCEIL DLVGFFHAAS ALEEFCGGSF NEPDEPDKYS
241 AVKFPPKLCC LGLSYMEKNV MSIVFPFASL LKKLDLLYAF
281 LGTEDHCVLV QRCPNLEVLE TRNVIGDRGL EALAQSCKLL
321 KRLRIERGAD EQGMEDVDGR VSHRGLIALA QGCLELEYIV
361 VYVSDITNAA LEHMGTYSKN LNDFRLVLLE QEERITDLPL
401 DNGVRALLRG CEKLQRFGLY LRPGGLTDVG LGYIGQYSRR
441 VRWMILGSVG ESDEGLLAFS RGCPSLQKLE MRACCFSESA
481 LARAALQLTS LRYLWVHGYR ETSTGHRDLL TMVRPFWNIE
521 LIPSRKVESV NEAGENIVSE NPAHILAYYS LAGPRTDFPD
561 TVRPLDPANI VAA
```

An example of a nucleotide (cDNA) sequence that encodes the *Populus trichocarpa* SEQ ID NO:35 COI1 protein (NCBI cDNA accession number XM_002312104.1 (GI:224101094)) is shown below as SEQ ID NO:37.

```
   1 ATGCCGTACA TAAACGACCC GCGGGACCGC GACGCCGTTT
  41 CGTTAGTTTG CCGGAGATGG TACGAGCTAG ATGCGTTAAC
  81 ACGGAAGAAC GTGACTATAG CTTTTTGTTA CAGTACAAGT
 121 CCAGATCGAT TACGACGTCG TTTTAATGAC ATTGAATCAT
 161 TAAAGCTAAA AGGGAAACCC CGGGCTGCTA TGTTTTTTAA
 201 TTTGATACCG GAGGATTGGG GAGGGTTTGT GACTCCATGG
 241 GTTAATGAAA TAGCGGAGAG TTTTAATTGC TTGAAATCGC
 281 TTCATTTTAG AAGGATGATT GTTAAAGATT CGGATCTGGA
 321 GTTACTTGCT AGGTCCAGAG GGAGACTTTT GCAGGTTTTG
 361 AAGCTTGATA AGTGCTCTGG GTTTTCCACG GATGGCCTTT
 401 CGCACATCGG TCGCTCTTGC AGGCAATTGA GAACATTATT
 441 CTTGGAAGAG AGTGCAATTG TTGAGAGAGA TGGTGACTGG
 481 CTCCATGAGC TTGCTACGAA CAATACAGTT CTCGAGACTC
 521 TAAATTTTTA CATGACAGAA CTTACCAGAG TCAGATCGGA
 561 AGACCTTGAG CTTCTTGCCA GGAACTGTCG TTCATTAGTC
 601 TCTGTAAAGG TTAGCGACTG TGAAATCTTG GATCTTGTTG
 641 GTTTCTTTCA TGCTGCATCT GCTTTAGAGG AATTTTGTGG
 681 AGGTTCCTTC AATGAGCCAG ATGAACCAGA CAAATACTCT
 721 GCTGTCAAAT TCCCCCCAAA ATTATGCTGT TTGGGTCTTA
 761 GCTATATGGA GAAGAACGTA ATGTCAATAG TGTTTCCTTT
 801 TGCATCCCTG CTCAAAAAGC TGGATCTCCT CTACGCTTTT
 841 CTTGGCACGG AAGATCATTG TGTTTTAGTC CAAAGGTGCC
 881 CCAACTTAGA AGTTCTCGAG ACAAGAAATG TTATTGGAGA
 921 TAGAGGGTTG GAAGCCCTTG CCCAGAGTTG TAAGCTACTA
 961 AAGAGGCTTC GAATAGAGCG TGGTGCCGAT GAGCAGGGAA
1001 TGGAGGATGT GGATGGCCGA GTTTCACATA GAGGATTAAT
1041 TGCCTTGGCT CAAGGCTGCT TAGAACTCGA GTACATCGCC
1081 GTTTATGTTT CTGATATTAC CAATGCAGCT CTAGAACATA
1121 TGGGCACATA CTCAAAGAAC CTCAATGATT TCCGCCTGGT
1161 CTTGCTTGAG CAAGAAGAGA GGATAACCGA CCTGCCCCTT
1201 GACAATGGAG TTCGAGCTCT ATTAAGGGGC TGTGAAAAGC
1241 TCCAAAGGTT CGGTCTGTAT CTCCGACCAG GGGGTTTGAC
1281 TGATGTGGGT CTTGGATATA TTGGACAGTA CAGCAGACGA
1321 GTAAGATGGA TGATTCTAGG TAGTGTTGGG GAGTCTGATG
1361 AAGGGCTTTT GGCGTTTTCT AGAGGCTGTC CTAGCCTGCA
1401 AAAACTTGAA ATGAGGGCCT GTTGCTTCAG TGAGAGTGCA
1441 CTGGCTAGAG CTGCCTTGCA ACTGACTTCT CTGAGGTACT
1481 TGTGGGTGCA TGGTTATAGA GAGACCTCTA CTGGTCATCG
1521 TGATCTCTTA ACAATGGTTC GCCCATTTTG GAACATCGAA
1561 TTGATTCCTT CTAGGAAGGT TGAGTCGGTT AATGAAGCTG
1601 GAGAAAATAT TGTTTCCGAG AATCCAGCCC ACATTCTTGC
```

```
1641 ATATTACTCC CTTGCTGGAC CAAGAACAGA CTTTCCAGAT

1681 ACTGTGAGAC CACTGGATCC AGCGAACATA GTTGCTGCGT

1721 AGAGCTGTAT ATGAAGTTGA TGTCATGTTC TTTTTATTGC

1761 CACGCCCTGT TTATAGATTT ATCCATCTTT TTATCATTTG

1801 GGTAAGAGTG TTTCGGTTTA ATTTTAAATT TCTATTTTAC

1841 TTAGACCGTT GTCCTGTAAT AAGTCTACGT TCTCTGCTGT

1881 AATTTAGCAC TTCCGCTCTA GGTACACTAC TGTCTTTTCT

1921 GTCGTCTGTG GCAGTTAGCT TAACCTTTTG GTGACTTTGT

1961 ATTTCATCTG CTTCAATGTT GGAAATGTTG CTAGAATTTT

2001 GGCTGCTTTT TATTGATAAA TACACAGATT TTCACTTGCA
```

An example of a COI1 protein from *Arachis hypogaeal* (peanut) with NCBI accession number AGH62009.1 (GI: 469609864) has the following sequence (SEQ ID NO:38).

```
  1 RHCKKLQRLW IMDSIGDKGL GVVANTCKEL QELRVFPSDN

41 IGQHAAVTEK GLVAISMGCP KLHSLLYFCH QMTNAALITV

81 AKNCPNFIRF RLAILDATKP DPDTNQPLDE GFGAIVQSCR

121 RLRRLSLSGQ LTDKVFLYIG MYAEQLEMLS IAFAGESDKG

161 MLYVLNGCKK LRKLEIRDCP FGNTALLTDV GKYETMRSLW

201 MSSCEVTVGA CKVLAMKMPR LNVEIFNENE PADCEPDDVQ

241 KVEKMYLYRT LAGKRKDAPE YVWTL
```

A comparison of the *Arabidopsis thaliana* COI1 SEQ ID NO:1 sequence and the *Arachis hypogaeal* COI1 SEQ ID NO:38 sequence is shown below, illustrating that the two proteins have at least 31% sequence identity. In addition, the location of the alanine at position 384 that can be replaced, for example with a valine, to generate a modified COI1 protein is also identified in bold and with underlining. As illustrated, instead of an alanine, the *Arachis hypogaeal* COI1 sequence has a leucine at the equivalent position (66). Such a leucine at position 66 of the *Arachis hypogaeal* COI1 protein (SEQ ID NO:38) sequence can be modified and in some cases, it can be replaced with a valine.

```
31.0% identity in 274 residues overlap; Score: 312.0; Gap frequency:
4.7%
Seq1   317 CPNLEVLETRNVIGDRGLEVLAQYCKQLKRLRIERGADEQGMEDEEGLVSQRGLIALAQG
Seq38    3 CKKLQRLWIMDSIGDKGLGYVANTCKELQELRVFP-SDNIG---QHAAVTEKGLVAISMG
           *  *  *     *** ** * *  ** *  **     *  *       *   ** *   *

Seq1   377 CQELEYMAVYVSDITNESLESIGTYLKNLCDFRLVLLD--REERITDLPLDNGVRSLLIG
Seq38   59 CPKLKSLLYFCHQMTNAALITVAKNCPNFIRFRLAILDATKPDPDTNQPLDEGFGAIVQS
           *  *          **  *        *   ***  **       *  *** *

Seq1   435 CKKLRRFAFYLRQGGLTDLGLSYIGQYSPNVRWMLLGYVGESDEGIMEFSRGCPNLQKLE
Seq38  119 CRRLRRLSL---SGQLTDKVFLYIGMYAEQLEMLSIAFAGESDKGMLYVLNGCKKLRKLE
           *  ***       * ***    *** *            **** *      **  * ***

Seq1   495 MRGCCFSERAIAAAVTKLPSLRYLWVQGYRASMTGQDLMQMARPYWNIELIPSRRVPEVN
Seq38  176 IRDCPFGNTALLTDVGKYETMRSLWMSSCEVTVGACKVLAMKMPRLNVEIF-NENEPADC
           *  ***       * ***    *** *            **** *      **  * ***

Seq1   555 QQGEIREMEHPAHILAYYSLAGQRTDCPTTVRVL
Seq38  235 EPDDVQKVE---KMYLYRTLAGKRKDAPEYVWTL
                   *       *  *** * * *  *  *
```

An example of a modified *Arachis hypogaeal* (peanut) COI1 protein with a valine instead of a leucine has the following sequence (SEQ ID NO:39).

```
  1 RHCKKLQRLW IMDSIGDKGL GVVANTCKEL QELRVFPSDN

41 IGQHAAVTEK GLVAISMGCP KLHSLVYFCH QMTNAALITV

81 AKNCPNFIRF RLAILDATKP DPDTNQPLDE GFGAIVQSCR

121 RLRRLSLSGQ LTDKVFLYIG MYAEQLEMLS IAFAGESDKG

161 MLYVLNGCKK LRKLEIRDCP FGNTALLTDV GKYETMRSLW

201 MSSCEVTVGA CKVLAMKMPR LNVEIFNENE PADCEPDDVQ

241 KVEKMYLYRT LAGKRKDAPE YVWTL
```

An example of a nucleotide (cDNA) sequence that encodes the *Arachis hypogaeal* SEQ ID NO:38 COI1 protein (with NCBI cDNA accession number KC355791.1 (GI:469609863)) is shown below as SEQ ID NO:40.

```
  1 CGTCACTGCA AGAAACTTCA GCGCTTATGG ATAATGGATT

41 CCATTGGAGA TAAAGGGCTA GGTGTTGTAG CTAACACATG

81 TAAGGAATTG CAAGAATTGA GGGTTTTTCC TTCCGACAAC

121 ATTGGTCAGC ATGCGGCTGT CACAGAGAAG GGATTGGTTG

161 CGATATCTAT GGGCTGCCCG AAACTTCACT CATTGCTCTA

201 CTTCTGCCAC CAGATGACAA ATGCTGCCCT AATAACTGTG

241 GCCAAGAACT GCCCGAATTT TATCCGCTTT AGGTTGGCCA

281 TCCTTGACGC AACAAAACCC GACCCCGACA CAAATCAGCC

321 ACTGGATGAA GGTTTTGGGG CGATTGTGCA ATCTTGCAGG

361 CGTCTTAGGC GGCTTTCCCT CTCTGGCCAG CTGACTGATA

401 AGGTATTCCT CTACATCGGA ATGTATGCTG AGCAGCTTGA

441 GATGTTGTCC ATTGCCTTTG CCGGGGAGAG CGACAAGGGG

481 ATGCTCTATG TTCTGAACGG ATGCAAGAAG CTCCGCAAGC

521 TTGAGATCAG GGACTGCCCT TTCGGCAACA CGGCACTTCT

561 GACAGACGTA GGGAAGTATG AAACAATGCG ATCCCTTTGG
```

```
601 ATGTCGTCGT GCGAAGTAAC CGTCGGAGCA TGCAAGGTGC

641 TAGCAATGAA GATGCCGAGG CTAAATGTTG AGATCTTCAA

681 CGAGAATGAG CCAGCCGACT GCGAGCCGGA TGATGTGCAG

721 AAGGTGGAGA AGATGTACTT GTACCGGACA TTGGCTGGGA

761 AGAGGAAAGA TGCACCGGAA TATGTATGGA CCCTTTAGGT

801 GCATTTTTAG GTCAATTTTA ATTTTATTGT TATTATTGAG

841 CAGTTTGTAC GTTAGGCTGA CTTATTAATG CAATTTTAGC

881 CTTGTGTAGT GGTTGGTTTG
```

An example of a COI1 protein from *Physcomitrella patens* (earthmoss) with NCBI accession number XP_001776814.1 (GI:168048721) has the following sequence (SEQ ID NO:41).

```
  1 MGREKRPSGS GTGLSDETLA CVLKYVESAE DRASVSLVCK

41 QWRLVDGATR KFVTIAYMYS TSPEMLTRRF KRLEGLKLKG

61 KPRAAEYDLL VPDWGGYAEP WIRDLGRAYT SLQTLQLRRC

121 QVSNADLTLI ASSPCQASLQ VLYLHKCAGF STAGLLPVAK

161 SCRSLKSLSV EDSDVTDEGG EWLFELARNN SVLEVLNFAV

201 LGLEDVDAAD LVLLVERCKS LVSLKVGEVE MVDMISAISR

241 ASSLTEFGTG SCNFFGDEDS RTHVSISLPS SLTGLSGLWA

281 MSDPGLAMVL PIAPNLRKLD LKFTLLSRKA YCQLFSQCHA

321 LEELQVRNAV GDEGMEVIGK TCKSLRRLRV EHDNAGAITQ

361 RGVVAVAQGC ARMQQLIVYV SDITNAALAM LGQCCAQLTD

401 FRLVLETAAR RVVDLPLDDG IKLLLKGCRK ISKLAVYLRH

441 GGLTDRGMGY IGEFGTNLKW LLLGCTGESD IGLASLAYKA

481 QRIERLECRD CPFGEAGLAA AVVAMSSLKF IWIQGYRAPW

521 AGEHLLALSR PYLNIEVISS TDTQPGQLIA HYTTVGPRTD

561 NPLEVKQLTL NPDDHLQEMR PSLHSPGSTR H
```

A comparison of the *Arabidopsis thaliana* COI1 SEQ ID NO:1 sequence and the *Physcomitrella patens* COI1 SEQ ID NO:41 sequence is shown below, illustrating that the two proteins have at least 40% sequence identity. In addition, the location of the alanine at position 384 that can be replaced, for example with a valine, to generate a modified COI1 protein is also identified in bold and with underlining. As illustrated, instead of an alanine, the *Physcomitrella patens* COI1 SEQ ID NO:41 sequence has a isoleucine at the equivalent position (377). Such an isoleucine at position 377 of the *Physcomitrella patens* COI1 protein (SEQ ID NO:41) sequence can be modified and in some cases, it can be replaced with a valine.

```
41.5% identity in 544 residues overlap; Score: 1109.0; Gap frequency: 2.0%

Seq1    7 KRCKLSCVATVDDVIEQVMTYITDPKDRDSASLVCRRWFKIDSETREHVTMALCYTATPD
Seq41   5 KRPSGSGTGLSDETLACVLKYVESAEDRASVSLVCKQWRLVDGATRKFVTIAYMYSTSPE
           **  *       *    *   ** ****  *    *  **  ***  **  *     *

Seq1   67 RLSRRFPNLRSLKLKGKPRAAMFNLIPENWGGYVTPWVTEISNNLRQLKSVHFRRMIVSD
Seq41  65 MLTRRFKRLEGLKLKGKPRAAEYDLLVPDWGGYAEPWIRDLGRAYTSLQTLQLRRCQVSN
            ***  *   **********   * * *  ****  **         *     **  **

Seq1  127 LDLDRLAKARAD-DLETLKLDKCSGFTTDGLLSIVTHCRKIKTLLMEESSFSEKDGKWLH
Seq41 125 ADLTLIASSPCQASLQVLYLHKCAGFSTAGLLPVAKSCRSLKSLSVEDSDVTDEGGEWLF
           **     *        *  * ** *** ***   * *** *  *     *  * * ***

Seq1  186 ELAQHNTSLEVLNFYMTEFAKISPKDLETIARNCRSLVSVKVGDFEILELVGFFKAAANL
Seq41 185 ELARNNSVLEVLNFAVLGLEDVDAADLVLLVERCKSLVSLKVGEVEMVDMISAISRASSL
          ***   * ******         **     **  **** ***    *     *    * *

Seq1  246 EEFCGGSLNEDIGMPEK-YMNLVFPRKLCRL-GLSYMGPNEMPILFPFAAQIRKLDLLYA
Seq41 245 TEFGTGSCNFFGDEDSRTHVSISLPSSLTGLSGLWAMSDPGLAMVLPIAPNLRKLDLKFT
           ** ** **  *    *    * *   * **     *       ** *   **   ****

Seq1  304 LLETEDHCTLIQKCPNLEVLETRNVIGDRGLEVLAQYCKQLKRLRIERGADEQGMEDEEG
Seq41 305 LLSRKAYCQLFSQCHALEELQVRNAVGDEGMEVIGKTCKSLRRLRVEH--------DNAG
          **     *  *  *    **  ** ** * ***   **  ****  **             * *

Seq1  364 LVSQRGLIALAQGCQELEYMAVYVSDITNESLESIGTYLKNLCDFRLVLLDREERITDLP
Seq41 357 AITQRGVVAVAQGCARMQQLIVYVSDITNAALAMLGQCCAQLTDFRLVLETAARRVVDLP
           *** *     * **** ********                 *   ******       * ***

Seq1  424 LDNGVRSLLIGCKKLRRFAFYLRQGGLTDLGLSYIGQYSPNVRWMLLGYVGESDEGLMEF
Seq41 417 LDDGIKLLLKGCRKISKLAVYLRHGGLTDRGMGYIGEFGTNLKWLLLGCTGESDIGLASL
          ** *  * ** **    * ****  *****  * ***   *   *****  ****  * *

Seq1  484 SRGCPNLQKLEMRGCCFSERAIAAAVTKLPSLRYLWVQGYRASMTGQDLMQMARPYWNIE
Seq41 477 AYKAQRIERLECRDCPFGEAGLAAAVVAMSSLKFIWIQGYRAPWAGEHLLALSRPYLNIE
            *   *   *       *  * *****    * ***   **    ***  **   *** ***

Seq1  544 LIPS
Seq41 537 VISS
             * *
```

An example of a modified COI1 *Physcomitrella patens* protein with a valine instead of an isoleucine at position 377 has the following sequence (SEQ ID NO:42).

```
  1 MGREKRPSGS GTGLSDETLA CVLKYVESAE DRASVSLVCK
 41 QWRLVDGATR KFVTIAYMYS TSPEMLTRRF KRLEGLKLKG
 61 KPRAAEYDLL VPDWGGYAEP WIRDLGRAYT SLQTLQLRRC
121 QVSNADLTLI ASSPCQASLQ VLYLHKCAGF STAGLLPVAK
161 SCRSLKSLSV EDSDVTDEGG EWLFELARNN SVLEVLNFAV
201 LGLEDVDAAD LVLLVERCKS LVSLKVGEVE MVDMISAISR
241 ASSLTEFGTG SCNFFGDEDS RTHVSISLPS SLTGLSGLWA
281 MSDPGLAMVL PIAPNLRKLD LKFTLLSRKA YCQLFSQCHA
321 LEELQVRNAV GDEGMEVIGK TCKSLRRLRV EHDNAGAITQ
361 RGVVAVAQGC ARMQQLVVYV SDITNAALAM LGQCCAQLTD
401 FRLVLETAAR RVVDLPLDDG IKLLLKGCRK ISKLAVYLRH
441 GGLTDRGMGY IGEFGTNLKW LLLGCTGESD IGLASLAYKA
481 QRIERLECRD CPFGEAGLAA AVVAMSSLKF IWIQGYRAPW
521 AGEHLLALSR PYLNIEVISS TDTQPGQLIA HYTTVGPRTD
561 NPLEVKQLTL NPDDHLQEMR PSLHSPGSTR H
```

An example of a nucleotide (cDNA) sequence that encodes the *Physcomitrella patens* SEQ ID NO:40 COI1 protein (with NCBI cDNA accession number KC355791.1 (GI:469609863)) is shown below as SEQ ID NO:43.

```
   1 ATGGGGCGAG AGAAGAGACC ATCAGGATCT GGGACGGGCT
  41 TATCCGACGA GACCCTGGCG TGTGTGTTGA AGTATGTGGA
  81 GAGTGCGGAG GATAGAGCGT CAGTCTCCCT GGTGTGCAAG
 121 CAATGGCGAC TCGTGGATGG TGCCACGAGG AAGTTTGTAA
 161 CGATAGCTTA CATGTACTCC ACTAGCCCTG AGATGCTCAC
 201 CCGACGCTTC AAGCGCCTGG AAGGGCTTAA GCTGAAGGGG
 241 AAGCCTCGCG CTGCGGAATA TGATTTACTA GTACCCGATT
 281 GGGGTGGATA TGCTGAGCCC TGGATTCGGG ATCTGGGGCG
 321 CGCATATACA AGTCTGCAAA CGCTGCAACT GCGTCGGTGC
 361 CAGGTTTCTA ATGCGGATTT GACCTTAATT GCGTCTTCTC
 401 CCTGTCAAGC GTCTCTGCAA GTTTTGTATT TACATAAATG
 441 CGCTGGGTTT TCCACCGCTG GCCTCCTCCC TGTTGCTAAG
 481 TCCTGCCGGT CTCTGAAGTC TTTGAGCGTA GAGGACAGCG
 521 ATGTAACTGA TGAAGGTGGA GAGTGGCTAT TCGAGCTGGC
 561 CCGCAACAAT TCCGTGTTGG AGGTCCTGAA TTTTGCTGTA
 601 CTTGGTCTTG AGGATGTTGA TGCAGCTGAC TTGGTGTTGC
 641 TAGTGGAGAG GTGCAAATCA CTGGTTTCTC TAAAAGTTGG
 681 TGAAGTTGAA ATGGTGGACA TGATAAGTGC CATTAGCAGA
 721 GCGTCTTCTT TGACTGAATT CGGCACAGGC TCTTGCAATT
 761 TCTTCGGGGA CGAGGACAGC AGGACACATG TATCTATATC
 801 TTTACCTTCA AGCTTGACGG GTTTGTCAGG TTTGTGGGCC
 841 ATGTCCGACC CTGGATTGGC TATGGTTCTT CCCATAGCAC
 881 CAAACTTGAG AAAACTGGAC CTGAAGTTCA CGCTTTTGAG
 921 CAGAAAAGCT TACTGCCAAC TTTTCAGTCA GTGCCATGCT
 961 TTGGAAGAGC TTCAGGTTCG CAACGCAGTT GGGGACGAGG
1001 GCATGGAAGT TATCGGCAAG ACATGCAAGA GCCTCAGGCG
1041 ATTACGCGTG GAGCACGATA ATGCAGGAGC TATCACTCAA
1081 CGAGGCGTTG TTGCTGTTGC CCAAGGGTGT GCACGAATGC
1121 AGCAGTTGAT CGTGTACGTG TCCGACATCA CCAACGCCGC
1161 GCTGGCGATG CTGGGACAAT GCTGCGCACA GCTGACGGAC
1201 TTCCGTCTCG TGCTGGAGAC CGCTGCAAGA CGCGTCGTCG
1241 ACCTGCCGTT GGACGATGGA ATCAAGCTCC TGCTCAAAGG
1281 CTGCCGAAAA ATATCCAAGC TTGCTGTATA TCTTCGGCAC
1321 GGGGGCTTGA CAGACAGAGG AATGGGTTAC ATCGGGGAGT
1361 TTGGCACGAA TTTGAAATGG TTATTGTTGG GATGCACAGG
1401 CGAATCCGAC ATTGGATTGG CCAGTTTGGC ATACAAAGCG
1441 CAGCGCATTG AAAGGTTAGA GTGTCGGGAT TGTCCGTTTG
1481 GGGAGGCAGG TCTTGCGGCA GCAGTAGTGG CGATGAGCTC
1521 GCTCAAGTTT ATATGGATTC AAGGCTATAG GGCTCCATGG
1561 GCAGGAGAGC ATCTACTGGC CTTATCACGA CCGTATCTGA
1601 ACATAGAAGT TATCTCCTCA ACAGACACCC AACCAGGCCA
1641 GCTCATAGCC CACTATACCA CTGTCGGGCC TCGCACTGAT
1681 AACCCTTTGG AGGTAAAGCA GCTGACGTTA AACCCGGACG
1721 ATCACCTGCA GGAAATGCGA CCGAGTTTAC ACTCACCTGG
1761 ATCTACGCGG CACTAAGCAG AGATTAGGCC AAGCGTCATT
1801 GCTTTCAGGC CCTCTATTGA TTTCTGTCTT CTAGCCGCGG
1841 ATGGTCGCAG TGCGCCGTTG GATACCCTAC CAGAAGCGTG
1881 GCTATTAATA CTAATGAGTG TTTGCCAGAA CGGCCCTTGA
1921 TTGTGGTCTG TGGTGGACGT TTACTGACAG CAGGAGGTGT
1961 ACGAGAGATT GCCCCTCATT GTAAAATCTG TATTAGGACA
2001 GCTAGGCTAC CAATGCTGCT GTTTCAAGTC CTTGAAACAG
2041 TGAAGATGTT GCATGCGTAC GAGGACTGCC TACTACTGTA
2081 TAAGTGTAGT GCAATGTGAA AGTGTAATGT AGTGTATTGA
2121 AATTGGGCAA GGAGTTATGG GAAAGGCTAT GTAGCTGACA
2161 CAGTTGAATG TACCTATTGT GCATTTTGGA GAAA
```

An example of a COI1 protein from *Oryza sativa Japonica* Group (rice) with NCBI accession number XP_015639870.1 (GI:1002271090) has the following sequence (SEQ ID NO:44).

```
  1 MGGEAPEARR LDRAMSFGGA GSIPEEALHL VLGYVDDPRD
 41 REAVSLVCRR WHRIDALTRK HVTVPFCYAA SPAHLLARFP
 81 RLESLAVKGK PRAAMYGLIP EDWGAYARPW VAELAAPLEC
121 LKALHLRRMV VTDDDLAALV RARGHMLQEL KLDKCSGFST
```

```
161 DALRLVARSC RSLRTLFLEE CSIADNGTEW LHDLAVNNPV

201 LETLNFHMTE LTVVPADLEL LAKKCKSLIS LKISDCDFSD

241 LIGFFRMAAS LQEFAGGAFI EQGELTKYGN VKFPSRLCSL

281 GLTYMGTNEM PIIFPFSALL KKLDLQYTFL TTEDHCQLIA

321 KCPNLLVLAV RNVIGDRGLG VVADTCKKLQ RLRVERGDDD

361 PGLQEEQGGV SQVGLTTVAV GCRELEYIAA YVSDITNGAL

401 ESIGTFCKNL CDFRLVLLDR EERITDLPLD NGVRALLRGC

441 TKLRRFALYL RPGGLSDTGL GYIGQYSGII QYMLLGNVGE

481 TDDGLIRFAL GCENLRKLEL RSCCFSEQAL ARAIRSMPSL

521 RYVWVQGYKA SKTGHDLMLM ARPFWNIEFT PPSSENANRM

561 REDGEPCVDS QAQILAYYSL AGKRSDCPRS VVPLYPA
```

A comparison of the *Arabidopsis thaliana* COI1 SEQ ID NO:1 sequence and the *Oryza sativa* COI1 SEQ ID NO:44 sequence is shown below, illustrating that the two proteins have at least 59% sequence identity. In addition, the location of the alanine at position 384 that can be replaced, for example with a valine, to generate a modified COI1 protein is also identified in bold and with underlining. As illustrated, the *Oryza sativa* COI1 SEQ ID NO:44 sequence has an alanine at the equivalent position (389). Such an alanine at position 389 of the *Oryza sativa* COI1 protein (SEQ ID NO:44) sequence can be modified and in some cases, it can be replaced with a valine.

An example of a modified COI1 *Oryza sativa* protein with a valine instead of an alanine at position 389 has the following sequence (SEQ ID NO:45).

```
  1 MGGEAPEARR LDRAMSFGGA GSIPEEALHL VLGYVDDPRD

41 REAVSLVCRR WHRIDALTRK HVTVPFCYAA SPAHLLARFP

81 RLESLAVKGK PRAAMYGLIP EDWGAYARPW VAELAAPLEC

121 LKALHLRRMV VTDDDLAALV RARGHMLQEL KLDKCSGFST

161 DALRLVARSC RSLRTLFLEE CSIADNGTEW LHDLAVNNPV

201 LETLNFHMTE LTVVPADLEL LAKKCKSLIS LKISDCDFSD

241 LIGFFRMAAS LQEFAGGAFI EQGELTKYGN VKFPSRLCSL

281 GLTYMGTNEM PIIFPFSALL KKLDLQYTFL TTEDHCQLIA

321 KCPNLLVLAV RNVIGDRGLG VVADTCKKLQ RLRVERGDDD

361 PGLQEEQGGV SQVGLTTVAV GCRELEYIVA YVSDITNGAL

401 ESIGTFCKNL CDFRLVLLDR EERITDLPLD NGVRALLRGC

441 TKLRRFALYL RPGGLSDTGL GYIGQYSGII QYMLLGNVGE

481 TDDGLIRFAL GCENLRKLEL RSCCFSEQAL ARAIRSMPSL

521 RYVWVQGYKA SKTGHDLMLM ARPFWNIEFT PPSSENANRM

561 REDGEPCVDS QAQILAYYSL AGKRSDCPRS VVPLYPA
```

An example of a nucleotide (cDNA) sequence that encodes the *Oryza sativa* SEQ ID NO:44 COI1 protein (with

```
59.1% identity in 570 residues overlap; Score: 1768.0; Gap frequency:
0.9%
Seq1     18 DDVIEQVMTYITDPKDRDSASLVCRRWFKIDSETREHVTMALCYTATPDRLSRRFPNLRS
Seq44    25 EEALHLVLGYVDDPRDREAVSLVCRRWHRIDALTRKHVTVPFCYAASPAHLLARFPRLES
             *  *  ** **  *******  **  ** *** **   *  *    *** *  *

Seq1     78 LKLKGKPRAAMFNLIPENWGGYVTPWVTEISNNLRQLKSVHFRRMIVSDLDLDRLAKARA
Seq44    85 LAVKGEPRAAMYGLIPEDWGAYARPWVAELAAPLECLKALHLRRMVVTDDDLAALVRARG
             *  *** *******   *  *  * * ***  *    *      * ***  *  *  **

Seq1    138 DDLETLKLDKCSGFTTDGLLSIVTHCRKIKTLLMEESSFSEKDGKWLHELAQHNTSLEVL
Seq44   145 HMLQELKLDKCSGFSTDALRLVARSCRSLRTLFLEECSIADNGTEWLHDLAVNNPVLETL
              * *********  **    *   **   **  ***   ** *  *** *  *   * *

Seq1    198 NFYMTEFAKISPKDLETIARNCRSLVSVKVGDFEILELVGFFKAAANLEEFCGGSLNEDI
Seq44   205 NFHMTELTVV-PADLELLAKKCKSLISLKISDCDFSDLIGFFRMAASLQEFAGGAFIEQ-
             ** ***     *** *  *  * *** **  *  *  ****   *** *** *   *

Seq1    258 GMPEKYMNLVFPRKLCRLGLSYMGPNEMPILFPFAAQIRKLDLLYALLETEDHCTLIQKC
Seq44   263 GELTKYGNVKFPSRLCSLGLTYMGTNEMPIIPPFSALLKKLDLQYTFLTTEDHCQLIAKC
              *  **  * **  *** *** *** ****   **      ****  *  ***** ** *

Seq1    318 PNLEVLETRNVIGDRGLEVLAQYCKQLKRLRIERGADEQGMEDEEGLVSQRGLIALAQGC
Seq44   323 PNLLVLAVRNVIGDRGLGVVADTCKKLQRLRVERGDDDPGLQEEQGGVSQVGLTTVAVGC
             ***  **  ******** *   ** * *** ***     *     *  * **     **

Seq1    378 QELEYMAVYVSDITNESLESIGTYLKNLCDFRLVLLDREERITDLPLDNGVRSLLIGCKK
Seq44   383 RELEYIAAYVSDITNGALESIGTFCKNLCDFRLVLLDREERITDLPLDNGVRALLRGCTK
             *****  ******* **  ****  **********************  ** ** * *

Seq1    438 LRRFAFYLRQGGLTDLGLSYIGQYSPNVRWMLLGYVGESDEGLMEFSRGCPNLQKLEMRG
Seq44   443 LRRFALYLRPGGLSDTGLGYIGQYSGIIQYMLLGNVGETDDGLIRFALGCENLRKLELRS
             *****  *** ** * ** ******    **** ***  ***  *   ** ** ** *

Seq1    498 CCFSERAIAAAVTKLPSLRYLWVQGYRASMTGQDLMQMARPYWNIELIP--SRRVPEVNQ
Seq44   503 CCFSEQALARAIRSMPSLRYVWVQGYKASKTGHDLMLMARPFWNIEFTPPSSENANRMRE
             *****  *   *    ****  ***** ** ****  ****  ***          *

Seq1    556 QGEIREMEHPAHILAYYSLAGQRTDCPTTV
Seq44   563 DGEPC-VDSQAQILAYYSLAGKRSDCPRSV
              **     *  * ******** * ***  *
```

NCBI cDNA accession number XM_015784384.1 (GI: 1002271089)) is shown below as SEQ ID NO:46.

```
   1 CTGCGATTGC CATCCCGGCC ACCTCCAAAG GCTTTAGCCG
  41 GCGGGGGACA AAGGGCGGCC CACCCCCTGC GTGCGCCAAG
  81 CAATTTGGCC GCCTGACCCC GTGCCGACGT GGCCCGGCAT
 121 CCCCTAGCTG GATCCCGCAG AAGTAAACGC CCGCCTCCTC
 161 CCCCAATCCC CATCTCCTCT CCACTCTTCT TCTCCCTCCA
 201 ATAATTCTCT CCCCTCTCCT CCTCTTCACC ACCACCACCA
 241 CCACCAGCAG CAGCAGAGAG CACCATCTCC ATCCAATAAT
 281 CCCCATGCTT GCGCACCACT CCCGGCCACA TCCCGCGCGA
 321 GGAGGAGGAG GAGGAGGAGG GTGTGCTTGA TCCGCGCTCC
 361 CGCCTGGTTG GTGGTGGTGG GGTGAGGGGG GAGGGATGGG
 401 AGGGGAGGCA CCGGAGGCGC GGCGGTTGGA CCGCGCGATG
 441 AGCTTCGGCG GCGCGGGCAG CATCCCGGAG GAGGCGCTGC
 481 ACCTGGTGCT GGGGTACGTG GACGACCCGC GGGACAGGGA
 521 GGCGGTGTCG CTCGTGTGCC GCCGCTGGCA CCGCATCGAC
 561 GCGCTCACGC GGAAGCACGT CACCGTGCCC TTCTGCTACG
 601 CCGCGTCGCC CGCGCACCTG CTCGCGCGGT TCCCGCGGCT
 641 GGAGTCGCTC GCGGTCAAGG GGAAGCCGCG CGCCGCCATG
 681 TACGGGCTCA TCCCGGAGGA CTGGGGCGCC TACGCGCGCC
 721 CCTGGGTCGC CGAGCTCGCC GCGCCGCTCG AGTGCCTCAA
 761 GGCGCTCCAC CTGCGCCGCA TGGTCGTCAC CGACGACGAC
 801 CTCGCCGCGC TCGTCCGCGC CCGCGGCCAC ATGCTGCAGG
 841 AGCTCAAGCT CGACAAGTGC TCCGGCTTCT CCACCGACGC
 881 TCTCCGCCTC GTCGCCCGCT CCTGCAGATC ACTGAGAACA
 921 TTATTTCTGG AGGAATGCTC AATTGCTGAT AATGGTACTG
 961 AATGGCTCCA CGACCTTGCT GTCAACAATC CTGTTCTGGA
1001 GACATTGAAC TTCCACATGA CCGAACTCAC AGTGGTGCCA
1041 GCTGACCTGG AGCTTCTCGC AAAGAAGTGC AAGTCACTAA
1081 TTTCATTGAA GATCAGTGAC TGTGACTTTT CAGATTTAAT
1121 TGGATTTTTC CGGATGGCTG CATCATTGCA AGAGTTTGCG
1161 GGAGGGGCAT TCATTGAGCA AGGGGAGCTC ACTAAGTATG
1201 GAAATGTTAA ATTCCCTTCA AGACTGTGCT CCTTAGGACT
1241 TACGTACATG GGGACAAACG AGATGCCCAT TATCTTCCCT
1281 TTCTCTGCAT TACTCAAGAA GCTGGACTTG CAGTACACTT
1321 TTCTCACCAC TGAAGATCAC TGCCAACTCA TTGCAAAATG
1361 TCCCAACTTA CTAGTTCTTG CGGTGAGGAA TGTGATTGGA
1401 GATAGAGGAT TAGGGGTTGT TGCAGACACA TGCAAGAAGC
1441 TACAAAGACT CAGAGTTGAG CGAGGAGATG ATGATCCAGG
1481 TTTGCAAGAA GAACAAGGAG GAGTCTCTCA AGTCGGGTTG
1521 ACAACTGTAG CCGTAGGATG CCGTGAACTG GAATACATAG
1561 CTGCCTATGT GTCTGATATC ACAAATGGGG CCCTGGAGTC
1601 TATTGGGACT TTCTGCAAAA ATCTTTGCGA CTTCCGTCTT
1641 GTCCTACTCG ATAGAGAAGA GAGGATAACA GATTTGCCCT
1681 TAGACAATGG TGTCCGTGCA CTGCTGAGGG GCTGCACGAA
1721 ACTTCGGAGG TTTGCTCTAT ACTTGAGACC AGGGGGACTT
1761 TCAGATACAG GCCTTGGCTA TATTGGACAG TACAGTGGAA
1801 TTATCCAATA CATGCTTCTG GGTAATGTTG GGGAAACAGA
1841 TGATGGTCTG ATCCGGTTTG CATTGGGGTG TGAGAACCTG
1881 CGGAAGCTTG AGCTAAGGAG TTGTTGCTTC AGTGAGCAAG
1921 CTTTAGCCCG CGCTATACGG AGTATGCCTT CCCTGAGATA
1961 CGTGTGGGTA CAGGGCTACA AGGCTTCTAA GACTGGTCAC
2001 GATCTCATGC TCATGGCCAG GCCCTTCTGG AACATAGAGT
2041 TTACACCTCC CAGTTCTGAG AATGCAAATC GAATGAGAGA
2081 AGATGGTGAA CCTTGTGTAG ATAGTCAAGC TCAGATACTT
2121 GCATACTACT CCCTTGCCGG GAAGAGGTCG GACTGCCCAC
2161 GATCTGTGGT TCCTTTGTAT CCTGCGTGAC TGTAAATACC
2201 GATATGGTAT CTCTCTGCTT CGTTCTTGCC TCTTGCCTTT
2241 TTTGGGTGAT ATGTTGATAT GTGGTTATTG TATGGGTCTA
2281 GAACTCTAGA TGGCTAGCTG CTATGTACCG TAATAAGCTA
2321 CTGGTAGCTG AGATGTACTG GAATAAGCAC TTCTATTTCC
2361 CACTCTACTA CTATCTAATC CTAGGAAGAT GTATACTAAG
2401 GAACACTCTG TGCCACTACT CCTTGCTTGT TCATGCTCCC
2441 GTCCTGGTTT GTTACCATTG GAGGTATAAG AATACCTGGT
2481 TTTGGCAGTC CTTAA
```

An example of a COI1 protein from *Sorghum bicolor* (*sorghum*) with NCBI accession number XP_002439888.1 (GI:242088111) has the following sequence (SEQ ID NO:47).

```
  1 MGGEAPEPRR LTRALSIGGG DGGWVPEEML HLVMGFVEDP
 41 RDREAASLVC RRWHRVDALS RKHVTVPFCY AVSPARLLAR
 81 FPRLESLAIK GKPRAAMYGL IPDDWGAYAR PWVAELAAPL
121 ECLKALHLRR MVVTDDDLAE LVRARGHMLQ ELKLDKCTGF
161 STDGLRLVAR SCRSLRTLFL EECQINDKGS EWIHDLADGC
201 PVLTTLNFHM TELQVMPADL EFLARSCKSL ISLKISDCDV
241 SDLIGFFQFA TALEEFAGGT FNEQGELTMY GNVRFPSRLC
281 SLGLTFMGTN EMPIIFPFSA ILKKLDLQYT VLTTEDHCQL
321 IAKCPNLLVL AVRNVIGDRG LGVVADTCKK LQRLRIERGD
361 DEGGVQEEQG GVSQVGLTAI AVGCRELEYI AAYVSDITNG
401 ALESIGTFCK KLYDFRLVLL DREERITELP LDNGVRALLR
441 GCTKLRRFAL YLRPGGLSDA GLGYIGQCSG NIQYMLLGNV
481 GETDDGLFSF ALGCVNLRKL ELRSCCFSER ALALAILRMP
```

```
521 SLRYVWVQGY KASQTGRDLM LMARPFWNIE FTPPSSENAG

561 RLMEDGEPCV DSHAQILAYH SLAGKRLDCP QSVVPLYPA
```

A comparison of the *Arabidopsis thaliana* COI1 SEQ ID NO:1 sequence and the *Sorghum bicolor* COI1 SEQ ID NO:47 sequence is shown below, illustrating that the two proteins have at least 58% sequence identity. In addition, the location of the alanine at position 384 that can be replaced, for example with a valine, to generate a modified COI1 protein is also identified in bold and with underlining. As illustrated, the *Sorghum bicolor* COI1 SEQ ID NO:47 sequence has an alanine at the equivalent position (391). Such an alanine at position 391 of the *Sorghum bicolor* COI1 protein (SEQ ID NO:47) sequence can be modified and in some cases, it can be replaced with a valine.

```
201 PVLTTLNFHM TELQVMPADL EFLARSCKSL ISLKISDCDV

241 SDLIGFFQFA TALEEFAGGT FNEQGELTMY GNVRFPSRLC

281 SLGLTFMGTN EMPIIFPFSA ILKKLDLQYT VLTTEDHCQL

321 IAKCPNLLVL AVRNVIGDRG LGVVADTCKK LQRLRIERGD

361 DEGGVQEEQG GVSQVGLTAI AVGCRELEYI VAYVSDITNG

401 ALESIGTFCK KLYDFRLVLL DREERITELP LDNGVRALLR

441 GCTKLRRFAL YLRPGGLSDA GLGYIGQCSG NIQYMLLGNV

481 GETDDGLFSF ALGCVNLRKL ELRSCCFSER ALALAILRMP

521 SLRYVWVQGY KASQTGRDLM LMARPFWNIE FTPPSSENAG

561 RLMEDGEPCV DSHAQILAYH SLAGKRLDCP QSVVPLYPA
```

```
58.4% identity in 570 residues overlap; Score: 1740.0; Gap frequency:
0.9%
Seq1    18 DDVIEQVMTYITDPKDRDSASLVCRRWFKIDSETREHVTMALCYTATPDRLSRRFPNLRS
Seq47   27 EEMLHLVMGFVEDPRDREAASLVCRRWHRVDALSRKHVTVPFCYAVSPARLLARFPRLES
              **   ** ** ********  *   * ***   **    * **  ***   * *

Seq1    78 LKLKGKPRAAMFNLIPENWGGYVTPWVTEISNNLRQLKSVHFRRMIVSDLDLDRLAKARA
Seq47   87 LAIKGKPRAAMYGLIPDDWGAYARPWVAELAAPLECLKALHLRRMVVTDDDLAELVRARG
            * ********  ** ***  **  *    *    *  ** * ***  * *  * **

Seq1   138 DDLETLKLDKCSGFTTDGLLSIVTHCRKIKTLLMEESSFSEKDGKWLHELAQHNTSLEVL
Seq47  147 HMLQELKLDKCTGFSTDGLRLVARSCRSLRTLFLEECQINDKGSEWIHDLADGCPVLTTL
              * ****** ** ****   **   **     *  **    *     *   *  * *

Seq1   198 NFYMTEFAKISPKDLETIARNCRSLVSVKVGDFEILELVGFFKAAANLEEFCGGSLNEDI
Seq47  207 NFHMTEL-QVMPADLEFLARSCKSLISLKISDCDVSDLIGFFQFATALEEFAGGTFNEQ-
           ** ***       *** * **  *** * * *   * ****  *  * **** ** **

Seq1   258 GMPEKYMNLVFPRKLCRLGLSYMGPNEMPILFPFAAQIRKLDLLYALLETEDHCTLIQKC
Seq47  265 GELTMYGNVRFPSRLCSLGLTFMGTNEMPIIFPFSAILKKLDLQYTVLTTEDHCQLIAKC
             *    *  **  ***  **  ** ****** *** *  ****  *  ****  ** **

Seq1   318 PNLEVLETRNVIGDRGLEVLAQYCKQLKRLRIERGADEQGMEDEEGLVSQRGLIALAQGC
Seq47  325 PNLLVLAVRNVIGDRGLGVVADTCKKLQRLRIERGDDEGGVQEEQGGVSQVGLTAIAVGC
           *** **  ********* *    ** * ******* **    *  * **** * * * **

Seq1   378 QELEYMAVYVSDITNESLESIGTYLKNLCDFRLVLLDREERITDLPLDNGVRSLLIGCKK
Seq47  385 RELEYIAAYVSDITNGALESIGTFCKKLYDFRLVLLDREERITELPLDNGVRALLRGCTK
            **** * ******* *******  * *  ************* ********  * **  *

Seq1   438 LRRFAFYLRQGGLTDLGLSYIGQYSPNVRWMLLGYVGESDEGLMEFSRGCPNLQKLEMRG
Seq47  445 LRRFALYLRPGGLSDAGLGYIGQCSGNIQYMLLGNVGETDDGLFSFALGCVNLRKLELRS
           *****  *** ***  ** ****   *   ***** ** * ***  *   * ** ** * *

Seq1   498 CCFSERAIAAAVTKLPSLRYLWVQGYRASMTGQDLMQMARPYWNIELIP--SRRVPEVNQ
Seq47  505 CCFSERALALAILRMPSLRYVWVQGYKASQTGRDLMLMARPFWNIEFTPPSSENAGRLME
           *******  *   * ***** ***** ** ** *** ***** * **  *     *

Seq1   556 QGEIREMEHPAHILAYYSLAGQRTDCPTTV
Seq47  565 DGEPCVDSH-AQILAYHSLAGKRLDCPQSV
              **     *  * **** **** *  *** *
```

An example of a modified COI1 *Sorghum bicolor* protein with a valine instead of an alanine at position 391 has the following sequence (SEQ ID NO:48).

```
  1 MGGEAPEPRR LTRALSIGGG DGGWVPEEML HLVMGFVEDP

41 RDREAASLVC RRWHRVDALS RKHVTVPFCY AVSPARLLAR

81 FPRLESLAIK GKPRAAMYGL IPDDWGAYAR PWVAELAAPL

121 ECLKALHLRR MVVTDDDLAE LVRARGHMLQ ELKLDKCTGF

161 STDGLRLVAR SCRSLRTLFL EECQINDKGS EWIHDLADGC
```

An example of a nucleotide (cDNA) sequence that encodes the *Sorghum bicolor* SEQ ID NO:47 COI1 protein (with NCBI cDNA accession number XM_002439843.1 (GI:242088110)) is shown below as SEQ ID NO:49.

```
  1 CTCGTCCGTC CTCCTCTCCA CTCTCTCTTC TCCCTCCAAT

41 AATTCTCTCC TCTCTCTCTG CACTCTGCTT GCTCCACCTC

81 CAAGCACCAC CGAATCAGGG CCAGTGGGAG CAGCAGCAGC

121 AGCGAGTGGG AGCAGAGGAG GGCAGAGAAT CCCATGTCTC
```

-continued

```
 161 CGCCCCTCGC TAGAGCAGAT CCTCGGCGAG CCGGGCGTGG
 201 AGCTGCTTCG GTAGAAAAGC GAGCCAACTG AGCCTGCGAG
 241 CGCCTGATCC GCCCGCGGCC CGATCGGGAT CGATGGGCGG
 281 TGAGGCGCCG GAGCCCCGGC GGCTGACCCG CGCGCTGAGC
 321 ATCGGCGGCG GCGACGGCGG CTGGGTCCCC GAGGAGATGC
 361 TGCACCTGGT GATGGGGTTC GTCGAGGACC CGCGCGACCG
 401 GGAGGCCGCG TCGCTGGTGT GCCGCCGGTG GCACCGCGTC
 441 GACGCGCTGT CGCGGAAGCA CGTCACGGTG CCCTTCTGCT
 481 ACGCCGTGTC CCCGGCGCGC CTGCTCGCGC GGTTCCCGCG
 521 GCTCGAGTCG CTGGCCATCA AGGGGAAGCC CCGCGCGGCC
 561 ATGTACGGCC TCATACCGGA CGACTGGGGC GCCTACGCCC
 601 GCCCCTGGGT CGCCGAGCTC GCCGCGCCGC TCGAGTGCCT
 641 CAAGGCGCTC CACCTCCGAC GCATGGTCGT CACGGACGAC
 681 GACCTCGCCG AGCTCGTCCG TGCCAGGGGA CACATGCTGC
 721 AGGAGCTCAA GCTCGACAAG TGCACCGGCT TCTCCACGGA
 761 TGGACTCCGC CTCGTTGCGC GCTCCTGCAG ATCACTGAGA
 801 ACTTTGTTTC TGGAAGAATG TCAAATTAAT GATAAAGGCA
 841 GTGAATGGAT CCACGATCTT GCAGACGGTT GTCCTGTTCT
 881 GACAACATTG AATTTCCACA TGACTGAGCT TCAAGTGATG
 921 CCAGCTGACC TAGAGTTTCT TGCAAGGAGC TGCAAGTCAC
 961 TGATTTCCTT GAAGATTAGC GACTGTGATG TTTCAGATTT
1001 GATAGGGTTC TTCCAATTTG CCACAGCACT GGAAGAATTT
1041 GCTGGAGGGA CATTCAATGA GCAAGGGGAA CTCACCATGT
1081 ATGGGAATGT CAGATTTCCA TCAAGACTAT GCTCCTTGGG
1121 ACTTACTTTC ATGGGAACAA ATGAAATGCC TATTATATTT
1161 CCTTTTTCTG CAATACTGAA GAAGCTGGAT TTGCAGTACA
1201 CTGTCCTCAC CACTGAAGAC CATTGCCAGC TTATTGCAAA
1241 ATGTCCGAAC TTACTAGTTC TCGCGGTGAG GAATGTGATT
1281 GGAGATAGAG GATTAGGAGT TGTTGCAGAT ACATGCAAGA
1321 AGCTCCAAAG GCTCAGAATT GAGCGAGGAG ACGATGAAGG
1361 AGGTGTGCAA GAAGAGCAGG GAGGGGTCTC TCAAGTGGGC
1401 TTGACGGCTA TAGCCGTCGG TTGCCGTGAA CTGGAATACA
1441 TAGCTGCCTA TGTGTCTGAT ATAACCAATG GGGCCCTGGA
1481 ATCTATCGGG ACATTCTGCA AAAAACTCTA TGACTTCCGG
1521 CTTGTTCTGC TTGATAGAGA AGAGAGGATA ACAGAATTGC
1561 CACTGGACAA TGGTGTCCGA GCTTTGTTGA GGGGCTGCAC
1601 CAAACTTCGG AGGTTTGCTC TGTACTTGAG ACCAGGAGGG
1641 CTCTCAGATG CAGGTCTCGG CTACATTGGA CAGTGCAGTG
1681 GAAACATCCA ATACATGCTT CTCGGTAATG TTGGGGAAAC
1721 TGATGATGGA TTGTTCAGTT TCGCATTGGG ATGCGTAAAC
1761 CTGCGGAAGC TTGAACTCAG GAGTTGTTGC TTCAGCGAGC
1801 GAGCTCTGGC CCTCGCCATA CTACGCATGC CTTCCCTGAG
1841 GTACGTATGG GTTCAGGGCT ACAAAGCGTC TCAAACCGGC
1881 CGAGACCTCA TGCTCATGGC GAGGCCCTTC TGGAACATAG
1921 AGTTTACACC TCCCAGTTCC GAGAACGCAG GTCGGTTGAT
1961 GGAAGATGGG GAACCTTGTG TAGATAGTCA TGCTCAGATA
2001 CTCGCATACC ACTCCCTCGC CGGTAAGAGG TTGGACTGCC
2041 CACAATCCGT GGTCCCTTTG TATCCTGCCT GAGTGTAAAT
2081 AGACTAAGCT GGTGTTTTTC TCCCTCATCC CTGCTTCCTT
2121 AGCCTCCTGG TCAACAAGAA CGATGTTGAT GACTTGATAT
2161 GTGGTTATTG TATGGATCTA GATGGCTAGC TGCTACGTAC
2201 TGTAATAAGC TACTAGTAGC TGAGATGTCC TGGAATAAGC
2241 CCTTGCTATT TTCGCCTGTA CTGCTATCTA ATCCTAGGAA
2281 GATGTATACT ACTAAGTAAC GGTGGAAGAT GTGAGTCTTG
2321 CTTGCTCGCC CTGATTTGTA CTATTGGAGG TATAAGAATA
2361 CCTGGGTTTT TGCCGCCTAC TTTGAGCATT GAGATGTGTC
2401 T
```

In some cases, the modified COI1 protein can have a sequence related to SEQ ID NO:1, 2, 5, 8, 10, 13, 16, 19, 22, 25, 28, 31, 33, 36, 39, 42, 45, or 48. However, the modified COI1 protein can have some sequence variation relative to SEQ ID NO:1, 2, 5, 8, 10, 13, 16, 19, 22, 25, 28, 31, 33, 36, 39, 42, 45, or 48. For example, a modified COI1 protein can have an amino acid sequence that has at least 90%, or at least 95%, or at least 96%, or at least 97%, at least 98%, or at least 99% sequence identity to SEQ ID NO:1, 2, 5, 8, 10, 13, 16, 19, 22, 25, 28, 31, 33, 36, 39, 42, 45, or 48.

Transformation of Plant Cells

Plant cells can be modified to include expression cassettes or transgenes that can express any of the modified COI1 proteins described herein. Such an expression cassette or transgene can include a promoter operably linked to a nucleic acid segment that encodes any of the modified COI1 proteins described herein.

Promoters provide for expression of mRNA from the COI1 nucleic acids. In some cases the promoter can be a COI1 native promoter. However, the promoter can in some cases be heterologous to the COI1 nucleic acid segment. In other words, such a heterologous promoter may not be naturally linked to such a COI1 nucleic acid segment. Instead, some expression cassettes and expression vectors have been recombinantly engineered to include a COI1 nucleic acid segment operably linked to a heterologous promoter. A COI1 nucleic acid is operably linked to the promoter, for example, when it is located downstream from the promoter.

A variety of promoters can be included in the expression cassettes and/or expression vectors. In some cases, the endogenous COIL promoter can be employed. Promoter regions are typically found in the flanking DNA upstream from the coding sequence in both prokaryotic and eukaryotic cells. A promoter sequence provides for regulation of transcription of the downstream gene sequence and typically includes from about 50 to about 2,000 nucleotide base pairs. Promoter sequences can also contain regulatory sequences such as enhancer sequences that can influence the level of gene expression. Some isolated promoter sequences can provide for gene expression of heterologous DNAs, that is a DNA different from the native or homologous DNA.

Promoters can be strong or weak, or inducible. A strong promoter provides for a high level of gene expression, whereas a weak promoter provides for a very low level of gene expression. An inducible promoter is a promoter that provides for the turning on and off of gene expression in response to an exogenously added agent, or to an environmental or developmental stimulus. For example, a bacterial promoter such as the $P_{tac}$ promoter can be induced to vary levels of gene expression depending on the level of isothiopropylgalactoside added to the transformed cells. Promoters can also provide for tissue specific or developmental regulation. A strong promoter for heterologous DNAs can be advantageous because it provides for a sufficient level of gene expression for easy detection and selection of transformed cells and provides for a high level of gene expression when desired. In some cases, the promoter within such expression cassettes/vectors can be functional during plant development or growth.

Expression cassettes/vectors can include, but are not limited to, a plant promoter such as the CaMV 35S promoter (Odell et al., *Nature*. 313:810-812 (1985)), or others such as CaMV 19S (Lawton et al., *Plant Molecular Biology*. 9:315-324 (1987)), nos (Ebert et al., *Proc. Natl. Acad. Sci. USA*. 84:5745-5749 (1987)), Adh1 (Walker et al., *Proc. Natl. Acad. Sci. USA*. 84:6624-6628 (1987)), sucrose synthase (Yang et al., *Proc. Natl. Acad. Sci. USA*. 87:4144-4148 (1990)), α-tubulin, ubiquitin, actin (Wang et al., *Mol. Cell. Biol.* 12:3399 (1992)), cab (Sullivan et al., *Mol. Gen. Genet.* 215:431 (1989)), PEPCase (Hudspeth et al., *Plant Molecular Biology*. 12:579-589 (1989)) or those associated with the R gene complex (Chandler et al., *The Plant Cell.* 1:1175-1183 (1989)). Further suitable promoters include the poplar xylem-specific secondary cell wall specific cellulose synthase 8 promoter, cauliflower mosaic virus promoter, the Z10 promoter from a gene encoding a 10 kD zein protein, a Z27 promoter from a gene encoding a 27 kD zein protein, inducible promoters, such as the light inducible promoter derived from the pea rbcS gene (Coruzzi et al., *EMBO J.* 3:1671 (1971)) and the actin promoter from rice (McElroy et al., *The Plant Cell.* 2:163-171 (1990)). Seed specific promoters, such as the phaseolin promoter from beans, may also be used (Sengupta-Gopalan, *Proc. Natl. Acad. Sci. USA.* 83:3320-3324 (1985). Other promoters useful in the practice of the invention are available to those of skill in the art.

Alternatively, novel tissue specific promoter sequences may be employed in the practice of the present invention. cDNA clones from a particular tissue can be isolated and those clones which are expressed specifically in that tissue are identified, for example, using Northern blotting. Preferably, the gene isolated is not present in a high copy number, but is relatively abundant in specific tissues. The promoter and control elements of corresponding genomic clones can then be localized using techniques well known to those of skill in the art.

A COI1 nucleic acid can be combined with the promoter by standard methods to yield an expression cassette or transgene, for example, as described in Sambrook et al. (MOLECULAR CLONING: A LABORATORY MANUAL. Second Edition (Cold Spring Harbor, N.Y.: Cold Spring Harbor Press (1989); MOLECULAR CLONING: A LABORATORY MANUAL. Third Edition (Cold Spring Harbor, N.Y.: Cold Spring Harbor Press (2000)). Briefly, a plasmid containing a promoter such as the 35S CaMV promoter can be constructed as described in Jefferson (*Plant Molecular Biology Reporter* 5:387-405 (1987)) or obtained from Clontech Lab in Palo Alto, Calif. (e.g., pBI121 or pBI221). Typically, these plasmids are constructed to have multiple cloning sites having specificity for different restriction enzymes downstream from the promoter. The COI1 nucleic acids can be subcloned downstream from the promoter using restriction enzymes and positioned to ensure that the DNA is inserted in proper orientation with respect to the promoter so that the DNA can be expressed as sense or antisense RNA. Once the COI1 nucleic acid is operably linked to a promoter, the expression cassette so formed can be subcloned into a plasmid or other vector (e.g., an expression vector).

In some embodiments, a cDNA clone encoding a COI1 protein is synthesized, isolated, and/or obtained from a selected cell. In other embodiments, cDNA clones from other species (that encode a COI1 protein) are isolated from selected plant tissues. For example, the nucleic acid encoding a COI1 protein can be any nucleic acid with a coding region that hybridizes to SEQ ID NO:3 and that has COI1 activity. In another example, the COI1 nucleic acid can encode a COI1 protein with an amino acid sequence that has at least 90%, or at least 95%, or at least 96%, or at least 97%, at least 98%, or at least 99% sequence identity to SEQ ID NO:1, 2, 5, 8, 10, 13, 16, 19, 22, 25, 28, 31, 33, 36, 39, 42, 45, or 48. Using restriction endonucleases, the entire coding sequence for the COI1 nucleic acid is subcloned downstream of the promoter in a 5' to 3' sense orientation.

In some cases, an endogenous COI1 gene can be modified to generate plant cells and plants that can express a modified COI1 protein. Mutations can be introduced into COI1 plant genomes by introducing targeting vectors, T-DNA, transposons, nucleic acids encoding TALENS, CRISPR, or ZFN nucleases, and combinations thereof into a recipient plant cell to create a transformed cell.

In some cases the endogenous COI1 gene can be deleted and plant cells with such a deleted endogenous COI1 gene can be can be transformed to include a modified COI transgene, for example, by transformation of the plant cells with a COI1 expression cassette or expression vector.

The frequency of occurrence of cells taking up exogenous (foreign) DNA can sometimes be low. However, certain cells from virtually any dicot or monocot species can be stably transformed, and these cells can be regenerated into transgenic plants, through the application of the techniques disclosed herein. The plant cells, plants, and seeds can therefore be monocotyledons or dicotyledons.

The cell(s) that undergo transformation may be in a suspension cell culture or may be in an intact plant part, such as an immature embryo, or in a specialized plant tissue, such as callus, such as Type I or Type II callus.

Transformation of the cells of the plant tissue source can be conducted by any one of a number of methods available to those of skill in the art. Examples are: Transformation by direct DNA transfer into plant cells by electroporation (U.S. Pat. No. 5,384,253 and 5,472,869, Dekeyser et al., The Plant Cell. 2:591 602 (1990)); direct DNA transfer to plant cells by PEG precipitation (Hayashimoto et al., Plant Physiol. 93:857 863 (1990)); direct DNA transfer to plant cells by microprojectile bombardment (McCabe et al., Bio/Technology. 6:923 926 (1988), Gordon Kamm et al., The Plant Cell. 2:603 618 (1990); U.S. Pat. Nos. 5,489,520; 5,538,877; and 5,538,880) and DNA transfer to plant cells via infection with *Agrobacterium*. Methods such as microprojectile bombardment or electroporation can be carried out with "naked" DNA where the expression cassette may be simply carried on any *E. coli* derived plasmid cloning vector. In the case of viral vectors, it is desirable that the system retain replication functions, but lack functions for disease induction.

One method for dicot transformation, for example, involves infection of plant cells with *Agrobacterium tumefaciens* using the leaf disk protocol (Horsch et al., Science 227:1229 1231 (1985). Monocots such as *Zea mays* can be transformed via microprojectile bombardment of embryogenic callus tissue or immature embryos, or by electroporation following partial enzymatic degradation of the cell wall with a pectinase containing enzyme (U.S. Pat. Nos. 5,384,253; and 5,472,869). For example, embryogenic cell lines derived from immature *Zea mays* embryos can be transformed by accelerated particle treatment as described by Gordon Kamm et al. (The Plant Cell. 2:603 618 (1990)) or U.S. Pat. Nos. 5,489,520 ; 5,538,877 and 5,538,880, cited above. Excised immature embryos can also be used as the target for transformation prior to tissue culture induction, selection and regeneration as described in U.S. application Ser. No. 08/112,245 and PCT publication WO 95/06128. Furthermore, methods for transformation of monocotyledonous plants utilizing *Agrobacterium tumefaciens* have been described by Hiei et al. (European Patent 0 604 662, 1994) and Saito et al. (European Patent 0 672 752, 1995).

Methods such as microprojectile bombardment or electroporation are carried out with "naked" DNA where the expression cassette may be simply carried on any *E. coli* derived plasmid cloning vector. In the case of viral vectors, it is desirable that the system retain replication functions, but lack functions for disease induction.

The choice of plant tissue source for transformation will depend on the nature of the host plant and the transformation protocol. Useful tissue sources include callus, suspension culture cells, protoplasts, leaf segments, stem segments, tassels, pollen, embryos, hypocotyls, tuber segments, meristematic regions, and the like. The tissue source is selected and transformed so that it retains the ability to regenerate whole, fertile plants following transformation, i.e., contains totipotent cells. Type I or Type II embryonic maize callus and immature embryos are preferred *Zea mays* tissue sources. Selection of tissue sources for transformation of monocots is described in detail in U.S. application Ser. No. 08/112,245 and PCT publication WO 95/06128.

The transformation is carried out under conditions directed to the plant tissue of choice. The plant cells or tissue are exposed to the DNA or RNA carrying the targeting vector and/or other nucleic acids for an effective period of time. This may range from a less than one second pulse of electricity for electroporation to a 2-3 day co cultivation in the presence of plasmid bearing *Agrobacterium* cells. Buffers and media used will also vary with the plant tissue source and transformation protocol. Many transformation protocols employ a feeder layer of suspended culture cells (tobacco or Black Mexican Sweet corn, for example) on the surface of solid media plates, separated by a sterile filter paper disk from the plant cells or tissues being transformed.

Where one wishes to introduce DNA by means of electroporation, it is contemplated that the method of Krzyzek et al. (U.S. Pat. No. 5,384,253) may be advantageous. In this method, certain cell wall degrading enzymes, such as pectin degrading enzymes, are employed to render the target recipient cells more susceptible to transformation by electroporation than untreated cells. Alternatively, recipient cells can be made more susceptible to transformation, by mechanical wounding.

To effect transformation by electroporation, one may employ either friable tissues such as a suspension cell cultures, or embryogenic callus, or alternatively, one may transform immature embryos or other organized tissues directly. The cell walls of the preselected cells or organs can be partially degraded by exposing them to pectin degrading enzymes (pectinases or pectolyases) or mechanically wounding them in a controlled manner. Such cells would then be receptive to DNA uptake by electroporation, which may be carried out at this stage, and transformed cells then identified by a suitable selection or screening protocol dependent on the nature of the newly incorporated DNA.

A further advantageous method for delivering transforming DNA segments to plant cells is microprojectile bombardment. In this method, microparticles may be coated with DNA and delivered into cells by a propelling force. Exemplary particles include those comprised of tungsten, gold, platinum, and the like.

It is contemplated that in some instances DNA precipitation onto metal particles would not be necessary for DNA delivery to a recipient cell using microprojectile bombardment. In an illustrative embodiment, non-embryogenic cells were bombarded with intact cells of the bacteria *E. coli* or *Agrobacterium tumefaciens* containing plasmids with either the β-glucoronidase or bar gene engineered for expression in maize. Bacteria were inactivated by ethanol dehydration prior to bombardment. A low level of transient expression of the β-glucoronidase gene was observed 24-48 hours following DNA delivery. In addition, stable transformants containing the bar gene were recovered following bombardment with either *E. coli* or *Agrobacterium tumefaciens* cells. It is contemplated that particles may contain DNA rather than be coated with DNA. Hence it is proposed that particles may increase the level of DNA delivery but are not, in and of themselves, necessary to introduce DNA into plant cells.

An advantage of microprojectile bombardment, in addition to being an effective means of reproducibly stably transforming monocots, is that the isolation of protoplasts (Christou et al., PNAS. 84:3962 3966 (1987)), the formation of partially degraded cells, or the susceptibility to *Agrobacterium* infection is not required. An illustrative embodiment of a method for delivering DNA into maize cells by acceleration is a Biolistics Particle Delivery System, which can be used to propel particles coated with DNA or cells through a screen, such as a stainless steel or Nytex screen, onto a filter surface covered with maize cells cultured in suspension (Gordon Kamm et al., The Plant Cell. 2:603 618 (1990)). The screen disperses the particles so that they are not delivered to the recipient cells in large aggregates. It is believed that a screen intervening between the projectile apparatus and the cells to be bombarded reduces the size of projectile aggregate and may contribute to a higher frequency of transformation, by reducing damage inflicted on the recipient cells by an aggregated projectile.

For bombardment, cells in suspension are preferably concentrated on filters or solid culture medium. Alternatively, immature embryos or other target cells may be arranged on solid culture medium. The cells to be bombarded are positioned at an appropriate distance below the macroprojectile stopping plate. If desired, one or more screens are also positioned between the acceleration device and the cells to be bombarded. Through the use of techniques set forth here in one may obtain up to 1000 or more foci of cells transiently expressing a marker gene. The number of cells in a focus which express the exogenous gene product 48 hours post bombardment often range from about 1 to 10 and average about 1 to 3.

In bombardment transformation, one may optimize the prebombardment culturing conditions and the bombardment parameters to yield the maximum numbers of stable transformants. Both the physical and biological parameters for bombardment can influence transformation frequency.

Physical factors are those that involve manipulating the DNA/microprojectile precipitate or those that affect the path and velocity of either the macroprojectiles or microprojectiles. Biological factors include all steps involved in manipulation of cells before and immediately after bombardment, the osmotic adjustment of target cells to help alleviate the trauma associated with bombardment, and also the nature of the transforming DNA, such as linearized DNA or intact supercoiled plasmid DNA.

One may wish to adjust various bombardment parameters in small scale studies to fully optimize the conditions and/or to adjust physical parameters such as gap distance, flight distance, tissue distance, and helium pressure. One may also minimize the trauma reduction factors (TRFs) by modifying conditions which influence the physiological state of the recipient cells and which may therefore influence transformation and integration efficiencies. For example, the osmotic state, tissue hydration and the subculture stage or cell cycle of the recipient cells may be adjusted for optimum transformation. Execution of such routine adjustments will be known to those of skill in the art.

Examples of plants and/or plant cells that can be modified as described herein include alfalfa (e.g., forage legume alfalfa), algae, apple, avocado, balsam, barley, broccoli, Brussels sprouts, cabbage, canola, cassava, cauliflower, cocoa, cole vegetables, collards, corn, cottonwood, crucifers, earthmoss, grain legumes, grasses (e.g., forage grasses), jatropa, kale, kohlrabi, maize, miscanthus, moss, mustards, nut, nut sedge, oats, oil firewood trees, oilseeds, peach, peanut, poplar, potato, radish, rape, rapeseed, rice, rutabaga, *sorghum*, soybean, sugar beets, sugarcane, sunflower, switchgrass, tobacco, tomato, turnips, and wheat. In some embodiments, the plant is a *Brassicaceae* or other *Solanaceae* species. In some embodiments, the plant or cell can be a maize plant or maize cell. In some cases, the plant or plant cell can be a soybean plant or plant cell. In some embodiments, the plant is not a species of *Arabidopsis*, for example, in some embodiments, the plant is not *Arabidopsis thaliana*.

An exemplary embodiment of methods for identifying transformed cells involves exposing the bombarded cultures to a selective agent, such as a metabolic inhibitor, an antibiotic, herbicide or the like. Cells which have been transformed and have stably integrated a marker gene conferring resistance to the selective agent used, will grow and divide in culture. Sensitive cells will not be amenable to further culturing.

To use the bar-bialaphos or the EPSPS-glyphosate selective system, bombarded tissue is cultured for about 0-28 days on nonselective medium and subsequently transferred to medium containing from about 1-3 mg/l bialaphos or about 1-3 mM glyphosate, as appropriate. While ranges of about 1-3 mg/l bialaphos or about 1-3 mM glyphosate can be employed, it is proposed that ranges of at least about 0.1-50 mg/l bialaphos or at least about 0.1-50 mM glyphosate will find utility in the practice of the invention. Tissue can be placed on any porous, inert, solid or semi-solid support for bombardment, including but not limited to filters and solid culture medium. Bialaphos and glyphosate are provided as examples of agents suitable for selection of transformants, but the technique of this invention is not limited to them.

An example of a screenable marker trait is the red pigment produced under the control of the R-locus in maize. This pigment may be detected by culturing cells on a solid support containing nutrient media capable of supporting growth at this stage and selecting cells from colonies (visible aggregates of cells) that are pigmented. These cells may be cultured further, either in suspension or on solid media. The R-locus is useful for selection of transformants from bombarded immature embryos. In a similar fashion, the introduction of the C1 and B genes will result in pigmented cells and/or tissues.

The enzyme luciferase is also useful as a screenable marker in the context of the present invention. In the presence of the substrate luciferin, cells expressing luciferase emit light which can be detected on photographic or X-ray film, in a luminometer (or liquid scintillation counter), by devices that enhance night vision, or by a highly light sensitive video camera, such as a photon counting camera. All of these assays are nondestructive and transformed cells may be cultured further following identification. The photon counting camera is especially valuable as it allows one to identify specific cells or groups of cells which are expressing luciferase and manipulate those in real time.

It is further contemplated that combinations of screenable and selectable markers may be useful for identification of transformed cells. For example, selection with a growth inhibiting compound, such as bialaphos or glyphosate at concentrations below those that cause 100% inhibition followed by screening of growing tissue for expression of a screenable marker gene such as luciferase would allow one to recover transformants from cell or tissue types that are not amenable to selection alone. In an illustrative embodiment embryogenic Type II callus of *Zea mays* L. can be selected with sub-lethal levels of bialaphos. Slowly growing tissue was subsequently screened for expression of the luciferase gene and transformants can be identified.

Regeneration and Seed Production

Cells that survive the exposure to the selective agent, or cells that have been scored positive in a screening assay, are cultured in media that supports regeneration of plants. One example of a growth regulator that can be used for such purposes is dicamba or 2,4-D. However, other growth regulators may be employed, including NAA, NAA+ 2,4-D or perhaps even picloram. Media improvement in these and like ways can facilitate the growth of cells at specific developmental stages. Tissue can be maintained on a basic media with growth regulators until sufficient tissue is available to begin plant regeneration efforts, or following repeated rounds of manual selection, until the morphology of the tissue is suitable for regeneration, at least two weeks, then transferred to media conducive to maturation of embryoids. Cultures are typically transferred every two weeks on this medium. Shoot development signals the time to transfer to medium lacking growth regulators.

The transformed cells, identified by selection or screening and cultured in an appropriate medium that supports regeneration, can then be allowed to mature into plants. Developing plantlets are transferred to soilless plant growth mix, and hardened, e.g., in an environmentally controlled chamber at about 85% relative humidity, about 600 ppm $CO_2$, and at about 25-250 microeinsteins/sec·m² of light. Plants can be matured either in a growth chamber or greenhouse. Plants are regenerated from about 6 weeks to 10 months after a transformant is identified, depending on the initial tissue. During regeneration, cells are grown on solid media in tissue culture vessels. Illustrative embodiments of such vessels are petri dishes and Plant Con™. Regenerating plants can be grown at about 19° C. to 28° C. After the regenerating plants have reached the stage of shoot and root development, they may be transferred to a greenhouse for further growth and testing.

Mature plants are then obtained from cell lines that are known to have the mutations. In some embodiments, the regenerated plants are self-pollinated. In addition, pollen obtained from the regenerated plants can be crossed to seed grown plants of agronomically important inbred lines. In some cases, pollen from plants of these inbred lines is used to pollinate regenerated plants. The trait is genetically characterized by evaluating the segregation of the trait in first and later generation progeny. The heritability and expression in plants of traits selected in tissue culture are of particular importance if the traits are to be commercially useful.

Regenerated plants can be repeatedly crossed to inbred plants in order to introgress the mutations into the genome of the inbred plants. This process is referred to as backcross conversion. When a sufficient number of crosses to the recurrent inbred parent have been completed in order to produce a product of the backcross conversion process that is substantially isogenic with the recurrent inbred parent except for the presence of the introduced expression cassette encoding a modified COI1, the plant is self-pollinated at least once in order to produce a homozygous backcross converted inbred containing the mutations. Progeny of these plants are true breeding.

Alternatively, seed from transformed mutant plant lines regenerated from transformed tissue cultures is grown in the field and self-pollinated to generate true breeding plants.

Seed from the fertile transgenic plants can then be evaluated for the presence of the desired COI1 genomic modification (e.g., mutation), e.g., the desired COI1 expression cassette, and/or the expression of the desired modified COI1 protein. Transgenic plant and/or seed tissue can be analyzed using standard methods such as SDS polyacrylamide gel electrophoresis, liquid chromatography (e.g., HPLC) or other means of detecting a mutation.

Once a transgenic plant with a mutant sequence and having improved growth and pathogen resistance is identified, seeds from such plants can be used to develop true breeding plants. The true breeding plants are used to develop a line of plants with improved growth and pathogen resistance relative to wild type, and acceptable insect resistance while still maintaining other desirable functional agronomic traits. Adding the mutation to other plants can be accomplished by back-crossing with this trait and with plants that do not exhibit this trait and studying the pattern of inheritance in segregating generations. Those plants expressing the target trait (e.g., herbicide and pathogen resistance, good growth) in a dominant fashion are preferably selected. Back-crossing is carried out by crossing the original fertile transgenic plants with a plant from an inbred line exhibiting desirable functional agronomic characteristics while not necessarily expressing the trait of increased herbicide and pathogen resistance and good plant growth. The resulting progeny are then crossed back to the parent that expresses the increased herbicide and pathogen resistance and good plant growth. The progeny from this cross will also segregate so that some of the progeny carry the trait and some do not. This back-crossing is repeated until an inbred line with the desirable functional agronomic traits, and with expression of the trait involving an increase in herbicide and pathogen resistance and good plant growth. Such herbicide and pathogen resistance as well as good plant growth can be expressed in a dominant fashion.

The new transgenic plants can also be evaluated for a battery of functional agronomic characteristics such as growth, lodging, kernel hardness, yield, resistance to disease and insect pests, drought resistance, and/or herbicide resistance.

Plants that may be improved by these methods include but are not limited to agricultural plants of all types, oil and/or starch plants (canola, potatoes, lupins, sunflower and cottonseed), forage plants (alfalfa, clover and fescue), grains (maize, wheat, barley, oats, rice, *sorghum*, millet and rye), grasses (switchgrass, prairie grass, wheat grass, sudangrass, *sorghum*, straw-producing plants), softwood, hardwood and other woody plants (e.g., those used for paper production such as poplar species, pine species, and eucalyptus). In some embodiments the plant is a gymnosperm. Examples of plants useful for pulp and paper production include most pine species such as loblolly pine, Jack pine, Southern pine, Radiata pine, spruce, Douglas fir and others. Hardwoods that can be modified as described herein include aspen, poplar, eucalyptus, and others. Plants useful for making biofuels and ethanol include corn, grasses (e.g., miscanthus, switchgrass, and the like), as well as trees such as poplar, aspen, willow, and the like. Plants useful for generating dairy forage include legumes such as alfalfa, as well as forage grasses such as bromegrass, and bluestem.

Determination of Stably Transformed Plant Tissues

To confirm the presence of COI1 mutations and/or a COI1 expression cassette in the regenerating plants, or seeds or progeny derived from the regenerated plant, a variety of assays may be performed. Such assays include, for example, molecular biological assays available to those of skill in the art, such as Southern and Northern blotting and PCR; biochemical assays, such as detecting the presence of a protein product, e.g., by immunological means (ELISAs and Western blots) or by enzymatic function; plant part assays, such as leaf, seed or root assays; and also, by analyzing the phenotype of the whole regenerated plant.

Whereas DNA analysis techniques may be conducted using DNA isolated from any part of a plant, RNA may only be expressed in particular cells or tissue types and so RNA for analysis can be obtained from those tissues. PCR techniques may also be used for detection and quantification of RNA produced from introduced COI1 mutation(s) or of RNA expressed from an introduced expression cassette encoding a modified COI1. For example, PCR also be used to reverse transcribe RNA into DNA, using enzymes such as reverse transcriptase, and then this DNA can be amplified through the use of conventional PCR techniques.

For example, if no amplification of COI1 mRNAs is observed, then a deletion mutation has successfully been introduced.

Information about mutations can also be obtained by primer extension or single nucleotide polymorphism (SNP) analysis.

Further information about the nature of the RNA product may be obtained by Northern blotting. This technique will demonstrate the presence of an RNA species and give information about the integrity of that RNA. The presence of some mutations can be detected by Northern blotting. The presence or absence of an RNA species (e.g., COI1 RNA) can also be determined using dot or slot blot Northern hybridizations. These techniques are modifications of Northern blotting and also demonstrate the presence or absence of an RNA species.

While Southern blotting and PCR may be used to detect the presence of mutations or the presence of a COI1 expression cassette, they do not provide information as to whether the preselected DNA segment is being expressed. Expression may be evaluated by specifically identifying the protein products of the introduced COI1 expression cassette or the introduced mutations, by detecting expression of modified COI proteins, or evaluating the phenotypic changes brought about by such mutation.

Assays for the production and identification of specific proteins may make use of physical-chemical, structural, functional, or other properties of the proteins. Unique physical-chemical or structural properties allow the proteins to be separated and identified by electrophoretic procedures, such as native or denaturing gel electrophoresis or isoelectric focusing, or by chromatographic techniques such as ion exchange, liquid chromatography or gel exclusion chromatography. The unique structures of individual proteins offer opportunities for use of specific antibodies to detect their presence in formats such as an ELISA assay. Combinations of approaches may be employed with even greater specificity such as Western blotting in which antibodies are used to locate individual gene products, or the absence thereof, that have been separated by electrophoretic techniques. Additional techniques may be employed to absolutely confirm the identity of a mutation such as evaluation by screening for reduced transcription (or no transcription) of wild type COI1 and/or modified (mutant) COI1 mRNAs, by screening for wild type and/or mutant (modified) COI1 mRNA or COI1 protein expression. Amino acid sequencing following purification can also be employed. The Examples of this application also provide assay procedures for detecting and quantifying infection and plant growth. Other procedures may be additionally used.

The expression of a gene product can also be determined by evaluating the phenotypic results of its expression. These assays also may take many forms including but not limited to analyzing changes in the resistance to infection, resistance to herbicides, growth characteristics, or other physiological properties of the plant. Expression of selected DNA segments encoding different amino acids or having different sequences and may be detected by amino acid analysis or sequencing.

The following Examples describe some of the experiments performed in the development of the invention.

EXAMPLE 1

Materials and Methods

This Example illustrates some of the materials and methods employed during development of the invention.

All experiments were performed three or more times with similar results. For computer modeling, coordinates for JA-Ile or coronatine (COR) were obtained from the crystal structures of COI1-JA-Ile/COR-JAZ degron peptide complex (PDB ID codes 3OGL and 3OGK, respectively). Structures of (3R,7S) JA-Ile and coronatine are shown below:

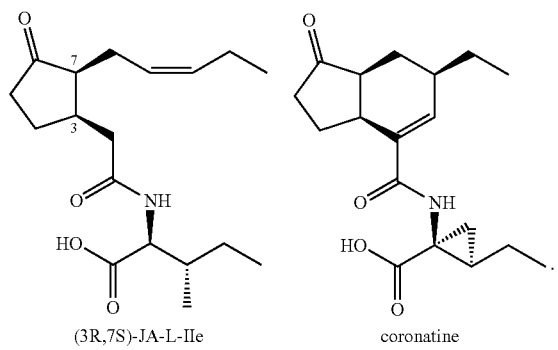

(3R,7S)-JA-L-Ile        coronatine

In Y2H and in planta assays, the relative potencies of different ligands used (COR, MeJA, and JA-Ile) were standardized before a new set of experiments. Because of the limited amounts of JA-Ile available for this study, other forms of JA were used if the use of JA-Ile was not absolutely needed. For example, MeJA can be converted to JA-Ile in planta and is commonly used in the study of JA signaling (Staswick et al., Plant Cell 16(8): 2117-2127 (2004)). Therefore, MeJA was used instead of JA-Ile, for in planta assays.

Computational Modeling

Coordinates for JA-Ile or COR were obtained from the crystal structures of COI1-JA-Ile/COR-JAZ degron peptide complex (PDB ID codes 3OGL and 3OGK, respectively) and the hydrogen atoms were added using xleap module in the Ambertools. Force field parameters and charges were derived using Antechamber module and GAFF in Ambertools (Wand et al., Antechamber, *An Accessory Software Package for Molecular Mechanical Calculation*. Abstracts of Papers, 222nd *National Meeting of the American Chemical Society*, Chicago, Ill., Aug. 2630, 2001; American Chemical Society: Washington, DC:U403 (2001)).

The force field ff99SB was used to represent the molecular mechanical potential. The system consisting of COR or JA-Ile along with COI1 and part of the JAZ degron peptide were minimized in two stages using a combination of steepest descent (15,000 steps) and conjugated gradient (5,000 steps) methods (Case et al., AMBER 12 (University of California, San Francisco). Available at ambermd.org/doc 12/Amber12.pdf. (2012)). A strong positional restraint (20 kcal/mole) was applied on all protein and ligand heavy atoms during the first stage of minimization. The protein-ligand complex was minimized again in the second stage, without any positional restraint. In silico mutations for A86 and A384 were introduced in COI1 using Pymol (DeLano Scientific).

Gene Cloning, Site-Direct Mutagenesis, and Plasmid Construction

The coding sequences of AtCOI1 and AtJAZ9 were amplified from total mRNA extract of *Arabidopsis* Col-0 leaf tissue and cloned into the pCR2.1-TOPO plasmid or pENTR-D TOPO Gateway entry vector (Life Technologies). Specific mutations were introduced into the AtCOI1 coding sequence directly through the QuickChangeII site directed mutagenesis kit (Agilent Technologies). For Y2H assays, the bait and prey vectors pGILDA and pB42AD (Clontech) were first converted to Gateway cloning-compatible pGILD-AattR and pB42ADattR vectors by inserting an attR cassette (Life Technologies) into their multiple cloning sites, respectively. Next, the wild-type and mutated COI1 coding sequences in the entry vector were recombined into pGILD-AattR using LR ClonaseII (Life Technologies) to generate C-terminal fusions to the LexA DNA binding domain. The JAZ9 coding sequences were recombined into pB42ADattR to generate C-terminal fusions to the B42 transcriptional activation domain.

For plant transformation, the AtCOI1 without stop codon was first cloned into pENTR4A to create pENCOI1C. Next, the native promoter of AtCOI1 (pCOI1; a genomic DNA fragment 1,807 bp upstream of the COI1 start codon) was cloned into pENCOI1C to create a pENpCOI1:COI1 entry vector. COI1A384V was introduced into this vector to create pENpCOI1:COI1A384V. Both pCOI1: COI1WT and pCOI1:COI1A384V were recombined into pGWB516 vector (containing a hygromycin resistance gene and a C-terminal 4×c-Myc epitope tag) (Nakagawa et al., Biol Rev Camb Philos Soc 82(4):591-605 (2007)) using LR ClonaseII. Confirmed constructs were introduced into *Agrobacterium tumefaciens* (GV3101) by electroporation.

Y2H Assays for Protein-Protein Interaction

For some Y2H experiments JA-Ile was used, because JA or MeJA are not active in yeast (Thines et al., Nature 448(7154):661-665 (2007); Melotto et al., Plant J 55(6):979-988 (2008)).

Yeast EGY48 strain carrying the p8Op:LacZ reporter plasmid was co-transformed with pGilda:COI1 (or COI1 mutants) and pB42AD:JAZ9 (or other JAZs) (Clontech). Colonies were selected on SD minimal plates (BD Biosciences) supplemented with the—uracil (U)/-tryptophan (W)/-histidine (H) amino acid drop out solution (Clontech). Yeast colonies were cultured overnight in liquid SD-UWH medium, harvested, washed twice in sterile water, and the absorbance ($OD_{600}$) of the cultures was adjusted to 0.2 in liquid SD galactose/raffinose-UWH medium (BD Biosciences).

For Y2H assays on plates, 10-μL culture was spotted onto SD galactose/raffinose-UWH plates with 80 μg/mL X-gal and 10 μM COR (Sigma-Aldrich). Blue color indicated protein-protein interactions after 5-7 days of incubation at 30° C.

For liquid Y2H assays, cultures were supplemented with designated concentrations of JA-Ile (10 or 30 μM), COR (1 μM), or DMSO. After 16-h incubation with ligands, the liquid cultures were processed through the Beta-Glo Assay system (Promega) for detecting the β-galactosidase activity. The JA-Ile stock consisted of cis- and trans-isomers, the cis-form being more active. Initial chemical analysis showed 6.8% of the cis-form after synthesis. Protein expression in yeast was detected using anti-LexA antibody (1:5,000; Upstate Biotechnology) for detection of COI1 expression from pGilda vector and anti-HA (1:5,000; Roche Life Science) antibody for detection of JAZ9 expression in pB42AD vector.

*Arabidopsis* Transformation and Screening pCOI1:COI1WT/A384V-4xc-Myc constructs were transformed into coil-30 mutant *Arabidopsis* plants (Yang et al., Proc Natl Acad Sci USA 109(19): E1192-E1200. (2012)). Because homozygous coi1-30 plants are male-sterile, heterozygous plants were identified through genotyping and used for *A. turnefaciens*-mediated *Arabidopsis* transformation. Half-strength Murashige and Skoog (MS) medium with 50 μg/mL hygromycin was used to select transgenic T1 seedlings containing the pCOI1:COI1WT/A384V-4xc-Myc transgene. Hygromycin-resistant seedlings were transplanted and genotyping was carried out to identify transgenic plants with the homozygous coil-30 background. Further screening of T2 or T3 plants were performed for homozygous transgene. Primers were:

```
SALK035548_LP1:
                             (SEQ ID NO: 50)
CGAATAAATCACACAGCTTATTGG,

SALK035548_RP1:
                             (SEQ ID NO: 51)
GATATGGTTCTTTGTACAACGACG,

LBb1.3:
                             (SEQ ID NO: 52)
ATTTTGCCGATTTCGGAAC,
and

SALK035548_RP:
                             (SEQ ID NO: 53)
CTGCAGTGTGTAACGATGCTC.
```

Protein Immunoblot Analysis

Proteins were extracted from 10-day-old to 12-day-old seedlings by protein extraction buffer (50 mM Tris.HCl, pH7.5, 150mMNaCl, 1% Nonidet P-40, 1% sodium deoxycholate, 0.1% SDS). Protein concentrations were measured using the RC/DC protein assay kit (Bio-Rad) with BSA as the standard (Bio-Rad). Protein samples with the same total protein concentration were used for immunoblot with rabbit polyclonal anti-c-Myc primary antibodies (1:5,000, Clontech) and goat anti-rabbit secondary antibody (1:20,000).

Coreceptor Pull-Down Assay

Pull-down assays were performed with protein extracts from 4-mg pCOI1:COI1WT/A384V-4xc-Myc plants and 25 μg recombinant MBP-JAZ9-8×His. Assays were performed in the presence of JA-Ile or COR at various concentrations and incubated for 30 min at 4° C. in the binding buffer (Katsir et al., Proc Natl Acad Sci USA 105(19):7100-7105 (2008)). Eighty microliters of Ni resin (Invitrogen) were added, followed by an additional 15-min incubation period at 4° C. MBP-JAZ9-8×Hisbound Ni resin was washed three times on microcentrifuge spin columns with 0.25 mL binding buffer at 4° C. MBP-JAZ9-8×His was eluted from the resin with 100 μL of 300 mM imidazole. Proteins bound to MBP-JAZ9-8×His were analyzed by immunoblotting for the presence of COI1WT/A384V-4xc-Myc using anti-cMyc antibody. MBP-JAZ9-8×His recovered by the Ni affinity resin was detected by Coomassie blue staining.

RNA Isolation and qPCR Assays

Col-0 and transgenic seeds were germinated on half-strength MS medium. Five-day-old seedlings were transferred into liquid half-strength MS medium. Segregating coil-30 seeds were germinated on half-strength MS medium with 10 μM MeJA. and MeJA-resistant 5-d-old seedlings were transferred into liquid half-strength MS medium. Next, 10 μM MeJA (Sigma), 0.2 μM COR or 0.1% DMSO were applied to 12-d-old seedlings. Samples were collected after 3 h and total RNA was extracted using Qiagen RNeasy Mini kit (Qiagen). M-MLV Reverse transcriptase (Life Technologies) and SYBR Green master mix (Life Technologies) were used for reverse-transcription and real-time PCR. Primers used were:

```
PP2AA3_qRT_F1:
                             (SEQ ID NO: 54)
GGTTACAAGACAAGGTTCACTC,

PP2AA3_qRT_R1:
                             (SEQ ID NO: 55)
CATTCAGGACCAAACTCTTCAG,

JAZ9_qRT_F1:
                             (SEQ ID NO: 56)
ATGAGGTTAACGATGATGCTG,

JAZ9_qRT_R1:
                             (SEQ ID NO: 57)
CTTAGCCTCCTGGAAATCTG,

PR1_qRT_F1:
                             (SEQ ID NO: 58)
GGCTAACTACAACTACGCTG,

PR1_qRT_R1:
                             (SEQ ID NO: 59)
TCTCGTTCACATAATTCCCAC,

SID2_qRT_F2:
                             (SEQ ID NO: 60)
ACTTACTAACCAGTCCGAAAGACGA,
and SID2_qRT_R2:
                             (SEQ ID NO: 61)
ACAACAACTCTGTCACATATACCGT.
```

Root Growth Inhibition Assays

Col-0, segregating COI1-30, transgenic COI1WT, and COI1A384V seeds were surface-sterilized, cold-stratified, and germinated on half-strength MS agar media containing MeJA, COR, or DMSO at the indicated concentrations. Seedlings were grown under long-day light conditions (16-h light at 100 µE·m$^2$·s, and 8-h dark) for 10-12 days before scanning images of roots. Root lengths were measured using ImageJ software (see website at rsbweb.nih.gov/ij/).

Bacterial Infection Assays

The *Pseudomonas syringae* infection assays in *Arabidopsis* were performed as described by Yao et al. (Methods Mol Biol 1011:63-81 (2013)). In brief, 4- to 5-wk-old (12-h light/12-h dark) *Arabidopsis* plants were dip-inoculated with bacterial suspension (1×10$^8$ cfu/mL Pst DC3000 or Psm ES4326 in 0.25 mM MgCl$_2$ solution with 0.025% Silwet-77) or syringe-infiltrated with bacterial suspension (1×10$^6$ cfu/mL Pst DC3118 or DB29 in 0.25 mM MgCl$_2$ solution). Bacterial growth was determined by serial dilutions of plant extracts 3 or 4 days after inoculation. Homozygous COI1-30 plants were selected by genotyping before bacterial infection.

Insect Feeding Assays

Insect bioassays were performed as described by Herde et al. (Methods Mol Biol 1011:51-61 (2013)). Briefly, eggs of *Spodoptera exigua* were obtained from Benzon Research, and four neonate *Spodoptera exigua* larvae were transferred to the center of each 6-wk-old *Arabidopsis* host plant. Plants were grown under 8-hour light (100 µE·m$^2$·s) and 16-h dark and covered with cup cages. Larval weights were determined after 9-12 days of feeding.

EXAMPLE 2

Targeted COI1 Alanine Substitution Mutagenesis

Higher plants synthesize different forms of JA, including the most bioactive form jasmonoyl-L-isoleucine (JA-Ile). Targeted alanine substitution mutagenesis of the COI1 protein was conducted to identify amino acid residues that can differentially affect the actions of JA-Ile against COR. At the onset of this study, the crystal structure of the COI1-JAZ coreceptor was not available. However, the crystal structure of the TIR1-AUX/IAA [for TRANSPORT INHIBITOR RESPONSE 1 (TIR1)-AUXIN/INDOLE 3-ACETIC ACID (AUX/IAA)] coreceptor involved in the perception of the plant hormone auxin was available (Tan et al., Nature 446(7136):640-645 (2007)). Auxin and JA signaling pathways are highly analogous in hormone sensing and response (Pauwels et al., Nature 464(7289):788-791 (2010); Santner & Estelle, Nature 459(7250):1071-1078 (2009)). Comparative genomic analysis suggested that auxin and JA signaling pathways may have originated from a common ancestor that duplicated and diverged into TIR1 and COI1 for different hormone signaling pathways (Wang et al., Plant Physiol 167(3):872-886 (2015)).

The inventors hypothesized that ligand-binding surfaces in COI1 may be similarly positioned to those in TIR1, and key differences in these conserved residues might confer specificity to the differential recognition of the respective ligands (i.e., JA-Ile/COR vs. auxin). Based on these initial criteria, thirty-two amino acids were selected for site-direct mutagenesis to alanine (Table 1).

TABLE 1

Amino acids for Site-Directed Mutagenesis to Alanine

| COI1 amino acid | Interaction with JAZ9* | Role in COI1 ligand binding pocket† | Homologous TIR1 amino acid‡ | Role in TIR1 ligand binding pocket‡ |
|---|---|---|---|---|
| Histidine 54§ | +++ | $PO_4$ contacting | Lysine | Not known |
| Serine 77§ | +++ | $PO_4$ contacting | Serine | Not known |
| Lysine 79§ | +++ | $PO_4$ contacting | Glutamate | Not known |
| Lysine 81 | +++ | $PO_4$ contacting | Lysine | IP6 coordination |
| Arginine 85 | +++ | JA-Ile and $PO_4$ contacting | Histidine | Auxin binding, IP6 coordination |
| Methionine 88 | No | JAZ1 and $PO_4$ contacting | Aspartate | Aux/IAA binding |
| Phenylalanine 89 | No | JA-Ile and JAZ1 contacting | Phenylalanine | Auxin and AUX/IAA binding |
| Leucine 91 | No | JA-Ile and JAZ1 contacting | Leucine | Aux/IAA binding |
| Histidine 118§ | +++ | $PO_4$ contacting | Arginine | Not known |
| Arginine 121 | No | $PO_4$ contacting | Arginine | IP6 coordination |
| Lysine 144§ | +++ | $PO_4$ contacting | Valine | Not known |
| Lysine 147 | ++++ | $PO_4$ contacting | Serine | Aux/IAA binding |
| Glutamate 173 | ++ | JAZ1 contacting | Glutamate | Aux/IAA binding |
| Methionine 201§ | +++ | JAZ1 contacting | Cysteine | Not known |
| Leucine 301§ | +++ | JAZ1 contacting | Serine | Not known |
| Tyrosine 302§ | No | JAZ1 contacting | Tyrosine | Not known |
| Arginine 326§ | No | JAZ1 contacting | Leucine | Not known |
| Arginine 348 | No | JA-Ile, JAZ1 and $PO_4$ contacting | Arginine | IP6 coordination |
| Arginine 351 | No | JAZ1 contacting | Proline | AUX/IAA binding |
| Aspartate 354 | No | JAZ1 contacting | Glutamate | AUX/IAA binding |
| Glutamate 355 | +++ | JAZ1 contacting | Proline | AUX/IAA binding |
| Glutamine 356 | +++ | Non | Phenylalanine | AUX/IAA binding |
| Glycine 357 | ++ | Non | Valine | AUX/IAA binding |
| Tyrosine 386 | No | JA-Ile and JAZ1 contacting | Phenylalanine | Auxin and AUX/IAA binding |
| Aspartate 407 | No | Non | Arginine | IP6 coordination |
| Arginine 409 | No | JA-Ile and $PO_4$ contacting | Arginine | Auxin and AUX/IAA binding |
| Leucine 410 | No | Non | Leucine | Auxin binding |

TABLE 1-continued Amino acids for Site-Directed Mutagenesis to Alanine

| COI1 amino acid | Interaction with JAZ9* | Role in COI1 ligand binding pocket† | Homologous TIR1 amino acid‡ | Role in TIR1 ligand binding pocket‡ |
|---|---|---|---|---|
| Valine 411 | No | JA-Ile and JAZ1 contacting | Cysteine | Auxin and AUX/IAA binding |
| Leucine 412 | No | Non | Isoleucine | AUX/IAA binding |
| Leucine 413 | No | JAZ1 contacting | Isoleucine | AUX/IAA binding |
| Arginine 415 | ++ | Non | Proline | AUX/IAA binding |
| Arginine 440 | ++ | Non | Arginine | IP6 coordination |
| Phenylalanine 443 | No | Non | Leucine | Auxin binding |
| Tyrosine 444§ | No | JA-Ile and JAZ1 contacting | None | Not known |
| Tryptophan 467 | +++ | Non | Methionine | IP6 coordination |
| Leucine 469 | No | JA-Ile contacting | Serine | Auxin binding |
| Leucine 470 | No | Non | Valine | Auxin binding |
| Tyrosine 472 | +++ | PO4 contacting | Phenylalanine | AUX/IAA binding |
| Glutamine 491 | +++ | Non | Arginine | IP6 coordination |
| Lysine 492 | +++ | PO4 contacting | Lysine | IP6 coordination |
| Arginine 496 | +++ | JA-Ile and JAZ1 contacting | Arginine | Auxin and AUX/IAA binding |
| Arginine 516 | No | Non | Arginine | IP6 coordination |

*Y2H assays were conducted with 10 µM COR in the medium. The strength of mutant COI1-JAZ9 interactions was scored relative to COI1-JAZ9 (designated as +++).
†COI1 amino acids and their roles in the JAZ1-COI1-JA-Ile interaction.
‡TIR1 amino acids corresponding to those in COI1 and roles in ligand-receptor interaction.
§Additional COI1 amino acids selected for mutagenesis based on the crystal structure of the COI1-JAZ1 complex with COR or JA-Ile.

Y2H assays showed that 56% (18 of 32) of the alanine substitution mutants abolished COR-dependent interaction between COI1 and JAZ9 (FIG. 1A and Table 1). When the 18 residues were mapped to the crystal structure of the COI1-JAZ1 coreceptor, which became available after some of the earlier studies, 12 were found to make contacts with ligand, Ins(1,2,4,5,6)P5 (InsP5) or JAZ1 in the ligand-binding pocket. The crystal structure of COI1-JAZ1 coreceptor also shows several additional amino acids in the ligand-binding pocket, which could contribute to the interactions between COI1-ligand, COI1-JAZ, and COI1 interaction with InsP5 (Sheard et al., Nature 468(7322): 400-405 (2010)).

Ten additional amino acids were selected for site-directed mutagenesis to alanine (Table 1). Y2H assays showed that three alanine substitutions, Y302A, R326A, and Y444A, disrupted the COR-dependent COI1-JAZ9 interaction (FIG. 1B). As a result of such studies, a total of 21 COI1 residues were identified to be important for COR-induced formation of the COI1-JAZ coreceptor complex in yeast.

Figure 2B:
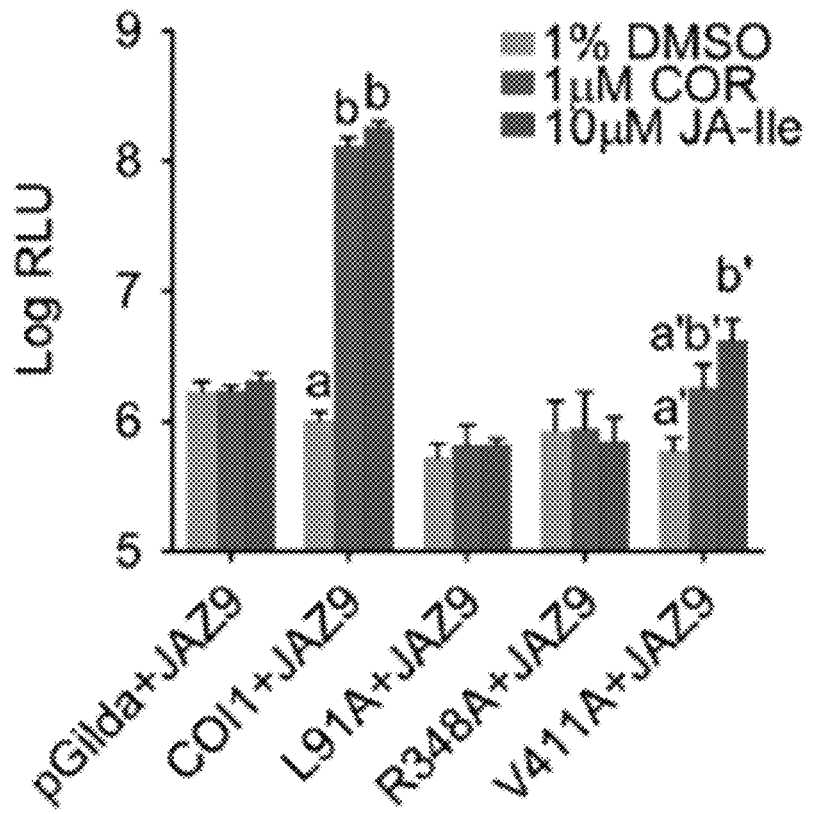

To determine whether substitutions that affected COR-dependent COI1-JAZ9 interaction could differentially affect JA-Ile-dependent COI1-JAZ9 interaction, quantitative liquid Y2H assays were conducted with COI11 mutants having one of ten alanine substitutions for the amino acids that directly contact JA-Ile (FIG. 2A-2B). These results show that: (i) seven alanine substitutions disrupted both JA-Ile-dependent and COR-dependent COI1-JAZ9 interaction, (ii) R409A substitution exhibited reduced COI1-JAZ9 interaction in the presence of JA-Ile or COR, and (iii) the R85A and R496A substitutions affect JAIle-dependent interaction more than COR-dependent interaction. No substitution was found to disrupt only COR-dependent interaction and still maintain JA-Ile-dependent COI1-JAZ9 interaction. However, none of the mutations disrupted only COR-dependent interaction but still maintained JAIle-dependent COI1-JAZ9 interaction (FIGS. 2A-2B).

These results show that COR is a remarkable mimic of JA-Ile and that most, if not all, of COI1 residues that are important for the action of JA-Ile are also important for COR action.

EXAMPLE 3

Structure-Guided Modeling of JA-Ile/COR Binding Sites in COI1

The initial mutagenesis described in Example 2 was based on alanine substitution of COI1 amino acids, which resulted in a reduction of the side-chain size for all of the amino acid residues targeted for mutagenesis, except for G357A. This Example describes experiments involving increasing the side-chain sizes of residues in COI1 that are in contact with JA-Ile/COR.

Although COR and JA-Ile are highly similar in structure, the flexibilities of COR and JA-Ile in the binding pocket are different. The structures of (3R,7S) JA-Ile and coronatine (COR) are shown below:

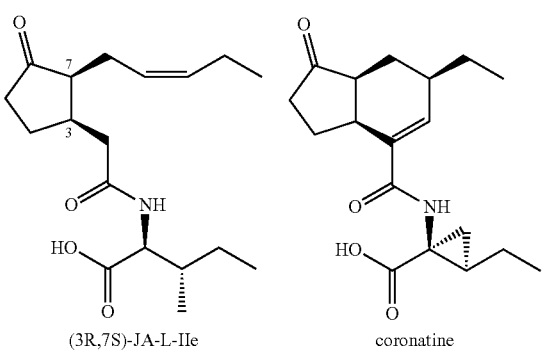

(3R,7S)-JA-L-Ile    coronatine

For example, the cyclohexene ring and the ethyl-cyclopropane group of COR appear more rigid than the equivalent parts (the pentenyl side-chain and the isoleucine side-chain, respectively) of JA-Ile (see, Sheard et al. Nature 468(7322): 400-405 (2010)). In view of the foregoing results, the inventors hypothesized that the higher rigidity of the cyclohexene ring and the ethylcyclopropane group of COR may be more prone than the equivalent parts of JA-Ile to physical hindrance from an increased size of the amino acid side-chain with which COR/JA-Ile are in direct contact.

Figure 2C:
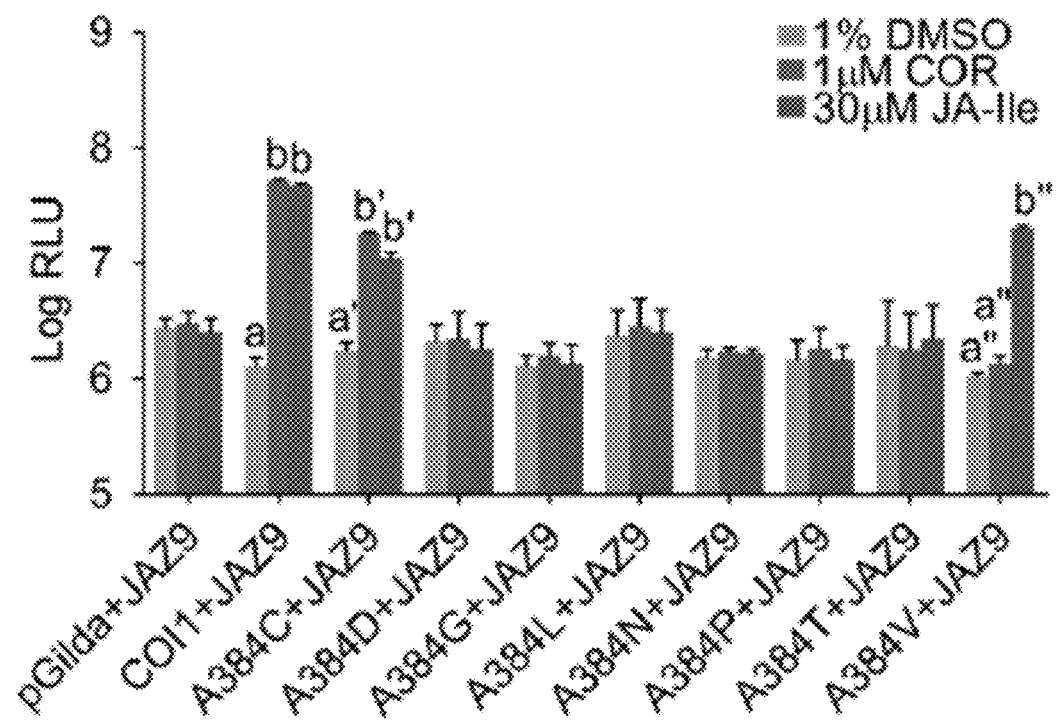
Figure 2D:
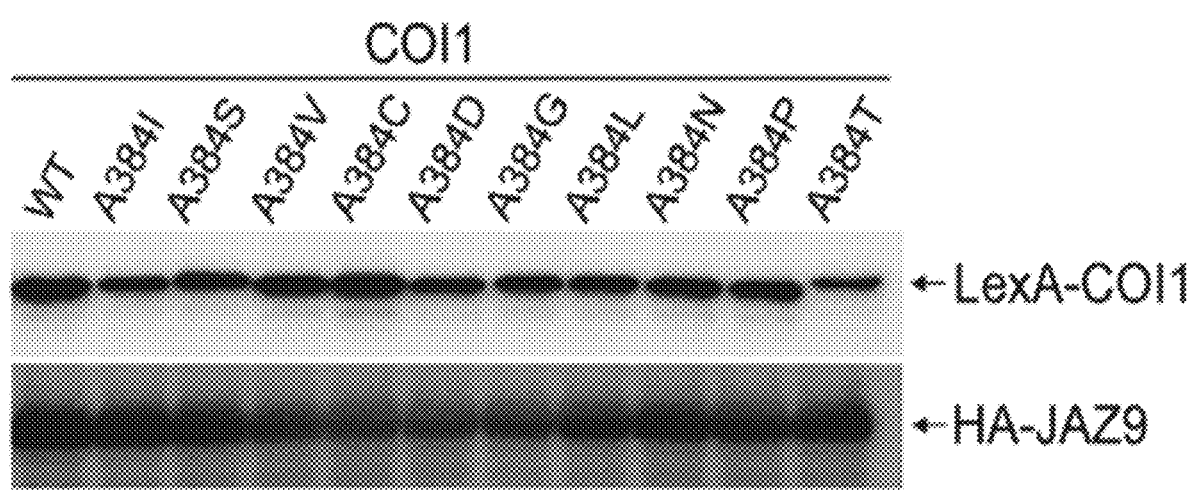
Figure 2E:
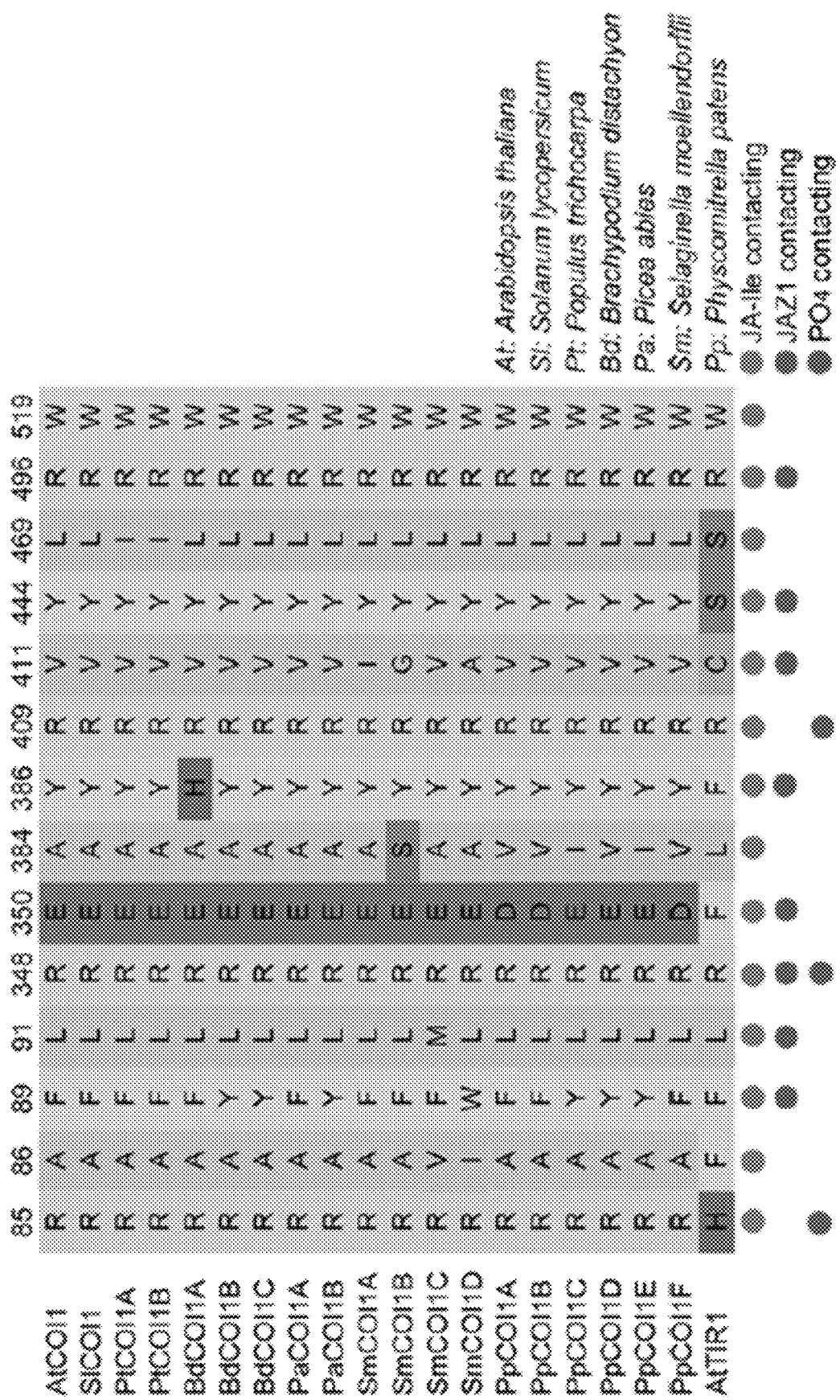

Based on such a hypothesis, COI1 residues A86 and A384 were viewed to be potential targets for mutagenesis for two reasons. First, in silico analysis of the putative JA-Ile binding pockets in diverse plant species for which the COI1 protein sequences are available revealed that, although most residues in the JA binding site are highly conserved across various taxa, residues at positions 86 and 384 exhibit a higher degree of polymorphism (FIG. 2E). In the moss species *Physcomitrella patens*, for example, isoleucine or valine occupy the corresponding position of A384 (FIG. 2E). Positions of A86 and A384 in *Selaginella moellendorffii* are replaced by isoleucine/valine and serine, respectively (FIG. 2E). Previous studies have shown that, although core JA signaling genes are found in *P. palens* (Wang et al. Plant Physiol 167(3):872-886 (2015)), neither JA nor JA-Ile could be detected in *P. patens* (Stumpe et al. New Phytol 188(3): 740-749 (2010)). On the other hand, (9S, 13 S)-12-oxophytodienoic acid [cis-(+)-OPDA], which is the precursor of JA biosynthesis, is synthesized in *P. patens*, suggesting that *P. patens* may produce an alternative, OPDA-related ligand (Stumpe (2010)).

The inventors speculated that, during plant evolution, polymorphism(s) at positions 86 and 384 in the putative COI1 binding pocket may provide a basis for accommodating related ligands of distinct structural features. If so, mutations at these amino acid positions may produce differential effects on different ligands compared with more highly conserved residues, which are expected to affect different ligands similarly.

Figure 3:
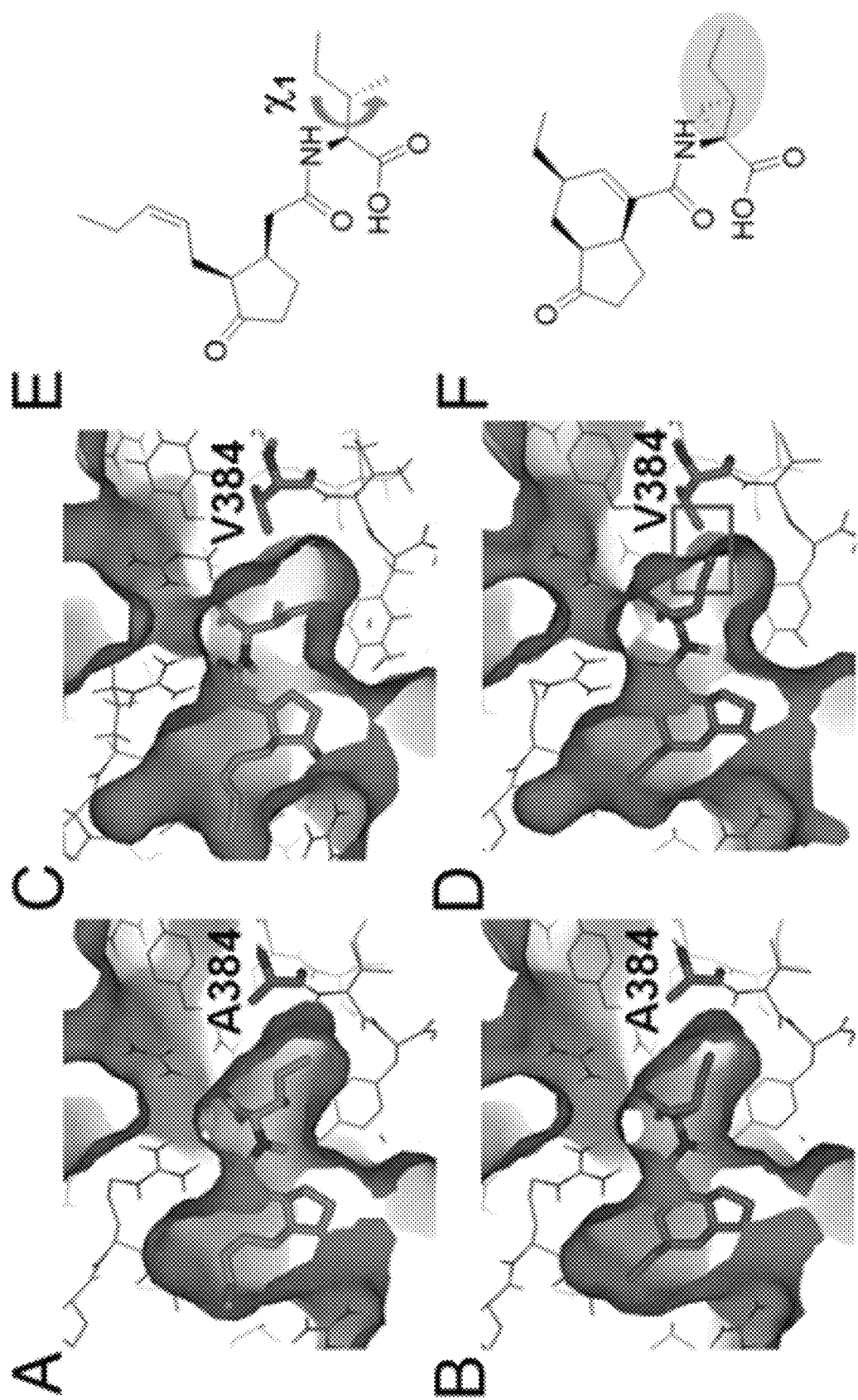
FIG. 3 illustrates structures of JA-Ile or COR in the ligand-binding site of COI1 or COI1A384V. Panels A and B illustrate the binding pose of JA-Ile (panel A) and COR (panel B) in the ligand-binding site of COI1 in the crystal structures of the COI1-JAZ1 complex (PDB ID codes 3OGL and 3OGK, respectively). Amino acid contacts in the ligand pocket were described by Sheard et al. (Nature 468(7322): 400-405 (2010)). Panels C and D illustrate structures of the A384V substitution COI1 mutant showing expected steric clash with the isoleucine side-chain of JA-Ile or the ethyl group attached to the cyclopropane moiety of COR. The isoleucine side-chain of JA-Ile can be adjusted in the mutant ligand binding site by rotation of the side-chain dihedral angle, $\chi 1$ of isoleucine (panel C). In contrast, the steric clash (highlighted in red box) impairs COR binding in the ligand-binding site because the rotatable bond at the equivalent position is absent in COR (panel D). The ligand-binding site in COI1 is shown in gray-colored surface representation. Ligands and A384/V384 residues are shown in stick representation, whereas all other atoms in the protein are shown in line representation. C-atoms in the wild type and mutant COI1 proteins are shown in green and cyan, respectively; those in JA-Ile and COR are shown in yellow and magenta, respectively. In protein and ligand molecules N—, O—, and H-atoms are colored in blue, red, and gray, respectively, and, for clarity, nonpolar H-atoms are not shown. Panel E illustrates the molecular structure of JA-Ile with the $\chi 1$ torsion angle shown by the cyan arrow. Panel F illustrates the molecular structure of COR in which the cyclopropane moiety can restrict the rotational freedom of the terminal ethyl group. The cyclopropane moiety along with the ethyl substitution is highlighted in yellow.

Second, in the JA-Ile/COR-binding pocket, the A86 and A384 residues make direct contacts with the ligand (FIG. 2E) and are situated close to the cyclohexene ring and the ethylcyclopropane group of COR or the equivalent parts of JA-Ile, the pentenyl side-chain, and the isoleucine side-chain, respectively (FIG. 3 panels A and B). The CB atom of A86 is 3.6 Å from the nearest C-atom in the pentenyl side-chain of JA-Ile and 3.7 Å from the ethyl group attached to the cyclohexene ring of COR in their respective crystal structures. The Cβ atom of A384 is 4.0 Å from the nearest C-atom of the isoleucine side chain of JA-Ile and 3.6 Å from the ethyl-cyclopropane group of COR. In silico mutagenesis followed by energy minimization revealed that the A384V substitution, in particular, would create steric clash with the isoleucine side-chain of JA-Ile or the ethyl group attached to the cyclopropane moiety of COR (FIG. 3 panels C and D). However, the flexibility of the isoleucine side-chain of JA-Ile would likely allow for its readjustment to fit the mutated ligand-binding pocket, whereas the rigidity of the ethyl-cyclopropane group of COR would not (FIG. 3 panels E and F).

Taken together, the in silico and structural modeling analyses indicate that mutating alanine to valine at position 384 may result in a ligand-binding pocket that is more unfavorable to the chemical structure of COR than that of JA-Ile.

EXAMPLE 4

Effects of Amino Acid Substitutions at Positions 86 and 384 on JA-Ile/COR-Dependent Formation of the COI1-JAZ9 Coreceptor To test the hypothesis that mutating A384 or A86 may create a ligand-binding pocket that is more unfavorable to COR than to that of JA-Ile, these two alanine residues were first substituted with the corresponding residues found in lower plant species *P. patens* and *S. moellendorffii* (FIG. 2E). Specifically, the following COI1 mutants were generated: COI1A86I, COI1A86V, COI1A384I, COI1A384S, and COI1A384V.

Figures 4A, 4B:
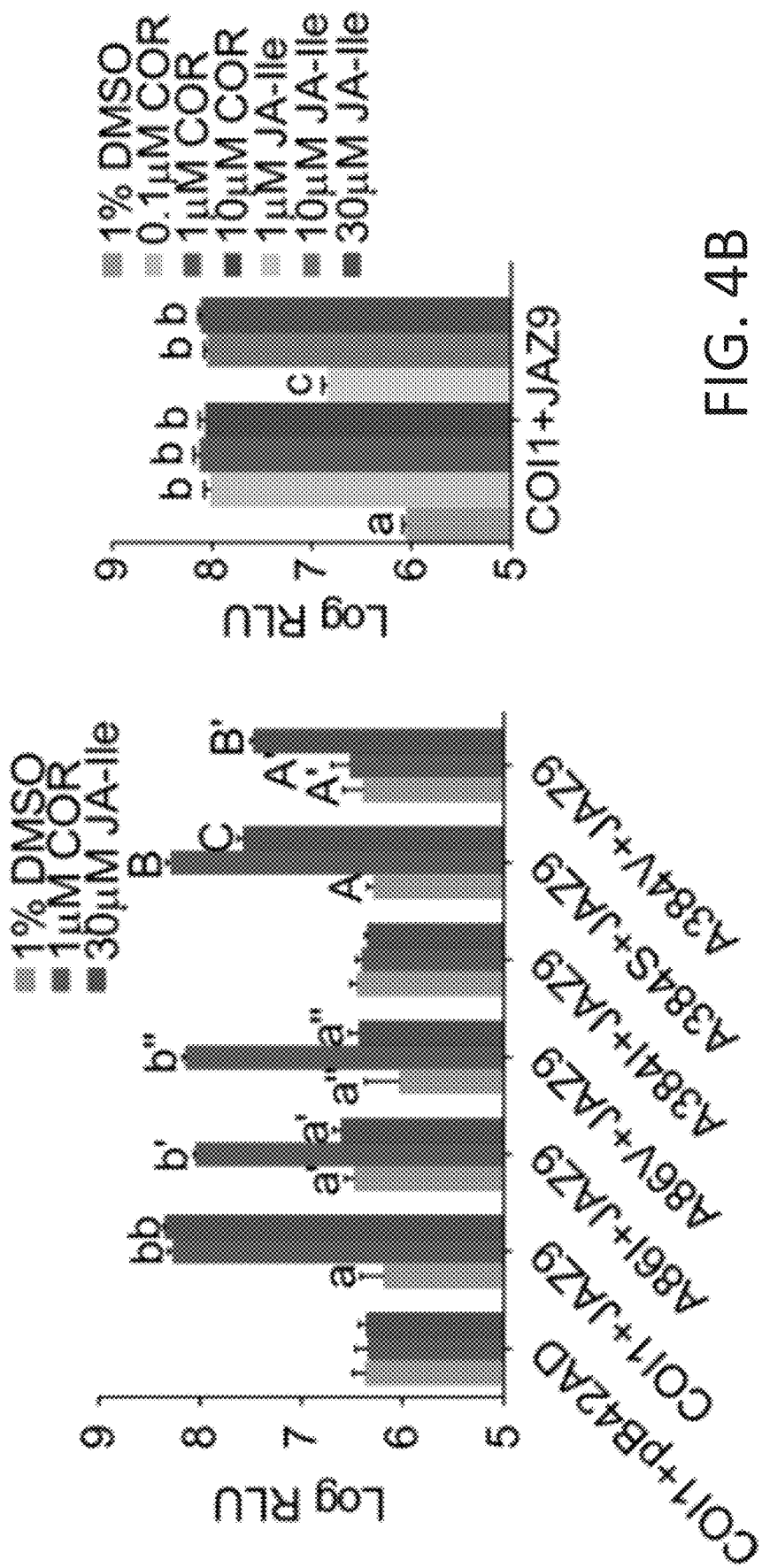
FIG. 4A-4C shows graphs of Y2H and pull-down assay results illustrating the physical interactions between COI1 and JAZ9 proteins.

Quantitative liquid Y2H assays revealed that both COI1A86I and COI1A86V abolished JA-Ile-dependent COI1-JAZ9 interaction, and reduced COR-dependent COI1-JAZ9 interaction (FIG. 4A). These results indicated that A86 may be needed for the action of both JA-Ile and COR, albeit more critical for JA-Ile than COR.

Substitutions at position 384 exhibited more diverse effects than those at position 86 on JA-Ile/COR-dependent COI1-JAZ9 interaction (FIG. 4A). COI1A384I disrupted both JA-Ile-dependent and COR-dependent interaction, whereas COI1A384S only reduced JA-Ile-dependent interaction. Most interestingly, COI1A384V greatly reduced COR-dependent interaction, but had less effect on JAIle-dependent COI1-JAZ9 interaction (FIG. 4A). As illustrated in FIG. 4B, 10 µM JA-Ile, which contains a mixture of active and inactive isomers of JA-Ile, was equivalent to 0.1 µM pure COR in promoting the COI1-JAZ9 interaction in yeast.

Seven additional substitutions at A384 were made to determine whether these substitutions would have an effect similar to that of COI1A384V. Of these seven substitutions (representing different types of side-chains), A384C reduced, and A384D, A384G, A384L, A384N, A384P, and A384T completely disrupted JA-Ile-dependent and COR-dependent interaction (FIG. 2C). In all, no additional substitutions affected COR-dependent COI1-JAZ9 interaction more than JA-Ile-dependent COI1-JAZ9 interaction.

Therefore, through extensive mutagenesis efforts a specific amino acid substitution, A384V, was identified in the JA-Ile binding pocket that preferably affects COR-dependent COI1-JAZ9 interaction, compared with JA-Ile-dependent COI1-JAZ9 interaction in yeast.

EXAMPLE 5

Transgenic *Arabidopsis* Plants Expressing COI1A384V are Fertile but Exhibit Differential Sensitivities to Methyl Jasmonate and COR In Vivo To determine the physiological relevance of the results from Y2H assays, transgenic *Arabidopsis* plants (in COI1-30-null mutant background) were produced that express COI1A384V from the COI1 native promoter (pCOI1:COI1A384V-4×c-Myc; COI1A384V hereafter). As controls, transgenic lines were also generated that express wild type COI1 in the COI1-30-null background (pCOI1:COI1WT-4× c-Myc; COI1WT hereafter).

Figure 5A:
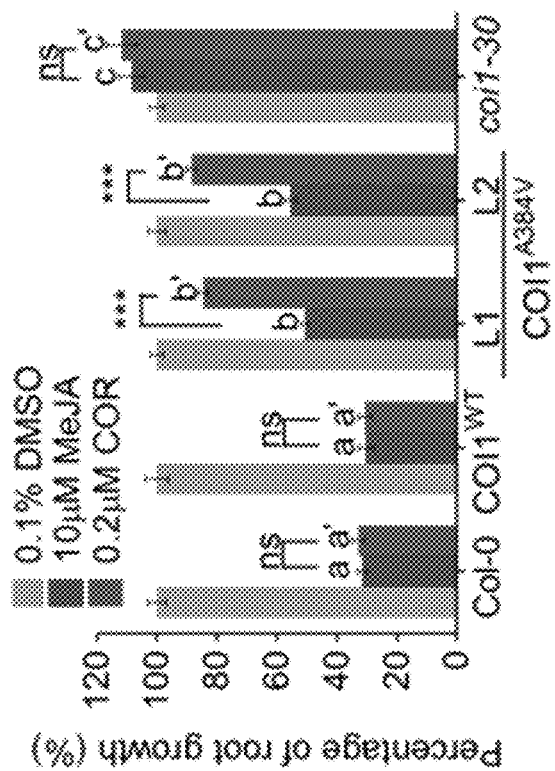
FIG. 5A-5F illustrate the phenotypes of transgenic COI1WT and COI1A384V plants.
Figure 5B:
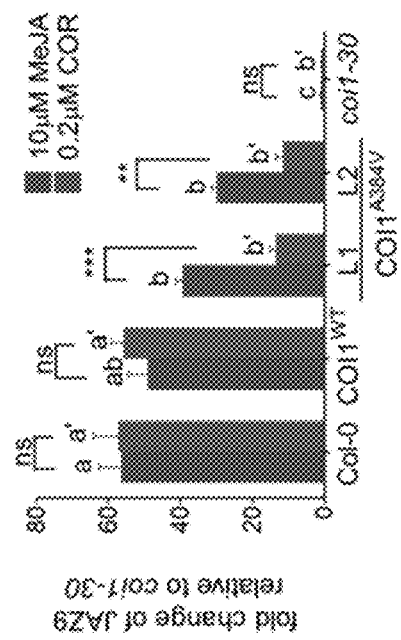

First, experiments were performed to determine whether COI1A384V complements the male sterile phenotype in COI1-30. JA is essential for male fertility and COI1 mutants are male sterile (Feys et al. Plant Cell 6(5):751-759 (1994)). Consistent with Y2H results showing that COI1A384V maintained substantial JA-Ile interaction, 83% of COI1A384V lines (10 of 12 lines analyzed) were fertile (FIG. 5A). Four fertile COI1A384V lines were randomly chosen for protein expression analysis and all were found to produce the c-Myc-tagged COI1A384V protein (FIG. 5B). No fertility penalty was detected in COI1A384V plants, as judged by the number of developed siliques and the number of seeds per silique, which are similar to wild-type plants (Table 2).

TABLE 2

Fertility of Col-0, COI1WT, COIA384V, and coil-30 plants

| Plant | No. of fertile flowers* | No. of seeds/silique† |
|---|---|---|
| Col-0 | 50/50 | 62 ± 4 |
| coil-30/COI1$^{WT}$ | 50/50 | 57 ± 8 |
| coil-30/COI1$^{A384V}$ L1 | 50/50 | 58 ± 6 |
| coil-30 | 0/50 | 0 |

No statistically significant differences were found by ANOVA (P = 0.411072) between Col-0, coil-30/COI1WT, and coil-30/COI1A384V L1.
*Number of flowers that produce siliques/number of total flowers examined. Ten flowers of each plant and five plants of each genotype were examined.
†Five siliques of each plant and a total of five plants were examined.

Figure 4C:
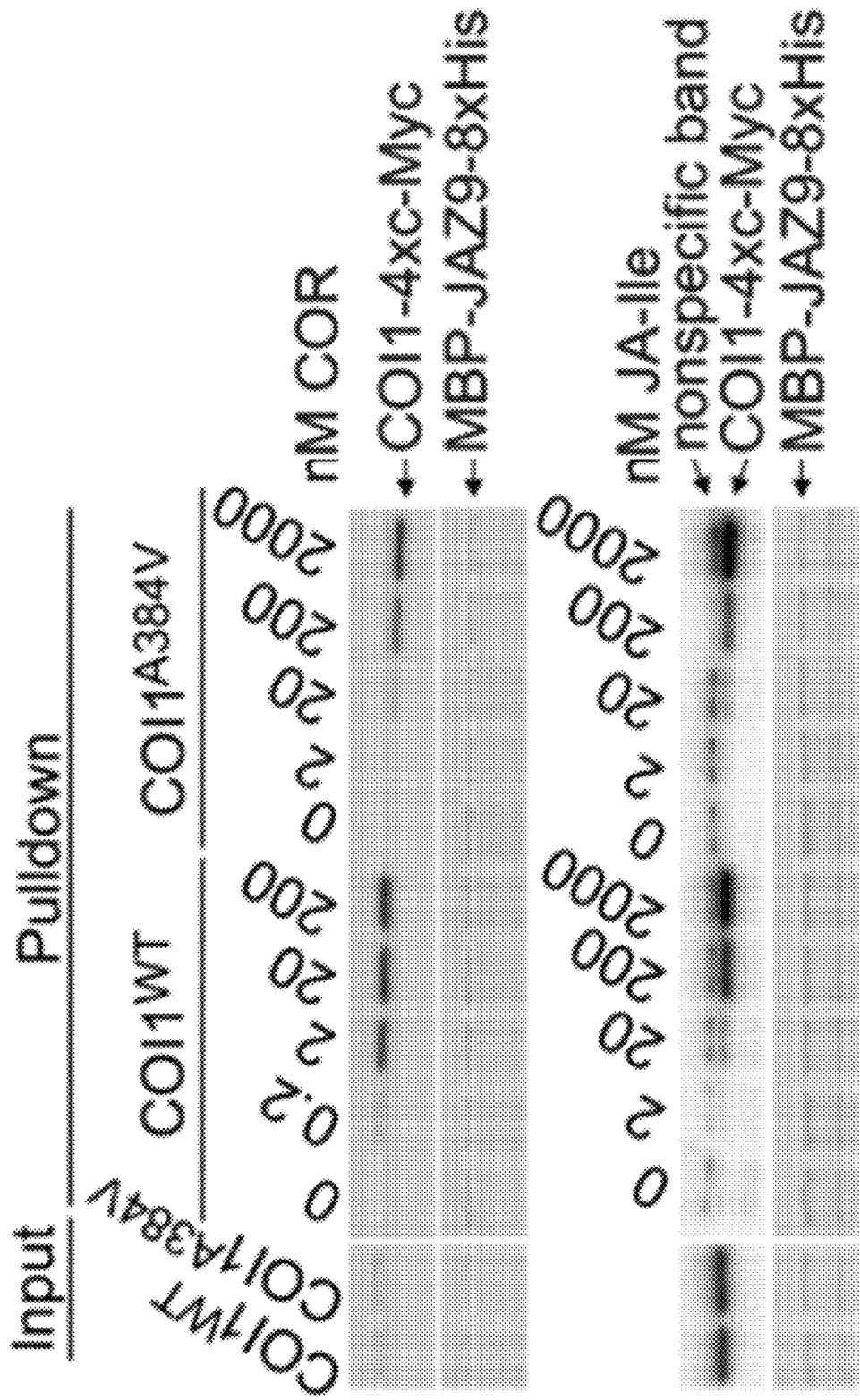

Next, COI1-JAZ9 pull-down experiments were performed to compare the responsiveness of plant-expressed COI1WT and COI1A384V proteins to serial concentrations of JA-Ile and COR using *Escherichia coli*-expressed JAZ9 protein, following the procedure reported by Katsir et al. (Proc Natl Acad Sci USA 105(19):7100-7105 (2008)). These experiments confirmed that a much higher (~100-fold) concentration of COR was required for robust formation of the COI1A384V-JAZ9 co-receptor than for the COI1WT-JAZ9 co-receptor, whereas similar concentrations of JA-Ile were needed to promote the formation of the COI1A384V-JAZ9 and COI1WT-JAZ9 co-receptors (FIG. 4C). Hence, the modified COI1A384V protein does not form a complex with JAZ and COR, as readily as it complexes with JAZ and jasmonic acid (e.g., JA-Ile).

Figure 5C:
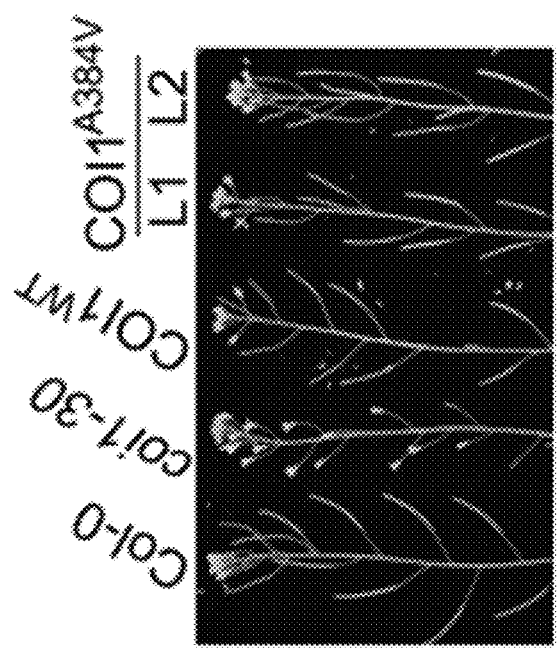

Further analyses were performed with two representative COI1A384V lines, L1 and L2, to determine their responses to JA-induced or COR-induced root growth inhibition. Dose-response experiments showed that the effect of 10 μM methyl jasmonate (MeJA), which is converted to the active form JA-Ile in planta, was equivalent to that of 0.2 μM COR in wild-type Col-0 plants (FIG. 5C). Unlike wild-type Col-0 plants, the root growth inhibition of COI1A384V plants was significantly less sensitive to 0.2 μM COR than to 10 μM MeJA (FIG. 5C). The potency of 0.2 μM COR in inhibiting root growth in COI1A384V plants was comparable to 0.1 μM MeJA, indicating that 0.2 μM COR was about 100-fold less effective in COI A384V than in Col-0 and COI1WT.

These results were consistent with the differential effects of the A384V substitution on JA-Ile-dependent vs. COR-dependent formation of the COI1-JAZ9 coreceptor observed in both Y2H and COI1-JAZ9 coreceptor pull-down assays. These results also confirmed that COI1A384V transgenic plants are differentially sensitive to MeJA vs. COR in vivo. COI A384V transgenic plants are thus more sensitive in vivo to MeJA than to COR.

EXAMPLE 6

Transgenic *Arabidopsis* Plants Expressing COI1A384V Exhibit Differential Expression of JA Response Marker Genes in Response to MeJA Vs. COR Gene expression responses in COI1A384V transgenic plants were examined by evaluating the expression of the JA-responsive marker gene JAZ9 by quantitative PCR (qPCR).

Figure 5D:
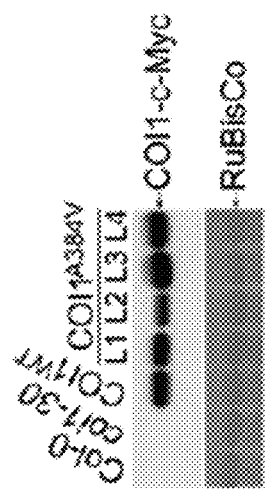

As illustrated in FIG. 5D, JAZ9 gene expression was induced in Col-0 and COI1WT plants after application of MeJA or COR. In COI1A384V lines, however, JAZ9 gene expression in response to COR treatment was significantly reduced compared with Col-0 or COI1WT plants, whereas JAZ9 expressions in response to MeJA treatment was less affected in this same comparison (FIG. 5D). For example, in plants of the COI1A384V L1 line, MeJA treatment induced the expression of JAZ9 by 38-fold compared with that in COI1-30 (COI1-null mutant) plants. However, induction of JAZ9 gene expression in COI1A384VL1 was only eight-fold higher than that in COI1-30 plants after COR treatment.

These results indicate that the A384V substitution significantly affects the action of COR, while maintaining JA signaling required for substantial JA responses in gene expression.

Figure 5F:
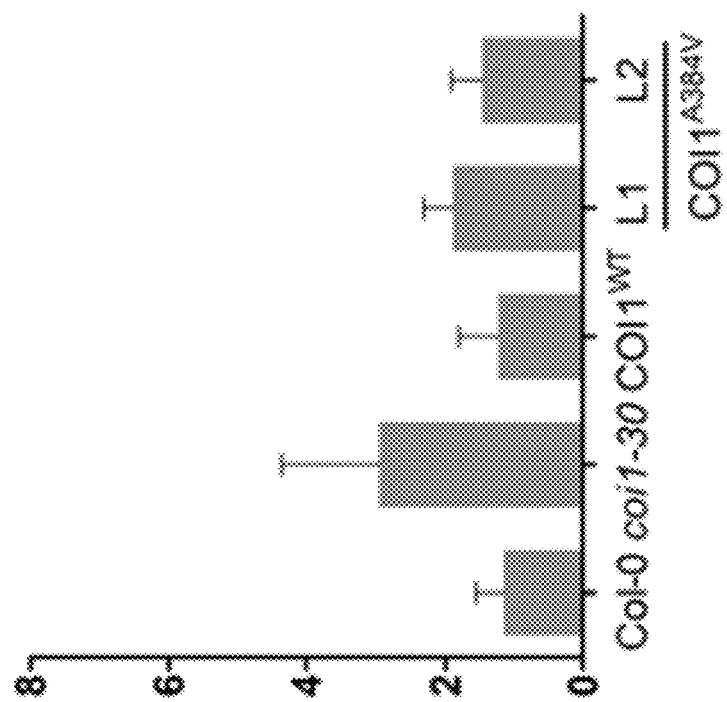
Figure 5E:
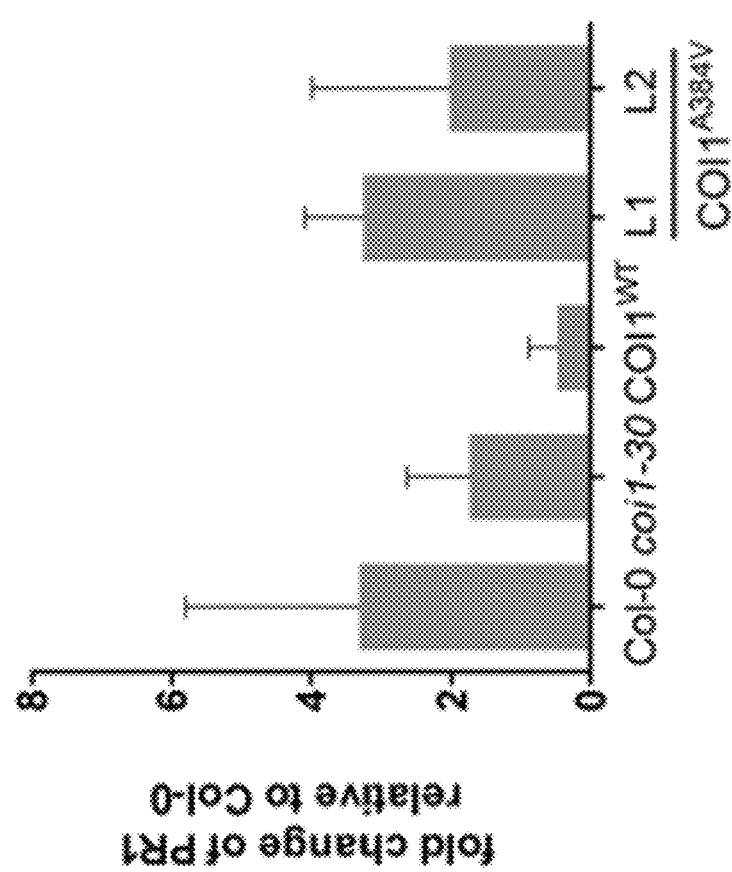

The expression of SA-responsive genes PATHOGENESIS-RELATED GENE 1 (PR1) and SALICYLIC ACID INDUCTION DEFICIENT 2 (SID2) was examined in COI1A384V plants. As illustrated in FIGS. 5E-5F, expression of PR1 and SID2 genes was similarly low in Col-0, COI1WT and COI1A384V plants. These results indicate that the SA signaling pathway remained quiescent in COI1A384V plants, in a manner that was similar to SA signaling in Col-0 and COI1WT plants.

EXAMPLE 7

COI1A384V Transgenic Plants Gained Resistance to Pst DC3000 and Psm ES4326, while Maintaining High-Level Defense Against Chewing Insects The data described above indicate that the inventors have succeeded in engineering a modified JA receptor that substantially uncouples endogenous hormone signaling from pathogen hijacking via COR. This Example describes experiments to test whether COI1A384V transgenic plants also gain resistance to COR-producing bacterial pathogens, while retaining substantial defense against chewing insects.

To test this possibility, bioassays were conducted using *Pseudomonas syringae* pv tomato (Pst) DC3000 and *Pseudomona syringe* pv maculicola (Psm) ES4326, two well-known COR-producing hemibiotrophic pathogens that infect *Arabidopsis* (Whalen et al. Plant Cell 3(1):49-59 (1991); Dong et al. Plant Cell 3(1):61-72 (1991)), and *Spodoptera exigua*, a generalist chewing insect that is susceptible to COI1-dependent defenses in *Arabidopsis* (Chung et al. Plant Physiol 146(3):952-964 (2008)).

Figure 6A:
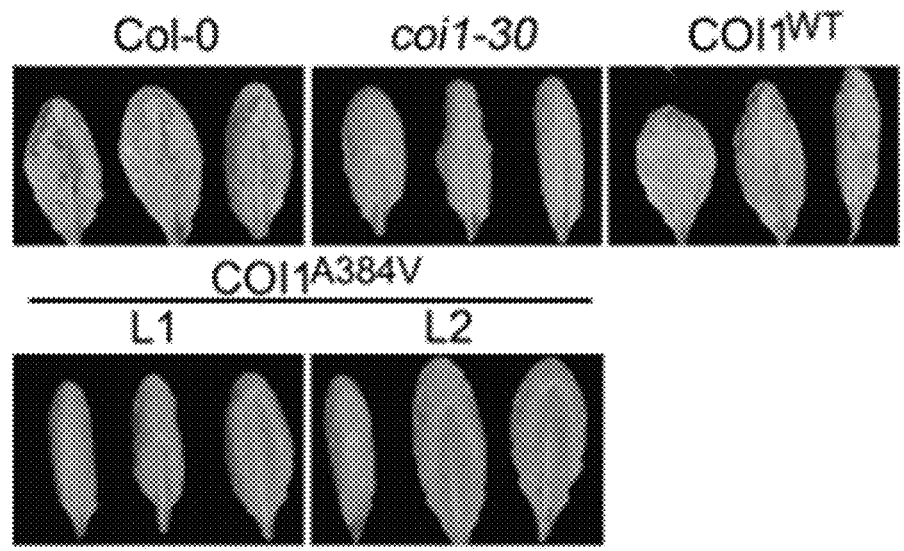
FIG. 6A-6F illustrates the effects of bacterial infections by Pseudomonas syringae pv tomato (Pst) DC3000, Pseudomonas syringae pv maculicola (Psm) ES4326, Pseudomonas syringae pv tomato DC3118 and Pseudomonas syringae pv tomato DB29. The Pseudomonas syringae pv tomato DC3118 and Pseudomonas syringae pv tomato DB29 strains are two COR-deficient mutants of Pseudomonas syringae pv tomato DC3000.
Figure 6B:
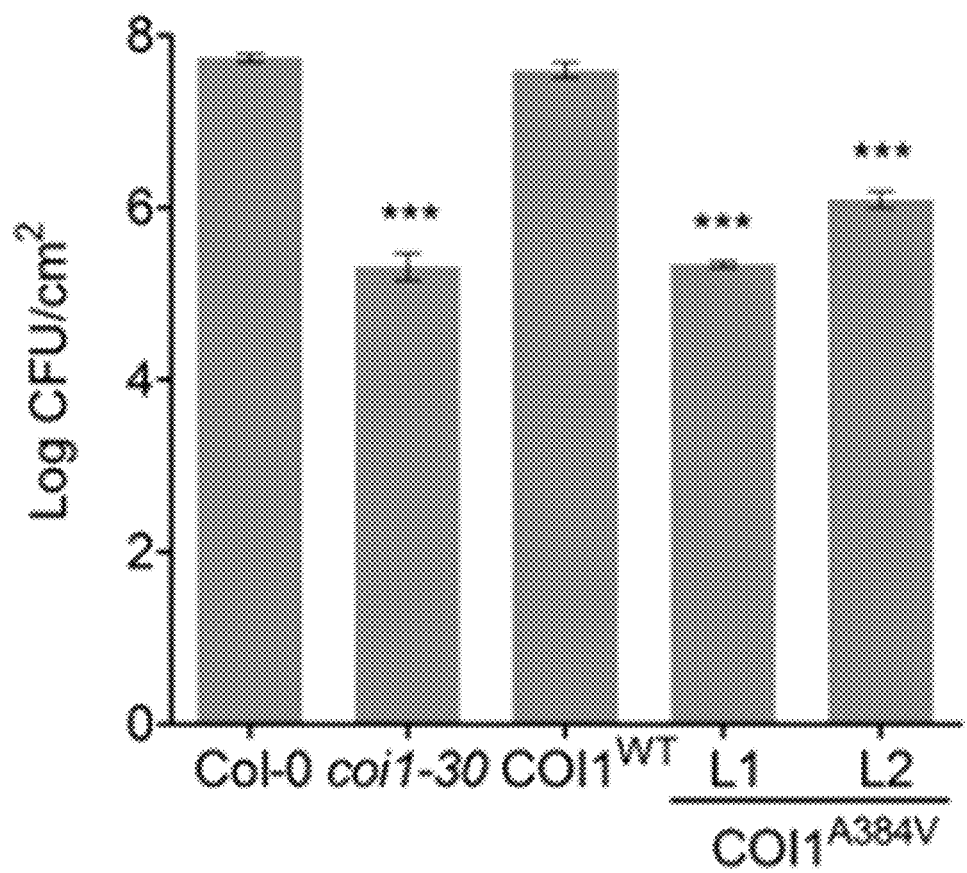
Figure 6C:
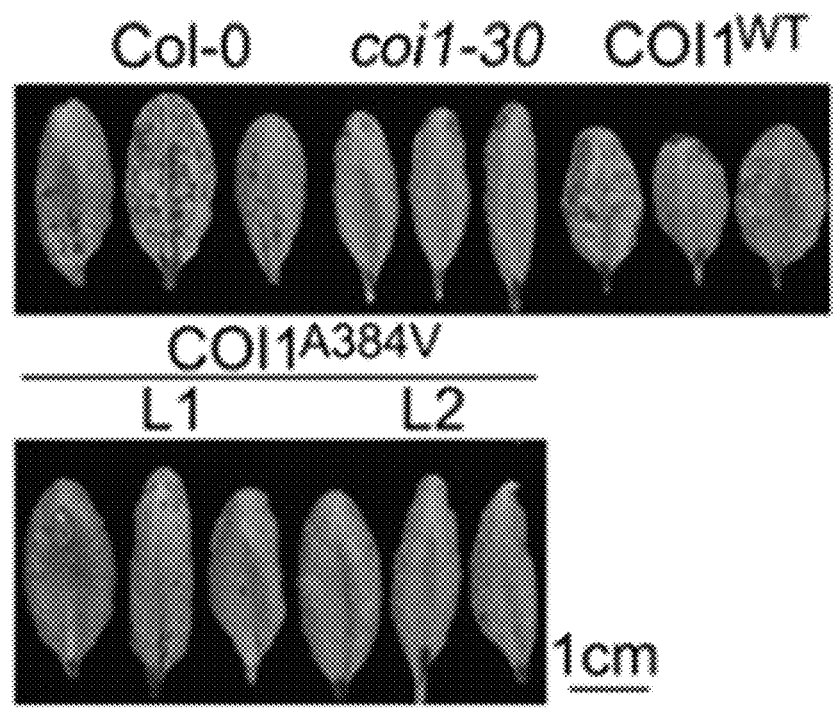
Figure 6D:
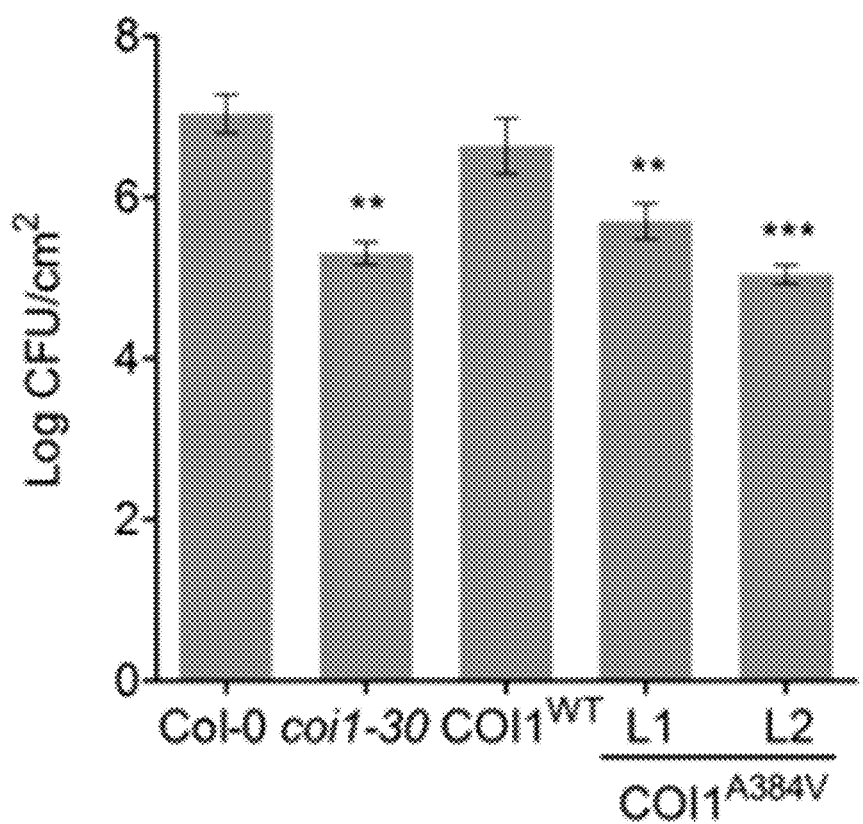

Col-0 and COI1WT plants were highly susceptible to Pst DC3000 (FIG. 6A-6B). COI1A384V plants, however, exhibited significantly increased resistance to Pst DC3000, as evidenced by greatly reduced bacterial growth and disease symptoms (FIG. 6A-6B). Quantitatively, Pst DC3000 populations in COI1A384V lines were 254-fold to 42-fold lower than those in Col-0 plants and 189-fold to 31-fold lower than those in COI1WT transgenic plants (FIG. 6B). Similarly, COI1A384V plants exhibited significantly increased resistance to Psm ES4326 compared with wild-type Col-0 or COI1WT plants (FIG. 6C-6D). Control experiments showed that COI1-30 plants were highly resistant to both pathogens in these assays (FIGS. 6B and 6D).

Figure 6E:
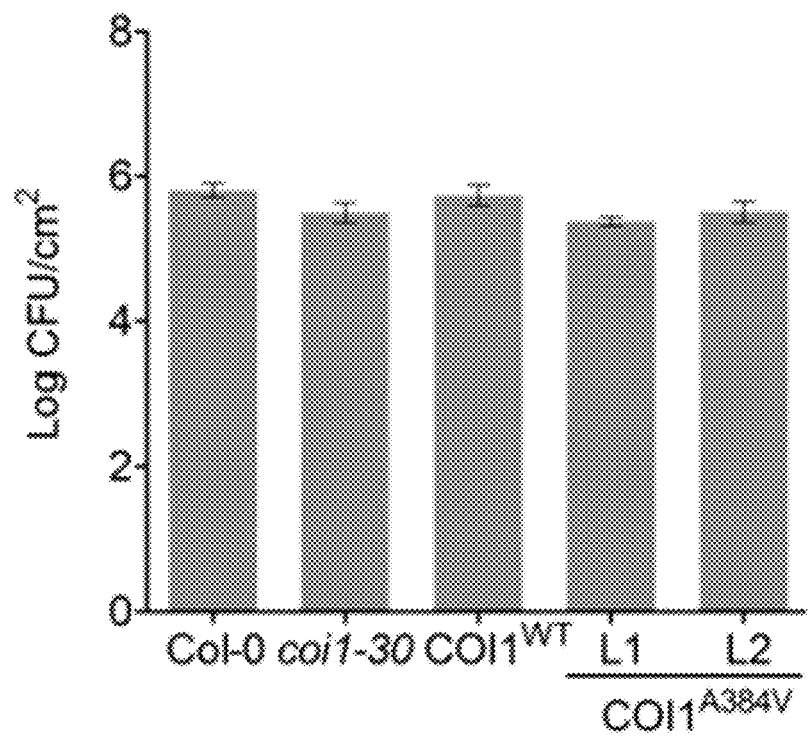
Figure 6F:
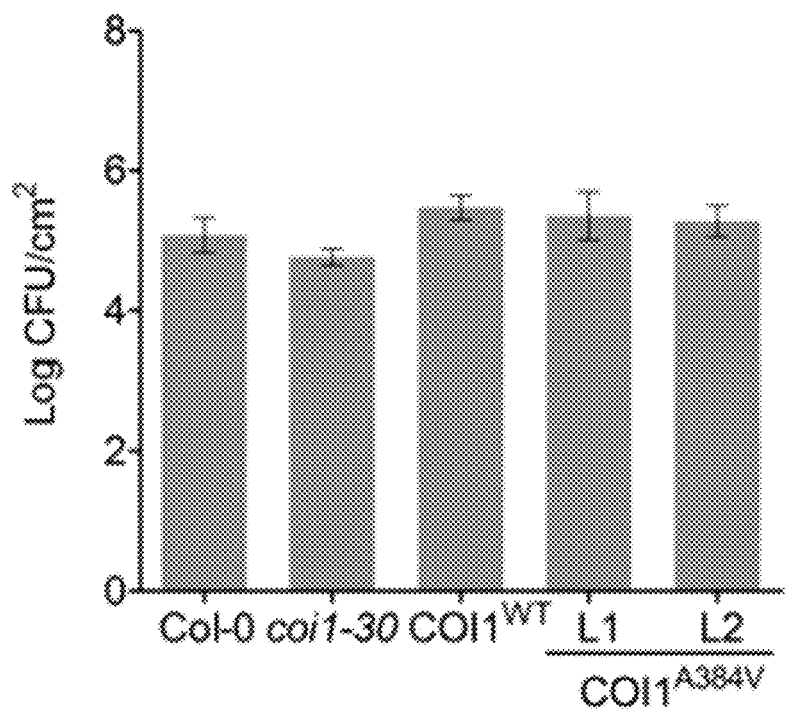

Disease assays were conducted using Psi DC3118 and DB29, which are mutants of Pst DC3000 defective in COR production (Brooks et al. Mol Plant Microbe Interact 17(2): 162-174 (2004); Zeng et al., PLoS Pathog 7(10): e1002291 (2011)). Similar levels of bacterial growth were observed in Col-0, COI1WT, and COI1A384V plants, indicating that the resistance gained in COI1A384V plants to Pst DC3000 was largely COR-dependent (FIG. 6E-6F).

Figures 7A, 7B:
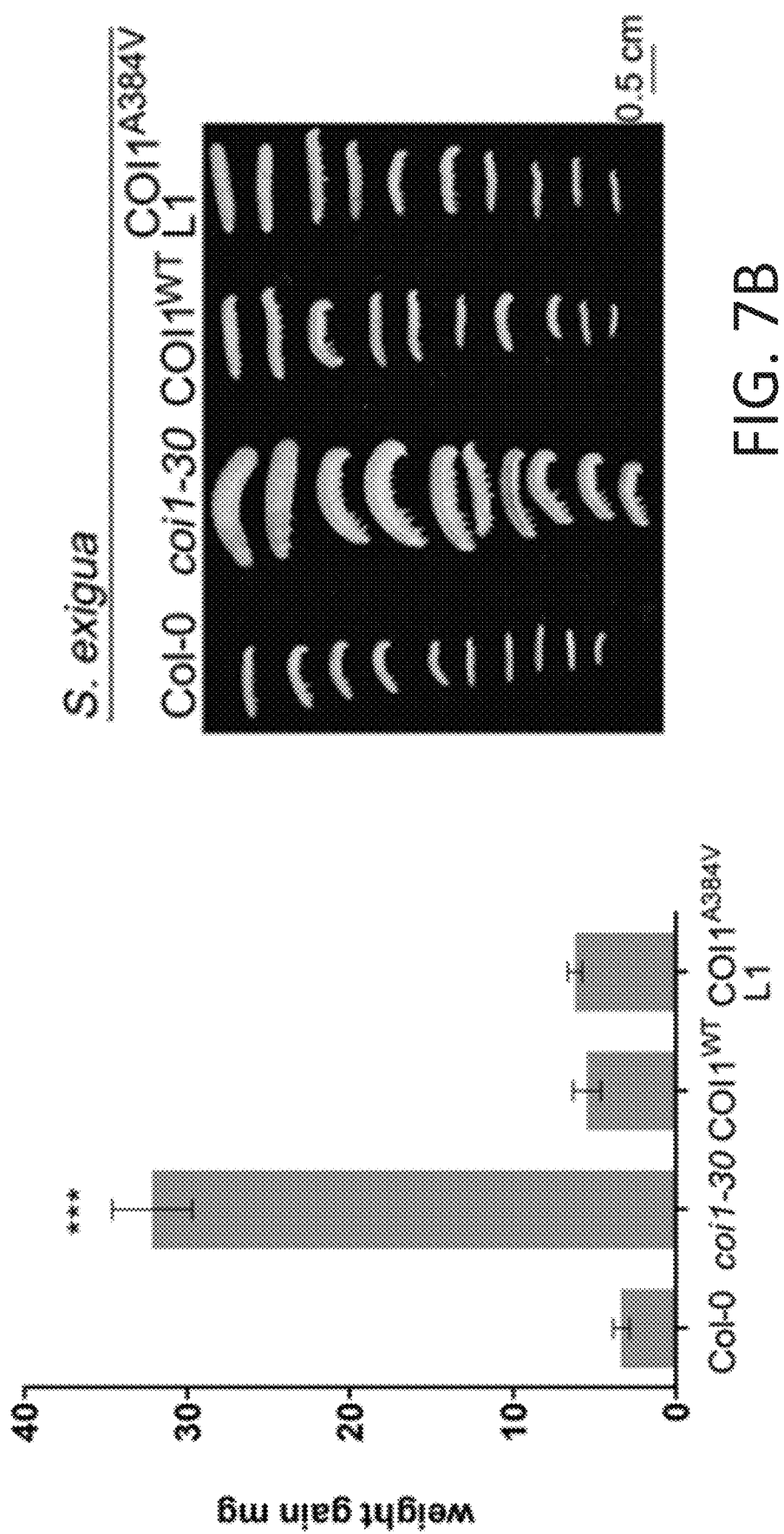
FIGS. 7A-7C illustrate the amount of insect feeding on COI1WT and COI1A384V plants.
Figure 7C:
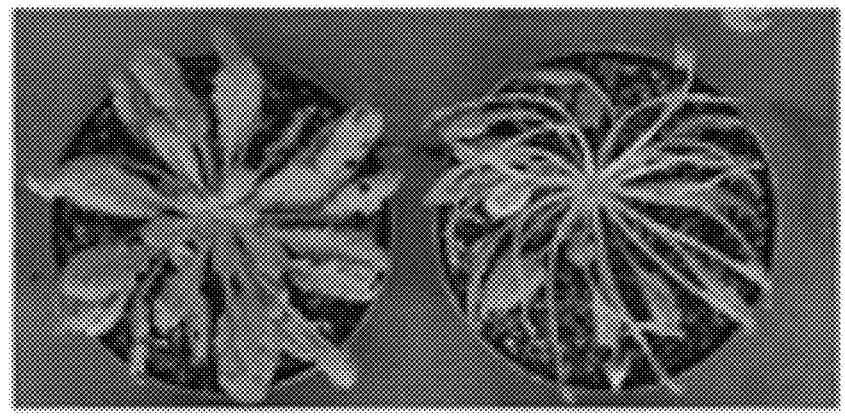
Figure 7C:
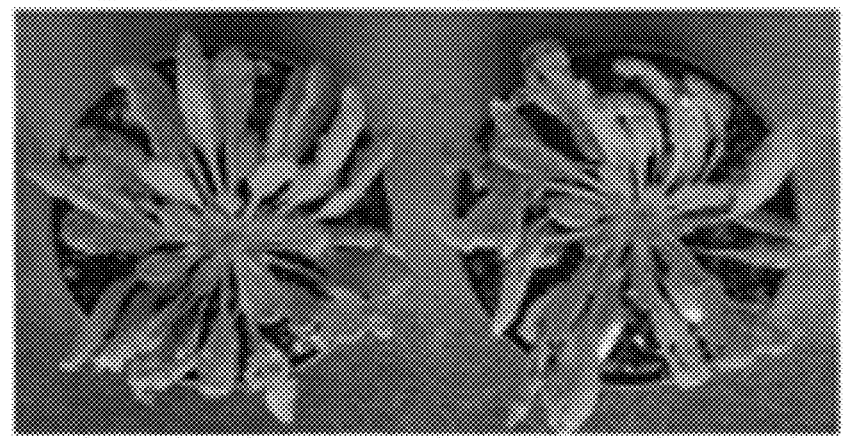

Insect feeding assays were performed using *S. exigua* neonate larvae. As illustrated FIG. 7, *S. exigua* grew much more slowly on Col-0 plants than on COI1-30 mutant plants. The average weight of larvae feeding on COI1-30 plants was six-fold higher than larvae reared on COI1WT plants and five-fold higher than those grown on COI1A384V plants (FIG. 7A). Thus, COI1A384V plants maintained an almost wild-type levels of defense against *S. exigua*.

REFERENCES

1. Robert-Seilaniantz A, Grant M, Jones J D (2011) Hormone crosstalk in plant disease and defense: More than just jasmonate-salicylate antagonism. Annu Rev Phytopathol 49:317-343.
2. Thaler J S, Humphrey P T, Whiteman N K (2012) Evolution of jasmonate and salicylate signal crosstalk. Trends Plant Sci 17(5):260-270.
3. Glazebrook J (2005) Contrasting mechanisms of defense against biotrophic and necrotrophic pathogens. Annu Rev Phytopathol 43:205-227.
4. Xin X F, He S Y (2013) *Pseudomonas syringae* pv. tomato DC3000: A model pathogen for probing disease susceptibility and hormone signaling in plants. Annu Rev Phytopathol 51:473-498.
5. Dou D, Zhou J M (2012) Phytopathogen effectors subverting host immunity: Different foes, similar battleground. Cell Host Microbe 12(4):484-495.
6. Block A, et al. (2014) The *Pseudomonas syringae* type III effector HopD1 suppresses effector-triggered immunity, localizes to the endoplasmic reticulum, and targets the *Arabidopsis* transcription factor NTL9. New Phytol 201 (4): 1358-1370.
7. Fonseca S, et al. (2009) (+)-7-iso-Jasmonoyl-L-isoleucine is the endogenous bioactive jasmonate. Nat Chem Biol 5(5):344-350.
8. Wasternack C (2007) Jasmonates: An update on biosynthesis, signal transduction and action in plant stress response, growth and development. Ann Bot (Lond) 100 (4): 681-697.
9. Wasternack C, Hause B (2013) Jasmonates: Biosynthesis, perception, signal transduction and action in plant stress response, growth and development. An update to the 2007 review in Annals of Botany. Ann Bot (Lond) 111(6): 1021-1058.
10. Browse J (2009) Jasmonate passes muster: A receptor and targets for the defense hormone. Annu Rev Plant Biol 60:183-205.
11. Staswick P E, Tiryaki 1 (2004) The oxylipin signal jasmonic acid is activated by an enzyme that conjugates it to isoleucine in *Arabidopsis*. Plant Cell 16(8):2117-2127.
12. Thines B, et al. (2007) JAZ repressor proteins are targets of the SCF(COI1) complex during jasmonate signalling. Nature 448(7154):661-665.
13. Katsir L, Schilmiller A L, Staswick P E, He S Y, Howe G A (2008) COI1 is a critical component of a receptor for jasmonate and the bacterial virulence factor coronatine. Proc Natl Acad Sci USA 105(19):7100-7105.
14. Chini A, Fonseca S, Chico J M, Fernandez-Calvo P, Solano R (2009) The ZIM domain mediates homo- and heteromeric interactions between *Arabidopsis* JAZ proteins. Plant J 59(1):77-87.
15. Melotto M, et al. (2008) A critical role of two positively charged amino acids in the Jas motif of *Arabidopsis* JAZ proteins in mediating coronatine- and jasmonoyl isoleucine-dependent interactions with the COI F-box protein. Plant J 55(6):979-988.
16. Yan Y, et al. (2007) A downstream mediator in the growth repression limb of the jasmonate pathway. Plant Cell 19(8):2470-2483.
17. Pauwels L, et al. (2010) NINJA connects the co-repressor TOPLESS to jasmonate signalling. Nature 464 (7289):788-791.
18. Chung H S, Howe G A (2009) A critical role for the TIFY motif in repression of jasmonate signaling by a stabilized splice variant of the JASMONATE ZIM-domain protein JAZ10 in *Arabidopsis*. Plant Cell 21(1):131-145.
19. Zhang F, et al. (2015) Structural basis of JAZ repression of MYC transcription factors in jasmonate signaling. Nature 525(7568):269-273.
20. Pauwels L, Goossens A (2011) The JAZ proteins: A crucial interface in the jasmonate signaling cascade. Plant Cell 23(9):3089-3100.
21. Xu L, et al. (2002) The SCF(COI1) ubiquitin-ligase complexes are required for jasmonate response in *Arabidopsis*. Plant Cell 14(8):1919-1935.
22. Tsuda K. Somssich I E (2015) Transcriptional networks in plant immunity. New Phytol 206(3):932-947.
23. Vidhyasekaran P (2015) Jasmonate signaling system in plant innate immunity. Signaling and Communication in Plants 2: Plant Hormone Signaling Systems in Plant Innate Immunity (Springer, The Netherlands), pp 123-194.
24. Song S, Qi T, Wasternack C, Xie D (2014) Jasmonate signaling and crosstalk with gibberellin and ethylene. Curr Opin Plant Biol 21:112-119.
25. Pieterse C M, Van der Does D, Zamioudis C, Leon-Reyes A, Van Wees S C (2012) Hormonal modulation of plant immunity. Annu Rev Cell Dev Biol 28:489-521.
26. Zheng X Y, et al. (2012) Coronatine promotes *Pseudomonas syringae* virulence in plants by activating a signaling cascade that inhibits salicylic acid accumulation. Cell Host Microbe 11(6):587-596.
27. Groen S C, et al. (2013) Pathogen-triggered ethylene signaling mediates systemic-induced susceptibility to herbivory in *Arabidopsis*. Plant Cell 25(11):4755-4766.
28. Cui J, et al. (2005) *Pseudomonas syringae* manipulates systemic plant defenses against pathogens and herbivores. Proc Natl Acad Sci USA 102(5):1791-1796.
29. Geng X, Jin L, Shimada M, Kim M G, Mackey D (2014) The phytotoxin coronatine is a multifunctional component of the virulence armament of *Pseudomonas syringae*. Planta 240(6): 1149-1165.
30. Bender C L, Alarcón-Chaidez F, Gross D C (1999) *Pseudomonas syringae* phytotoxins: Mode of action, regulation, and biosynthesis by peptide and polyketide synthetases. Microbiol Mol Biol Rev 63(2):266-292.
31. Fyans J K, Altowairish M S, Li Y, Bignell D R (2015) Characterization of the coronatine-like phytotoxins produced by the common scab pathogen *Streptomyces* scabies. Mol Plant Microbe Interact 28(4):443-454.
32. Plett J M, et al. (2014) Effector MiSSP7 of the mutualistic fungus Laccaria bicolor stabilizes the Populus JAZ6 protein and represses jasmonic acid (JA) responsive genes. Proc Natl Acad Sci USA 111(22):8299-8304.
33. Jiang S, et al. (2013) Bacterial effector activates jasmonate signaling by directly targeting JAZ transcriptional repressors. PLoS Pathog 9(10):e1003715.

34. Gimenez-Ibanez S, et al. (2014) The bacterial effector HopX1 targets JAZ transcriptional repressors to activate jasmonate signaling and promote infection in *Arabidopsis*. PLoS Biol 12(2):e1001792.
35. Yan J, et al. (2009) The *Arabidopsis* CORONATINE INSENSITIVE1 protein is a jasmonate receptor. Plant Cell 21(8):2220-2236.
36. Sheard L B, et al. (2010) Jasmonate perception by inositol-phosphate-potentiated COI1-JAZ co-receptor. Nature 468(7322):400-405.
37. Monte I, et al. (2014) Rational design of a ligand-based antagonist of jasmonate perception. Nat Chem Biol 10(8): 671-676.
38. Wang C, Liu Y, Li S S, Han G Z (2015) Insights into the origin and evolution of the plant hormone signaling machinery. Plant Physiol 167(3):872-886.
39. Stumpe M, et al. (2010) The moss *Physcomitrella patens* contains cyclopentenones but no jasmonates: Mutations in allene oxide cyclase lead to reduced fertility and altered sporophyte morphology. New Phytol 188(3):740-749.
40. Feys B, Benedetti C E, Penfold C N, Turner J G (1994) *Arabidopsis* mutants selected for resistance to the phytotoxin coronatine are male sterile, insensitive to methyl jasmonate, and resistant to a bacterial pathogen. Plant Cell 6(5):751-759.
41. Whalen M C, Innes R W, Bent A F, Staskawicz B J (1991) Identification of *Pseudomonas syringae* pathogens of *Arabidopsis* and a bacterial locus determining avirulence on both *Arabidopsis* and soybean. Plant Cell 3(1): 49-59.
42. Dong X, Mindrinos M, Davis K R, Ausubel F M (1991) Induction of *Arabidopsis* defense genes by virulent and avirulent *Pseudomonas syringae* strains and by a cloned avirulence gene. Plant Cell 3(1):61-72.
43. Chung H S, et al. (2008) Regulation and function of *Arabidopsis* JASMONATE ZIM-domain genes in response to wounding and herbivory. Plant Physiol 146 (3):952-964.
44. Brooks D M, et al. (2004) Identification and characterization of a well-defined series of coronatine biosynthetic mutants of *Pseudomonas syringae* pv. tomato DC3000. Mol Plant Microbe Interact 17(2): 162-174.
45. Zeng W, et al. (2011) A genetic screen reveals *Arabidopsis* stomatal and/or apoplastic defenses against *Pseudomonas syringae* pv. tomato DC3000. PLoS Pathog 7(10): e1002291.
46. Cipollini D, Enright S, Traw M B, Bergelson J (2004) Salicylic acid inhibits jasmonic acid-induced resistance of *Arabidopsis thaliana* to *Spodoptera exigua*. Mol Ecol 13(6): 1643-1653.
47. Mewis I, Appel H M, Hom A, Raina R, Schultz J C (2005) Major signaling pathways modulate *Arabidopsis* glucosinolate accumulation and response to both phloem-feeding and chewing insects. Plant Physiol 138(2):1 149-1162.
48. Qi M, Wang D, Bradley C A, Zhao Y (2011) Genome sequence analyses of *Pseudomonas savastanoi* pv. *glycinea* and subtractive hybridization-based comparative genomics with nine pseudomonads. PLoS One 6(1): e16451.
49. Bell K S, et al. (2004) Genome sequence of the enterobacterial phytopathogen *Erwinia carotovora* subsp. *atroseptica* and characterization of virulence factors. Proc Natl Acad Sci USA 101(30):11105-11110.
50. Park S Y, et al. (2015) Agrochemical control of plant water use using engineered abscisic acid receptors. Nature 520(7548):545-548.
51. Tan X, et al. (2007) Mechanism of auxin perception by the TIR1 ubiquitin ligase. Nature 446(7136):640-645.
52. Santner A, Estelle M (2009) Recent advances and emerging trends in plant hormone signalling. Nature 459(7250): 1071-1078.
53. Wang J, Wang W, Kollmann P, Case D (2001) Antechamber, An Accessory Software Package For Molecular Mechanical Calculation. Abstracts of Papers, 222nd National Meeting of the American Chemical Society, Chicago, Ill., Aug. 26-30, 2001, American Chemical Society: Washington, DC:U403.
54. Case D A, et al. (2012) AMBER 12 (University of California, San Francisco). Available at ambermd.org/doc 12/Amber12.pdf. Accessed Oct. 20, 2015.
55. Nakagawa S, Cuthill I C (2007) Effect size, confidence interval and statistical significance: A practical guide for biologists. Biol Rev Camb Philos Soc 82(4):591-605.
56. Yang D L, et al. (2012) Plant hormone jasmonate prioritizes defense over growth by interfering with gibberellin signaling cascade. Proc Natl Acad Sci USA 109(19): E1192-E1200.
57. Clough S J, Bent A F (1998) Floral dip: A simplified method for *Agrobacterium*-mediated transformation of *Arabidopsis thaliana*. Plant J 16(6):735-743.
58. Yao J, Withers J, He S Y (2013) *Pseudomonas syringae* infection assays in *Arabidopsis*. Methods Mol Biol 1011: 63-81.
59. Herde M, Koo A J, Howe G A (2013) Elicitation of jasmonate-mediated defense responses by mechanical wounding and insect herbivory. Methods Mol Biol 1011: 51-61.

All patents and publications referenced or mentioned herein are indicative of the levels of skill of those skilled in the art to which the invention pertains, and each such referenced patent or publication is hereby specifically incorporated by reference to the same extent as if it had been incorporated by reference in its entirety individually or set forth herein in its entirety. Applicants reserve the right to physically incorporate into this specification any and all materials and information from any such cited patents or publications.

The following statements are intended to describe and summarize various embodiments of the invention according to the foregoing description in the specification.

Statements:
1. A modified CORONATINE INSENSITIVE 1 (COI1) protein comprising an amino acid sequence with at least one amino acid substitution, replacement, deletion, or insertion relative to a native (wild type) COI1 protein amino acid sequence that reduces complex formation between coronatine and a JAZ repressor protein.
2. The modified COI1 protein of statement 1, wherein the at least one amino acid substitution, replacement, deletion, or insertion is within a jasmonate binding pocket of the COI1 protein.
3. The modified COI1 protein of statement 1 or 2, wherein the at least one amino acid substitution, replacement, deletion, or insertion is not a direct contact jasmonate binding pocket of the COI1 protein.
4. The modified COI1 protein of statement 1, 2, or 3, wherein the native (wild type) COI1 protein is an *Arabidopsis thaliana* protein, a *Solanum lycopersicum* protein, a *Populus trichocarpa* protein, a *Brachypodium distachyon* protein, a *Picea abies* protein, a *Selaginella moellendorffii* protein, a *Physcomitrella patens* protein, a *Brassicaceae* protein, a grass protein, a

*Lolium* (ryegrass) protein, a *Glycine max* protein, a *Zea mays* protein, a *Triticum* spp. protein, a *Brassica rapa* protein, a *Brassica napus* protein, a *Triticum aestivum* plant, a *Populus trichocarpa* plant, an *Arachis hypogaeal* plant, or a *Physcomitrella patens* plant.

5. The modified COI1 protein of statement 1-3 or 4, wherein the modified COI1 protein is a modified *Arabidopsis thaliana* protein, a *Solanum lycopersicum* protein, a *Populus trichocarpa* protein, a *Brachypodium distachyon* protein, a *Picea abies* protein, a *Selaginella moellendorffii* protein, a *Physcomitrella patens* protein, a *Brassicaceae* protein, a grass protein, a *Lolium* (ryegrass) protein, a *Glycine max* protein, a *Zea mays* protein, a *Triticum* spp. protein, a *Brassica rapa* protein, a *Brassica napus* protein, a *Triticum aestivum* plant, a *Populus trichocarpa* plant, an *Arachis hypogaeal* plant, or a *Physcomitrella patens* plant.

6. The modified COI1 protein of statements 1-4 or 5, wherein the modified COI1 protein has a hydrophobic amino acid that is not alanine at the position of an alanine in the native (wild type) COI1 protein.

7. The modified COI1 protein of statements 1-5 or 6, wherein the modified COI1 protein has at least one amino acid substitution within about 0-10 amino acid positions of amino acid position 384 where the amino acid that is replaced in the native (wild type) COI1 protein is an alanine, and the replacement is a hydrophobic amino acid.

8. The modified COI1 protein of statements 1-6 or 7, wherein the modified COI1 protein has an A384V (alanine at position 384 replaced by a valine).

9. The modified COI1 protein of statement 1-7 or 8, with greater binding affinity for jasmonate, methyljasmonate, or jasmonate-Ile, than for a plant toxin that forms a complex with a wild type (native) COIL protein and a JAZ protein.

10. The modified COI1 protein of statement 1-8 or 9, which binds jasmonate, methyljasmonate, or jasmonate-Ile with greater affinity than it binds a plant toxin produced by *Pseudomonas syringae* pv tomato, *Pseudomonas syringae* pv maculicola, *Pseudomonas syringe* pv atropurpurea, *Pseudomonas syringae* pv glycinea, *Pseudomonas syringae* pv morsprunorum, *Pseudomonas syringae* pv porri, *Pseudomonas cannabina* pv alisalensis, *Streptomyces scabies*, *Xanthomonas campestris* pv phormiicola, *Pseudomonas savastanoi* pv glycinea, *Pectobacterium atrosepticum* (syn. *Erwinia carotovora* subsp. *atroseptica*, or *Nectria* sp. DA060097.

11. The modified COI1 protein of statement 1-9 or 10, with greater binding affinity for jasmonate, methyljasmonate, or jasmonate-Ile, than for coronatine or cinnacidin.

12. The modified COI1 protein of statement 1-10 or 11, with greater binding affinity for jasmonate, methyljasmonate, or jasmonate-Ile, than for a compound of formula I:

wherein:
$R_1$ can be a three to six carbon ($C_3$ to $C_6$) alkyl that can have one double bond, or $R_1$ can be a $C_3$ to $C_6$ alkylene that can have one double bond and that links to $R_2$ to form a cycloalkyl ring;
$R_2$ can be a $CH_2$ or a CH;
A is a cyclopentyl ring;
B can be a $C_3$ to $C_6$ cycloalkyl ring or a heterocycloalkyl ring; and
$R_3$ can be a $C_1$ to $C_3$ alkyl; and
$R_4$ can be hydrogen or $C_1$ to $C_3$ alkyl.

13. The modified COI1 protein of statement 1-11 or 12, wherein at least 10-fold, or at least 20-fold, or at least 30-fold, or at least 40-fold, or at least 50-fold, or at least 60-fold, or at least 70-fold, at least 75-fold, at least 80-fold, at least 85-fold, at least 90-fold, or at least 95-fold, at least 100-fold, at least 110, or at least 125-fold, at least 150-fold, or at least 175-fold higher concentration of coronatine, cinnacidin, or a compound of formula I is required for formation of the COI1A384V-JAZ9 co-receptor than for the COI1WT-JAZ9 co-receptor.

14. The modified COI1 protein of statement 1-12 or 13, wherein treatment with methyljasmonate induces expression of JAZ9 in cells expressing the modified COI1 protein by at least 10-fold, by at least 15-fold, by at least 20-fold, by at least 25-fold, by at least 30-fold, by at least 35-fold, at least 40-fold, or at least 50-fold compared with that in COI1-30 (COI1-null mutant) plants.

15. The modified COI1 protein of statement 1-13 or 14, wherein treatment with coronatine or a compound of formula I induces expression of JAZ9 in cells expressing the modified COI1 protein by less than 10-fold, or by less than 9-fold, or by about 8-fold than COI1-30 plants after COR treatment or treatment with a compound of formula I.

16. The modified COI1 protein of statement 1-14 or 15, wherein plants expressing the modified protein have increased resistance to bacteria compared to parental or wild type plants under the same conditions.

17. The modified COI1 protein of statement 1-15 or 16, wherein plants expressing the modified protein have increased resistance to *Pseudomonas syringae* pv tomato (Pst) DC3000 and/or *Pseudomonas syringae* pv maculicola (Psm) ES4326 bacteria compared to parental or wild type plants under the same conditions.

18. The modified COI1 protein of statement 1-16 or 17, wherein plants expressing the modified protein have at least 10-fold, or at least 15-fold, or at least 20-fold, or at least 25-fold, or at least 30-fold, or at least 35-fold, or at least 40-fold, or at least 45-fold, or at least 50-fold, or at least 60-fold, or at least 75-fold, or at least 100-fold, or at least 150-fold, or at least 200-fold, or at least 250-fold fewer *Pseudomonas syringae* pv tomato (Pst) DC3000 and/or *Pseudomonas syringae* pv maculicola (Psm) ES4326 bacteria compared to parental or wild type plants under the same conditions.

19. The modified COI1 protein of statement 1-17 or 18, wherein plants expressing the modified protein retain insect resistance similar to plants expressing wild type or unmodified COI1.

20. The modified COI1 protein of statement 1-8 or 19, wherein plants expressing the modified protein have at least 2-fold, or at least 3-fold, or at least 4-fold, or at least 5-fold less insect *Spodoptera exigua* larvae by weight than COI1-30 plants.

21. The modified COI1 protein of statement 1-19 or 20, which when expressed in plants exhibits at least 2-fold, at least 5-fold, at least 10-fold, at least 25-fold, at least 50-fold, at least 75-fold, at least 90-fold, at least 100-fold less inhibition of root growth in the presence of coronatine or a compound of formula I, than an unmodified parental or wild type COI1 protein expressed in a plant under the same conditions.

22. The modified COI1 protein of statement 1-20 or 21, wherein root growth is inhibited in a plant expressing an unmodified parental or wild type COI1 protein of by at least 2-fold, at least 5-fold, at least 10-fold, at least 25-fold, at least 50-fold, at least 75-fold, at least 90-fold, at least 100-fold greater than root growth is inhibited in a plant expressing the modified COI1 protein under the same conditions, where the conditions comprise contacting the plant with coronatine or a compound of formula I.

23. The modified COI1 protein of statement 1-21 or 22, wherein a plant expressing the modified COI1 protein is fertile.

24. The modified COI1 protein of statement 1-22 or 23, wherein at least 50%, or at least 60%, or at least 70%, or at least 75%, or at least 80%, or at least 85%, or at least 90%, or at least 95% of plants in a population of plants expressing the modified COI1 protein are fertile.

25. The modified COI1 protein of statement 1-23 or 24, with an amino acid substitution, replacement, or deletion at a position equivalent to position 384 of a SEQ ID NO:1 COI1 protein.

26. The modified COI1 protein of statement 1-24 or 25, with an amino acid sequence that has at least 90%, or at least 95%, or at least 96%, or at least 97%, at least 98%, or at least 99%/0 sequence identity to SEQ ID NO:1, 2, 5, 8, 10, 13, 16, 19, 22, 25, 28, 31, 33, 36, 39, 42, 45, or 48.

27. A transgene or expression cassette comprising a promoter operably linked to a nucleic acid segment encoding the modified COI1 protein of statement 1-24 or 25.

28. The transgene or expression cassette of statement 27, wherein the promoter is an endogenous COI1 promoter operably linked to the nucleic acid segment encoding the modified COI1 protein.

29. The transgene or expression cassette of statement 27 or 28, wherein the promoter is heterologous to the nucleic acid segment encoding the modified COI1 protein.

30. A cell comprising the transgene or expression cassette of statement 27, 28, or 29.

31. The cell of statement 30, which is a plant cell.

32. The cell of statement 30 or 31 which is a monocotyledon or dicotyledon cell.

33. The cell of statement 30, 31, or 32, which is a *Brassicaceae* or other *Solanaceae* cell.

34. The cell of statement 30-32 or 33, which is an alfalfa, forage legume alfalfa, algae, apple, avocado, balsam, barley, broccoli, Brussels sprout, cabbage, canola, cassava, cauliflower, cocoa, cole vegetable, collard, corn, cottonwood, crucifers, earthmoss, grain legumes, grass, forage grass, jatropa, kale, kohlrabi, maize, miscanthus, moss, mustard, nut, nut sedge, oat, oil firewood trees, oilseed, peach, peanut, potato, radish, rape, rapeseed, rice, rutabaga, *sorghum*, soybean, sugar beet, sugarcane, sunflower, switchgrass, tobacco, tomato, turnip, or wheat cell.

35. A plant comprising the cell of statement 30-33 or 34.

36. The plant of statement 35, which has increased resistance to bacteria compared to parental or wild type plants under the same conditions.

37. The plant of statement 35 or 36, which has increased resistance to *Pseudomonas syringae* pv tomato (Psi) DC3000 and/or *Pseudomonas syringae* pv maculicola (Psm) ES4326 bacteria compared to parental or wild type plants under the same conditions.

38. The plant of statement 35, 36, or 37, which has at least 10-fold, or at least 15-fold, or at least 20-fold, or at least 25-fold, or at least 30-fold, or at least 35-fold, or at least 40-fold, or at least 45-fold, or at least 50-fold, or at least 60-fold, or at least 75-fold, or at least 100-fold, or at least 150-fold, or at least 200-fold, or at least 250-fold fewer *Pseudomonas syringae* pv tomato (Pst) DC3000 and/or *Pseudomonas syringae* pv *maculicola* (Psm) ES4326 bacteria compared to parental or wild type plants under the same conditions.

39. The plant of statement 35-37 or 38 which has at least 2-fold, or at least 3-fold, or at least 4-fold, or at least 5-fold fewer insect *Spodoptera exigua* larvae by weight than COI1-30 plants under the same conditions.

40. The plant of statement 35-38 or 39, which has at least 2-fold, at least 5-fold, at least 10-fold, at least 25-fold, at least 50-fold, at least 75-fold, at least 90-fold, at least 100-fold less inhibition of root growth in the presence of coronatine or a compound of formula I, than an unmodified parental or wild type COI1 protein expressed in a plant under the same conditions, where the conditions comprise contacting the plant with coronatine or a compound of formula I.

41. The plant of statement 35-39 or 40, wherein root growth is inhibited in a plant expressing an unmodified parental or wild type COI1 protein by at least 2-fold, at least 5-fold, at least 10-fold, at least 25-fold, at least 50-fold, at least 75-fold, at least 90-fold, at least 100-fold greater than root growth is inhibited in a plant expressing the modified COI1 protein under the same conditions, where the conditions comprise contacting the plant with coronatine or a compound of formula I.

42. The plant of statement 35-40 or 41, which is fertile.

43. The plant of statement 35-41 or 42, wherein at least 50%, or at least 60%, or at least 70%, or at least 75%, or at least 80%, or at least 85%, or at least 90%, or at least 95% of plants are fertile in a population of plants expressing the modified COI1 protein.

44. A method comprising applying a herbicide to a crop comprising the plant of statement 35-42 or 43 to kill or inhibit growth of plants that do not express the modified COI1 protein.

45. The method of statement 44, wherein the herbicide is a compound of formula I:

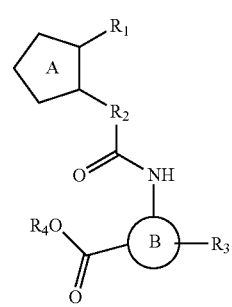

wherein:
R₁ can be a three to six carbon ($C_3$ to $C_6$) alkyl that can have one double bond, or $R_1$ can be a $C_3$ to $C_6$ alkylene that can have one double bond and that links to $R_2$ to form a cycloalkyl ring;
$R_2$ can be a $CH_2$ or a CH;
A is a cyclopentyl ring;
B can be a $C_3$ to $C_6$ cycloalkyl ring or a heterocycloalkyl ring; and
$R_3$ can be a $C_1$ to $C_3$ alkyl; and
$R_4$ can be hydrogen or $C_1$ to $C_3$ alkyl.

46. The method of statement 44 or 45, wherein the herbicide is coronatine.
47. The method of statement 44, wherein the herbicide is cinnacidin.
48. The method of statement 44, wherein the herbicide is a cinnacidin analog selected from compound 2 and 11 shown below:

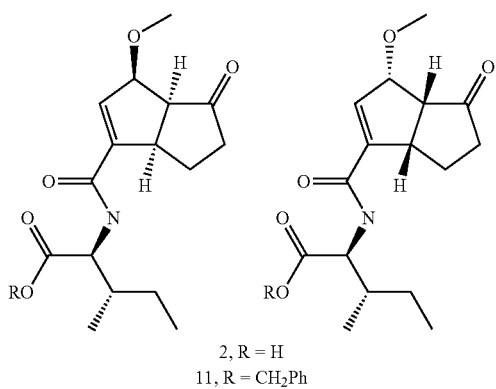

2, R = H
11, R = CH₂Ph

49. The method of statement 44-47 or 48, wherein a herbicidally effective amount of the herbicide is applied.
50. The method of statement 49, wherein the herbicidally effective amount of the herbicide is at least 50 g per hectacre, at least 100 g per hectacre, at least 125 g per hectacre, at least 150 g per hectacre, at least 200 g per hectacre, at least 250 g per hectacre, at least 300 g per hectacre, at least 400 g per hectacre, at least 500 g per hectacre, at least 700 g per hectacre, at least 1000 g per hectacre, at least 1500 g per hectacre, or at least 2000 g per hectacre.
51. The method of statement 49 or 50, wherein the herbicidally effective amount of the herbicide is less than 2500 g per hectacre, or less than 2000 g per hectacre, or less than 1500 g per hectacre, or less than 1000 g per hectacre.
52. The method of statement 44-50 or 51, wherein the crop comprises seedlings.
53. The method of statement 44-51 or 52, wherein the crop comprises a seeded field.
54. The method of statement 44-52 or 53, further comprising planting seeds comprising the transgene or expression cassette of statement 27, 28, or 29 to provide the crop.
55. The method of statement 44-53 or 54, further comprising planting seeds comprising a modified COI1 gene that encodes the modified protein.

The specific products, compositions, and methods described herein are representative, exemplary and not intended as limitations on the scope of the invention. Other objects, aspects, and embodiments will occur to those skilled in the art upon consideration of this specification, and are encompassed within the spirit of the invention as defined by the scope of the claims. It will be readily apparent to one skilled in the art that varying substitutions and modifications may be made to the invention disclosed herein without departing from the scope and spirit of the invention. The terms and expressions that have been employed are used as terms of description and not of limitation, and there is no intent in the use of such terms and expressions to exclude any equivalent of the features shown and described or portions thereof, but it is recognized that various modifications are possible within the scope of the invention as claimed. Thus, it will be understood that although the present invention has been specifically disclosed by embodiments and optional features, modification and variation of the concepts herein disclosed may be resorted to by those skilled in the art, and that such modifications and variations are considered to be within the scope of this invention as defined by the appended claims and statements of the invention.

The invention illustratively described herein may be practiced in the absence of any element or elements, or limitation or limitations, which is not specifically disclosed herein as essential. The methods and processes illustratively described herein may be practiced in differing orders of steps, and the methods and processes are not necessarily restricted to the orders of steps indicated herein or in the claims.

As used herein and in the appended claims, the singular forms "a," "an," and "the" include plural reference unless the context clearly dictates otherwise. Thus, for example, a reference to "a plant" or "a seed" or "a cell" includes a plurality of such plants, seeds or cells, and so forth. In this document, the term "or" is used to refer to a nonexclusive or, such that "A or B" includes "A but not B," "B but not A," and "A and B," unless otherwise indicated.

Under no circumstances may the patent be interpreted to be limited to the specific examples or embodiments or methods specifically disclosed herein. Under no circumstances may the patent be interpreted to be limited by any statement made by any Examiner or any other official or employee of the Patent and Trademark Office unless such statement is specifically and without qualification or reservation expressly adopted in a responsive writing by Applicants.

The invention has been described broadly and generically herein. Each of the narrower species and subgeneric groupings falling within the generic disclosure also form part of the invention. This includes the generic description of the invention with a proviso or negative limitation removing any subject matter from the genus, regardless of whether or not the excised material is specifically recited herein. In addition, where features or aspects of the invention are described in terms of Markush groups, those skilled in the art will recognize that the invention is also thereby described in terms of any individual member or subgroup of members of the Markush group.

What is claimed:

1. A modified CORONATINE INSENSITIVE 1 (COI1) protein comprising an amino acid sequence with at least one amino acid substitution or replacement at a position equivalent to position 384 of a SEQ ID NO: 1 COI1 protein, which is within a jasmonate binding pocket of the COI1 protein, wherein the at least one amino acid substitution reduces complex formation between the modified COI1 protein, coronatine, and a JAZ repressor protein compared to the native (wild types) COI1 protein.

2. The modified COI1 protein of claim 1, wherein the modified COI1 protein has a hydrophobic amino acid that is not alanine at the position of an alanine in the native (wild type) COI1 protein.

3. The modified COI1 protein of claim 1, wherein the modified COI1 protein has at least one amino acid substitution within about 0-10 amino acid positions of amino acid position 384 where the amino acid that is replaced in the native (wild type) COI1 protein is an alanine, and the replacement is a hydrophobic amino acid.

4. The modified COI1 protein of claim 1, wherein the modified COI1 protein has a valine substitution or replacement at a position equivalent to position 384 of SEQ ID NO:1.

5. The modified COI1 protein of claim 1, with greater binding affinity for jasmonate, methyljasmonate, or jasmonate-Ile, than for a plant toxin that forms a complex with a wild type (native) COI1 protein and a JAZ protein.

6. The modified COI1 protein of claim 1, which binds jasmonate, methyljasmonate, or jasmonate-Ile with greater affinity than it binds a plant toxin produced by *Pseudomonas syringae* pv tomato, *Pseudomonas syringae* pv maculicola, *Pseudomonas syringae* pv atropurpurea, *Pseudomonas syringae* pv glycinea, *Pseudomonas syringae* pv morsprunorum, *Pseudomonas syringae* pv porri, *Pseudomonas cannabina* pv alisalensis, *Streptomyces scabies*, *Xanthomonas campestris* pv phormiicola, *Pseudomonas savastanoi* pv glycinea, *Pectobacterium atrosepticum*(syn. *Erwinia carotovora* subsp. *atroseptica*, or *Nectria* sp. DA060097.

7. The modified COI1 protein of claim 1, with greater binding affinity for jasmona methyljasmonate, or jasmonate-Ile, than for a compound of formula I:

$$\text{I}$$

wherein:

$R_1$ can be a three to six carbon ($C_3$ to $C_6$)alkyl that can have one double bond, or $R_1$ can be a $C_3$ to $C_6$ alkylene that can have one double bond and that links to $R_2$ to form a cycloalkyl ring;

$R_2$ can be a $CH_2$ or a CH;

A is a cyclopentyl ring;

B can be a $C_3$ to $C_6$ cycloalkyl ring or a heterocycloalkyl ring; and $R_3$ can be a $C_1$ to $C_3$ alkyl; and $R_4$ can be hydrogen or $C_1$ to $C_3$ alkyl.

8. The modified COI1 protein of claim 7, wherein at least 10-fold higher concentration of coronatirie, cinnacidin, or a compound of formula I is required for formation of a COI1 A 384V-JAZ9 co-receptor in the presence of the coronatine, cinnacidin, or a compound of formula I, than for a COI1WT-JAZ9 co-receptor in the presence of coronatine, cinnacidin, or a compound of formula I.

9. The modified COI1 protein of claim 1, wherein plants expressing the modified protein have increased resistance to bacteria compared to parental or wild type plants under the same conditions.

10. The modified COI1 protein of claim 1, wherein plants expressing the modified protein have increased resistance to *Pseudomonas syringae* pv tomato (Pst) DC3000 and/or *Pseudomonas syringae* pv maculicola (Psm) ES4326 bacteria compared to parental or wild type plants under the same conditions.

11. The modified COI1 protein of claim 1, wherein plants expressing the modified protein have at least 10-fold fewer *Pseudomonas syringae* pv tomato (Pst) DC3000 and/or *Pseudomonas syringae* pv maculicola (Psm) ES4326 bacteria compared to parental or wild type plants under the same conditions.

12. The modified COI1 protein of claim 1, wherein plants expressing the modified protein retain insect resistance of plants expressing wild type or unmodified COI1, or have increased insect resistance compared to plants expressing (native) wild type or unmodified COI1.

13. The modified COI1 protein of claim 1, wherein plants expressing the modified protein have at least 2-fold less insect *Spodoptera exigua* larvae by weight than coil-30 plants.

14. The modified COI1 protein of claim 1, wherein plants expressing the modified protein exhibit at least 2-fold less inhibition of root growth in the presence of coronatine or a compound of formula I, than an unmodified parental or wild type COI1 protein exhibits in a plan under the same conditions.

15. The modified COI1 protein of claim 1, with an amino acid sequence that has at least 95% sequence identity to SEQ ID NO: 2, 5, 8, 10, 13, 16, 19, 22, 25, 28, 31, 33, 36, 39, 42, 45, or 48.

16. A cell comprising modified COI1 protein of claim 1.

17. The cell of claim 16, which is an alfalfa, forage legume alfalfa, algae, apple, avocado, balsam, barley, broccoli, Brussels sprout, cabbage, canola, cassava, cauliflower, cocoa, cote vegetable, collard, corn, cottonwood, crucifers, earthmoss, grain legumes, grass, forage grass, jatropa, kale, kohlrabi, maize, miscanthus, moss, mustard, nut, nut sedge, oat, oil firewood trees, oilseed, peach, peanut, potato, radish, rape, rapeseed, rice, rutabaga, sorghum, soybean, sugar beet, sugarcane, sunflower, switchgrass, tobacco, tomato, turnip, or wheat cell.

18. A transgene or expression cassette comprising a promoter operably linked to a nucleic acid segment encoding the modified COI1 protein of claim 1.

19. The transgene or expression cassette of claim 18, wherein the promoter is an endogenous COI1 promoter operably linked to the nucleic acid segment encoding the modified COI1 protein.

20. The transgene or expression cassette of claim 18, wherein the promoter is heterologous to the nucleic acid segment encoding the modified COI1 protein.

21. A plant comprising the modified COI1 protein of claim 1.

22. The plant of claim 21, which has at least 10-fold increased resistance to *Pseudomonas syringae* pv tomato (Pst) DC3000 and/or *Pseudomonas syringae* pv maculicola (Psm) ES4326 bacteria compared to parental or wild type plants under the same conditions.

23. The plant of claim 21, which has at least 2-fold fewer *Spodoptera exigua* larvae by weight than coil-30 plants under the same conditions.

24. The plant of claim 21, which has at least 2-fold less inhibition of root growth in the presence of coronatine or a compound of formula I, than an unmodified parental or wild type COI1 protein expressed in a plant under the same conditions, where the conditions comprise contacting the plant with coronatine or a compound of formula I:

wherein:
$R_1$ can be a three to six carbon ($C_3$ to $C_6$) alkyl that can have one double bond, or $R_1$ can be a $C_3$ to $C_6$ alkylene that can have one double bond and that links to $R_2$ to form a cycloalkyl ring;
$R_2$ can be a $CH_2$ or a CH;
A is a cyclopentyl ring;
B can be a $C_3$ to $C_6$ cycloalkyl ring or a heterocycloalkyl ring; and
$R_3$ can be a $C_1$ to $C_3$ alkyl; and
$R_4$ can be hydrogen or $C_1$ to $C_3$ alkyl.

25. The plant of claim 21, which is fertile.

26. A method comprising applying a herbicide composition comprisil coronatine to a crop comprising one or more plants expressing a modified COI1 protein to kill or inhibit growth of plants that do not express the modified COI1 protein, wherein the modified COI1 protein comprises an amino acid sequence with at least one amino acid substitution or replacement at a position equivalent to position 384 of a SEQ ID NO: 1 COI1 protein, which is within a jasmonate binding pocket of the COI1 protein, wherein the at least one amino acid substitution reduces complex formation between coronatine and a JAZ repressor protein.

27. The method of claim 26, wherein the plant expressing the modified COI1 protein grows in the presence of the herbicide.

28. The method of claim 26, wherein plant expressing a modified COI1 protein is fertile.

* * * * *

UNITED STATES PATENT AND TRADEMARK OFFICE
CERTIFICATE OF CORRECTION

PATENT NO. : 10,584,350 B2  
APPLICATION NO. : 15/796311  
DATED : March 10, 2020  
INVENTOR(S) : He et al.

Page 1 of 1

It is certified that error appears in the above-identified patent and that said Letters Patent is hereby corrected as shown below:

In the Claims

In Column 231, Line 57, in Claim 6, delete "syringaepv" and insert --syringae pv-- therefor In Column 231, Line 60, in Claim 6, delete "syringaepv" and insert --syringae pv-- therefor In Column 231, Line 66, in Claim 7, delete "jasmona" and insert --jasmonate,-- therefor In Column 232, Line 53, in Claim 8, delete "coronatirie," and insert --coronatine,-- therefor In Column 233, Line 20, in Claim 14, delete "plan" and insert --plant-- therefor In Column 233, Line 26, in Claim 16, after "comprising", insert --the--

In Column 233, Line 30, in Claim 17, delete "cote" and insert --cole-- therefor

In Column 233, Line 50, in Claim 22, delete "syringaepv" and insert --syringae pv-- therefor In Column 234, Line 38, in Claim 26, delete "comprisil" and insert --comprising-- therefor In Column 234, Line 51, in Claim 28, after "wherein", insert --the--

Signed and Sealed this  
Twentieth Day of October, 2020

Andrei Iancu  
*Director of the United States Patent and Trademark Office*